US010577411B2

(12) United States Patent
Trauger et al.

(10) Patent No.: US 10,577,411 B2
(45) Date of Patent: Mar. 3, 2020

(54) ANGIOPOIETIN-LIKE 4 ANTIBODIES AND METHODS OF USE

(71) Applicant: Novartis AG, Basel (CH)

(72) Inventors: John Trauger, Cambridge, MA (US); Andrei Igorevich Voznesensky, Arlington, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 15/686,454

(22) Filed: Aug. 25, 2017

(65) Prior Publication Data

US 2018/0044410 A1 Feb. 15, 2018

Related U.S. Application Data

(62) Division of application No. 14/819,680, filed on Aug. 6, 2015, now Pat. No. 9,771,417.

(60) Provisional application No. 62/034,409, filed on Aug. 7, 2014.

(51) Int. Cl.
C07K 16/18 (2006.01)
C07K 16/22 (2006.01)
A61K 39/00 (2006.01)

(52) U.S. Cl.
CPC .............. C07K 16/18 (2013.01); C07K 16/22 (2013.01); A61K 2039/505 (2013.01); C07K 2317/24 (2013.01); C07K 2317/33 (2013.01); C07K 2317/565 (2013.01); C07K 2317/71 (2013.01); C07K 2317/76 (2013.01); C07K 2317/92 (2013.01); C07K 2317/94 (2013.01)

(58) Field of Classification Search
None
See application file for complete search history.

(56) References Cited

U.S. PATENT DOCUMENTS

| | | | |
|---|---|---|---|
| 6,005,091 A | 12/1999 | Blackburn et al. |
| 7,001,766 B2 | 2/2006 | Shimkets et al. |
| 7,217,794 B2 | 5/2007 | Abdel-Meguid et al. |
| 7,368,531 B2 | 5/2008 | Rosen et al. |
| 7,371,384 B2 | 5/2008 | Gerber et al. |
| 7,459,564 B2 | 12/2008 | Corte et al. |
| 7,501,404 B2 | 3/2009 | Bannister et al. |
| 7,544,699 B2 | 6/2009 | Mjalli et al. |
| 7,612,181 B2 | 11/2009 | Wu et al. |
| 7,626,039 B2 | 12/2009 | Pinto et al. |
| 7,655,762 B2 | 2/2010 | Lee et al. |
| 7,740,846 B2 | 6/2010 | Gerber et al. |
| 8,092,796 B2 | 1/2012 | Lee et al. |
| 8,168,586 B1 | 5/2012 | Fang et al. |
| 8,236,316 B2 | 8/2012 | Gruber et al. |
| 8,258,268 B2 | 9/2012 | Wu et al. |
| 8,354,103 B2 | 1/2013 | Sleeman et al. |
| 8,524,238 B2 | 9/2013 | Fang et al. |
| 8,591,891 B2 | 11/2013 | Lee et al. |
| 8,604,185 B2 | 12/2013 | Gerber et al. |
| 8,633,155 B2 | 1/2014 | Gerber et al. |
| 8,722,859 B2 | 5/2014 | Miller et al. |
| 9,120,851 B2 | 9/2015 | Sleeman et al. |
| 2002/0004587 A1 | 1/2002 | Miller et al. |
| 2004/0180855 A1 | 9/2004 | Schumacher et al. |
| 2005/0143317 A1 | 6/2005 | Abdel-Meguid et al. |
| 2006/0025576 A1 | 2/2006 | Miller et al. |
| 2006/0093606 A1 | 5/2006 | Gerber et al. |
| 2006/0093607 A1 | 5/2006 | Gerber et al. |
| 2006/0222645 A1 | 10/2006 | Lee et al. |
| 2007/0026002 A1 | 2/2007 | Gerber et al. |
| 2007/0041905 A1 | 2/2007 | Hoffman et al. |
| 2007/0054859 A1 | 3/2007 | Aubin et al. |
| 2007/0071675 A1 | 3/2007 | Wu et al. |
| 2007/0081996 A1 | 4/2007 | Hoffman et al. |
| 2008/0146811 A1 | 6/2008 | Deng et al. |
| 2008/0299120 A1 | 12/2008 | Miller et al. |
| 2010/0047239 A1 | 2/2010 | Wu et al. |
| 2010/0137414 A1 | 6/2010 | Freier et al. |
| 2010/0172915 A1 | 7/2010 | Gerber et al. |
| 2011/0008359 A1 | 1/2011 | Lee et al. |
| 2011/0110852 A1 | 5/2011 | Miller et al. |
| 2011/0159006 A1 | 6/2011 | Hack |
| 2011/0159015 A1 | 6/2011 | Sleeman et al. |
| 2011/0311524 A1 | 12/2011 | Gerber et al. |
| 2012/0171217 A1 | 7/2012 | Lee et al. |
| 2012/0201746 A1 | 8/2012 | Liu et al. |
| 2012/0207770 A1 | 8/2012 | Tan et al. |
| 2012/0238728 A1 | 9/2012 | Miller et al. |
| 2013/0004416 A1 | 1/2013 | Wu et al. |
| 2013/0078253 A1 | 3/2013 | Fang et al. |

(Continued)

FOREIGN PATENT DOCUMENTS

EP 1846452 B1 8/2014
WO 1995017420 A1 6/1995

(Continued)

OTHER PUBLICATIONS

Vajdos et al. Comprehensive functional maps of the antigen-binding site of an anti-ErbB2 antibody obtained with shotgun scanning mutagenesis. J Mol Biol., 320(2):415-28, (2002).
Brown et al. Tolerance of single, but not multiple, amino acid replacements in antibody VH CDR 2: a means of minimizing B cell wastage from somatic hypermutation? J. Immuno., 3285-91. (1996).
Rudikoff et al Single amino acid substitution altering antigen-binding specificity. Proc Natl Acad Sci U S A., 79(6):1979-83 (1982).
Paul "Fundamental Immunology", 3rd Edition, (1993) pp. 292-295.

(Continued)

Primary Examiner — Marianne P Allen
(74) Attorney, Agent, or Firm — Meghan S. Adams

(57) ABSTRACT

The present invention relates to monoclonal antibodies binding to human angiopoietin-like 4 protein (hereinafter, sometimes referred to as "ANGPTL4"), and pharmaceutical compositions and methods of treatment comprising the same.

13 Claims, 12 Drawing Sheets

Specification includes a Sequence Listing.

(56) References Cited

U.S. PATENT DOCUMENTS

| | | |
|---|---|---|
| 2013/0266574 A1 | 10/2013 | Sleeman et al. |
| 2014/0099310 A1 | 4/2014 | Fang et al. |
| 2014/0100359 A1 | 4/2014 | Wu et al. |
| 2014/0154256 A1 | 6/2014 | Wu et al. |
| 2014/0213768 A1 | 7/2014 | Wu et al. |
| 2014/0296493 A1 | 10/2014 | Hoffman et al. |
| 2014/0322221 A1 | 10/2014 | Miller et al. |
| 2014/0377805 A1 | 12/2014 | Wu et al. |
| 2015/0004167 A1 | 1/2015 | Wu et al. |
| 2015/0056202 A1 | 2/2015 | Wu et al. |
| 2015/0071941 A1 | 3/2015 | Sodhi et al. |
| 2015/0086554 A1 | 3/2015 | Wu et al. |
| 2015/0099298 A1 | 4/2015 | Wilmen et al. |
| 2015/0147327 A1 | 5/2015 | Wu et al. |
| 2015/0210758 A1 | 7/2015 | Lescar et al. |
| 2016/0145326 A1 | 5/2016 | Trauger et al. |

FOREIGN PATENT DOCUMENTS

| | | |
|---|---|---|
| WO | 9915654 A2 | 4/1999 |
| WO | 11046515 A1 | 10/2001 |
| WO | 200177342 A1 | 10/2001 |
| WO | 2006014678 A2 | 2/2006 |
| WO | 2006014729 A2 | 2/2006 |
| WO | 2006074228 A1 | 7/2006 |
| WO | 2007024705 A2 | 3/2007 |
| WO | 2007024715 A2 | 3/2007 |
| WO | 2007109307 A2 | 9/2007 |
| WO | 2008024188 A2 | 2/2008 |
| WO | 2009114677 A1 | 9/2009 |
| WO | 2010066836 A2 | 6/2010 |
| WO | 11079257 A2 | 6/2011 |
| WO | 12088302 A2 | 6/2012 |
| WO | 13155512 A2 | 10/2013 |
| WO | 2013167669 A1 | 11/2013 |
| WO | 14027959 A1 | 2/2014 |
| WO | 2016020880 A2 | 2/2016 |
| WO | 2016020882 A2 | 2/2016 |

OTHER PUBLICATIONS

Kim, "Hepatic expression, synthesis and secretion of a novel fibrinogen/angiopoietin-related protein that prevents endothelial-cell apoptosis", Biochem J. (2000) 346:603-610.

Yoon et al., "Peroxisome Proliferator-Activated Receptor y Target Gene Encoding a Novel Angiopoietin-Related Protein Associated with Adipose Differentiation", Molecular and Cellular Biology, (2000) 20:14:5343-5349.

Lee et al., "Identification of a New Functional Domain in Angiopoietin-like 3 (ANGPTL3) and Angiopoitin-like 4 (ANGPTL4) Involved in Binding and Inhibition of Lipoprotein Lipase (LPL)", The Journal of Biological Chemistry, (2009) 284(20):13735-13745.

Boder et al., "Directed evolution of antibody fragments with monovalent femtomolar antigen-binding affinity", PNAS, (2000) 97(20):10701-10705.

Yoshida et al., "Angiopoietin-like protein 4 is a potent hyperlipidemia-inducing factor in mice and inhibitor of lipoprotein lipase", Journal of Lipid Research, (2002) 43(11):1770-1772.

Drager L.F. et al "Chronic intermittent hypoxia induces atherosclerosis via activation of adipose angiopoietin-like 4" Am J Respir Crit Care Med., (2013), vol. 188, No. 2, pp. 240-248.

Leabman et al., "Effects of altered Fc[gamma]R binding on antiody pharmacokinetics in cynomolgus monkeys", mAbs, 5(6):896-903 (2013).

(A)

(B)

(C)

(D)

(A)

(B)

SEQUENCE LISTING

```
<160> NUMBER OF SEQ ID NOS: 233

<210> SEQ ID NO 1
<211> LENGTH: 406
<212> TYPE: PRT
<213> ORGANISM: Homo sapiens

<400> SEQUENCE: 1

Met Ser Gly Ala Pro Thr Ala Gly Ala Ala Leu Met Leu Cys Ala Ala
1               5                   10                  15

Thr Ala Val Leu Leu Ser Ala Gln Gly Gly Pro Val Gln Ser Lys Ser
                20                  25                  30

Pro Arg Phe Ala Ser Trp Asp Glu Met Asn Val Leu Ala His Gly Leu
            35                  40                  45

Leu Gln Leu Gly Gln Gly Leu Arg Glu His Ala Glu Arg Thr Arg Ser
        50                  55                  60

Gln Leu Ser Ala Leu Glu Arg Arg Leu Ser Ala Cys Gly Ser Ala Cys
65                  70                  75                  80

Gln Gly Thr Glu Gly Ser Thr Asp Leu Pro Leu Ala Pro Glu Ser Arg
                85                  90                  95

Val Asp Pro Glu Val Leu His Ser Leu Gln Thr Gln Leu Lys Ala Gln
            100                 105                 110

Asn Ser Arg Ile Gln Gln Leu Phe His Lys Val Ala Gln Gln Gln Arg
        115                 120                 125

His Leu Glu Lys Gln His Leu Arg Ile Gln His Leu Gln Ser Gln Phe
    130                 135                 140

Gly Leu Leu Asp His Lys His Leu Asp His Glu Val Ala Lys Pro Ala
145                 150                 155                 160

Arg Arg Lys Arg Leu Pro Glu Met Ala Gln Pro Val Asp Pro Ala His
                165                 170                 175

Asn Val Ser Arg Leu His Arg Leu Pro Arg Asp Cys Gln Glu Leu Phe
            180                 185                 190

Gln Val Gly Glu Arg Gln Ser Gly Leu Phe Glu Ile Gln Pro Gln Gly
        195                 200                 205

Ser Pro Pro Phe Leu Val Asn Cys Lys Met Thr Ser Asp Gly Gly Trp
    210                 215                 220

Thr Val Ile Gln Arg Arg His Asp Gly Ser Val Asp Phe Asn Arg Pro
225                 230                 235                 240

Trp Glu Ala Tyr Lys Ala Gly Phe Gly Asp Pro His Gly Glu Phe Trp
                245                 250                 255

Leu Gly Leu Glu Lys Val His Ser Ile Thr Gly Asp Arg Asn Ser Arg
            260                 265                 270

Leu Ala Val Gln Leu Arg Asp Trp Asp Gly Asn Ala Glu Leu Leu Gln
        275                 280                 285
```

```
        Phe Ser Val His Leu Gly Gly Glu Asp Thr Ala Tyr Ser Leu Gln Leu
            290                 295                 300

Thr Ala Pro Val Ala Gly Gln Leu Gly Ala Thr Thr Val Pro Pro Ser
        305                 310                 315                 320

Gly Leu Ser Val Pro Phe Ser Thr Trp Asp Gln Asp His Asp Leu Arg
                        325                 330                 335

Arg Asp Lys Asn Cys Ala Lys Ser Leu Ser Gly Gly Trp Trp Phe Gly
                        340                 345                 350

Thr Cys Ser His Ser Asn Leu Asn Gly Gln Tyr Phe Arg Ser Ile Pro
                    355                 360                 365

Gln Gln Arg Gln Lys Leu Lys Lys Gly Ile Phe Trp Lys Thr Trp Arg
                    370                 375                 380

Gly Arg Tyr Tyr Pro Leu Gln Ala Thr Thr Met Leu Ile Gln Pro Met
        385                 390                 395                 400

Ala Ala Glu Ala Ala Ser
                        405

<210> SEQ ID NO 2
<211> LENGTH: 1225
<212> TYPE: DNA
<213> ORGANISM: Homo sapiens

<400> SEQUENCE: 2
atgagcggtg ctccgacggc cggggcagcc ctgatgctct cgccgccac cgccgtgcta      60 ctgagcgctc agggcggacc cgtgcagtcc aagtcgccgc gctttgcgtc ctgggacgag     120
atgaatgtcc tggcgcacgg actcctgcag ctcggccagg ggctgcgcga acacgcggag     180
cgcacccgca gtcagctgag cgcgctggag cggcgcctga gcgcgtgcgg gtccgcctgt    240
cagggaaccg aggggtccac cgacctcccg ttagcccctg agagccgggt ggaccctgag    300
gtccttcaca gcctgcagac acaactcaag gctcagaaca gcaggatcca gcaactcttc    360
cacaaggtgg cccagcagca gcggcacctg gagaagcagc acctgcgaat tcagcatctg    420
caaagccagt ttggcctcct ggaccacaag cacctagacc atgaggtggc caagcctgcc    480
cgaagaaaga ggctgcccga gatggcccag ccagttgacc cggctcacaa tgtcagccgc    540
ctgcaccggc tgcccaggga ttgccaggag ctgttccagg ttggggagag cagagtggga    600
ctatttgaaa tccagcctca ggggtctccg ccatttttgg tgaactgcaa gatgacctca    660
gatggaggct ggacagtaat tcagaggcgc acgatggct cagtggactt caaccggccc    720
tgggaagcct acaaggcggg gtttggggat cccacggcg agttctggct gggtctggag    780
aaggtgcata gcatcacggg ggaccgcaac agccgcctgg ccgtgcagct gcgggactgg    840
gatggcaacg ccgagttgct gcagttctcc gtgcacctgg gtggcgagga cacggcctat    900
agcctgcagc tcactgcacc cgtggccggc cagctgggcg ccaccaccgt cccacccagc    960
ggcctctccg tacccttctc cacttgggac caggatcacg acctccgcag ggacaagaac   1020
tgcgccaaga gcctctctgg aggctggtgg tttggcacct gcagccattc caacctcaac   1080
ggccagtact tccgctccat cccacagcag cggcagaagc ttaagaaggg aatcttctgg   1140
aagacctggc ggggccgcta ctaccgctg caggccacca ccatgttgat ccagcccatg   1200
gcagcagagg cagcctccta gcgtc                                          1225

<210> SEQ ID NO 3
<211> LENGTH: 406
<212> TYPE: PRT
```

<213> ORGANISM: Macaca fascicularis

<400> SEQUENCE: 3

Met Arg Gly Ala Pro Thr Ala Gly Ala Ala Leu Met Leu Cys Val Ala
1               5                   10                  15

Thr Ala Val Leu Leu Arg Ala Gln Gly Gly Pro Val Gln Ser Lys Ser
            20                  25                  30

Pro Arg Phe Ala Ser Trp Asp Glu Met Asn Val Leu Ala His Gly Leu
        35                  40                  45

Leu Gln Leu Gly Gln Gly Leu Arg Glu His Ala Glu Arg Thr Arg Ser
    50                  55                  60

Gln Leu Asn Ala Leu Glu Arg Arg Leu Ser Ala Cys Gly Ser Ala Cys
65                  70                  75                  80

Gln Gly Thr Glu Gly Ser Thr Ala Leu Pro Leu Ala Pro Glu Ser Arg
                85                  90                  95

Val Asp Pro Glu Val Leu His Ser Leu Gln Thr Gln Leu Lys Ala Gln
            100                 105                 110

Asn Ser Arg Ile Gln Gln Leu Phe His Lys Val Ala Gln Gln Gln Arg
        115                 120                 125

His Leu Glu Lys Gln His Leu Arg Ile Gln Arg Leu Gln Ser Gln Val
    130                 135                 140

Gly Leu Leu Asp Pro Lys His Leu Asp His Glu Val Ala Lys Pro Ala
145                 150                 155                 160

Arg Arg Lys Arg Arg Pro Glu Met Ala Gln Pro Val Asp Ser Ala His
                165                 170                 175

Asn Ala Ser Arg Leu His Arg Leu Pro Arg Asp Cys Gln Glu Leu Phe
            180                 185                 190

Glu Asp Gly Glu Arg Gln Ser Gly Leu Phe Glu Ile Gln Pro Gln Gly
        195                 200                 205

Ser Pro Pro Phe Leu Val Asn Cys Lys Met Thr Ser Asp Gly Gly Trp
    210                 215                 220

Thr Val Ile Gln Arg Arg His Asp Gly Ser Val Asp Phe Asn Arg Pro
225                 230                 235                 240

Trp Glu Ala Tyr Lys Ala Gly Phe Gly Asp Pro Gln Gly Glu Phe Trp
                245                 250                 255

Leu Gly Leu Glu Lys Val His Ser Ile Thr Gly Asp Arg Asn Ser Arg
            260                 265                 270

Leu Ala Val Gln Leu Gln Asp Trp Asp Gly Asn Ala Glu Ser Leu Gln
        275                 280                 285

Phe Ser Val His Leu Gly Gly Glu Asp Thr Ala Tyr Ser Leu Gln Leu
    290                 295                 300

Thr Glu Pro Val Ala Ser Gln Leu Gly Ala Thr Thr Val Pro Pro Ser
305                 310                 315                 320

Gly Leu Ser Val Pro Phe Ser Thr Trp Asp Gln Asp His Asp Leu Arg
                325                 330                 335

Arg Asp Lys Asn Cys Ala Lys Ser Leu Ser Gly Gly Trp Trp Phe Gly
            340                 345                 350

Thr Cys Ser His Ser Asn Leu Asn Gly Gln Tyr Phe Arg Ser Ile Pro
        355                 360                 365

Gln Gln Arg Gln Glu Leu Lys Lys Gly Ile Phe Trp Lys Thr Trp Arg
    370                 375                 380

Gly Arg Tyr Tyr Pro Leu Gln Ala Thr Thr Met Leu Ile Gln Pro Thr
385                 390                 395                 400

Ala Ala Glu Ala Ala Ser
            405

<210> SEQ ID NO 4
<211> LENGTH: 1221
<212> TYPE: DNA
<213> ORGANISM: Macaca fascicularis

<400> SEQUENCE: 4

| | | | | | |
|---|---|---|---|---|---|
| atgcgcggtg | ctccgacggc | cggagcagcc | ctgatgctct | cgtcgccac | ggccgtgctg | 60 |
| ctgagagctc | agggcggccc | ggtgcagtcc | aagtctccgc | gctttgcgtc | ctgggacgag | 120 |
| atgaatgtcc | tggcgcacgg | actcctgcag | ctaggccagg | ggctgcgcga | acacgcggag | 180 |
| cgcacccgca | gtcagctgaa | cgcgctggag | cggcgcctca | gcgcttgcgg | gtctgcctgc | 240 |
| cagggaaccg | aggggtccac | cgccctcccg | ttagccctg | agaccgggt | ggaccctgag | 300 |
| gtccttcaca | gcctgcagac | acaactcaag | gctcagaaca | gcaggatcca | gcaactcttc | 360 |
| cacaaggtgg | cccagcagca | gcggcacctg | gagaagcagc | acctgcgaat | tcagcgtctg | 420 |
| caaagccagg | ttggcctcct | ggaccccaag | cacctagacc | atgaggtggc | caagcctgcc | 480 |
| cgaagaaaga | ggcggcccga | gatggcccag | ccagttgact | cggctcacaa | tgccagccgc | 540 |
| ctgcaccggc | tgcccaggga | ttgccaggag | ctgtttgaag | atggggagag | gcagagtgga | 600 |
| ctatttgaga | tccagcctca | ggggtctccg | ccattttgg | tgaactgcaa | gatgaccctca | 660 |
| gatggaggct | ggacagtaat | tcagaggcgc | cacgatggct | ctgtggactt | caaccggccc | 720 |
| tgggaagcct | acaaggcggg | gtttggggat | ccccaaggcg | agttctggct | gggcctggag | 780 |
| aaggtgcata | gcatcacagg | ggaccgcaac | agccgcctgg | ccgtgcagct | gcaggactgg | 840 |
| gatggcaacg | ccgagtcgct | gcagttctct | gtgcacctgg | gtggcgagga | cacggcttac | 900 |
| agcctgcagc | tcaccgagcc | cgtggccagc | cagttgggtg | ccaccaccgt | cccgcctagc | 960 |
| ggcctctccg | tacccttctc | cacttgggac | caggatcacg | acctccgcag | ggacaagaac | 1020 |
| tgcgccaaga | gcctctctgg | aggctggtgg | tttggcacct | gcagccattc | aacctcaat | 1080 |
| ggccagtact | tccgctccat | cccacagcag | cggcaggagc | ttaagaaagg | aatcttctgg | 1140 |
| aagacctggc | ggggccgcta | ctacccgctg | caggccacca | ccatgttgat | ccagcccacg | 1200 |
| gcggcagagg | cagcctccta | g | | | | 1221 |

<210> SEQ ID NO 5
<211> LENGTH: 460
<212> TYPE: PRT
<213> ORGANISM: Homo sapiens

<400> SEQUENCE: 5

Met Phe Thr Ile Lys Leu Leu Phe Ile Val Pro Leu Val Ile Ser
1               5                   10                  15

Ser Arg Ile Asp Gln Asp Asn Ser Ser Phe Asp Ser Leu Ser Pro Glu
            20                  25                  30

Pro Lys Ser Arg Phe Ala Met Leu Asp Asp Val Lys Ile Leu Ala Asn
        35                  40                  45

Gly Leu Leu Gln Leu Gly His Gly Leu Lys Asp Phe Val His Lys Thr
    50                  55                  60

Lys Gly Gln Ile Asn Asp Ile Phe Gln Lys Leu Asn Ile Phe Asp Gln
65                  70                  75                  80

Ser Phe Tyr Asp Leu Ser Leu Gln Thr Ser Glu Ile Lys Glu Glu Glu
                85                  90                  95

```
Lys Glu Leu Arg Arg Thr Thr Tyr Lys Leu Gln Val Lys Asn Glu Glu
                100                 105                 110

Val Lys Asn Met Ser Leu Glu Leu Asn Ser Lys Leu Glu Ser Leu Leu
        115                 120                 125

Glu Glu Lys Ile Leu Leu Gln Gln Lys Val Lys Tyr Leu Glu Glu Gln
    130                 135                 140

Leu Thr Asn Leu Ile Gln Asn Gln Pro Glu Thr Pro Glu His Pro Glu
145                 150                 155                 160

Val Thr Ser Leu Lys Thr Phe Val Glu Lys Gln Asp Asn Ser Ile Lys
                165                 170                 175

Asp Leu Leu Gln Thr Val Glu Asp Gln Tyr Lys Gln Leu Asn Gln Gln
            180                 185                 190

His Ser Gln Ile Lys Glu Ile Glu Asn Gln Leu Arg Arg Thr Ser Ile
        195                 200                 205

Gln Glu Pro Thr Glu Ile Ser Leu Ser Ser Lys Pro Arg Ala Pro Arg
    210                 215                 220

Thr Thr Pro Phe Leu Gln Leu Asn Glu Ile Arg Asn Val Lys His Asp
225                 230                 235                 240

Gly Ile Pro Ala Glu Cys Thr Thr Ile Tyr Asn Arg Gly Glu His Thr
                245                 250                 255

Ser Gly Met Tyr Ala Ile Arg Pro Ser Asn Ser Gln Val Phe His Val
            260                 265                 270

Tyr Cys Asp Val Ile Ser Gly Ser Pro Trp Thr Leu Ile Gln His Arg
        275                 280                 285

Ile Asp Gly Ser Gln Asn Phe Asn Glu Thr Trp Glu Asn Tyr Lys Tyr
    290                 295                 300

Gly Phe Gly Arg Leu Asp Gly Glu Phe Trp Leu Gly Leu Glu Lys Ile
305                 310                 315                 320

Tyr Ser Ile Val Lys Gln Ser Asn Tyr Val Leu Arg Ile Glu Leu Glu
                325                 330                 335

Asp Trp Lys Asp Asn Lys His Tyr Ile Glu Tyr Ser Phe Tyr Leu Gly
            340                 345                 350

Asn His Glu Thr Asn Tyr Thr Leu His Leu Val Ala Ile Thr Gly Asn
        355                 360                 365

Val Pro Asn Ala Ile Pro Glu Asn Lys Asp Leu Val Phe Ser Thr Trp
    370                 375                 380

Asp His Lys Ala Lys Gly His Phe Asn Cys Pro Glu Gly Tyr Ser Gly
385                 390                 395                 400

Gly Trp Trp Trp His Asp Glu Cys Gly Glu Asn Asn Leu Asn Gly Lys
                405                 410                 415

Tyr Asn Lys Pro Arg Ala Lys Ser Lys Pro Glu Arg Arg Arg Gly Leu
            420                 425                 430

Ser Trp Lys Ser Gln Asn Gly Arg Leu Tyr Ser Ile Lys Ser Thr Lys
        435                 440                 445

Met Leu Ile His Pro Thr Asp Ser Glu Ser Phe Glu
    450                 455                 460

<210> SEQ ID NO 6
<211> LENGTH: 1380
<212> TYPE: DNA
<213> ORGANISM: Homo sapiens

<400> SEQUENCE: 6
atgttcacaa ttaagctcct tcttttatt gttcctctag ttatttcctc cagaattgat      60
```

-continued

```
caagacaatt catcatttga ttctctatct ccagagccaa aatcaagatt tgctatgtta    120
gacgatgtaa aaattttagc caatggcctc cttcagttgg gacatggtct taaagacttt    180
gtccataaga cgaagggcca aattaatgac atatttcaaa aactcaacat atttgatcag    240 tcttttatg atctatcgct gcaaaccagt gaaatcaaag aagaagaaaa ggaactgaga     300
agaactacat ataaactaca agtcaaaaat gaagaggtaa agaatatgtc acttgaactc    360
aactcaaaac ttgaaagcct cctagaagaa aaaattctac ttcaacaaaa agtgaaatat    420
ttagaagagc aactaactaa cttaattcaa aatcaacctg aaactccaga cacccagaa     480 gtaacttcac ttaaaacttt tgtagaaaaa caagataata gcatcaaaga ccttctccag    540
accgtggaag accaatataa acaattaaac caacagcata gtcaaataaa agaaatagaa    600
aatcagctca gaaggactag tattcaagaa cccacagaaa tttctctatc ttccaagcca    660
agagcaccaa gaactactcc ctttcttcag ttgaatgaaa taagaaatgt aaaacatgat    720
ggcattcctg ctgaatgtac caccatttat aacagaggtg aacatacaag tggcatgtat    780
gccatcagac ccagcaactc tcaagttttt catgtctact gtgatgttat atcaggtagt    840
ccatggacat taattcaaca tcgaatagat ggatcacaaa acttcaatga acgtgggag     900 aactacaaat atggttttgg gaggcttgat ggagaatttt ggttgggcct agagaagata    960
tactccatag tgaagcaatc taattatgtt ttacgaattg agttggaaga ctggaaagac    1020
aacaaacatt atattgaata ttcttttttac ttgggaaatc acgaaaccaa ctatacgcta   1080
catctagttg cgattactgg caatgtcccc aatgcaatcc cggaaaacaa agatttggtg    1140
ttttctactt gggatcacaa agcaaaagga cacttcaact gtccagaggg ttattcagga    1200
ggctggtggt ggcatgatga gtgtggagaa acaacctaa atggtaaata taacaaacca    1260
agagcaaaat ctaagccaga gaggagaaga ggattatctt ggaagtctca aaatggaagg    1320
ttatactcta taaaatcaac caaaatgttg atccatccaa cagattcaga aagctttgaa    1380
```

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 7

Ser Ser Trp Met Gln
1               5

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 8

Glu Ile Asp Pro Ser Asp Asn Tyr Ala Asn Tyr Asn Gln Lys Phe Gln
1               5                   10                  15

Gly

<210> SEQ ID NO 9
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 9

Gly Ser Tyr Phe Ser Asn Phe Phe Asp Tyr
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Tyr Thr Phe Thr Ser Ser
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Pro Ser Asp Asn Tyr
1               5

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Ser Tyr Phe Ser Asn Phe Phe Asp Tyr
1               5                   10

<210> SEQ ID NO 13
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Ala Tyr Thr Phe Thr Ser Ser
                20                  25                  30

Trp Met Gln Trp Val Arg Gln Ala Pro Gly Gln Gly Leu Glu Trp Met
            35                  40                  45

Gly Glu Ile Asp Pro Ser Asp Asn Tyr Ala Asn Tyr Asn Gln Lys Phe
        50                  55                  60

Gln Gly Arg Val Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Ser Gly Ser Tyr Phe Ser Asn Phe Phe Asp Tyr Trp Gly Gln Gly
            100                 105                 110

Thr Leu Val Thr Val Ser Ser
        115

<210> SEQ ID NO 14
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
caggtgcagc tggtgcagtc tggcgccgaa gtgaagaaac caggcgccag cgtgaaggtg      60
tcctgcaagg ccagcgccta cacctttacc agcagctgga tgcagtgggt gcgccaggct     120
cctggacagg gcctggaatg gatgggcgag atcgacccca gcgacaacta cgccaactac     180
aaccagaaat tccagggcag agtgaccctg accgtggaca ccagcaccct caccgcctac     240
atggaactga gcagcctgcg gagcgaggac accgccgtgt actattgtgc cagcggcagc     300
tacttcagca acttcttcga ctactgggc cagggcaccc tcgtgaccgt gtcatct        357

<210> SEQ ID NO 15
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Ala Tyr Thr Phe Thr Ser Ser
            20                  25                  30

Trp Met Gln Trp Val Arg Gln Ala Pro Gly Gln Gly Leu Glu Trp Met
        35                  40                  45

Gly Glu Ile Asp Pro Ser Asp Asn Tyr Ala Asn Tyr Asn Gln Lys Phe
    50                  55                  60

Gln Gly Arg Val Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Ser Tyr Phe Ser Asn Phe Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

```
Ser Asn Thr Lys Val Asp Lys Arg Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 16
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
caggtgcagc tggtgcagtc tggcgccgaa gtgaagaaac caggcgccag cgtgaaggtg      60
tcctgcaagg ccagcgccta cacctttacc agcagctgga tgcagtgggt gcgccaggct     120
cctggacagg gcctggaatg gatgggcgag atcgacccca gcgacaacta cgccaactac     180
aaccagaaat tccagggcag agtgaccctg accgtggaca ccagcaccte caccgcctac     240 atggaactga gcagcctgcg gagcgaggac accgccgtgt actattgtgc cagcggcagc     300
tacttcagca acttcttcga ctactggggc cagggcaccc tcgtgaccgt gtcatctgct     360
agcaccaagg gcccagcgt gttccccctg gccccagca gcaagagcac cagcggcggc     420
acagccgccc tgggctgcct ggtgaaggac tacttccccg agcccgtgac cgtgtcctgg     480
aacagcggag ccctgaccte cggcgtgcac accttcccg ccgtgctgca gagcagcggc     540
ctgtacagcc tgtccagcgt ggtgacagtg cccagcagca gcctgggcac ccagacctac     600
```

```
atctgcaacg tgaaccacaa gcccagcaac accaaggtgg acaagagagt ggagcccaag    660
agctgcgaca agacccacac ctgccccccc tgcccagccc cagagctgct gggcggaccc    720
tccgtgttcc tgttcccccc caagcccaag gacaccctga tgatcagcag gaccccgag    780 gtgacctgcg tggtggtgga cgtgagccac gaggacccag aggtgaagtt caactggtac    840
gtggacggcg tggaggtgca caacgccaag accaagccca gagaggagca gtacaacagc    900
acctacaggg tggtgtccgt gctgaccgtg ctgcaccagg actggctgaa cggcaaggaa    960
tacaagtgca aggtctccaa caaggccctg ccagccccca tcgaaaagac catcagcaag   1020
gccaagggcc agccacggga gccccaggtg tacaccctgc cccccctccg ggaggagatg   1080
accaagaacc aggtgtccct gacctgtctg gtgaagggct ctacccccag cgacatcgcc   1140
gtggagtggg agagcaacgg ccagcccgag aacaactaca agaccacccc cccagtgctg   1200
gacagcgacg gcagcttctt cctgtacagc aagctgaccg tggacaagtc caggtggcag   1260
cagggcaacg tgttcagctg cagcgtgatg cacgaggccc tgcacaacca ctacacccag   1320
aagagcctga gcctgtcccc cggcaag                                      1347
```

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Ala Ser Gln Asp Ile Gly Ser Asn Leu Asn
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Val Ser Asn Arg Gly Pro
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Gln Tyr Ala Ser Ser Pro Trp Thr
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser Gln Asp Ile Gly Ser Asn
1               5

<210> SEQ ID NO 21
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Val Ser
1

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Tyr Ala Ser Ser Pro Trp
1               5

<210> SEQ ID NO 23
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Asp Ile Gly Ser Asn
            20                  25                  30

Leu Asn Trp Leu Gln Gln Lys Pro Gly Gln Ala Pro Arg Arg Leu Ile
        35                  40                  45

Tyr Ala Val Ser Asn Arg Gly Pro Gly Ile Pro Ala Arg Phe Ser Gly
    50                  55                  60

Ser Arg Ser Gly Ser Glu Tyr Thr Leu Thr Ile Ser Ser Leu Gln Ser
65                  70                  75                  80

Glu Asp Phe Ala Val Tyr Tyr Cys Leu Gln Tyr Ala Ser Ser Pro Trp
                85                  90                  95

Thr Phe Gly Gln Gly Thr Lys Val Glu Ile Lys
            100                 105

<210> SEQ ID NO 24
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
gagatcgtga tgacacagag ccccgccacc ctgtccgtgt ctccaggcga aagagccacc    60
ctgagctgca aagccagcca ggacatcggc agcaacctga actggctgca gcagaaacca   120
ggccaggccc ccagaaggct gatctacgct gtttccaacc gtggtcctgg catccccgcc   180

```
agattttccg gcagcagatc cggcagcgag tacaccctga ccatcagcag cctgcagagc    240
gaggacttcg ccgtgtacta ctgcctgcag tacgccagca gccctggac atttggccag     300 ggcaccaagg tggaaatcaa g                                               321
```

<210> SEQ ID NO 25  
<211> LENGTH: 214  
<212> TYPE: PRT  
<213> ORGANISM: Artificial Sequence  
<220> FEATURE:  
<223> OTHER INFORMATION: Description of Artificial Sequence: Synthetic polypeptide

<400> SEQUENCE: 25

```
Glu Ile Val Met Thr Gln Ser Pro Ala Thr Leu Ser Val Ser Pro Gly
1               5                  10                  15

Glu Arg Ala Thr Leu Ser Cys Lys Ala Ser Gln Asp Ile Gly Ser Asn
            20                  25                  30

Leu Asn Trp Leu Gln Gln Lys Pro Gly Gln Ala Pro Arg Arg Leu Ile
        35                  40                  45

Tyr Ala Val Ser Asn Arg Gly Pro Gly Ile Pro Ala Arg Phe Ser Gly
50                  55                  60

Ser Arg Ser Gly Ser Glu Tyr Thr Leu Thr Ile Ser Ser Leu Gln Ser
65                  70                  75                  80

Glu Asp Phe Ala Val Tyr Tyr Cys Leu Gln Tyr Ala Ser Ser Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 26  
<211> LENGTH: 642  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 26

```
gagatcgtga tgacacagag ccccgccacc ctgtccgtgt ctccaggcga aagagccacc    60
ctgagctgca aagccagcca ggacatcggc agcaacctga actggctgca gcagaaacca    120
ggccaggccc ccagaaggct gatctacgct gtttccaacc gtggtcctgg catccccgcc    180
agattttccg gcagcagatc cggcagcgag tacaccctga ccatcagcag cctgcagagc    240
```

-continued

```
gaggacttcg ccgtgtacta ctgcctgcag tacgccagca gccctggac atttggccag     300 ggcaccaagg tggaaatcaa gcgtacggtg gccgctccca gcgtgttcat cttcccccc      360 agcgacgagc agctgaagag cggcaccgcc agcgtggtgt gcctgctgaa caacttctac     420
ccccgggagg ccaaggtgca gtggaaggtg gacaacgccc tgcagagcgg caacagccag    480
gagagcgtca ccgagcagga cagcaaggac tccacctaca gcctgagcag caccctgacc    540
ctgagcaagg ccgactacga gaagcataag gtgtacgcct gcgaggtgac ccaccagggc    600
ctgtccagcc ccgtgaccaa gagcttcaac aggggcgagt gc                       642
```

<210> SEQ ID NO 27
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 27

```
caggtgcagc tggtgcagtc aggcgccgaa gtgaagaaac ccggcgctag tgtgaaagtc     60
agctgtaaag ctagtgccta caccttcacc tctagctgga tgcagtgggt cagacaggcc    120
ccaggtcagg gcctggagtg gatgggcgag atcgacccta gcgataacta cgctaactat    180
aatcagaagt ttcagggtag agtcaccctg accgtggaca ctagcactag caccgcctat    240
atggaactgt ctagcctgag atcagaggac accgccgtct actactgcgc tagtggtagc    300
tacttctcta acttcttcga ctactggggt cagggcaccc tggtcaccgt gtctagc       357
```

<210> SEQ ID NO 28
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

```
Gln Val Gln Leu Val Gln Ser Gly Ala Glu Val Lys Lys Pro Gly Ala
1               5                   10                  15

Ser Val Lys Val Ser Cys Lys Ala Ser Ala Tyr Thr Phe Thr Ser Ser
            20                  25                  30

Trp Met Gln Trp Val Arg Gln Ala Pro Gly Gln Gly Leu Glu Trp Met
        35                  40                  45

Gly Glu Ile Asp Pro Ser Asp Asn Tyr Ala Asn Tyr Asn Gln Lys Phe
    50                  55                  60

Gln Gly Arg Val Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Ser Tyr Phe Ser Asn Phe Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
```

```
                    165                 170                 175
        Gln Ser Ser Gly Leu Tyr Ser Leu Ser Ser Val Thr Val Pro Ser
                    180                 185                 190

Ser Leu Gly Thr Gln Thr Tyr Ile Cys Asn Val Asn His Lys Pro
                    195                 200                 205

Ser Asn Thr Lys Val Asp Lys Arg Val Glu Pro Lys Ser Cys Asp Lys
                    210                 215                 220

Thr His Thr Cys Pro Pro Cys Pro Ala Pro Glu Ala Ala Gly Gly Pro
        225                 230                 235                 240

Ser Val Phe Leu Phe Pro Pro Lys Pro Lys Asp Thr Leu Met Ile Ser
                            245                 250                 255

Arg Thr Pro Glu Val Thr Cys Val Val Val Asp Val Ser His Glu Asp
                            260                 265                 270

Pro Glu Val Lys Phe Asn Trp Tyr Val Asp Gly Val Glu Val His Asn
                            275                 280                 285

Ala Lys Thr Lys Pro Arg Glu Glu Gln Tyr Asn Ser Thr Tyr Arg Val
                            290                 295                 300

Val Ser Val Leu Thr Val Leu His Gln Asp Trp Leu Asn Gly Lys Glu
        305                 310                 315                 320

Tyr Lys Cys Lys Val Ser Asn Lys Ala Leu Pro Ala Pro Ile Glu Lys
                            325                 330                 335

Thr Ile Ser Lys Ala Lys Gly Gln Pro Arg Glu Pro Gln Val Tyr Thr
                            340                 345                 350

Leu Pro Pro Ser Arg Glu Glu Met Thr Lys Asn Gln Val Ser Leu Thr
                            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
        385                 390                 395                 400

Asp Ser Asp Gly Ser Phe Phe Leu Tyr Ser Lys Leu Thr Val Asp Lys
                            405                 410                 415

Ser Arg Trp Gln Gln Gly Asn Val Phe Ser Cys Ser Val Met His Glu
                            420                 425                 430

Ala Leu His Asn His Tyr Thr Gln Lys Ser Leu Ser Leu Ser Pro Gly
                            435                 440                 445

Lys

<210> SEQ ID NO 29
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
caggtgcagc tggtgcagtc aggcgccgaa gtgaagaaac ccggcgctag tgtgaaagtc       60
agctgtaaag ctagtgccta caccttcacc tctagctgga tgcagtgggt cagacaggcc     120
ccaggtcagg gcctggagtg gatgggcgag atcgacccta gcgataacta cgctaactat     180
aatcagaagt ttcagggtag agtcaccctg accgtggaca ctagcactag caccgcctat     240
atggaactgt ctagcctgag atcagaggac accgccgtct actactgcgc tagtggtagc     300
tacttctcta acttcttcga ctactggggt cagggcaccc tggtcaccgt gtctagcgct     360
agcactaagg gccccctcgt gttccctctg gcccttccag gcaagtctac ctccggcggc     420
```

```
acagctgctc tgggctgcct ggtcaaggac tacttccctg agcctgtgac agtgtcctgg    480
aactctggcg ccctgacctc tggcgtgcac accttccctg ccgtgctgca gtcctccggc    540
ctgtactccc tgtcctccgt ggtcacagtg ccttcaagca gcctgggcac ccagacctat    600
atctgcaacg tgaaccacaa gccttccaac accaaggtgg acaagcgggt ggagcctaag    660
tcctgcgaca agacccacac ctgtcctccc tgccctgctc ctgaagctgc tggcggccct    720
tctgtgttcc tgttccctcc aaagcccaag gacaccctga tgatctcccg gacccctgaa    780
gtgacctgcg tggtggtgga cgtgtcccac gaggatcctg aagtgaagtt caattggtac    840
gtggacggcg tggaggtgca caacgccaag accaagcctc gggaggaaca gtacaactcc    900
acctaccggg tggtgtccgt gctgaccgtg ctgcaccagg actggctgaa cggcaaagag    960
tacaagtgca aagtctccaa caaggccctg cctgccccta tcgaaaagac aatctccaag   1020
gccaagggcc agcctaggga accccaggtg tacaccctgc acccagccg ggaggaaatg   1080 accaagaacc aggtgtccct gacctgtctg gtcaagggct tctaccctc cgatatcgcc   1140 gtggagtggg agtctaacgg ccagcctgag aacaactaca agaccacccc tcctgtgctg   1200
gactccgacg gctccttctt cctgtactcc aaactgaccg tggacaagtc ccggtggcag   1260
cagggcaacg tgttctcctg ctccgtgatg cacgaggccc tgcacaacca ctacacccag   1320
aagtccctgt ccctgtctcc cggcaag                                        1347

<210> SEQ ID NO 30
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
gagatcgtga tgactcagtc acccgctacc ctgagcgtca gccctggcga gcgggctaca     60
ctgagctgta aagcctctca ggatatcggc tctaacctga ctggctgca gcagaagccc    120 ggtcaggccc ctagacggct gatctacgcc gtgtctaata gaggccccgg aatccccgct    180
aggtttagcg gctctaggtc aggttcagag tacaccctga ctatctctag cctgcagtca    240
gaggacttcg ccgtctacta ctgcctgcag tacgcctcta gccccctggac cttcggtcag    300 ggcactaagg tcgagattaa g                                               321

<210> SEQ ID NO 31
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
gagatcgtga tgactcagtc acccgctacc ctgagcgtca gccctggcga gcgggctaca     60
ctgagctgta aagcctctca ggatatcggc tctaacctga ctggctgca gcagaagccc    120 ggtcaggccc ctagacggct gatctacgcc gtgtctaata gaggccccgg aatccccgct    180
aggtttagcg gctctaggtc aggttcagag tacaccctga ctatctctag cctgcagtca    240
gaggacttcg ccgtctacta ctgcctgcag tacgcctcta gccccctggac cttcggtcag    300 ggcactaagg tcgagattaa gcgtacggtg gccgctccca gcgtgttcat cttccccccc    360
```

```
agcgacgagc agctgaagag cggcaccgcc agcgtggtgt gcctgctgaa caacttctac    420
ccccgggagg ccaaggtgca gtggaaggtg acaacgccc tgcagagcgg caacagccag    480
gagagcgtca ccgagcagga cagcaaggac tccacctaca gcctgagcag caccctgacc    540
ctgagcaagg ccgactacga gaagcataag gtgtacgcct gcgaggtgac ccaccagggc    600
ctgtccagcc ccgtgaccaa gagcttcaac aggggcgagt gc                      642
```

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ser Ser Trp Met Gln
1               5

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Glu Ile Asp Pro Ser Asp Asn Tyr Ala Asn Tyr Asn Gln Lys Phe Gln
1               5                   10                  15

Gly

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Ser Tyr Phe Ser Asn Phe Phe Asp Tyr
1               5                   10

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Tyr Thr Phe Thr Ser Ser
1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Asp Pro Ser Asp Asn Tyr
1               5

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Ser Tyr Phe Ser Asn Phe Phe Asp Tyr
1               5                   10

<210> SEQ ID NO 38
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Ala Tyr Thr Phe Thr Ser Ser
            20                  25                  30

Trp Met Gln Trp Val Arg Gln Ala Pro Gly Gln Gly Leu Glu Trp Met
        35                  40                  45

Gly Glu Ile Asp Pro Ser Asp Asn Tyr Ala Asn Tyr Asn Gln Lys Phe
    50                  55                  60

Gln Gly Arg Val Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Ser Tyr Phe Ser Asn Phe Phe Asp Tyr Trp Gly Gln Gly
            100                 105                 110

Thr Leu Val Thr Val Ser Ser
        115

<210> SEQ ID NO 39
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
caggtgcagc tggtgcagtc tggcgccgaa gtgaagaaac caggcgccag cgtgaaggtg      60
tcctgcaagg ccagcgccta cacctttacc agcagctgga tgcagtgggt gcgccaggct     120
cctggacagg gcctggaatg gatgggcgag atcgacccca gcgacaacta cgccaactac     180
aaccagaaat tccagggcag agtgaccctg accgtggaca ccagcaccag caccgcctac     240
atggaactga gcagcctgcg gagcgaggac accgccgtgt actattgtgc cagcggcagc     300
tacttcagca acttcttcga ctactggggc cagggcaccc tcgtgaccgt gtcatct       357

<210> SEQ ID NO 40
<211> LENGTH: 449
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Ala Tyr Thr Phe Thr Ser Ser
            20                  25                  30

Trp Met Gln Trp Val Arg Gln Ala Pro Gly Gln Gly Leu Glu Trp Met
        35                  40                  45

Gly Glu Ile Asp Pro Ser Asp Asn Tyr Ala Asn Tyr Asn Gln Lys Phe
    50                  55                  60

Gln Gly Arg Val Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Ser Tyr Phe Ser Asn Phe Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

```
Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
            435                 440                 445

Lys

<210> SEQ ID NO 41
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
caggtgcagc tggtgcagtc tggcgccgaa gtgaagaaac caggcgccag cgtgaaggtg      60
tcctgcaagg ccagcgccta cacctttacc agcagctgga tgcagtgggt gcgccaggct     120
cctggacagg gcctggaatg gatgggcgag atcgacccca gcgacaacta cgccaactac     180
aaccagaaat tccagggcag agtgaccctg accgtggaca ccagcaccag caccgcctac     240
atggaactga gcagcctgcg gagcgaggac accgccgtgt actattgtgc cagcggcagc     300
tacttcagca acttcttcga ctactgggc cagggcaccc tcgtgaccgt gtcatctgct     360
agcaccaagg gcccagcgt gttccccctg gcccccagca gcaagagcac cagcggcggc     420
acagccgccc tgggctgcct ggtgaaggac tacttccccg agcccgtgac cgtgtcctgg     480
aacagcggag ccctgacctc cggcgtgcac accttccccg ccgtgctgca gagcagcggc     540
ctgtacagcc tgtccagcgt ggtgacagtg cccagcagca gcctgggcac ccagacctac     600
atctgcaacg tgaaccacaa gcccagcaac accaaggtgg acaagagagt ggagcccaag     660
agctgcgaca gaacccacac ctgcccccc tgcccagccc cagagctgct gggcggaccc     720
tccgtgttcc tgttcccccc caagcccaag gacaccctga tgatcagcag gacccccgag     780
gtgacctgcg tggtggtgga cgtgagccac gaggacccag aggtgaagtt caactggtac     840
gtggacggcg tggaggtgca caacgccaag accaagccca gagaggagca gtacaacagc     900
acctacaggg tggtgtccgt gctgaccgtg ctgcaccagg actggctgaa cggcaaggaa     960
tacaagtgca aggtctccaa caaggccctg ccagccccca tcgaaaagac catcagcaag    1020
gccaagggcc agccacggga gccccaggtg tacaccctgc cccctcccg ggaggagatg     1080 accaagaacc aggtgtccct gacctgtctg gtgaagggct cctacccag cgacatcgcc    1140 gtggagtggg agagcaacgg ccagcccgag aacaactaca gaccacccc cccagtgctg    1200 gacagcgacg gcagcttctt cctgtacagc aagctgaccg tggacaagtc caggtggcag    1260
cagggcaacg tgttcagctg cagcgtgatg cacgaggccc tgcacaacca ctacacccag    1320
aagagcctga gcctgtcccc cggcaag                                        1347

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 42

Lys Ala Ser Gln Asp Ile Gly Ser Asn Leu Asn
1               5                   10

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ala Ala Ser Val Arg Glu Pro
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Leu Gln Tyr Ala Ser Ser Pro Trp Thr
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ser Gln Asp Ile Gly Ser Asn
1               5

<210> SEQ ID NO 46
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Ala Ser
1

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Tyr Ala Ser Ser Pro Trp
1               5

<210> SEQ ID NO 48
<211> LENGTH: 107
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Asp Ile Gly Ser Asn
            20                  25                  30

Leu Asn Trp Leu Gln Gln Lys Pro Gly Gln Ala Pro Arg Arg Leu Ile
        35                  40                  45

Tyr Ala Ala Ser Val Arg Glu Pro Gly Ile Pro Ala Arg Phe Ser Gly
    50                  55                  60

Ser Arg Ser Gly Ser Glu Tyr Thr Leu Thr Ile Ser Ser Leu Gln Ser
65                  70                  75                  80

Glu Asp Phe Ala Val Tyr Tyr Cys Leu Gln Tyr Ala Ser Ser Pro Trp
                85                  90                  95

Thr Phe Gly Gln Gly Thr Lys Val Glu Ile Lys
            100                 105

<210> SEQ ID NO 49
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
gagatcgtga tgacacagag ccccgccacc ctgtccgtgt ctccaggcga aagagccacc      60
ctgagctgca aagccagcca ggacatcggc agcaacctga actggctgca gcagaaacca     120
ggccaggccc ccagaaggct gatctacgct gcttccgtcc gtgagcctgg catccccgcc     180
agattttccg gcagcagatc cggcagcgag tacaccctga ccatcagcag cctgcagagc     240
gaggacttcg ccgtgtacta ctgcctgcag tacgccagca gccctggac atttggccag      300 ggcaccaagg tggaaatcaa g                                                321

<210> SEQ ID NO 50
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Asp Ile Gly Ser Asn
            20                  25                  30

Leu Asn Trp Leu Gln Gln Lys Pro Gly Gln Ala Pro Arg Arg Leu Ile
        35                  40                  45

Tyr Ala Ala Ser Val Arg Glu Pro Gly Ile Pro Ala Arg Phe Ser Gly
    50                  55                  60

Ser Arg Ser Gly Ser Glu Tyr Thr Leu Thr Ile Ser Ser Leu Gln Ser
65                  70                  75                  80

Glu Asp Phe Ala Val Tyr Tyr Cys Leu Gln Tyr Ala Ser Ser Pro Trp
```

```
                    85                  90                  95
Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 51
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
gagatcgtga tgacacagag ccccgccacc ctgtccgtgt ctccaggcga aagagccacc        60
ctgagctgca agccagcca ggacatcggc agcaacctga actggctgca gcagaaacca       120
ggccaggccc ccagaaggct gatctacgct gcttccgtcc gtgagcctgg catccccgcc       180
agattttccg gcagcagatc cggcagcgag tacaccctga ccatcagcag cctgcagagc       240
gaggacttcg ccgtgtacta ctgcctgcag tacgccagca gcccctggac atttggccag       300
ggcaccaagg tggaaatcaa gcgtacggtg gccgctccca gcgtgttcat cttccccccc       360
agcgacgagc agctgaagag cggcaccgcc agcgtggtgt gcctgctgaa caacttctac       420
ccccgggagg ccaaggtgca gtggaaggtg gacaacgccc tgcagagcgg caacagccag       480
gagagcgtca ccgagcagga cagcaaggac tccacctaca gcctgagcag cacccctgacc      540 ctgagcaagg ccgactacga gaagcataag gtgtacgcct gcgaggtgac ccaccagggc       600
ctgtccagcc ccgtgaccaa gagcttcaac aggggcgagt gc                         642

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ser Tyr Thr Met His
1               5

<210> SEQ ID NO 53
<211> LENGTH: 17
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 53

Tyr Ile Asn Pro Ser Ser Gly Tyr Thr Lys Tyr Asn Gln Lys Phe Gln
1               5                   10                  15

Gly

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Trp Leu Leu Leu Ala Met Asp Tyr
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Tyr Thr Phe Thr Ser Tyr
1               5

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asn Pro Ser Ser Gly Tyr
1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Trp Leu Leu Leu Ala Met Asp Tyr
1               5

<210> SEQ ID NO 58
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Met
        35                  40                  45

Gly Tyr Ile Asn Pro Ser Ser Gly Tyr Thr Lys Tyr Asn Gln Lys Phe
    50                  55                  60

Gln Gly Arg Val Thr Met Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Glu Gly Trp Leu Leu Leu Ala Met Asp Tyr Trp Gly Gln Gly Thr
            100                 105                 110

Leu Val Thr Val Ser Ser
        115

<210> SEQ ID NO 59
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
caggtgcagc tggtgcagtc tggcgccgaa gtgaagaaac caggcgccag cgtgaaggtg     60
tcctgcaagg ccagcggcta cacctttacc agctacacca tgcactgggt gcgccaggct    120
ccaggccagg gactggaatg gatgggctac atcaaccca gcagcggcta taccaagtac    180
aaccagaaat tccagggccg cgtgaccatg accgccgaca agagcacaag caccgcctac    240
atggaactga gcagcctgcg gagcgaggac accgccgtgt actattgtgc cgagggctgg    300
ctgctgctgg ccatggatta ttggggccag ggcaccctcg tgaccgtgtc tagt          354

<210> SEQ ID NO 60
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Met
        35                  40                  45

Gly Tyr Ile Asn Pro Ser Ser Gly Tyr Thr Lys Tyr Asn Gln Lys Phe
    50                  55                  60

Gln Gly Arg Val Thr Met Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Glu Gly Trp Leu Leu Leu Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Gln Thr Tyr Ile Cys Asn Val Asn His Lys Pro Ser
    195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Arg Glu Glu Met Thr Lys Asn Gln Val Ser Leu Thr Cys
    355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
    435                 440                 445

<210> SEQ ID NO 61
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
caggtgcagc tggtgcagtc tggcgccgaa gtgaagaaac caggcgccag cgtgaaggtg      60
tcctgcaagg ccagcggcta cacctttacc agctacacca tgcactgggt gcgccaggct     120
ccaggccagg gactggaatg gatgggctac atcaaccccca gcagcggcta taccaagtac     180
aaccagaaat tccagggccg cgtgaccatg accgccgaca gagcacaag caccgcctac     240

```
atggaactga gcagcctgcg gagcgaggac accgccgtgt actattgtgc cgagggctgg    300
ctgctgctgg ccatggatta ttggggccag ggcaccctcg tgaccgtgtc tagtgctagc    360
accaagggcc ccagcgtgtt cccccctggcc cccagcagca agagcaccag cggcggcaca    420
gccgccctgg gctgcctggt gaaggactac ttccccgagc ccgtgaccgt gtcctggaac    480
agcggagccc tgacctccgg cgtgcacacc ttccccgccg tgctgcagag cagcggcctg    540
tacagcctgt ccagcgtggt gacagtgccc agcagcagcc tgggcaccca gacctacatc    600
tgcaacgtga accacaagcc cagcaacacc aaggtggaca agagagtgga gcccaagagc    660
tgcgacaaga cccacacctg ccccccctgc ccagccccag agctgctggg cggacccctcc   720 gtgttcctgt tccccccaaa gcccaaggac accctgatga tcagcaggac ccccgaggtg    780
acctgcgtgt ggtggacgt gagccacgag gacccagagg tgaagttcaa ctggtacgtg     840
gacggcgtgg aggtgcacaa cgccaagacc aagcccagag aggagcagta caacagcacc    900
tacagggtgg tgtccgtgct gaccgtgctg caccaggact ggctgaacgg caaggaatac    960
aagtgcaagg tctccaacaa ggcccctgcca gcccccatcg aaaagaccat cagcaaggcc    1020
aagggccagc cacgggagcc ccaggtgtac accctgcccc cctcccggga ggagatgacc    1080
aagaaccagg tgtccctgac ctgtctggtg aagggcttct accccagcga catcgccgtg    1140
gagtgggaga gcaacggcca gcccgagaac aactacaaga ccaccccccc agtgctggac    1200
agcgacggca gcttcttcct gtacagcaag ctgaccgtgg acaagtccag gtggcagcag    1260
ggcaacgtgt tcagctgcag cgtgatgcac gaggccctgc acaaccacta cacccagaag    1320
agcctgagcc tgtccccgg caag                                             1344
```

<210> SEQ ID NO 62
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Arg Ser Ser Thr Gly Ala Val Thr Thr Ser Asn Tyr Ala Ile
1               5                   10

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Thr Asn Asn Arg Ala Pro
1               5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ala Leu Trp Tyr Ser Asp His Trp Val

```
<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ser Thr Gly Ala Val Thr Thr Ser Asn Tyr
1               5                   10

<210> SEQ ID NO 66
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Thr Asn
1

<210> SEQ ID NO 67
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Trp Tyr Ser Asp His Trp
1               5

<210> SEQ ID NO 68
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Glu Ala Val Val Thr Gln Ser Pro Ala Thr Leu Ser Leu Ser Pro Gly
1               5                   10                  15

Glu Arg Ala Thr Leu Ser Cys Arg Ser Ser Thr Gly Ala Val Thr Thr
            20                  25                  30

Ser Asn Tyr Ala Ile Trp Val Gln Glu Lys Pro Gly Gln Ala Pro Arg
        35                  40                  45

Gly Leu Ile Gly Gly Thr Asn Asn Arg Ala Pro Gly Ile Pro Ala Arg
    50                  55                  60

Phe Ser Gly Ser Leu Ser Gly Asp Asp Ala Thr Leu Thr Ile Ser Ser
65                  70                  75                  80

Leu Gln Pro Glu Asp Phe Ala Val Tyr Phe Cys Ala Leu Trp Tyr Ser
                85                  90                  95

Asp His Trp Val Phe Gly Gln Gly Thr Lys Val Glu Ile Lys
                100                 105                 110

<210> SEQ ID NO 69
<211> LENGTH: 330
```

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
gaagccgtcg tgacacagag ccctgccacc ctgtcactga gccctggcga aagagccacc      60
ctgagctgca gatctagcac cggcgctgtg accaccagca actacgccat ctgggtgcag     120
gaaaagcccg gccaggctcc cagaggactg atcggcggca ccaacaatag agcccctggc     180
atccccgcca gattcagcgg atctctgtct ggcgacgacg ccacactgac catcagcagc     240
ctgcagcccg aggacttcgc cgtgtacttc tgcgccctgt ggtacagcga ccactgggtg     300
ttcggccagg gcaccaaggt ggaaatcaag                                      330

<210> SEQ ID NO 70
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70
```

Glu Ala Val Val Thr Gln Ser Pro Ala Thr Leu Ser Leu Ser Pro Gly
1               5                   10                  15

Glu Arg Ala Thr Leu Ser Cys Arg Ser Ser Thr Gly Ala Val Thr Thr
            20                  25                  30

Ser Asn Tyr Ala Ile Trp Val Gln Glu Lys Pro Gly Gln Ala Pro Arg
        35                  40                  45

Gly Leu Ile Gly Gly Thr Asn Asn Arg Ala Pro Gly Ile Pro Ala Arg
    50                  55                  60

Phe Ser Gly Ser Leu Ser Gly Asp Asp Ala Thr Leu Thr Ile Ser Ser
65                  70                  75                  80

Leu Gln Pro Glu Asp Phe Ala Val Tyr Phe Cys Ala Leu Trp Tyr Ser
                85                  90                  95

Asp His Trp Val Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

```
<210> SEQ ID NO 71
<211> LENGTH: 651
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 71

```
gaagccgtcg tgacacagag ccctgccacc ctgtcactga gccctggcga aagagccacc    60
ctgagctgca gatctagcac cggcgctgtg accaccagca actacgccat ctgggtgcag   120
gaaaagcccg gccaggctcc cagaggactg atcggcggca ccaacaatag agcccctggc   180
atccccgcca gattcagcgg atctctgtct ggcgacgacg ccacactgac catcagcagc   240
ctgcagcccg aggacttcgc cgtgtacttc tgcgccctgt ggtacagcga ccactgggtg   300
ttcggccagg gcaccaaggt ggaaatcaag cgtacggtgg ccgctcccag cgtgttcatc   360
ttcccccca gcgacgagca gctgaagagc ggcaccgcca gcgtggtgtg cctgctgaac   420
aacttctacc cccgggaggc caaggtgcag tggaaggtgg acaacgccct gcagagcggc   480
aacagccagg agagcgtcac cgagcaggac agcaaggact ccacctacag cctgagcagc   540
accctgaccc tgagcaaggc cgactacgag aagcataagg tgtacgcctg cgaggtgacc   600
caccagggcc tgtccagccc cgtgaccaag agcttcaaca ggggcgagtg c           651
```

<210> SEQ ID NO 72
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Asn Tyr Trp Ile Thr
1               5

<210> SEQ ID NO 73
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Asp Phe Tyr Pro Gly Gly Gly Ser Thr Asn Tyr Asn Ala Lys Leu Gln
1               5                   10                  15

Gly

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ser Pro Pro Gln Val Ala Pro Phe Asp Tyr
1               5                   10

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 75

Gly Tyr Thr Phe Asn Asn Tyr
1               5

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Tyr Pro Gly Gly Gly Ser
1               5

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ser Pro Pro Gln Val Ala Pro Phe Asp Tyr
1               5                   10

<210> SEQ ID NO 78
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Asn Tyr
            20                  25                  30

Trp Ile Thr Trp Val Arg Gln Ala Pro Gly Gln Gly Leu Glu Trp Met
        35                  40                  45

Gly Asp Phe Tyr Pro Gly Gly Gly Ser Thr Asn Tyr Asn Ala Lys Leu
    50                  55                  60

Gln Gly Arg Val Thr Leu Thr Val Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Pro Pro Gln Val Ala Pro Phe Asp Tyr Trp Gly Gln Gly
            100                 105                 110

Thr Leu Val Thr Val Ser Ser
        115

<210> SEQ ID NO 79
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79
```

```
caggtgcagc tggtgcagtc tggcgccgaa gtgaagaaac caggcgccag cgtgaaggtg      60
tcctgcaagg ccagcggcta cacctttaac aactactgga tcacctgggt gcgccaggcc     120
cctggacagg gactggaatg gatgggcgac ttctaccctg gcggcggcag caccaactac     180
aacgccaagc tgcagggcag agtgaccctg accgtggaca ccagcacctc caccgcctac     240
atggaactgc ggagcctgag aagcgacgac accgccgtgt attactgcgc tagaagccct     300
cctcaggtgg ccccttcga ttattggggc cagggcacac tcgtgaccgt gtcctct         357
```

<210> SEQ ID NO 80
<211> LENGTH: 449
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 80

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Asn Tyr
            20                  25                  30

Trp Ile Thr Trp Val Arg Gln Ala Pro Gly Gln Gly Leu Glu Trp Met
        35                  40                  45

Gly Asp Phe Tyr Pro Gly Gly Gly Ser Thr Asn Tyr Asn Ala Lys Leu
    50                  55                  60

Gln Gly Arg Val Thr Leu Thr Val Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Pro Pro Gln Val Ala Pro Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
```

```
                290              295              300
Val Ser Val Leu Thr Val Leu His Gln Asp Trp Leu Asn Gly Lys Glu
305              310              315              320

Tyr Lys Cys Lys Val Ser Asn Lys Ala Leu Pro Ala Pro Ile Glu Lys
                325              330              335

Thr Ile Ser Lys Ala Lys Gly Gln Pro Arg Glu Pro Gln Val Tyr Thr
                340              345              350

Leu Pro Pro Ser Arg Glu Glu Met Thr Lys Asn Gln Val Ser Leu Thr
                355              360              365

Cys Leu Val Lys Gly Phe Tyr Pro Ser Asp Ile Ala Val Glu Trp Glu
            370              375              380

Ser Asn Gly Gln Pro Glu Asn Asn Tyr Lys Thr Thr Pro Pro Val Leu
385              390              395              400

Asp Ser Asp Gly Ser Phe Phe Leu Tyr Ser Lys Leu Thr Val Asp Lys
                405              410              415

Ser Arg Trp Gln Gln Gly Asn Val Phe Ser Cys Ser Val Met His Glu
                420              425              430

Ala Leu His Asn His Tyr Thr Gln Lys Ser Leu Ser Leu Ser Pro Gly
            435              440              445

Lys

<210> SEQ ID NO 81
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
caggtgcagc tggtgcagtc tggcgccgaa gtgaagaaac caggcgccag cgtgaaggtg      60
tcctgcaagg ccagcggcta cacctttaac aactactgga tcacctgggt gcgccaggcc     120
cctggacagg gactggaatg gatgggcgac ttctaccctg gcggcggcag caccaactac     180
aacgccaagc tgcagggcag agtgaccctg accgtggaca ccagcacctc caccgcctac     240
atggaactgc ggagcctgag aagcgacgac accgccgtgt attactgcgc tagaagccct     300
cctcaggtgg cccccttcga ttattgggc cagggcacac tcgtgaccgt gtcctctgct     360
agcaccaagg gcccagcgt gttccccctg gcccccagca gcaagagcac cagcggcggc     420
acagccgccc tgggctgcct ggtgaaggac tacttcccg agcccgtgac cgtgtcctgg     480
aacagcggag ccctgacctc cggcgtgcac accttccccg ccgtgctgca gagcagcggc     540
ctgtacagcc tgtccagcgt ggtgacagtg cccagcagca gcctgggcac ccagacctac     600
atctgcaacg tgaaccacaa gcccagcaac accaaggtgg acaagagagt ggagcccaag     660
agctgcgaca gacccacac tgccccccc tgcccagccc cagagctgct gggcggaccc     720
tccgtgttcc tgttcccccc caagcccaag gacaccctga tgatcagcag gacccccgag     780
gtgacctgcg tggtggtgga cgtgagccac gaggacccag aggtgaagtt caactggtac     840
gtggacggcg tggaggtgca caacgccaag accaagccca gagaggagca gtacaacagc     900
acctacaggg tggtgtccgt gctgaccgtg ctgcaccagg actggctgaa cggcaaggaa     960
tacaagtgca aggtctccaa caaggccctg ccagccccca tcgaaaagac catcagcaag    1020
gccaagggca gccacggga gccccaggtg tacaccctgc cccctcccg ggaggagatg    1080 accaagaacc aggtgtccct gacctgtctg gtgaagggct tctaccccag cgacatcgcc    1140
```

```
gtggagtggg agagcaacgg ccagcccgag aacaactaca agaccacccc cccagtgctg    1200
gacagcgacg gcagcttctt cctgtacagc aagctgaccg tggacaagtc caggtggcag    1260
cagggcaacg tgttcagctg cagcgtgatg cacgaggccc tgcacaacca ctacacccag    1320
aagagcctga gcctgtcccc cggcaag                                        1347
```

<210> SEQ ID NO 82
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gln Ala Ser Asp Tyr Ile Tyr His Trp Leu Gly
1               5                   10

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Ala Ser Gly Leu Glu Thr
1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gln Gln Tyr Trp Ser Thr Pro Trp Thr
1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ser Asp Tyr Ile Tyr His Trp
1               5

<210> SEQ ID NO 86
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Ala Ser
1

<210> SEQ ID NO 87
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Tyr Trp Ser Thr Pro Trp
1               5

<210> SEQ ID NO 88
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Gln Ala Ser Asp Tyr Ile Tyr His Trp
            20                  25                  30

Leu Gly Trp Tyr Gln Gln Lys Pro Gly Lys Ala Pro Lys Leu Leu Ile
        35                  40                  45

Ser Gly Ala Ser Gly Leu Glu Thr Gly Val Pro Ser Arg Phe Ser Gly
    50                  55                  60

Ser Gly Ser Gly Lys Asp Tyr Thr Phe Thr Ile Ser Ser Leu Gln Pro
65                  70                  75                  80

Glu Asp Ile Ala Thr Tyr Tyr Cys Gln Gln Tyr Trp Ser Thr Pro Trp
                85                  90                  95

Thr Phe Gly Gln Gly Thr Lys Leu Glu Ile Lys
            100                 105

<210> SEQ ID NO 89
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89
gacatccaga tgacccagag ccccagcagc ctgtctgcca gcgtgggcga cagggtgacc      60
atcacctgtc aggccagcga ctacatctac cactggctgg gctggtatca gcagaagccc    120
ggcaaggccc ccaagctgct gattagcgga gcctccggtc tggaaaccgg cgtgccaagc    180 agatttccg gcagcggctc cggcaaggac tacaccttca ccatcagctc cctgcagccc     240
gaggatatcg ccacctacta ctgccagcag tactggtcca cccctggac ctttggccag     300 ggcaccaagc tggaaatcaa g                                               321

<210> SEQ ID NO 90
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Asp Tyr Ile Tyr His Trp
            20                  25                  30

Leu Gly Trp Tyr Gln Gln Lys Pro Gly Lys Ala Pro Lys Leu Leu Ile
        35                  40                  45

Ser Gly Ala Ser Gly Leu Glu Thr Gly Val Pro Ser Arg Phe Ser Gly
50                  55                  60

Ser Gly Ser Gly Lys Asp Tyr Thr Phe Thr Ile Ser Ser Leu Gln Pro
65                  70                  75                  80

Glu Asp Ile Ala Thr Tyr Tyr Cys Gln Gln Tyr Trp Ser Thr Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 91
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
gacatccaga tgacccagag ccccagcagc ctgtctgcca gcgtgggcga cagggtgacc      60
atcacctgtc aggccagcga ctacatctac cactggctgg gctggtatca gcagaagccc    120
ggcaaggccc ccaagctgct gattagcgga gcctccggtc tggaaaccgg cgtgccaagc    180
agattttccg gcagcggctc cggcaaggac tacaccttca ccatcagctc cctgcagccc    240
gaggatatcg ccacctacta ctgccagcag tactggtcca cccctggac ctttggccag     300
ggcaccaagc tggaaatcaa gcgtacggtg gccgctccca gcgtgttcat cttcccccc     360
agcgacgagc agctgaagag cggcaccgcc agcgtggtgt gcctgctgaa caacttctac    420
ccccgggagg ccaaggtgca gtggaaggtg gacaacgccc tgcagagcgg caacagccag    480
gagagcgtca ccgagcagga cagcaaggac tccacctaca gcctgagcag caccctgacc    540
ctgagcaagg ccgactacga aagcataag gtgtacgcct gcgaggtgac ccaccagggc     600
ctgtccagcc ccgtgaccaa gagcttcaac aggggcgagt gc                       642

<210> SEQ ID NO 92
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Asn Tyr Trp Ile Thr
1               5

<210> SEQ ID NO 93
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Asp Phe Tyr Pro Gly Gly Gly Asn Thr Asn Tyr Asn Ala Lys Leu Gln
1               5                   10                  15

Gly

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ser Pro Pro Gln Val Ala Pro Phe Asp Tyr
1               5                   10

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Tyr Thr Phe Thr Asn Tyr
1               5

<210> SEQ ID NO 96
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Tyr Pro Gly Gly Gly Asn
1               5

<210> SEQ ID NO 97
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97
```

```
Ser Pro Pro Gln Val Ala Pro Phe Asp Tyr
1               5                   10
```

<210> SEQ ID NO 98
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile Thr Trp Val Arg Gln Ala Pro Gly Gln Gly Leu Glu Trp Met
        35                  40                  45

Gly Asp Phe Tyr Pro Gly Gly Asn Thr Asn Tyr Asn Ala Lys Leu
50                  55                  60

Gln Gly Arg Val Thr Leu Thr Val Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Pro Pro Gln Val Ala Pro Phe Asp Tyr Trp Gly Gln Gly
            100                 105                 110

Thr Leu Val Thr Val Ser Ser
        115
```

<210> SEQ ID NO 99
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99

```
caggtgcagc tggtgcagtc tggcgccgaa gtgaagaaac caggcgccag cgtgaaggtg      60
tcctgcaagg ccagcggcta cacctttacc aactactgga tcacctgggt gcgccaggcc     120
cctggacagg gactggaatg gatgggcgac ttctaccctg gcggcggcaa caccaactac     180
aacgccaagc tgcagggcag agtgaccctg accgtggaca ccagcacctc caccgcctac     240
atggaactgc ggagcctgag aagcgacgac accgccgtgt attactgcgc tagaagccct     300
cctcaggtgg cccccttcga ttattggggc cagggcacac tcgtgaccgt gtcctct        357
```

<210> SEQ ID NO 100
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30
```

Trp Ile Thr Trp Val Arg Gln Ala Pro Gly Gln Gly Leu Glu Trp Met
            35                  40                  45

Gly Asp Phe Tyr Pro Gly Gly Asn Thr Asn Tyr Asn Ala Lys Leu
 50                  55                  60

Gln Gly Arg Val Thr Leu Thr Val Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Ser Pro Pro Gln Val Ala Pro Phe Asp Tyr Trp Gly Gln Gly
             100                 105                 110

Thr Leu Val Thr Val Ser Ser Ala Ser Thr Lys Gly Pro Ser Val Phe
         115                 120                 125

Pro Leu Ala Pro Ser Ser Lys Ser Thr Ser Gly Gly Thr Ala Ala Leu
     130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                 165                 170                 175

Gln Ser Ser Gly Leu Tyr Ser Leu Ser Ser Val Val Thr Val Pro Ser
             180                 185                 190

Ser Ser Leu Gly Thr Gln Thr Tyr Ile Cys Asn Val Asn His Lys Pro
         195                 200                 205

Ser Asn Thr Lys Val Asp Lys Arg Val Glu Pro Lys Ser Cys Asp Lys
     210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                 245                 250                 255

Arg Thr Pro Glu Val Thr Cys Val Val Val Asp Val Ser His Glu Asp
             260                 265                 270

Pro Glu Val Lys Phe Asn Trp Tyr Val Asp Gly Val Glu Val His Asn
         275                 280                 285

Ala Lys Thr Lys Pro Arg Glu Glu Gln Tyr Asn Ser Thr Tyr Arg Val
     290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                 325                 330                 335

Thr Ile Ser Lys Ala Lys Gly Gln Pro Arg Glu Pro Gln Val Tyr Thr
             340                 345                 350

Leu Pro Pro Ser Arg Glu Glu Met Thr Lys Asn Gln Val Ser Leu Thr
         355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                 405                 410                 415

Ser Arg Trp Gln Gln Gly Asn Val Phe Ser Cys Ser Val Met His Glu
             420                 425                 430

Ala Leu His Asn His Tyr Thr Gln Lys Ser Leu Ser Leu Ser Pro Gly
         435                 440                 445

Lys

<210> SEQ ID NO 101
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101

```
caggtgcagc tggtgcagtc tggcgccgaa gtgaagaaac caggcgccag cgtgaaggtg      60
tcctgcaagg ccagcggcta cacctttacc aactactgga tcacctgggt gcgccaggcc     120
cctggacagg gactggaatg gatgggcgac ttctaccctg gcggcggcaa caccaactac     180
aacgccaagc tgcagggcag agtgaccctg accgtggaca ccagcacctc caccgcctac     240
atggaactgc ggagcctgag aagcgacgac accgccgtgt attactgcgc tagaagccct     300
cctcaggtgg cccccttcga ttattggggc cagggcacac tcgtgaccgt gtcctctgct     360
agcaccaagg gccccagcgt gttccccctg gcccccagca gcaagagcac cagcggcggc     420
acagccgccc tgggctgcct ggtgaaggac tacttccccg agcccgtgac cgtgtcctgg     480
aacagcggag ccctgacctc cggcgtgcac accttccccg ccgtgctgca gagcagcggc     540
ctgtacagcc tgtccagcgt ggtgacagtg cccagcagca gcctgggcac ccagacctac     600
atctgcaacg tgaaccacaa gcccagcaac accaaggtgg acaagagagt ggagcccaag     660
agctgcgaca agacccacac ctgccccccc tgcccagccc cagagctgct gggcggaccc     720
tccgtgttcc tgttcccccc caagcccaag gacaccctga tgatcagcag gacccccgag     780
gtgacctgcg tggtggtgga cgtgagccac gaggacccag aggtgaagtt caactggtac     840
gtggacggcg tggaggtgca caacgccaag accaagccca gaggagca gtacaacagc     900 acctacaggg tggtgtccgt gctgaccgtg ctgcaccagg actggctgaa cggcaaggaa     960
tacaagtgca aggtctccaa caaggccctg ccagccccca tcgaaaagac catcagcaag    1020
gccaagggcc agccacggga gccccaggtg tacaccctgc ccccctcccg ggaggagatg    1080
accaagaacc aggtgtccct gacctgtctg gtgaagggct tctacccag cgacatcgcc    1140 gtggagtggg agagcaacgg ccagcccgag aacaactaca agaccacccc cccagtgctg    1200
gacagcgacg gcagcttctt cctgtacagc aagctgaccg tggacaagtc caggtggcag    1260
cagggcaacg tgttcagctg cagcgtgatg cacgaggccc tgcacaacca ctacacccag    1320
aagagcctga gcctgtcccc cggcaag                                        1347
```

<210> SEQ ID NO 102
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

```
Gln Ala Ser Glu Tyr Ile Tyr Asn Trp Leu Gly
1               5                   10
```

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 103

Gly Ala Ser Gly Leu Glu Thr
1               5

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gln Gln Tyr Trp Ser Thr Pro Trp Thr
1               5

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ser Glu Tyr Ile Tyr Asn Trp
1               5

<210> SEQ ID NO 106
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Ala Ser
1

<210> SEQ ID NO 107
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Tyr Trp Ser Thr Pro Trp
1               5

<210> SEQ ID NO 108
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Tyr Ile Tyr Asn Trp
            20                  25                  30

```
Leu Gly Trp Tyr Gln Gln Lys Pro Gly Lys Ala Pro Lys Leu Leu Ile
            35                  40                  45

Ser Gly Ala Ser Gly Leu Glu Thr Gly Val Pro Ser Arg Phe Ser Gly
 50                  55                  60

Ser Gly Ser Gly Lys Asp Tyr Thr Phe Thr Ile Ser Ser Leu Gln Pro
 65                  70                  75                  80

Glu Asp Ile Ala Thr Tyr Tyr Cys Gln Gln Tyr Trp Ser Thr Pro Trp
                85                  90                  95

Thr Phe Gly Gln Gly Thr Lys Leu Glu Ile Lys
            100                 105
```

<210> SEQ ID NO 109
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 109

```
gacatccaga tgacccagag ccccagcagc ctgtctgcca gcgtgggcga cagggtgacc      60
atcacctgtc aggccagcga atacatctac aactggctgg gctggtatca gcagaagccc     120
ggcaaggccc ccaagctgct gattagcgga gcctccggtc tggaaaccgg cgtgccaagc     180
agattttccg gcagcggctc cggcaaggac tacaccttca ccatcagctc cctgcagccc     240
gaggatatcg ccacctacta ctgccagcag tactggtcca cccctggac  ctttggccag     300
ggcaccaagc tggaaatcaa g                                                321
```

<210> SEQ ID NO 110
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 110

```
Asp Ile Gln Met Thr Gln Ser Pro Ser Ser Leu Ser Ala Ser Val Gly
 1               5                  10                  15

Asp Arg Val Thr Ile Thr Cys Gln Ala Ser Glu Tyr Ile Tyr Asn Trp
            20                  25                  30

Leu Gly Trp Tyr Gln Gln Lys Pro Gly Lys Ala Pro Lys Leu Leu Ile
            35                  40                  45

Ser Gly Ala Ser Gly Leu Glu Thr Gly Val Pro Ser Arg Phe Ser Gly
 50                  55                  60

Ser Gly Ser Gly Lys Asp Tyr Thr Phe Thr Ile Ser Ser Leu Gln Pro
 65                  70                  75                  80

Glu Asp Ile Ala Thr Tyr Tyr Cys Gln Gln Tyr Trp Ser Thr Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 111
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111
gacatccaga tgacccagag ccccagcagc ctgtctgcca gcgtgggcga cagggtgacc      60
atcacctgtc aggccagcga atacatctac aactggctgg ctggtatca gcagaagccc     120 ggcaaggccc ccaagctgct gattagcgga gcctccggtc tggaaaccgg cgtgccaagc    180
agattttccg gcagcggctc cggcaaggac tacaccttca ccatcagctc cctgcagccc    240
gaggatatcg ccacctacta ctgccagcag tactggtcca cccctggac ctttggccag     300 ggcaccaagc tggaaatcaa gcgtacggtg gccgctccca gcgtgttcat cttcccccc    360 agcgacgagc agctgaagag cggcaccgcc agcgtggtgt gcctgctgaa caacttctac    420
ccccgggagg ccaaggtgca gtggaaggtg gacaacgccc tgcagagcgg caacagccag    480
gagagcgtca ccgagcagga cagcaaggac tccacctaca gcctgagcag cacccctgacc   540 ctgagcaagg ccgactacga aagcataag gtgtacgcct gcgaggtgac ccaccagggc    600
ctgtccagcc ccgtgaccaa gagcttcaac aggggcgagt gc                       642

<210> SEQ ID NO 112
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Ser Phe Trp Ile Thr
1               5

<210> SEQ ID NO 113
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Asp Ile Tyr Pro Gly Gly Ala Thr Thr Asn Tyr Asn Glu Lys Leu Gln
1               5                   10                  15

Gly

<210> SEQ ID NO 114
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ser Pro Pro Gln Val Gly Pro Phe Asp Tyr
1               5                   10

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Tyr Thr Phe Thr Ser Phe
1               5

<210> SEQ ID NO 116
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Tyr Pro Gly Gly Ala Thr
1               5

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Ser Pro Pro Gln Val Gly Pro Phe Asp Tyr
1               5                   10

<210> SEQ ID NO 118
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Trp Ile Thr Trp Val Arg Gln Ala Pro Gly Gln Gly Leu Glu Trp Met
        35                  40                  45

Gly Asp Ile Tyr Pro Gly Gly Ala Thr Thr Asn Tyr Asn Glu Lys Leu
    50                  55                  60

Gln Gly Arg Val Thr Leu Thr Val Asp Thr Ser Thr Ser Thr Ala Tyr
65                  70                  75                  80
```

```
Met Glu Leu Arg Ser Leu Arg Ser Asp Asp Thr Ala Val Tyr Tyr Cys
                85                  90                  95

Ala Arg Ser Pro Pro Gln Val Gly Pro Phe Asp Tyr Trp Gly Gln Gly
            100                 105                 110

Thr Leu Val Thr Val Ser Ser
        115

<210> SEQ ID NO 119
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119
caggtgcagc tggtgcagtc tggcgccgaa gtgaagaaac caggcgccag cgtgaaggtg     60
tcctgcaagg ccagcggcta taccttcacc agcttttgga tcacctgggt gcgccaggcc    120
cctggacagg gactggaatg gatgggcgac atctaccctg gcggcgccac caccaactac    180
aacgagaagc tgcagggcag agtgaccctg accgtggaca ccagcacctc caccgcctac    240
atggaactgc ggagcctgag aagcgacgac accgccgtgt actactgcgc tagaagccct    300
cctcaggtgg gccccttcga ttattggggc cagggcacac tcgtgaccgt gtcctct       357

<210> SEQ ID NO 120
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Trp Ile Thr Trp Val Arg Gln Ala Pro Gly Gln Gly Leu Glu Trp Met
        35                  40                  45

Gly Asp Ile Tyr Pro Gly Gly Ala Thr Thr Asn Tyr Asn Glu Lys Leu
    50                  55                  60

Gln Gly Arg Val Thr Leu Thr Val Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Pro Pro Gln Val Gly Pro Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 121
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121
caggtgcagc tggtgcagtc tggcgccgaa gtgaagaaac caggcgccag cgtgaaggtg      60
tcctgcaagg ccagcggcta caccttcacc agcttttgga tcacctgggt gcgccaggcc     120
cctggacagg gactggaatg gatgggcgac atctaccctg gcggcgccac caccaactac     180
aacgagaagc tgcagggcag agtgaccctg accgtggaca ccagcacctc caccgcctac     240
atggaactgc ggagcctgag aagcgacgac accgccgtgt actactgcgc tagaagccct     300
cctcaggtgg gcccccttcga ttattggggc cagggcacac tcgtgaccgt gtcctctgct     360
agcaccaagg gcccagcgt gttccccctg gcccccagca gcaagagcac cagcggcggc     420
acagccgccc tgggctgcct ggtgaaggac tacttccccg agcccgtgac cgtgtcctgg     480
aacagcggag ccctgacctc cggcgtgcac accttccccg ccgtgctgca gagcagcggc     540

```
ctgtacagcc tgtccagcgt ggtgacagtg cccagcagca gcctgggcac ccagacctac    600
atctgcaacg tgaaccacaa gcccagcaac accaaggtgg acaagagagt ggagcccaag    660
agctgcgaca agacccacac ctgcccccccc tgcccagccc cagagctgct gggcggaccc    720
tccgtgttcc tgttcccccc caagcccaag gacaccctga tgatcagcag gaccccccgag    780 gtgacctgcg tggtggtgga cgtgagccac gaggacccag aggtgaagtt caactggtac    840
gtggacggcg tggaggtgca caacgccaag accaagccca gagaggagca gtacaacagc    900
acctacaggg tggtgtccgt gctgaccgtg ctgcaccagg actggctgaa cggcaaggaa    960
tacaagtgca aggtctccaa caaggccctg ccagccccca tcgaaaagac catcagcaag   1020
gccaagggcc agccacggga gccccaggtg tacaccctgc cccctcccg ggaggagatg   1080 accaagaacc aggtgtccct gacctgtctg gtgaagggct tctacccag cgacatcgcc   1140 gtggagtggg agagcaacgg ccagcccgag aacaactaca agaccacccc cccagtgctg   1200
gacagcgacg gcagcttctt cctgtacagc aagctgaccg tggacaagtc caggtggcag   1260
cagggcaacg tgttcagctg cagcgtgatg cacgaggccc tgcacaacca ctacacccag   1320
aagagcctga gcctgtcccc cggcaag                                       1347
```

<210> SEQ ID NO 122
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gln Ala Ser Asp Tyr Ile Tyr His Trp Leu Ala
1               5                   10

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gly Ala Ser Ser Leu Glu Thr
1               5

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gln Gln Tyr Trp Ser Ile Pro Trp Thr
1               5

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ser Asp Tyr Ile Tyr His Trp
1               5

<210> SEQ ID NO 126
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gly Ala Ser
1

<210> SEQ ID NO 127
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Tyr Trp Ser Ile Pro Trp
1               5

<210> SEQ ID NO 128
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Asp Ile Gln Met Thr Gln Ser Pro Ser Ser Leu Ser Ala Ser Val Gly
1               5                   10                  15

Asp Arg Val Thr Ile Thr Cys Gln Ala Ser Asp Tyr Ile Tyr His Trp
                20                  25                  30

Leu Ala Trp Tyr Gln Gln Lys Pro Gly Lys Ala Pro Lys Leu Leu Ile
            35                  40                  45

Ser Gly Ala Ser Ser Leu Glu Thr Gly Val Pro Ser Arg Phe Ser Gly
    50                  55                  60

Ser Gly Ser Gly Lys Asp Tyr Thr Phe Thr Ile Ser Ser Leu Gln Pro
65                  70                  75                  80

Glu Asp Ile Ala Thr Tyr Tyr Cys Gln Gln Tyr Trp Ser Ile Pro Trp
                85                  90                  95

Thr Phe Gly Gln Gly Thr Lys Leu Glu Ile Lys
            100                 105

<210> SEQ ID NO 129
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 129
gacatccaga tgacccagag ccccagcagc ctgtctgcca gcgtgggcga cagagtgacc      60
atcacctgtc aggccagcga ctacatctac cactggctgg cctggtatca gcagaagccc    120

```
ggcaaggccc ccaagctgct gattagcgga gcctccagtc tggaaaccgg cgtgccaagc    180
agattttccg gcagcggctc cggcaaggac tacaccttca ccatcagctc cctgcagccc    240
gaggatatcg ccacctacta ctgccagcag tactggtcca tccctggac ctttggccag    300 ggcaccaagc tggaaatcaa g                                              321
```

<210> SEQ ID NO 130
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 130

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Asp Tyr Ile Tyr His Trp
            20                  25                  30

Leu Ala Trp Tyr Gln Gln Lys Pro Gly Lys Ala Pro Lys Leu Leu Ile
        35                  40                  45

Ser Gly Ala Ser Ser Leu Glu Thr Gly Val Pro Ser Arg Phe Ser Gly
    50                  55                  60

Ser Gly Ser Gly Lys Asp Tyr Thr Phe Thr Ile Ser Ser Leu Gln Pro
65                  70                  75                  80

Glu Asp Ile Ala Thr Tyr Tyr Cys Gln Gln Tyr Trp Ser Ile Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 131
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 131

```
gacatccaga tgacccagag ccccagcagc ctgtctgcca gcgtgggcga cagagtgacc     60
atcacctgtc aggccagcga ctacatctac cactggctgg cctggtatca gcagaagccc    120
ggcaaggccc ccaagctgct gattagcgga gcctccagtc tggaaaccgg cgtgccaagc    180
```

```
agattttccg gcagcggctc cggcaaggac tacaccttca ccatcagctc cctgcagccc    240
gaggatatcg ccacctacta ctgccagcag tactggtcca tccctggac ctttggccag     300 ggcaccaagc tggaaatcaa gcgtacggtg ccgctccca gcgtgttcat cttccccccc    360
agcgacgagc agctgaagag cggcaccgcc agcgtggtgt gcctgctgaa caacttctac    420
ccccgggagg ccaaggtgca gtggaaggtg gacaacgccc tgcagagcgg caacagccag    480
gagagcgtca ccgagcagga cagcaaggac tccacctaca gcctgagcag cacctgacc    540 ctgagcaagg ccgactacga aagcataag gtgtacgcct gcgaggtgac ccaccagggc    600
ctgtccagcc ccgtgaccaa gagcttcaac aggggcgagt gc                       642
```

```
<210> SEQ ID NO 132
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ser Phe Trp Ile Thr
1               5

<210> SEQ ID NO 133
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Asp Ile Tyr Pro Gly Gly Ala Asn Thr Asn Tyr Asn Glu Lys Leu Gln
1               5                   10                  15

Gly

<210> SEQ ID NO 134
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ser Pro Pro Gln Val Gly Pro Phe Asp Tyr
1               5                   10

<210> SEQ ID NO 135
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gly Tyr Thr Phe Thr Ser Phe
1               5

<210> SEQ ID NO 136
<211> LENGTH: 6
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 136

Tyr Pro Gly Gly Ala Asn
1               5

<210> SEQ ID NO 137
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ser Pro Pro Gln Val Gly Pro Phe Asp Tyr
1               5                   10

<210> SEQ ID NO 138
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Trp Ile Thr Trp Val Arg Gln Ala Pro Gly Gln Gly Leu Glu Trp Met
        35                  40                  45

Gly Asp Ile Tyr Pro Gly Gly Ala Asn Thr Asn Tyr Asn Glu Lys Leu
    50                  55                  60

Gln Gly Arg Val Thr Leu Thr Val Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Pro Pro Gln Val Gly Pro Phe Asp Tyr Trp Gly Gln Gly
            100                 105                 110

Thr Leu Val Thr Val Ser Ser
        115

<210> SEQ ID NO 139
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 139
caggtgcagc tggtgcagtc tggcgccgaa gtgaagaaac caggcgccag cgtgaaggtg      60
tcctgcaagg ccagcggcta taccttcacc agcttttgga tcacctgggt gcgccaggcc     120
cctggacagg gactggaatg gatgggcgac atctaccctg gcggcgccaa caccaactac     180
aacgagaagc tgcagggcag agtgaccctg accgtggaca ccagcacctc caccgcctac     240
atggaactgc ggagcctgag aagcgacgac accgccgtgt actactgcgc tagaagccct     300
cctcaggtgg gccccttcga ttattggggc cagggcacac tcgtgaccgt gtcctct      357

<210> SEQ ID NO 140
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Ser Phe
            20                  25                  30

Trp Ile Thr Trp Val Arg Gln Ala Pro Gly Gln Gly Leu Glu Trp Met
        35                  40                  45

Gly Asp Ile Tyr Pro Gly Gly Ala Asn Thr Asn Tyr Asn Glu Lys Leu
    50                  55                  60

Gln Gly Arg Val Thr Leu Thr Val Asp Thr Ser Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Pro Pro Gln Val Gly Pro Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 141
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 141
caggtgcagc tggtgcagtc tggcgccgaa gtgaagaaac caggcgccag cgtgaaggtg      60
tcctgcaagg ccagcggcta ccttcacc agcttttgga tcacctgggt gcgccaggcc       120
cctggacagg gactggaatg gatgggcgac atctaccctg gcgccgccaa caccaactac    180
aacgagaagc tgcagggcag agtgaccctg accgtggaca ccagcacctc caccgcctac    240
atggaactgc ggagcctgag aagcgacgac accgccgtgt actactgcgc tagaagcccc    300
cctcaggtgg gccccttcga ttattgggc agggcacac tcgtgaccgt gtcctctgct     360
agcaccaagg gccccagcgt gttccccctg gccccagca gcaagagcac cagcggcggc     420
acagccgccc tgggctgcct ggtgaaggac tacttccccg agcccgtgac cgtgtcctgg    480
aacagcggag ccctgacctc cggcgtgcac accttccccg ccgtgctgca gagcagcggc    540
ctgtacagcc tgtccagcgt ggtgacagtg cccagcagca gcctgggcac ccagacctac    600
atctgcaacg tgaaccacaa gcccagcaac accaaggtgg acaagagagt ggagcccaag    660
agctgcgaca gacccacac tgccccccc tgcccagccc cagagctgct gggcggaccc      720
tccgtgttcc tgttcccccc caagcccaag gacaccctga tgatcagcag gaccccgag     780 gtgacctgcg tggtggtgga cgtgagccac gaggacccag aggtgaagtt caactggtac    840
gtggacggcg tggaggtgca caacgccaag accaagccca gagaggagca gtacaacagc    900
acctacaggg tggtgtccgt gctgaccgtg ctgcaccagg actggctgaa cggcaaggaa    960
tacaagtgca aggtctccaa caaggccctg ccagccccca tcgaaaagac catcagcaag    1020
gccaagggcc agccacggga gccccaggtg tacaccctgc cccctcccg ggaggagatg    1080 accaagaacc aggtgtccct gacctgtctg gtgaagggct ctaccccag cgacatcgcc    1140 gtggagtggg agagcaacgg ccagcccgag aacaactaca agaccacccc cccagtgctg   1200
gacagcgacg gcagcttctt cctgtacagc aagctgaccg tggacaagtc caggtggcag   1260
cagggcaacg tgttcagctg cagcgtgatg cacgaggccc tgcacaacca ctacacccag   1320
aagagcctga gcctgtcccc cggcaag                                        1347

<210> SEQ ID NO 142

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gln Ala Ser Glu Tyr Ile Ile Asn Trp Leu Ala
1               5                   10

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly Ala Thr Gly Leu Glu Thr
1               5

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gln Gln Tyr Trp Ser Ile Pro Trp Thr
1               5

<210> SEQ ID NO 145
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ser Glu Tyr Ile Ile Asn Trp
1               5

<210> SEQ ID NO 146
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gly Ala Thr
1

<210> SEQ ID NO 147
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147
```

Tyr Trp Ser Ile Pro Trp
1               5

<210> SEQ ID NO 148
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Tyr Ile Ile Asn Trp
            20                  25                  30

Leu Ala Trp Tyr Gln Gln Lys Pro Gly Lys Ala Pro Lys Leu Leu Ile
        35                  40                  45

Ser Gly Ala Thr Gly Leu Glu Thr Gly Val Pro Ser Arg Phe Ser Gly
    50                  55                  60

Ser Gly Ser Gly Lys Asp Tyr Thr Phe Thr Ile Ser Ser Leu Gln Pro
65                  70                  75                  80

Glu Asp Ile Ala Thr Tyr Tyr Cys Gln Gln Tyr Trp Ser Ile Pro Trp
                85                  90                  95

Thr Phe Gly Gln Gly Thr Lys Leu Glu Ile Lys
            100                 105

<210> SEQ ID NO 149
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 149
gacatccaga tgacccagag ccccagcagc ctgtctgcca gcgtgggcga cagagtgacc      60
atcacctgtc aggccagcga atacatcata aactggctgg cctggtatca gcagaagccc     120
ggcaaggccc ccaagctgct gattagcgga gccaccggtc tggaaaccgg cgtgccaagc     180 agatttccg gcagcggctc cggcaaggac tacaccttca ccatcagctc cctgcagccc      240
gaggatatcg ccacctacta ctgccagcag tactggtcca tcccctggac ctttggccag     300
ggcaccaagc tggaaatcaa g                                               321

<210> SEQ ID NO 150
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Tyr Ile Ile Asn Trp
            20                  25                  30

Leu Ala Trp Tyr Gln Gln Lys Pro Gly Lys Ala Pro Lys Leu Leu Ile
        35                  40                  45

Ser Gly Ala Thr Gly Leu Glu Thr Gly Val Pro Ser Arg Phe Ser Gly

```
          50                  55                  60
Ser Gly Ser Gly Lys Asp Tyr Thr Phe Thr Ile Ser Ser Leu Gln Pro
 65                  70                  75                  80

Glu Asp Ile Ala Thr Tyr Tyr Cys Gln Gln Tyr Trp Ser Ile Pro Trp
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 151
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 151

```
gacatccaga tgacccagag ccccagcagc ctgtctgcca gcgtgggcga cagagtgacc      60
atcacctgtc aggccagcga atacatcata aactggctgg cctggtatca gcagaagccc    120
ggcaaggccc ccaagctgct gattagcgga gccaccggtc tggaaaccgg cgtgccaagc    180
agattttccg gcagcggctc cggcaaggac tacaccttca ccatcagctc cctgcagccc    240
gaggatatcg ccacctacta ctgccagcag tactggtcca tccctggac ctttggccag    300
ggcaccaagc tggaaatcaa gcgtacggtg gccgctccca gcgtgttcat cttcccccc    360
agcgacgagc agctgaagag cggcaccgcc agcgtggtgt gcctgctgaa caacttctac    420
ccccgggagg ccaaggtgca gtggaaggtg acaacgccc tgcagagcgg caacagccag    480
gagagcgtca ccgagcagga cagcaaggac tccacctaca gcctgagcag caccctgacc    540
ctgagcaagg ccgactacga aagcataag gtgtacgcct gcgaggtgac ccaccagggc    600
ctgtccagcc ccgtgaccaa gagcttcaac aggggcgagt gc                       642
```

<210> SEQ ID NO 152
<211> LENGTH: 24
<212> TYPE: PRT
<213> ORGANISM: Homo sapiens

<400> SEQUENCE: 152

```
Met Lys Thr Phe Ile Leu Leu Trp Val Leu Leu Trp Val Ile
  1               5                  10                  15

Phe Leu Leu Pro Gly Ala Thr Ala
                 20
```

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Asp Tyr Lys Asp Asp Asp Asp Lys His
1               5

<210> SEQ ID NO 154
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 154

His His His His His His
1               5

<210> SEQ ID NO 155
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Gly Gly Gly Leu Asn Asp Ile Phe Glu Ala Gln Lys Ile Glu Trp His
1               5                   10                  15

Glu

<210> SEQ ID NO 156
<211> LENGTH: 438
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Met Lys Thr Phe Ile Leu Leu Leu Trp Val Leu Leu Leu Trp Val Ile
1               5                   10                  15

Phe Leu Leu Pro Gly Ala Thr Ala Gln Pro Gly Val Gln Ser Lys
                20                  25                  30

Ser Pro Arg Phe Ala Ser Trp Asp Glu Met Asn Val Leu Ala His Gly
                35                  40                  45

Leu Leu Gln Leu Gly Gln Gly Leu Arg Glu His Ala Glu Arg Thr Arg
        50                  55                  60

Ser Gln Leu Ser Ala Leu Glu Arg Arg Leu Ser Ala Cys Gly Ser Ala
65                  70                  75                  80

Cys Gln Gly Thr Glu Gly Ser Thr Asp Leu Pro Leu Ala Pro Glu Ser
                85                  90                  95

Arg Val Asp Pro Glu Val Leu His Ser Leu Gln Thr Gln Leu Lys Ala
                100                 105                 110

Gln Asn Ser Arg Ile Gln Gln Leu Phe His Lys Val Ala Gln Gln Gln
        115                 120                 125

Arg His Leu Glu Lys Gln His Leu Arg Ile Gln His Leu Gln Ser Gln
130                 135                 140

Phe Gly Leu Leu Asp His Lys His Leu Asp His Glu Val Ala Lys Pro
145                 150                 155                 160

Ala Arg Arg Lys Arg Leu Pro Glu Met Ala Gln Pro Val Asp Pro Ala
            165                 170                 175

His Asn Val Ser Arg Leu His Arg Leu Pro Arg Asp Cys Gln Glu Leu
            180                 185                 190

Phe Gln Val Gly Glu Arg Gln Ser Gly Leu Phe Glu Ile Gln Pro Gln
            195                 200                 205

Gly Ser Pro Pro Phe Leu Val Asn Cys Lys Met Thr Ser Asp Gly Gly
210                 215                 220

Trp Thr Val Ile Gln Arg Arg His Asp Gly Ser Val Asp Phe Asn Arg
225                 230                 235                 240

Pro Trp Glu Ala Tyr Lys Ala Gly Phe Gly Asp Pro His Gly Glu Phe
            245                 250                 255

Trp Leu Gly Leu Glu Lys Val His Ser Ile Thr Gly Asp Arg Asn Ser
            260                 265                 270

Arg Leu Ala Val Gln Leu Arg Asp Trp Asp Gly Asn Ala Glu Leu Leu
            275                 280                 285

Gln Phe Ser Val His Leu Gly Gly Glu Asp Thr Ala Tyr Ser Leu Gln
            290                 295                 300

Leu Thr Ala Pro Val Ala Gly Gln Leu Gly Ala Thr Thr Val Pro Pro
305                 310                 315                 320

Ser Gly Leu Ser Val Pro Phe Ser Thr Trp Asp Gln Asp His Asp Leu
            325                 330                 335

Arg Arg Asp Lys Asn Cys Ala Lys Ser Leu Ser Gly Gly Trp Trp Phe
            340                 345                 350

Gly Thr Cys Ser His Ser Asn Leu Asn Gly Gln Tyr Phe Arg Ser Ile
            355                 360                 365

Pro Gln Gln Arg Gln Lys Leu Lys Lys Gly Ile Phe Trp Lys Thr Trp
            370                 375                 380

Arg Gly Arg Tyr Tyr Pro Leu Gln Ala Thr Thr Met Leu Ile Gln Pro
385                 390                 395                 400

Met Ala Ala Glu Ala Ala Ser Asp Tyr Lys Asp Asp Asp Asp Lys His
            405                 410                 415

His His His His His Gly Gly Gly Leu Asn Asp Ile Phe Glu Ala Gln
            420                 425                 430

Lys Ile Glu Trp His Glu
            435

<210> SEQ ID NO 157
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Met Lys Thr Phe Ile Leu Leu Leu Trp Val Leu Leu Leu Trp Val Ile
1               5                   10                  15

Phe Leu Leu Pro Gly Ala Thr Ala Gln Pro Gly Pro Val Gln Ser Lys
            20                  25                  30

Ser Pro Arg Phe Ala Ser Trp Asp Glu Met Asn Val Leu Ala His Gly
        35                  40                  45

```
Leu Leu Gln Leu Gly Gln Gly Leu Arg Glu His Ala Glu Arg Thr Arg
         50                  55                  60

Ser Gln Leu Ser Ala Leu Glu Arg Arg Leu Ser Ala Cys Gly Ser Ala
 65                  70                  75                  80

Cys Gln Gly Thr Glu Gly Ser Thr Asp Leu Pro Leu Ala Pro Glu Ser
                 85                  90                  95

Arg Val Asp Pro Glu Val Leu His Ser Leu Gln Thr Gln Leu Lys Ala
             100                 105                 110

Gln Asn Ser Arg Ile Gln Gln Leu Phe His Lys Val Ala Gln Gln Gln
         115                 120                 125

Arg His Leu Glu Lys Gln His Leu Arg Ile Gln His Leu Gln Ser Gln
     130                 135                 140

Phe Gly Leu Leu Asp His Lys His Leu Asp His Glu Val Ala Lys Pro
145                 150                 155                 160

Ala Arg Arg Lys Arg Leu Pro Glu Met Ala Gln Pro Val Asp Pro Ala
                 165                 170                 175

His Asn Val Ser Arg Leu His Arg Leu Pro Arg Asp Tyr Lys Asp Asp
             180                 185                 190

Asp Asp Lys His His His His His Asp Tyr Lys Asp Asp Asp Asp
         195                 200                 205

Lys His His His His His Gly Gly Gly Leu Asn Asp Ile Phe Glu
     210                 215                 220

Ala Gln Lys Ile Glu Trp His Glu
225                 230

<210> SEQ ID NO 158
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
atccccgctc ccaggctac                                                  19

<210> SEQ ID NO 159
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
cagcaaggag tgaagctcca tgcc                                            24

<210> SEQ ID NO 160
<211> LENGTH: 438
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Met Lys Thr Phe Ile Leu Leu Leu Trp Val Leu Leu Leu Trp Val Ile
 1               5                  10                  15

Phe Leu Leu Pro Gly Ala Thr Ala Gln Pro Gly Pro Val Gln Ser Lys
             20                  25                  30
```

```
Ser Pro Arg Phe Ala Ser Trp Asp Glu Met Asn Val Leu Ala His Gly
            35                  40                  45

Leu Leu Gln Leu Gly Gln Gly Leu Arg Glu His Ala Glu Arg Thr Arg
 50                  55                  60

Ser Gln Leu Asn Ala Leu Glu Arg Arg Leu Ser Ala Cys Gly Ser Ala
 65                  70                  75                  80

Cys Gln Gly Thr Glu Gly Ser Thr Ala Leu Pro Leu Ala Pro Glu Ser
                 85                  90                  95

Arg Val Asp Pro Glu Val Leu His Ser Leu Gln Thr Gln Leu Lys Ala
                100                 105                 110

Gln Asn Ser Arg Ile Gln Gln Leu Phe His Lys Val Ala Gln Gln Gln
            115                 120                 125

Arg His Leu Glu Lys Gln His Leu Arg Ile Gln Arg Leu Gln Ser Gln
        130                 135                 140

Val Gly Leu Leu Asp Pro Lys His Leu Asp His Glu Val Ala Lys Pro
145                 150                 155                 160

Ala Arg Arg Lys Arg Pro Glu Met Ala Gln Pro Val Asp Ser Ala
                165                 170                 175

His Asn Ala Ser Arg Leu His Arg Leu Pro Arg Asp Cys Gln Glu Leu
                180                 185                 190

Phe Glu Asp Gly Glu Arg Gln Ser Gly Leu Phe Glu Ile Gln Pro Gln
        195                 200                 205

Gly Ser Pro Pro Phe Leu Val Asn Cys Lys Met Thr Ser Asp Gly Gly
        210                 215                 220

Trp Thr Val Ile Gln Arg Arg His Asp Gly Ser Val Asp Phe Asn Arg
225                 230                 235                 240

Pro Trp Glu Ala Tyr Lys Ala Gly Phe Gly Asp Pro Gln Gly Glu Phe
                245                 250                 255

Trp Leu Gly Leu Glu Lys Val His Ser Ile Thr Gly Asp Arg Asn Ser
                260                 265                 270

Arg Leu Ala Val Gln Leu Gln Asp Trp Asp Gly Asn Ala Glu Ser Leu
        275                 280                 285

Gln Phe Ser Val His Leu Gly Gly Glu Asp Thr Ala Tyr Ser Leu Gln
        290                 295                 300

Leu Thr Glu Pro Val Ala Ser Gln Leu Gly Ala Thr Thr Val Pro Pro
305                 310                 315                 320

Ser Gly Leu Ser Val Pro Phe Ser Thr Trp Asp Gln Asp His Asp Leu
                325                 330                 335

Arg Arg Asp Lys Asn Cys Ala Lys Ser Leu Ser Gly Gly Trp Trp Phe
                340                 345                 350

Gly Thr Cys Ser His Ser Asn Leu Asn Gly Gln Tyr Phe Arg Ser Ile
                355                 360                 365

Pro Gln Gln Arg Gln Glu Leu Lys Lys Gly Ile Phe Trp Lys Thr Trp
                370                 375                 380

Arg Gly Arg Tyr Tyr Pro Leu Gln Ala Thr Thr Met Leu Ile Gln Pro
385                 390                 395                 400

Thr Ala Ala Glu Ala Ala Ser Asp Tyr Lys Asp Asp Asp Asp Lys His
                405                 410                 415

His His His His Gly Gly Gly Leu Asn Asp Ile Phe Glu Ala Gln
            420                 425                 430

Lys Ile Glu Trp His Glu
            435
```

<210> SEQ ID NO 161
<211> LENGTH: 218
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 161

```
Met Lys Thr Phe Ile Leu Leu Leu Trp Val Leu Leu Leu Trp Val Ile
1               5                   10                  15

Phe Leu Leu Pro Gly Ala Thr Ala Gln Pro Gly Pro Val Gln Ser Lys
            20                  25                  30

Ser Pro Arg Phe Ala Ser Trp Asp Glu Met Asn Val Leu Ala His Gly
        35                  40                  45

Leu Leu Gln Leu Gly Gln Gly Leu Arg Glu His Ala Glu Arg Thr Arg
    50                  55                  60

Ser Gln Leu Asn Ala Leu Glu Arg Arg Leu Ser Ala Cys Gly Ser Ala
65                  70                  75                  80

Cys Gln Gly Thr Glu Gly Ser Thr Ala Leu Pro Leu Ala Pro Glu Ser
                85                  90                  95

Arg Val Asp Pro Glu Val Leu His Ser Leu Gln Thr Gln Leu Lys Ala
            100                 105                 110

Gln Asn Ser Arg Ile Gln Gln Leu Phe His Lys Val Ala Gln Gln Gln
        115                 120                 125

Arg His Leu Glu Lys Gln His Leu Arg Ile Gln Arg Leu Gln Ser Gln
    130                 135                 140

Val Gly Leu Leu Asp Pro Lys His Leu Asp His Glu Val Ala Lys Pro
145                 150                 155                 160

Ala Arg Arg Lys Arg Arg Pro Glu Met Ala Gln Pro Val Asp Ser Ala
                165                 170                 175

His Asn Ala Ser Arg Leu His Arg Leu Pro Arg Asp Tyr Lys Asp Asp
            180                 185                 190

Asp Asp Lys His His His His His His Gly Gly Gly Leu Asn Asp Ile
        195                 200                 205

Phe Glu Ala Gln Lys Ile Glu Trp His Glu
    210                 215
```

<210> SEQ ID NO 162
<211> LENGTH: 442
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 162

```
Met Lys Thr Phe Ile Leu Leu Leu Trp Val Leu Leu Leu Trp Val Ile
1               5                   10                  15

Phe Leu Leu Pro Gly Ala Thr Ala Gln Pro Arg Pro Ala Gln Pro Glu
            20                  25                  30

Pro Pro Arg Phe Ala Ser Trp Asp Glu Met Asn Leu Leu Ala His Gly
        35                  40                  45

Leu Leu Gln Leu Gly His Gly Leu Arg Glu His Val Glu Arg Thr Arg
    50                  55                  60

Gly Gln Leu Gly Ala Leu Glu Arg Arg Met Ala Ala Cys Gly Asn Ala
65                  70                  75                  80
```

```
Cys Gln Gly Pro Lys Gly Lys Asp Ala Pro Phe Lys Asp Ser Glu Asp
                 85                  90                  95

Arg Val Pro Glu Gly Gln Thr Pro Glu Thr Leu Gln Ser Leu Gln Thr
            100                 105                 110

Gln Leu Lys Ala Gln Asn Ser Lys Ile Gln Gln Leu Phe Gln Lys Val
        115                 120                 125

Ala Gln Gln Gln Arg Tyr Leu Ser Lys Gln Asn Leu Arg Ile Gln Asn
    130                 135                 140

Leu Gln Ser Gln Ile Asp Leu Leu Ala Pro Thr His Leu Asp Asn Gly
145                 150                 155                 160

Val Asp Lys Thr Ser Arg Gly Lys Arg Leu Pro Lys Met Thr Gln Leu
                165                 170                 175

Ile Gly Leu Thr Pro Asn Ala Thr His Leu His Arg Pro Pro Arg Asp
            180                 185                 190

Cys Gln Glu Leu Phe Gln Glu Gly Glu Arg His Ser Gly Leu Phe Gln
        195                 200                 205

Ile Gln Pro Leu Gly Ser Pro Pro Phe Leu Val Asn Cys Glu Met Thr
    210                 215                 220

Ser Asp Gly Gly Trp Thr Val Ile Gln Arg Arg Leu Asn Gly Ser Val
225                 230                 235                 240

Asp Phe Asn Gln Ser Trp Glu Ala Tyr Lys Asp Gly Phe Gly Asp Pro
                245                 250                 255

Gln Gly Glu Phe Trp Leu Gly Leu Glu Lys Met His Ser Ile Thr Gly
            260                 265                 270

Asn Arg Gly Ser Gln Leu Ala Val Gln Leu Gln Asp Trp Asp Gly Asn
        275                 280                 285

Ala Lys Leu Leu Gln Phe Pro Ile His Leu Gly Gly Glu Asp Thr Ala
    290                 295                 300

Tyr Ser Leu Gln Leu Thr Glu Pro Thr Ala Asn Glu Leu Gly Ala Thr
305                 310                 315                 320

Asn Val Ser Pro Asn Gly Leu Ser Leu Pro Phe Ser Thr Trp Asp Gln
                325                 330                 335

Asp His Asp Leu Arg Gly Asp Leu Asn Cys Ala Lys Ser Leu Ser Gly
            340                 345                 350

Gly Trp Trp Phe Gly Thr Cys Ser His Ser Asn Leu Asn Gly Gln Tyr
        355                 360                 365

Phe His Ser Ile Pro Arg Gln Arg Gln Glu Arg Lys Lys Gly Ile Phe
    370                 375                 380

Trp Lys Thr Trp Lys Gly Arg Tyr Tyr Pro Leu Gln Ala Thr Thr Leu
385                 390                 395                 400

Leu Ile Gln Pro Met Glu Ala Thr Ala Ala Ser Asp Tyr Lys Asp Asp
                405                 410                 415

Asp Asp Lys His His His His His Gly Gly Gly Leu Asn Asp Ile
            420                 425                 430

Phe Glu Ala Gln Lys Ile Glu Trp His Glu
            435                 440

<210> SEQ ID NO 163
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163
```

```
Met Lys Thr Phe Ile Leu Leu Trp Val Leu Leu Leu Trp Val Ile
1               5                   10                  15

Phe Leu Leu Pro Gly Ala Thr Ala Gln Pro Gln Gly Arg Pro Ala Gln
            20                  25                  30

Pro Glu Pro Arg Phe Ala Ser Trp Asp Glu Met Asn Leu Leu Ala
        35                  40                  45

His Gly Leu Leu Gln Leu Gly His Gly Leu Arg Glu His Val Glu Arg
    50                  55                  60

Thr Arg Gly Gln Leu Gly Ala Leu Glu Arg Arg Met Ala Ala Cys Gly
65                  70                  75                  80

Asn Ala Cys Gln Gly Pro Lys Gly Thr Asp Pro Lys Asp Arg Val Pro
                85                  90                  95

Glu Gly Gln Ala Pro Glu Thr Leu Gln Ser Leu Gln Thr Gln Leu Lys
                100                 105                 110

Ala Gln Asn Ser Lys Ile Gln Gln Leu Phe Gln Lys Val Ala Gln Gln
            115                 120                 125

Gln Arg Tyr Leu Ser Lys Gln Asn Leu Arg Ile Gln Asn Leu Gln Ser
        130                 135                 140

Gln Ile Asp Leu Leu Thr Pro Thr His Leu Asp Asn Gly Val Asp Lys
145                 150                 155                 160

Thr Ser Arg Gly Lys Arg Leu Pro Lys Met Ala Gln Leu Ile Gly Leu
                165                 170                 175

Thr Pro Asn Ala Thr Arg Leu His Arg Pro Pro Arg Asp Cys Gln Glu
                180                 185                 190

Leu Phe Gln Glu Gly Glu Arg His Ser Gly Leu Phe Gln Ile Gln Pro
            195                 200                 205

Leu Gly Ser Pro Pro Phe Leu Val Asn Cys Glu Met Thr Ser Asp Gly
        210                 215                 220

Gly Trp Thr Val Ile Gln Arg Arg Leu Asn Gly Ser Val Asp Phe Asn
225                 230                 235                 240

Gln Ser Trp Glu Ala Tyr Lys Asp Gly Phe Gly Asp Pro Gln Gly Glu
                245                 250                 255

Phe Trp Leu Gly Leu Glu Lys Met His Ser Ile Thr Gly Asp Arg Gly
                260                 265                 270

Ser Gln Leu Ala Val Gln Leu Gln Asp Trp Asp Gly Asn Ala Lys Leu
        275                 280                 285

Leu Gln Phe Pro Ile His Leu Gly Gly Glu Asp Thr Ala Tyr Ser Leu
        290                 295                 300

Gln Leu Thr Glu Pro Thr Ala Asn Glu Leu Gly Ala Thr Asn Val Ser
305                 310                 315                 320

Pro Asn Gly Leu Ser Leu Pro Phe Ser Thr Trp Asp Gln Asp His Asp
                325                 330                 335

Leu Arg Gly Asp Leu Asn Cys Ala Lys Ser Leu Ser Gly Gly Trp Trp
                340                 345                 350

Phe Gly Thr Cys Ser His Ser Asn Leu Asn Gly Gln Tyr Phe His Ser
            355                 360                 365

Ile Pro Arg Gln Arg Gln Gln Arg Lys Lys Gly Ile Phe Trp Lys Thr
        370                 375                 380

Trp Lys Gly Arg Tyr Tyr Pro Leu Gln Ala Thr Thr Leu Leu Ile Gln
385                 390                 395                 400

Pro Met Glu Ala Thr Ala Ala Ser Asp Tyr Lys Asp Asp Asp Asp Lys
                405                 410                 415
```

His His His His His Gly Gly Gly Leu Asn Asp Ile Phe Glu Ala
            420             425             430

Gln Lys Ile Glu Trp His Glu Thr
        435             440

<210> SEQ ID NO 164
<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Met Lys Thr Phe Ile Leu Leu Trp Val Leu Leu Trp Val Ile
1               5                   10                  15

Phe Leu Leu Pro Gly Ala Thr Ala Gln Pro Ser Arg Ile Asp Gln Asp
            20                  25                  30

Asn Ser Ser Phe Asp Ser Leu Ser Pro Glu Pro Lys Ser Arg Phe Ala
        35                  40                  45

Met Leu Asp Asp Val Lys Ile Leu Ala Asn Gly Leu Leu Gln Leu Gly
    50                  55                  60

His Gly Leu Lys Asp Phe Val His Lys Thr Lys Gly Gln Ile Asn Asp
65                  70                  75                  80

Ile Phe Gln Lys Leu Asn Ile Phe Asp Gln Ser Phe Tyr Asp Leu Ser
                85                  90                  95

Leu Gln Thr Ser Glu Ile Lys Glu Glu Lys Glu Leu Arg Arg Thr
            100                 105                 110

Thr Tyr Lys Leu Gln Val Lys Asn Glu Glu Val Lys Asn Met Ser Leu
        115                 120                 125

Glu Leu Asn Ser Lys Leu Glu Ser Leu Leu Glu Lys Ile Leu Leu
    130                 135                 140

Gln Gln Lys Val Lys Tyr Leu Glu Glu Gln Leu Thr Asn Leu Ile Gln
145                 150                 155                 160

Asn Gln Pro Glu Thr Pro Glu His Pro Glu Val Thr Ser Leu Lys Thr
                165                 170                 175

Phe Val Glu Lys Gln Asp Asn Ser Ile Lys Asp Leu Leu Gln Thr Val
            180                 185                 190

Glu Asp Gln Tyr Lys Gln Leu Asn Gln Gln His Ser Gln Ile Lys Glu
        195                 200                 205

Ile Glu Asn Gln Leu Arg Arg Thr Ser Ile Gln Glu Pro Thr Glu Ile
    210                 215                 220

Ser Leu Ser Ser Lys Pro Arg Ala Pro Arg Thr Thr Pro Phe Leu Gln
225                 230                 235                 240

Leu Asn Glu Ile Arg Asn Val Lys His Asp Gly Ile Pro Ala Glu Cys
                245                 250                 255

Thr Thr Ile Tyr Asn Arg Gly Glu His Thr Ser Gly Met Tyr Ala Ile
            260                 265                 270

Arg Pro Ser Asn Ser Gln Val Phe His Val Tyr Cys Asp Val Ile Ser
        275                 280                 285

Gly Ser Pro Trp Thr Leu Ile Gln His Arg Ile Asp Gly Ser Gln Asn
    290                 295                 300

Phe Asn Glu Thr Trp Glu Asn Tyr Lys Tyr Gly Phe Gly Arg Leu Asp
305                 310                 315                 320

Gly Glu Phe Trp Leu Gly Leu Glu Lys Ile Tyr Ser Ile Val Lys Gln
                325                 330                 335

```
Ser Asn Tyr Val Leu Arg Ile Glu Leu Glu Asp Trp Lys Asp Asn Lys
            340                 345                 350

His Tyr Ile Glu Tyr Ser Phe Tyr Leu Gly Asn His Glu Thr Asn Tyr
            355                 360                 365

Thr Leu His Leu Val Ala Ile Thr Gly Asn Val Pro Asn Ala Ile Pro
            370                 375                 380

Glu Asn Lys Asp Leu Val Phe Ser Thr Trp Asp His Lys Ala Lys Gly
385                 390                 395                 400

His Phe Asn Cys Pro Glu Gly Tyr Ser Gly Trp Trp Trp His Asp
            405                 410                 415

Glu Cys Gly Glu Asn Asn Leu Asn Gly Lys Tyr Asn Lys Pro Arg Ala
            420                 425                 430

Lys Ser Lys Pro Glu Arg Arg Arg Gly Leu Ser Trp Lys Ser Gln Asn
            435                 440                 445

Gly Arg Leu Tyr Ser Ile Lys Ser Thr Lys Met Leu Ile His Pro Thr
            450                 455                 460

Asp Ser Glu Ser Phe Glu Asp Tyr Lys Asp Asp Asp Lys His His
465                 470                 475                 480

His His His His Gly Gly Gly Leu Asn Asp Ile Phe Glu Ala Gln Lys
            485                 490                 495

Ile Glu Trp His Glu
            500

<210> SEQ ID NO 165
<211> LENGTH: 10
<212> TYPE: PRT
<213> ORGANISM: Homo sapiens

<400> SEQUENCE: 165

Gly Pro Val Gln Ser Lys Ser Pro Arg Phe
1               5                   10

<210> SEQ ID NO 166
<211> LENGTH: 11
<212> TYPE: PRT
<213> ORGANISM: Homo sapiens

<400> SEQUENCE: 166

Val Gln Ser Lys Ser Pro Arg Phe Ala Ser Trp
1               5                   10

<210> SEQ ID NO 167
<211> LENGTH: 8
<212> TYPE: PRT
<213> ORGANISM: Homo sapiens

<400> SEQUENCE: 167

Asn Val Leu Ala His Gly Leu Leu
1               5

<210> SEQ ID NO 168
<211> LENGTH: 10
<212> TYPE: PRT
<213> ORGANISM: Homo sapiens

<400> SEQUENCE: 168

Asn Val Leu Ala His Gly Leu Leu Gln Leu
1               5                   10
```

```
<210> SEQ ID NO 169
<211> LENGTH: 8
<212> TYPE: PRT
<213> ORGANISM: Homo sapiens

<400> SEQUENCE: 169

Leu Ala His Gly Leu Leu Gln Leu
1               5

<210> SEQ ID NO 170
<211> LENGTH: 13
<212> TYPE: PRT
<213> ORGANISM: Homo sapiens

<400> SEQUENCE: 170

Asn Val Leu Ala His Gly Leu Leu Gln Leu Gly Gln Gly
1               5                   10

<210> SEQ ID NO 171
<211> LENGTH: 14
<212> TYPE: PRT
<213> ORGANISM: Homo sapiens

<400> SEQUENCE: 171

Asn Val Leu Ala His Gly Leu Leu Gln Leu Gly Gln Gly Leu
1               5                   10

<210> SEQ ID NO 172
<211> LENGTH: 16
<212> TYPE: PRT
<213> ORGANISM: Homo sapiens

<400> SEQUENCE: 172

Asn Val Leu Ala His Gly Leu Leu Gln Leu Gly Gln Gly Leu Arg Glu
1               5                   10                  15

<210> SEQ ID NO 173
<211> LENGTH: 25
<212> TYPE: PRT
<213> ORGANISM: Homo sapiens

<400> SEQUENCE: 173

Asn Val Leu Ala His Gly Leu Leu Gln Leu Gly Gln Gly Leu Arg Glu
1               5                   10                  15

His Ala Glu Arg Thr Arg Ser Gln Leu
            20                  25

<210> SEQ ID NO 174
<211> LENGTH: 27
<212> TYPE: PRT
<213> ORGANISM: Homo sapiens

<400> SEQUENCE: 174

Asn Val Leu Ala His Gly Leu Leu Gln Leu Gly Gln Gly Leu Arg Glu
1               5                   10                  15

His Ala Glu Arg Thr Arg Ser Gln Leu Ser Ala
            20                  25

<210> SEQ ID NO 175
<211> LENGTH: 23
<212> TYPE: PRT
<213> ORGANISM: Homo sapiens

<400> SEQUENCE: 175
```

```
Leu Ala His Gly Leu Leu Gln Leu Gly Gln Gly Leu Arg Glu His Ala
1               5                   10                  15

Glu Arg Thr Arg Ser Gln Leu
            20
```

<210> SEQ ID NO 176
<211> LENGTH: 13
<212> TYPE: PRT
<213> ORGANISM: Homo sapiens

<400> SEQUENCE: 176

```
Ala His Gly Leu Leu Gln Leu Gly Gln Gly Leu Arg Glu
1               5                   10
```

<210> SEQ ID NO 177
<211> LENGTH: 22
<212> TYPE: PRT
<213> ORGANISM: Homo sapiens

<400> SEQUENCE: 177

```
Ala His Gly Leu Leu Gln Leu Gly Gln Gly Leu Arg Glu His Ala Glu
1               5                   10                  15

Arg Thr Arg Ser Gln Leu
            20
```

<210> SEQ ID NO 178
<211> LENGTH: 18
<212> TYPE: PRT
<213> ORGANISM: Homo sapiens

<400> SEQUENCE: 178

```
Leu Gln Leu Gly Gln Gly Leu Arg Glu His Ala Glu Arg Thr Arg Ser
1               5                   10                  15

Gln Leu
```

<210> SEQ ID NO 179
<211> LENGTH: 15
<212> TYPE: PRT
<213> ORGANISM: Homo sapiens

<400> SEQUENCE: 179

```
Gly Gln Gly Leu Arg Glu His Ala Glu Arg Thr Arg Ser Gln Leu
1               5                   10                  15
```

<210> SEQ ID NO 180
<211> LENGTH: 32
<212> TYPE: PRT
<213> ORGANISM: Homo sapiens

<400> SEQUENCE: 180

```
Leu Glu Arg Arg Leu Ser Ala Cys Gly Ser Ala Cys Gln Thr Glu Gly
1               5                   10                  15

Ser Thr Asp Leu Pro Ala Pro Glu Ser Arg Val Asp Pro Glu Val Leu
            20                  25                  30
```

<210> SEQ ID NO 181
<211> LENGTH: 25
<212> TYPE: PRT
<213> ORGANISM: Homo sapiens

<400> SEQUENCE: 181

```
Cys Gly Ser Ala Cys Gln Thr Glu Gly Ser Thr Asp Leu Pro Ala Pro
1               5                   10                  15
```

Glu Ser Arg Val Asp Pro Glu Val Leu
            20                  25

<210> SEQ ID NO 182
<211> LENGTH: 16
<212> TYPE: PRT
<213> ORGANISM: Homo sapiens

<400> SEQUENCE: 182

Ser Thr Asp Leu Pro Ala Pro Glu Ser Arg Val Asp Pro Glu Val Leu
1               5                   10                  15

<210> SEQ ID NO 183
<211> LENGTH: 7
<212> TYPE: PRT
<213> ORGANISM: Homo sapiens

<400> SEQUENCE: 183

Arg Val Asp Pro Glu Val Leu
1               5

<210> SEQ ID NO 184
<211> LENGTH: 7
<212> TYPE: PRT
<213> ORGANISM: Homo sapiens

<400> SEQUENCE: 184

His Ser Leu Gln Thr Gln Leu
1               5

<210> SEQ ID NO 185
<211> LENGTH: 10
<212> TYPE: PRT
<213> ORGANISM: Homo sapiens

<400> SEQUENCE: 185

Lys Ala Gln Asn Ser Arg Ile Gln Gln Leu
1               5                   10

<210> SEQ ID NO 186
<211> LENGTH: 26
<212> TYPE: PRT
<213> ORGANISM: Homo sapiens

<400> SEQUENCE: 186

Lys Ala Gln Asn Ser Arg Ile Gln Gln Leu Phe His Lys Val Ala Gln
1               5                   10                  15

Gln Gln Arg His Leu Glu Lys Gln His Leu
            20                  25

<210> SEQ ID NO 187
<211> LENGTH: 16
<212> TYPE: PRT
<213> ORGANISM: Homo sapiens

<400> SEQUENCE: 187

Phe His Lys Val Ala Gln Gln Gln Arg His Leu Glu Lys Gln His Leu
1               5                   10                  15

<210> SEQ ID NO 188
<211> LENGTH: 7
<212> TYPE: PRT
<213> ORGANISM: Homo sapiens

<400> SEQUENCE: 188

Gln Ser Gln Phe Gly Leu Leu
1               5

<210> SEQ ID NO 189
<211> LENGTH: 12
<212> TYPE: PRT
<213> ORGANISM: Homo sapiens

<400> SEQUENCE: 189

Phe Gly Leu Leu Asp His Lys His Leu Asp His Glu
1               5                   10

<210> SEQ ID NO 190
<211> LENGTH: 26
<212> TYPE: PRT
<213> ORGANISM: Homo sapiens

<400> SEQUENCE: 190

Leu Glu Arg Arg Leu Ser Ala Cys Gly Ser Ala Cys Gln Thr Glu Gly
1               5                   10                  15

Ser Thr Asp Leu Pro Leu Ala Pro Glu Ser
            20                  25

<210> SEQ ID NO 191
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Gly Pro Val Gln Ser Lys Ser Pro Arg Phe Ala Ser Trp Asp Glu
1               5                   10                  15

<210> SEQ ID NO 192
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Gln Ser Lys Ser Pro Arg Phe Ala Ser Trp Asp Glu Met Asn Val
1               5                   10                  15

<210> SEQ ID NO 193
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ser Pro Arg Phe Ala Ser Trp Asp Glu Met Asn Val Leu Ala His
1               5                   10                  15

<210> SEQ ID NO 194
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 194

Phe Ala Ser Trp Asp Glu Met Asn Val Leu Ala His Gly Leu Leu
1               5                   10                  15

<210> SEQ ID NO 195
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Trp Asp Glu Met Asn Val Leu Ala His Gly Leu Leu Gln Leu Gly
1               5                   10                  15

<210> SEQ ID NO 196
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Met Asn Val Leu Ala His Gly Leu Leu Gln Leu Gly Gln Gly Leu
1               5                   10                  15

<210> SEQ ID NO 197
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Leu Ala His Gly Leu Leu Gln Leu Gly Gln Gly Leu Arg Glu His
1               5                   10                  15

<210> SEQ ID NO 198
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Gly Leu Leu Gln Leu Gly Gln Gly Leu Arg Glu His Ala Glu Arg
1               5                   10                  15

<210> SEQ ID NO 199
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Gln Leu Gly Gln Gly Leu Arg Glu His Ala Glu Arg Thr Arg Ser
1               5                   10                  15

<210> SEQ ID NO 200

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Gln Gly Leu Arg Glu His Ala Glu Arg Thr Arg Ser Gln Leu Ser
1               5                   10                  15

<210> SEQ ID NO 201
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Arg Glu His Ala Glu Arg Thr Arg Ser Gln Leu Ser Ala Leu Glu
1               5                   10                  15

<210> SEQ ID NO 202
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Ala Glu Arg Thr Arg Ser Gln Leu Ser Ala Leu Glu Arg Arg Leu
1               5                   10                  15

<210> SEQ ID NO 203
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Thr Arg Ser Gln Leu Ser Ala Leu Glu Arg Arg Leu Ser Ala Ser
1               5                   10                  15

<210> SEQ ID NO 204
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Gln Leu Ser Ala Leu Glu Arg Arg Leu Ser Ala Ser Gly Ser Ala
1               5                   10                  15

<210> SEQ ID NO 205
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205
```

Ala Leu Glu Arg Arg Leu Ser Ala Ser Gly Ser Ala Ser Gln Gly
1               5                   10                  15

<210> SEQ ID NO 206
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Arg Arg Leu Ser Ala Ser Gly Ser Ala Ser Gln Gly Thr Glu Gly
1               5                   10                  15

<210> SEQ ID NO 207
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Ser Ala Ser Gly Ser Ala Ser Gln Gly Thr Glu Gly Ser Thr Asp
1               5                   10                  15

<210> SEQ ID NO 208
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Gly Ser Ala Ser Gln Gly Thr Glu Gly Ser Thr Asp Leu Pro Leu
1               5                   10                  15

<210> SEQ ID NO 209
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ser Gln Gly Thr Glu Gly Ser Thr Asp Leu Pro Leu Ala Pro Glu
1               5                   10                  15

<210> SEQ ID NO 210
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Thr Glu Gly Ser Thr Asp Leu Pro Leu Ala Pro Glu Ser Arg Val
1               5                   10                  15

<210> SEQ ID NO 211
<211> LENGTH: 15
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 211

Ser Thr Asp Leu Pro Leu Ala Pro Glu Ser Arg Val Asp Pro Glu
1               5                   10                  15

<210> SEQ ID NO 212
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Leu Pro Leu Ala Pro Glu Ser Arg Val Asp Pro Glu Val Leu His
1               5                   10                  15

<210> SEQ ID NO 213
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Ala Pro Glu Ser Arg Val Asp Pro Glu Val Leu His Ser Leu Gln
1               5                   10                  15

<210> SEQ ID NO 214
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Ser Arg Val Asp Pro Glu Val Leu His Ser Leu Gln Thr Gln Leu
1               5                   10                  15

<210> SEQ ID NO 215
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Asp Pro Glu Val Leu His Ser Leu Gln Thr Gln Leu Lys Ala Gln
1               5                   10                  15

<210> SEQ ID NO 216
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Val Leu His Ser Leu Gln Thr Gln Leu Lys Ala Gln Asn Ser Arg
1               5                   10                  15

```
<210> SEQ ID NO 217
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Ser Leu Gln Thr Gln Leu Lys Ala Gln Asn Ser Arg Ile Gln Gln
1               5                   10                  15

<210> SEQ ID NO 218
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Thr Gln Leu Lys Ala Gln Asn Ser Arg Ile Gln Gln Leu Phe His
1               5                   10                  15

<210> SEQ ID NO 219
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Lys Ala Gln Asn Ser Arg Ile Gln Gln Leu Phe His Lys Val Ala
1               5                   10                  15

<210> SEQ ID NO 220
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Asn Ser Arg Ile Gln Gln Leu Phe His Lys Val Ala Gln Gln Gln
1               5                   10                  15

<210> SEQ ID NO 221
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Ile Gln Gln Leu Phe His Lys Val Ala Gln Gln Gln Arg His Leu
1               5                   10                  15

<210> SEQ ID NO 222
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222
```

```
Leu Phe His Lys Val Ala Gln Gln Gln Arg His Leu Glu Lys Gln
1               5                   10                  15

<210> SEQ ID NO 223
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Lys Val Ala Gln Gln Gln Arg His Leu Glu Lys Gln His Leu Arg
1               5                   10                  15

<210> SEQ ID NO 224
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Gln Gln Gln Arg His Leu Glu Lys Gln His Leu Arg Ile Gln His
1               5                   10                  15

<210> SEQ ID NO 225
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Arg His Leu Glu Lys Gln His Leu Arg Ile Gln His Leu Gln Ser
1               5                   10                  15

<210> SEQ ID NO 226
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Glu Lys Gln His Leu Arg Ile Gln His Leu Gln Ser Gln Phe Gly
1               5                   10                  15

<210> SEQ ID NO 227
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

His Leu Arg Ile Gln His Leu Gln Ser Gln Phe Gly Leu Leu Asp
1               5                   10                  15

<210> SEQ ID NO 228
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 228

Ile Gln His Leu Gln Ser Gln Phe Gly Leu Leu Asp His Lys His
1               5                   10                  15

<210> SEQ ID NO 229
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Leu Gln Ser Gln Phe Gly Leu Leu Asp His Lys His Leu Asp His
1               5                   10                  15

<210> SEQ ID NO 230
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Gln Phe Gly Leu Leu Asp His Lys His Leu Asp His Glu Val Ala
1               5                   10                  15

<210> SEQ ID NO 231
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Leu Leu Asp His Lys His Leu Asp His Glu Val Ala Lys Pro Ala
1               5                   10                  15

<210> SEQ ID NO 232
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

His Lys His Leu Asp His Glu Val Ala Lys Pro Ala Arg Arg Lys
1               5                   10                  15

<210> SEQ ID NO 233
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Lys His Leu Asp His Glu Val Ala Lys Pro Ala Arg Arg Lys Arg
1               5                   10                  15
```

ANGIOPOIETIN-LIKE 4 ANTIBODIES AND METHODS OF USE

RELATED APPLICATIONS

This application is a divisional of U.S. patent application Ser. No. 14/819,680, filed Aug. 6, 2015, which claims priority to U.S. Provisional Patent Application No. 62/034,409, filed Aug. 7, 2014, the contents of which are incorporated herein by reference in their entireties.

SEQUENCE LISTING

The instant application contains a Sequence Listing which was submitted in ASCII format via EFS-Web on Jan. 26, 2016, in U.S. patent application Ser. No. 14/819,680, and is hereby incorporated by reference in its entirety.

BACKGROUND OF THE INVENTION

Angiopoietin-like 4 protein (ANGPTL4) is a member of the angiopoietin like family of secreted proteins. It is a homooligomeric protein, capable of forming dimers and tetramers, that is expressed by cell types including macrophages, adipose, muscle, and liver cells. ANGPTL4 is also known as hepatic fibrinogen/angiopoietin-related protein (HFARP) (Kim et al. (2000) Biochem. J. 346:603-610); PPAR gamma angiopoietin related protein (PGAR) (Yoon, et al. (2000) Mol. Cell Biol., 20:5343-5349), and fasting induced adipose factor (FIAF) (Kerten et al. (2000) J. Biol. Chem., 275:28488-28493). ANGPTL4 contains an N-terminal coiled-coil domain and a C-terminal fibrinogen (FBN)-like domain (Kim et al. (2000) Biochem. J. 346:603-610).

Lipoprotein lipase (LPL) has a central role in lipoprotein metabolism which includes the maintenance of lipoprotein levels in blood and, through tissue specific regulation of its activity. The coiled-coil region of ANGPTL4 is known to inhibit lipoprotein lipase (LPL)-mediated triglyceride (TG) clearance. Therefore, ANGPTL4 loss-of-function mutations (e.g., as seen in human subjects), genetic deletions (e.g., as seen in transgenic mice), and antibody inhibition (e.g., as seen in mice and cynomolgus monkeys) are all observed to decrease plasma triglycerides. Furthermore, ANGPTL4 antibodies are also known to activate LPL. Conversely, ANGPTL4 injection into mice produces a rapid increase in circulating triglycerides and this is at a higher rate than the injection of angiopoietin-like protein 3 (ANGPTL3) (Yoshida et al. (2002) J Lipid Res 43:1770-1772).

The anti-ANGPTL4 antibodies and antigen binding fragments described in this invention initiate, promote, or enhance activation of LPL, e.g., by blocking ANGPTL4 inhibition of LPL, thereby decreasing plasma triglycerides. These antibodies are expected to prevent and ameliorate the acute and chronic manifestations of diseases characterized by elevated triglyceride levels, e.g., primary dyslipidemia, hypertriglyceridemia, metabolic syndrome, type II diabetes, and the like.

SUMMARY OF THE INVENTION

The present invention relates to monoclonal antibodies binding to human Angiopoietin-like 4 protein (hereinafter, sometimes referred to as "ANGPTL4"), and pharmaceutical compositions and methods of treatment comprising the same.

The isolated anti-ANGPTL4 antibodies, or antigen binding fragments, described herein bind ANGPTL4, with an equilibrium dissociation constant ($K_D$) of less than or equal to 100 pM. For example, the isolated antibodies or antigen binding fragments described herein may bind to human ANGPTL4 with a $K_D$ of less than or equal to 150 nM, less than or equal to 50 nM, less than or equal to 10 nM, less than or equal to 750 pM, less than or equal to 600 pM, less than or equal to 500 pM, less than or equal to 400 pM, less than or equal to 300 pM, less than or equal to 200 pM, less than or equal to 100 pM, less than or equal to 75 pM, less than or equal to 65 pM, less than or equal to 60 pM, less than or equal to 55 pM. More specifically, the isolated antibodies or antigen binding fragments described herein may also bind human ANGPTL4 with a $K_D$ of less than or equal to 45 pM, as measured by ForteBio kinetic binding assays, or less than or equal to 24 pM, as measured by solution equilibrium titration assay (SET); and may also bind cynomolgus monkey ANGPTL4 with a $K_D$ of less than or equal to 87 pM, as measured by ForteBio kinetic binding assays, or less than or equal to 22 pM, as measured by SET.

The present invention relates to an isolated antibody, or antigen binding fragments thereof, that binds to human ANGPTL4. The present invention also relates to an isolated antibody, or antigen binding fragments thereof, that binds ANGPTL4 and further competes for binding with an antibody as described in Table 1. The present invention also further relates to an isolated antibody, or antigen binding fragments thereof, that binds the same epitope as an antibody as described in Table 1.

The binding affinity of isolated antibodies and antigen binding fragments described herein can be determined by solution equilibrium titration (SET). Methods for SET are known in the art and are described in further detail below. Alternatively, binding affinity of the isolated antibodies, or fragments, described herein can be determined by Biacore assay. Methods for Biacore kinetic assays are known in the art and are described in further detail below.

The isolated anti-ANGPTL4 antibodies and antigen binding fragments described herein can be used to inhibit ANGPTL4 binding to lipoprotein lipase (LPL) with an $EC_{50}$ of less than or equal to 100 nM, less than or equal to 50 nM, less than or equal to 35 nM, less than or equal to 25 nM, less than or equal to 10 nM, or less than or equal to 3 nM.

The isolated anti-ANGPTL4 antibodies, or antigen binding fragments thereof, may be used to reduce the levels of circulating triglycerides (TG).

The isolated anti-ANGPTL4 antibodies, or antigen binding fragments thereof, as described herein can be monoclonal antibodies, human or humanized antibodies, chimeric antibodies, single chain antibodies, Fab fragments, Fv fragments, F(ab')2 fragments, or scFv fragments, and/or IgG isotypes.

The isolated anti-ANGPTL4 antibodies, or antigen binding fragments thereof, as described herein can also include a framework in which an amino acid has been substituted into the antibody framework from the respective human VH or VL germline sequences.

Another aspect of the invention includes an isolated antibody or antigen binding fragments thereof having the full heavy and light chain sequences of humanized antibodies described in Table 1. More specifically, the isolated antibody or antigen binding fragments thereof can have the heavy and light chain sequences of NEG276, NEG276-LALA, NEG278, NEG310, NEG313, NEG315, NEG318, NEG319.

A further aspect of the invention includes an isolated antibody or antigen binding fragments thereof having the heavy and light chain variable domain sequences of humanized antibodies described in Table 1. More specifically, the isolated antibody or antigen binding fragment thereof can have the heavy and light chain variable domain sequences of NEG276, NEG276-LALA, NEG278, NEG310, NEG313, NEG315, NEG318, NEG319.

The invention also relates to an isolated antibody or antigen binding fragments thereof that includes a heavy chain CDR1 selected from the group consisting of SEQ ID NOs: 7, 32, 52, 72, 92, 112, and 132; a heavy chain CDR2 selected from the group consisting of SEQ ID NOs: 8, 33, 53, 73, 93, 113, and 133; and a heavy chain CDR3 selected from the group consisting of SEQ ID NOs: 9, 34, 54, 74, 94, 114, and 134, wherein the isolated antibody or antigen binding fragments thereof binds to human ANGPTL4. In another aspect, such isolated antibody or antigen binding fragments thereof further includes a light chain CDR1 selected from the group consisting of SEQ ID NOs: 17, 42, 62, 82, 102, 122, and 142; a light chain CDR2 selected from the group consisting of SEQ ID NOs: 18, 43, 63, 83, 103, 123, and 143; and a light chain CDR3 selected from the group consisting of SEQ ID NOs: 19, 44, 64, 84, 104, 124, and 144.

The invention also relates to an isolated antibody or antigen binding fragments thereof that includes a light chain CDR1 selected from the group consisting of SEQ ID NOs: 17, 42, 62, 82, 102, 122, and 142; a light chain CDR2 selected from the group consisting of SEQ ID NOs: 18, 43, 63, 83, 103, 123, and 143; and a light chain CDR3 selected from the group consisting of SEQ ID NOs: 19, 44, 64, 84, 104, 124, and 144, wherein the isolated antibody or antigen binding fragments thereof binds to human ANGPTL4.

The invention also relates to an isolated antibody or antigen binding fragments thereof that binds ANGPTL4 having HCDR1, HCDR2, and HCDR3 and LCDR1, LCDR2, and LCDR3, wherein HCDR1, HCDR2, and HCDR3 comprises SEQ ID NOs: 7, 8, and 9, and LCDR1, LCDR2, LCDR3 comprises SEQ ID NOs: 17, 18 and 19; or HCDR1, HCDR2, and HCDR3 comprises SEQ ID NOs: 32, 33, and 34 and LCDR1, LCDR2, LCDR3 comprises SEQ ID NOs: 42, 43 and 44; or HCDR1, HCDR2, and HCDR3 comprises SEQ ID NOs: 52, 53, and 54, and LCDR1, LCDR2, LCDR3 comprises SEQ ID NOs: 62, 63, and 64; or HCDR1, HCDR2, and HCDR3 comprises SEQ ID NOs: 72, 73, and 74, and LCDR1, LCDR2, LCDR3 comprises SEQ ID NOs: 82, 83, and 84; or HCDR1, HCDR2, and HCDR3 comprises SEQ ID NOs: 92, 93, and 94, and LCDR1, LCDR2, LCDR3 comprises SEQ ID NOs: 102, 103, and 104; or HCDR1, HCDR2, and HCDR3 comprises SEQ ID NOs: 112, 113, and 114, and LCDR1, LCDR2, LCDR3 comprises SEQ ID NOs: 122, 123, and 124; or HCDR1, HCDR2, and HCDR3 comprises SEQ ID NOs: 132, 133, and 134, and LCDR1, LCDR2, LCDR3 comprises SEQ ID NOs: 142, 143, and 144.

The invention also relates to an antibody or antigen binding fragment having HCDR1, HCDR2, and HCDR3 of the heavy chain variable domain of SEQ ID NOs: 13, 38, 58, 78, 98, 118, and 138, and the LCDR1, LCDR2 and LCDR3 of the light chain variable domain of SEQ ID NOs: 23, 48, 68, 88, 108, 128, and 148, as defined by Chothia. In another aspect of the invention the antibody or antigen binding fragment may have the HCDR1, HCDR2, and HCDR3 of the heavy chain variable domain sequence of SEQ ID NOs: 13, 38, 58, 78, 98, 118, and 138, and the LCDR1, LCDR2 and LCDR3 of the light chain variable domain sequence of SEQ ID NOs: 23, 48, 68, 88, 108, 128, and 148, as defined by Kabat.

In one aspect of the invention the isolated antibody or antigen binding fragments thereof includes a heavy chain variable domain sequence selected from the group consisting of SEQ ID NOs: 13, 38, 58, 78, 98, 118, and 138. The isolated antibody or antigen binding fragment further can comprise a light chain variable domain sequence wherein the heavy chain variable domain and light chain variable domain combine to form and antigen binding site for ANGPTL4. In particular the light chain variable domain sequence can be selected from SEQ ID NOs: 23, 48, 68, 88, 108, 128, and 148 wherein said isolated antibody or antigen binding fragments thereof binds ANGPTL4.

The invention also relates to an isolated antibody or antigen binding fragments thereof that includes a light chain variable domain sequence selected from the group consisting of SEQ ID NOs: 23, 48, 68, 88, 108, 128, and 148, wherein said isolated antibody or antigen binding fragments thereof binds to human ANGPTL4. The isolated antibody or antigen binding fragment may further comprise a heavy chain variable domain sequence wherein the light chain variable domain and heavy chain variable domain combine to form and antigen binding site for ANGPTL4.

In particular, the isolated antibody or antigen binding fragments thereof that binds ANGPTL4, may have heavy and light chain variable domains comprising the sequences of SEQ ID NOs: 13 and 23; 38 and 48; 58 and 68; 78 and 88; 98 and 108; 118 and 128; or 138 and 148, respectively.

The invention further relates to an isolated antibody or antigen binding fragments thereof, that includes a heavy chain variable domain having at least 90% sequence identity to a sequence selected from the group consisting of SEQ ID NOs: 13, 38, 58, 78, 98, 118, and 138, wherein said antibody binds to ANGPTL4. In one aspect, the isolated antibody or antigen binding fragments thereof also includes a light chain variable domain having at least 90% sequence identity to a sequence selected from the group consisting of SEQ ID NOs: 23, 48, 68, 88, 108, 128, and 148. In a further aspect of the invention, the isolated antibody or antigen binding fragment has an HCDR1, HCDR2, HCDR3, LCDR1, LCDR2 and LCDR3 as defined by Kabat and as described in Table 1.

The invention also relates to an isolated antibody or antigen binding fragments thereof, having a light chain variable domain having at least 90% sequence identity to a sequence selected from the group consisting of SEQ ID NOs: 23, 48, 68, 88, 108, 128, and 148, wherein said antibody binds ANGPTL4.

In another aspect of the invention, the isolated antibody, or antigen binding fragments thereof, that binds to ANGPTL4 may have a heavy chain comprising the sequence of SEQ ID NOs: 15, 28, 40, 60, 80, 100, 120, and 140. The isolated antibody can also includes a light chain that can combine with the heavy chain to form an antigen binding site to human ANGPTL4. In particular, the light chain may have a sequence comprising SEQ ID NOs: 25, 50, 70, 90, 110, 130, and 150. In particular, the isolated antibody or antigen binding fragments thereof that binds ANGPTL4, may have a heavy chain and a light chain comprising the sequences of SEQ ID NOs: 15 and 25; 28 and 25; 40 and 50; 60 and 70; 80 and 90; 100 and 110; 120 and 130; or 140 and 150, respectively.

The invention still further relates to an isolated antibody or antigen binding fragments thereof that includes a heavy chain having at least 90% sequence identity to a sequence selected from the group consisting of SEQ ID NOs: 15, 28, 40, 60, 80, 100, 120, and 140, wherein said antibody binds to ANGPTL4. In one aspect, the isolated antibody or antigen binding fragments thereof also includes a light chain having at least 90% sequence identity to a sequence selected from the group consisting of SEQ ID NOs: 25, 50, 70, 90, 110, 130, and 150.

The invention still further relates to an isolated antibody or antigen binding fragments thereof that includes a light chain having at least 90% sequence identity to a sequence selected from the group consisting of SEQ ID NOs: 25, 50, 70, 90, 110, 130, and 150, wherein said antibody binds ANGPTL4.

The invention still further relates to an isolated antibody or antigen binding fragment which competes for binding with the antibodies or antigen binding fragments described herein, e.g., with humanized antibodies NEG276, NEG276-LALA, NEG278, NEG310, NEG313, NEG315, NEG318, and NEG319. In one embodiment, the isolated antibody or antigen binding fragment of the invention is capable of inhibiting by more than 50% the binding of ANGPTL4 by a humanized antibody selected from NEG276, NEG276-LALA, NEG278, NEG310, NEG313, NEG315, NEG318, and NEG319, when the two antibodies or antigen binding fragments are present in equimolar concentrations.

In another embodiment, the isolated antibody or antigen binding fragment of the invention is capable of inhibiting by more than 80% the binding of ANGPTL4 by a humanized antibody selected from NEG276, NEG276-LALA, NEG278, NEG310, NEG313, NEG315, NEG318, and NEG319, when the two antibodies or antigen binding fragments are present in equimolar concentrations. In still other embodiments, the isolated antibody or antigen binding fragment of the invention is capable of inhibiting by more than 85% (or 90%, 95%, 98% or 99%) the binding of ANGPTL4 by a humanized antibody selected from NEG276, NEG276-LALA, NEG278, NEG310, NEG313, NEG315, NEG318, and NEG319, when the two antibodies or antigen binding fragments are present in equimolar concentrations.

The invention also relates to compositions comprising the isolated antibody, or antigen binding fragments thereof, described herein. As well as, antibody compositions in combination with a pharmaceutically acceptable carrier. Specifically, the invention further includes pharmaceutical compositions comprising an antibody or antigen binding fragments thereof of Table 1, such as, for example humanized antibodies NEG276, NEG276-LALA, NEG278, NEG310, NEG313, NEG315, NEG318, NEG319. The invention also relates to pharmaceutical compositions comprising a combination of two or more of the isolated antibodies or antigen binding fragments thereof of Table 1.

The invention also relates to an isolated nucleic acid sequence encoding the heavy chain variable domain having a sequence selected from SEQ ID NOs: 13, 38, 58, 78, 98, 118, and 138. In particular the nucleic acid has a sequence at least 90% sequence identity to a sequence selected from the group consisting of SEQ ID NOs: 14, 27, 39, 59, 79, 99, 119, and 139. In a further aspect of the invention the sequence is SEQ ID NOs: 14, 27, 39, 59, 79, 99, 119, or 139.

The invention also relates to an isolated nucleic acid sequence encoding the light chain variable domain having a sequence selected from SEQ ID NOs: 23, 48, 68, 88, 108, 128, and 148. In particular the nucleic acid has a sequence at least 90% sequence identity to a sequence selected from the group consisting of SEQ ID NOs: 24, 31, 49, 69, 89, 109, 129, and 149. In a further aspect of the invention the sequence is SEQ ID NOs: 24, 31, 49, 69, 89, 109, 129, or 149.

The invention also relates to an isolated nucleic acid comprising a sequence encoding a polypeptide that includes a light chain variable domain having at least 90% sequence identity to a sequence selected from the group consisting of SEQ ID NOs: 23, 48, 68, 88, 108, 128, and 148.

The invention also relates to a vector that includes one or more of the nucleic acid molecules described herein.

The invention also relates to an isolated host cell that includes a recombinant DNA sequence encoding a heavy chain of the antibody described above, and a second recombinant DNA sequence encoding a light chain of the antibody described above, wherein said DNA sequences are operably linked to a promoter and are capable of being expressed in the host cell. It is contemplated that the antibody can be a humanized antibody. It is also contemplated that the host cell is a non-human mammalian cell.

It is contemplated that the cell is a human cell. It is further contemplated that the cell is in a subject. In one embodiment, it is contemplated that the cell is an endothelial cell. In other embodiments, the cell may be one or more of adipose, muscle, and liver cells. It is still further contemplated that the subject is human.

The invention also relates to a method of treating, improving, or preventing a ANGPTL4-associated disorder in a patient, wherein the method includes the step of administering to the patient an effective amount of a composition comprising the antibody or antigen binding fragments thereof described herein. In one aspect, the ANGPTL4-associated disorder is associated with hypertriglyceridemia (e.g., severe hypertriglyceridemia (e.g., with plasma triglyceride concentration >500 mg/dL), hypertriglyceridemia associated with obesity, and type V hypertriglyceridemia). In other aspects, the ANGPTL4-associated disorder is associated with primary dyslipidemia, metabolic syndrome, type II diabetes. It is contemplated that the patient is human.

Any of the foregoing isolated antibodies or antigen binding fragments thereof may be a monoclonal antibody or antigen binding fragments thereof.

DEFINITIONS

Unless defined otherwise, all technical and scientific terms used herein have the same meaning as commonly understood by those of ordinary skill in the art to which this invention pertains.

The terms "ANGPTL4 protein" or "ANGPTL4 antigen" or "ANGPTL4" are used interchangeably, and refer to the Angiopoietin-like 4 (ANGPTL4) protein in different species. For example, human ANGPTL4 has the sequence as set out in Table 1 (SEQ ID NO: 1), and has been described in previous reports and literature Mol Cell Biol. 2000 July;20 (14):5343-9; J Lipid Res. 2002 November;43(11):1770-2; Genbank Accession No. NP_647475.1). ANGPTL4 contains an N-terminal coiled-coil domain and a C-terminal fibrinogen (FBN)-like domain (Kim et al. (2000) Biochem. J. 346:603-610). It is a homooligomeric protein, capable of forming dimers and tetramers, that is expressed by cell types including macrophages, adipose, muscle, and liver cells, and known to inhibit lipoprotein lipase (LPL)-mediated triglyceride (TG) clearance.

In addition, in the context of this invention, the term "ANGPTL4" includes mutants of the natural Angiopoietin-like 4 (ANGPTL4) protein, which have substantially the same amino acid sequence as that of the native primary structure (amino acid sequence) described in the above-mentioned reports. Herein, the term "mutants of the natural human Angiopoietin-like 4 (ANGPTL4) protein having substantially the same amino acid sequence" refers to such mutant proteins.

The term "antibody" as used herein means a whole antibody and any antigen binding fragment (i.e., "antigen-binding portion") or single chain thereof. A whole antibody is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen binding portion" or "antigen binding fragment" of an antibody, as used herein, refers to one or more fragments of an intact antibody that retain the ability to specifically bind to a given antigen (e.g., human oxidized LDL receptor (ANGPTL4)). Antigen binding functions of an antibody can be performed by fragments of an intact antibody. Examples of binding fragments encompassed within the term antigen binding portion or antigen binding fragment of an antibody include a Fab fragment, a monovalent fragment consisting of the VL, VH, CL and CH1 domains; a $F(ab)_2$ fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) fragment (Ward et al., 1989 Nature 341:544-546), which consists of a VH domain or a VL domain; and an isolated complementarity determining region (CDR).

Furthermore, although the two domains of the Fv fragment, VL and VH, are coded for by separate genes, they can be joined, using recombinant methods, by an artificial peptide linker that enables them to be made as a single protein chain in which the VL and VH regions pair to form monovalent molecules (known as single chain Fv (scFv); see, e.g., Bird et al., 1988 Science 242:423-426; and Huston et al., 1988 Proc. Natl. Acad. Sci. 85:5879-5883). Such single chain antibodies include one or more antigen binding portions or fragments of an antibody. These antibody fragments are obtained using conventional techniques known to those of skill in the art, and the fragments are screened for utility in the same manner as are intact antibodies.

Antigen binding fragments can also be incorporated into single domain antibodies, maxibodies, minibodies, intrabodies, diabodies, triabodies, tetrabodies, v-NAR and bis-scFv (see, e.g., Hollinger and Hudson, 2005, Nature Biotechnology, 23, 9, 1126-1136). Antigen binding portions of antibodies can be grafted into scaffolds based on polypeptides such as Fibronectin type III (Fn3) (see U.S. Pat. No. 6,703, 199, which describes fibronectin polypeptide monobodies).

Antigen binding fragments can be incorporated into single chain molecules comprising a pair of tandem Fv segments (VH—CH1-VH—CH1) which, together with complementary light chain polypeptides, form a pair of antigen binding regions (Zapata et al., 1995 Protein Eng. 8(10):1057-1062; and U.S. Pat. No. 5,641,870).

As used herein, the term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity. As used herein, the term "high affinity" for an antibody or antigen binding fragments thereof (e.g., a Fab fragment) generally refers to an antibody, or antigen binding fragment, having a KD of $10^{-9}$M or less.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "binding specificity" as used herein refers to the ability of an individual antibody combining site to react with only one antigenic determinant.

The phrase "specifically (or selectively) binds" to an antibody (e.g., a ANGPTL4-binding antibody) refers to a binding reaction that is determinative of the presence of a cognate antigen (e.g., a human ANGPTL4 or cynomolgus ANGPTL4) in a heterogeneous population of proteins and other biologics. The phrases "an antibody recognizing an antigen" and "an antibody specific for an antigen" are used interchangeably herein with the term "an antibody which binds specifically to an antigen."

The term "ANGPTL4 mediated" refers to the fact that ANGPTL4 is known to inhibit lipoprotein lipase (LPL)-mediated triglyceride (TG) clearance, and thereby increase triglyceride levels.

An "ANGPTL4-associated disorder," "ANGPTL4-associated condition," or similar terms as used herein, refer to any number of conditions or diseases in which ANGPTL4ANGPTL4 a reduction of ANGPTL4-mediated LPL inhibition and lipoprotein modulation is sought. These conditions include but are not limited to those involving lipid metabolism, such as hyperlipidemia, hyperlipoproteinemia and dyslipidemia, including atherogenic dyslipidemia, diabetic dyslipidemia, hypertriglyceridemia (e.g., severe hypertriglyceridemia (e.g., with plasma triglyceride concentration >500 mg/dL), hypertriglyceridemia associated with obesity, and type V hypertriglyceridemia), hypercholesterolemia, chylomicronemia, mixed dyslipidemia (obesity, metabolic syndrome, diabetes, etc.), lipodystrophy, lipoatrophy, and other conditions caused by, e.g., decreased LPL activity and/or LPL deficiency, decreased LDL receptor activity and/or LDL receptor deficiency, altered ApoC2, ApoE deficiency, increased ApoB, increased production and/or decreased elimination of very low-density lipoprotein (VLDL), certain drug treatment (e.g., glucocorticoid treatment-induced dyslipidemia), any genetic predisposition, diet, life style, and the like.

Other ANGPTL4-associated diseases or disorders associated with or resulting from hyperlipidemia, hyperlipoproteinemia, and/or dyslipidemia, include, but are not limited to, cardiovascular diseases or disorders, such as atherosclerosis, aneurysm, hypertension, angina, stroke, cerebrovascular diseases, congestive heart failure, coronary artery diseases, myocardial infarction, peripheral vascular diseases, and the like; acute pancreatitis; nonalcoholic steatohepatitis (NASH); blood sugar disorders, such as diabetes; obesity, and the like.

The term "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. For example, a mouse antibody can be modified by replacing its constant region with the constant region from a human immunoglobulin. Due to the replacement with a human constant region, the chimeric antibody can retain its specificity in recognizing the antigen while having reduced antigenicity in human as compared to the original mouse antibody.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some embodiments, the term "conservative sequence modifications" are used to refer to amino acid modifications that do not significantly affect or alter the binding characteristics of the antibody containing the amino acid sequence.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences. The human antibodies of the invention may include amino acid residues not encoded by human sequences (e.g., mutations introduced by random or site-specific mutagenesis in vitro or by somatic mutation in vivo).

A "humanized" antibody is an antibody that retains the antigen-specific reactivity of a non-human antibody, e.g., a mouse monoclonal antibody, while being less immunogenic when administered as a therapeutic in humans. See, e.g., Robello et al., Transplantation, 68: 1417-1420. This can be achieved, for instance, by retaining the non-human antigen-binding regions and replacing the remaining parts of the antibody with their human counterparts (i.e., the constant region as well as portions of the variable region not involved in binding). See, e.g., Morrison et al., Proc. Natl. Acad. Sci. USA, 81:6851-6855, 1984; Morrison and Oi, Adv. Immunol., 44:65-92, 1989; Verhoeyen et al., Science, 239:1534-1536, 1988; Padlan, Molec. Immun., 28:489-498, 1991; and Padlan, Molec. Immun., 31:169-217, 1994. Other examples of human engineering technology include, but are not limited to Xoma technology disclosed in U.S. Pat. No. 5,766, 886.

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch, J. Mol. Biol. 48:443, 1970, by the search for similarity method of Pearson and Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., Current Protocols in Molecular Biology, John Wiley & Sons, Inc. (Ringbou ed., 2003)).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol, Biol. 48:444-453, 1970) algorithm which has been incorporated into the GAP program in the GCG software package (available on the world wide web at gcg.com), using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "isolated antibody" refers to an antibody that is substantially free of other antibodies having different antigenic specificities (e.g., an isolated antibody that specifically binds ANGPTL4 is substantially free of antibodies that specifically bind antigens other than ANGPTL4). An isolated antibody that specifically binds ANGPTL4 may, however, have cross-reactivity to other antigens. Moreover, an isolated antibody may be substantially free of other cellular material and/or chemicals.

The term "isotype" refers to the antibody class (e.g., IgM, IgE, IgG such as IgG1 or IgG4) that is provided by the heavy chain constant region genes. Isotype also includes modified versions of one of these classes, where modifications have been made to alter the Fc function, for example, to enhance or reduce effector functions or binding to Fc receptors.

The term "$k_{assoc}$" or "$k_a$", as used herein, is intended to refer to the association rate of a particular antibody-antigen interaction, whereas the term "$k_{dis}$" or "$k_d$," as used herein, is intended to refer to the dissociation rate of a particular antibody-antigen interaction. The term "$K_D$", as used herein, is intended to refer to the dissociation constant, which is obtained from the ratio of $k_d$ to $k_a$ (i.e. $k_d/k_a$) and is expressed as a molar concentration (M). $K_D$ values for antibodies can be determined using methods well established in the art. Methods for determining the $K_D$ of an antibody include measuring surface plasmon resonance using a biosensor system such as a Biacore® system, or measuring affinity in solution by solution equilibrium titration (SET).

The terms "monoclonal antibody" or "monoclonal antibody composition" as used herein refer to a preparation of antibody molecules of single molecular composition. A monoclonal antibody composition displays a single binding specificity and affinity for a particular epitope.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., Nucleic Acid Res. 19:5081, 1991; Ohtsuka et al., J. Biol. Chem. 260:2605-2608, 1985; and Rossolini et al., Mol. Cell. Probes 8:91-98, 1994).

The term "operably linked" refers to a functional relationship between two or more polynucleotide (e.g., DNA) segments. Typically, the term refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

As used herein, the term, "optimized" means that a nucleotide sequence has been altered to encode an amino acid sequence using codons that are preferred in the production cell or organism, generally a eukaryotic cell, for example, a cell of Pichia, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in mammalian cells. However, optimized expression of these sequences in other eukaryotic cells or prokaryotic cells is also envisioned herein. The amino acid sequences encoded by optimized nucleotide sequences are also referred to as optimized.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "subject" includes human and non-human animals. Non-human animals include all vertebrates (e.g.: mammals and non-mammals) such as, non-human primates (e.g.: cynomolgus monkey), sheep, dog, cow, chickens, amphibians, and reptiles. Except when noted, the terms "patient" or "subject" are used herein interchangeably. As used herein, the terms "cyno" or "cynomolgus" refer to the cynomolgus monkey (Macaca fascicularis).

As used herein, the term "treating" or "treatment" of any disease or disorder (e.g., ANGPTL4 associated disorder) refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

"Prevention" as it relates to indications described herein, including, e.g., ANGPTL4 associated disorder, means any action that prevents or slows a worsening in e.g., ANGPTL4 associated disease parameters, as described below, in a patient at risk for said worsening.

The term "vector" is intended to refer to a polynucleotide molecule capable of transporting another polynucleotide to which it has been linked. One type of vector is a "plasmid", which refers to a circular double stranded DNA loop into which additional DNA segments may be ligated. Another type of vector is a viral vector, such as an adeno-associated viral vector (AAV, or AAV2), wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

DETAILED DESCRIPTION

Figure 1A:
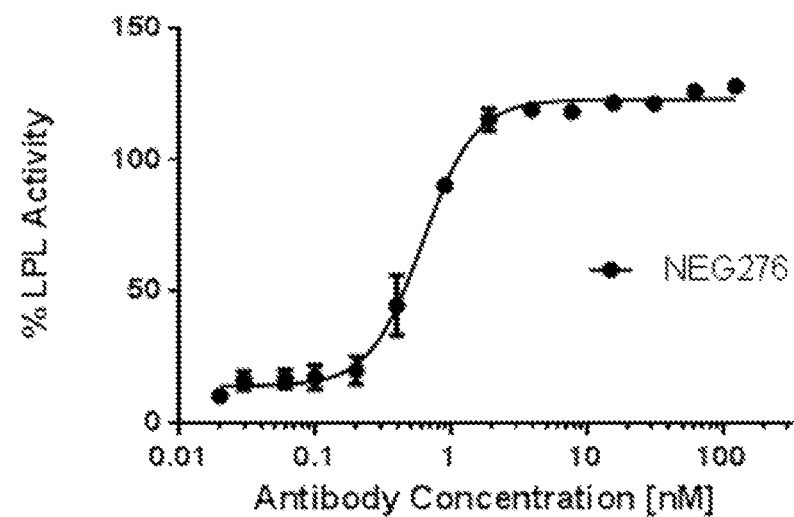
FIGS. 1A-1D depicts the reversal of ANGPTL4-mediated inhibition of human lipoprotein lipase (LPL) protein by selected ANGPTL4 antibodies of the invention.
Figure 1B:
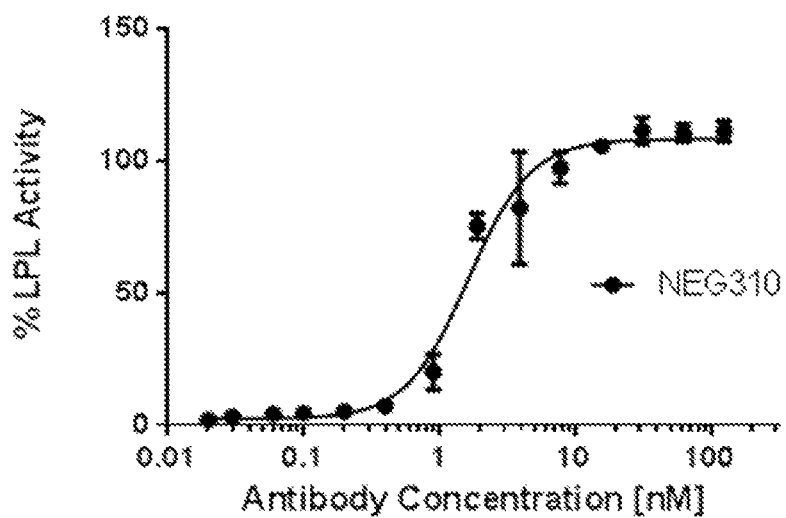
Figure 1C:
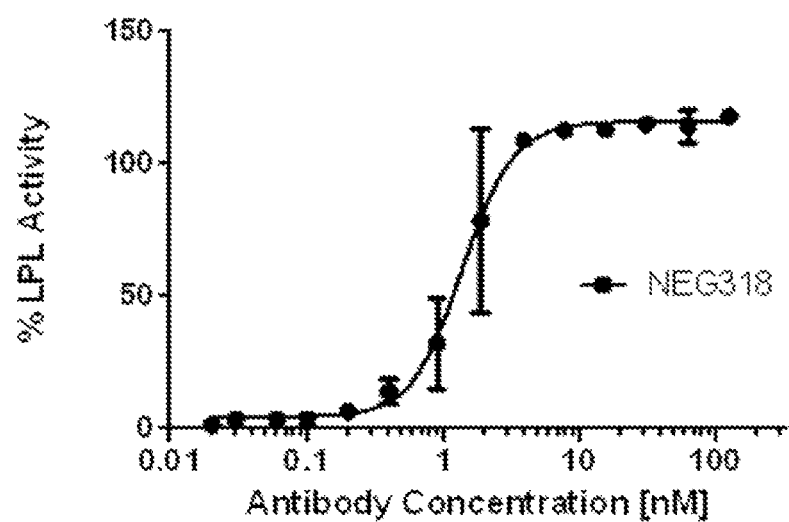
Figure 1D:
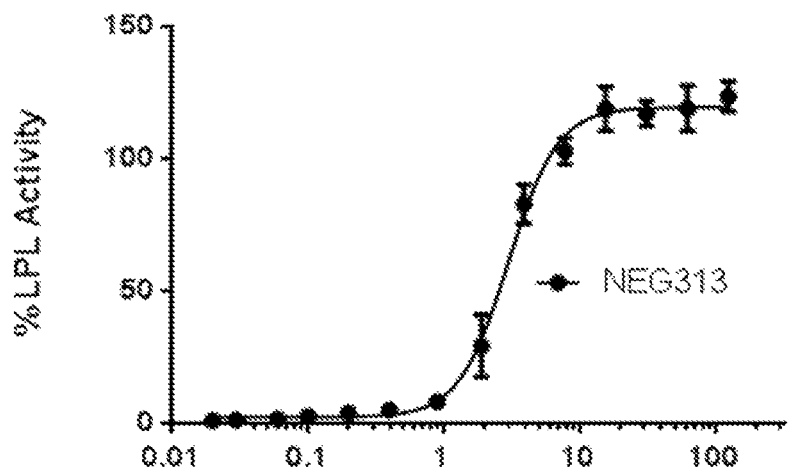

The present invention is based, in part, on the discovery of antibody molecules that specifically bind to ANGPTL4 and inhibit its biological activities. The invention relates to both full IgG format antibodies (e.g., humanized antibodies NEG276, NEG276-LALA, NEG278, NEG310, NEG313, NEG315, NEG318, NEG319) as well as antigen binding fragments thereof, such as Fab fragments.

Accordingly, the present invention provides antibodies that specifically bind to ANGPTL4 (e.g., human ANGPTL4), pharmaceutical compositions, production methods, and methods of use of such antibodies and compositions.

ANGPTL4 Proteins

The present invention provides antibodies that specifically bind to ANGPTL4 and inhibit its biological activities, including ability to activate lipoprotein lipase (LPL). Conversely, Angiopoietin-like 4 protein (ANGPTL4) is a member of the angiopoietin family of secreted proteins. It is a homooligomeric protein, capable of forming dimers and tetramers, that is expressed by cell types including macrophages, adipose, muscle, and liver cells. ANGPTL4 is also known as hepatic fibrinogen/angiopoietin-related protein (HFARP) (Kim et al. (2000) Biochem. J. 346:603-610); PPAR gamma angiopoietin related protein (PGAR)(Yoon, et al. (2000) Mol. Cell Biol., 20:5343-5349), and fasting induced adipose factor (FIAF)(Kerten et al. (2000) J. Biol. Chem., 275: 28488-28493). ANGPTL4 contains an N-terminal coiled-coil domain and a C-terminal fibrinogen (FBN)-like domain (Kim et al. (2000) Biochem. J. 346:603-610).

Lipoprotein lipase (LPL) has a central role in lipoprotein metabolism to maintain normal lipoprotein levels in blood and, through tissue specific regulation of its activity, to determine when and in what tissues triglycerides (TG) are unloaded. The coiled-coil region of ANGPTL4 is known to inhibit lipoprotein lipase (LPL)-mediated triglyceride (TG) clearance. Therefore, ANGPTL4 loss-of-function mutations (e.g., as seen in human subjects), genetic deletions (e.g., as seen in transgenic mice), and antibody inhibition (e.g., as seen in mice and cynomolgus monkeys) are all observed to decrease plasma triglycerides. Furthermore, ANGPTL4 antibodies are also known to activate LPL. Conversely, ANGPTL4 injection into mice produces a rapid increase in circulating triglycerides and this is at a higher rate than the injection of angiopoietin-like protein 3 (ANGPTL3) (Yoshida et al. (2002) J Lipid Res 43:1770-1772).

The anti-ANGPTL4 antibodies and antigen binding fragments described in this invention initiate, promote, or enhance activation of LPL, e.g., by blocking ANGPTL4 inhibition of LPL, thereby decreasing plasma triglycerides.

These antibodies are expected to prevent and ameliorate the acute and chronic manifestations of diseases characterized by elevated triglyceride levels, e.g., primary dyslipidemia, hypertriglyceridemia, metabolic syndrome, type II diabetes, and the like.

The anti-ANGPTL4 antibodies and antigen binding fragments described in this invention initiate, promote, or enhance activation of LPL, e.g., by blocking ANGPTL4 inhibition of LPL, thereby decreasing plasma triglycerides. These antibodies are expected to prevent and ameliorate the acute and chronic manifestations of diseases characterized by elevated triglyceride levels, e.g., primary dyslipidemia, hypertriglyceridemia, metabolic syndrome, type II diabetes, and the like.

ANGPTL4 Antibodies & Antigen Binding Fragments

The present invention provides antibodies that specifically bind to ANGPTL4. In some embodiments, the present invention provides antibodies that specifically bind to human and cynomolgus monkey ANGPTL4. Antibodies of the invention include, but are not limited to, the humanized antibodies and Fabs, isolated as described in the Examples.

The present invention provides antibodies that specifically bind a ANGPTL4 protein (e.g., human and cynomolgus monkey ANGPTL4), wherein the antibodies comprise a VH domain having an amino acid sequence of SEQ ID NOs: 13, 38, 58, 78, 98, 118, and 138. The present invention also provides antibodies that specifically bind to a ANGPTL4 protein, wherein the antibodies comprise a VH CDR having an amino acid sequence of any one of the VH CDRs listed in Table 1, infra. In particular, the invention provides antibodies that specifically bind to an ANGPTL4 protein (e.g., human and cynomolgus monkey ANGPTL4), wherein the antibodies comprise (or alternatively, consist of) one, two, three, or more VH CDRs having an amino acid sequence of any of the VH CDRs listed in Table 1, infra.

The present invention provides antibodies that specifically bind to a ANGPTL4 protein, said antibodies comprising a VL domain having an amino acid sequence of SEQ ID NOs: 23, 48, 68, 88, 108, 128, and 148. The present invention also provides antibodies that specifically bind to an ANGPTL4 protein (e.g., human and cynomolgus monkey ANGPTL4), said antibodies comprising a VL CDR having an amino acid sequence of any one of the VL CDRs listed in Table 2, infra. In particular, the invention provides antibodies that specifically bind to an ANGPTL4 protein (e.g., human and cynomolgus monkey ANGPTL4), said antibodies comprising (or alternatively, consisting of) one, two, three or more VL CDRs having an amino acid sequence of any of the VL CDRs listed in Table 1, infra.

Other antibodies of the invention include amino acids that have been mutated, yet have at least 60, 70, 80, 85, 90 or 95 percent identity in the CDR regions with the CDR regions depicted in the sequences described in Table 1. In some embodiments, it includes mutant amino acid sequences wherein no more than 1, 2, 3, 4 or 5 amino acids have been mutated in the CDR regions when compared with the CDR regions depicted in the sequence described in Table 1.

The present invention also provides nucleic acid sequences that encode VH, VL, the full-length heavy chain, and the full-length light chain of the antibodies that specifically bind to an ANGPTL4 protein (e.g., human and cynomolgus monkey ANGPTL4). Such nucleic acid sequences can be optimized for expression in mammalian cells (for example, Table 1 shows the optimized nucleic acid sequences for the heavy chain and light chain of antibodies of the invention).

TABLE 1

Examples of ANGPTL4 Antibodies, Fabs and ANGPTL4 Proteins

| Sequence Description | Sequence Identifier (SEQ ID NO.) | Amino acid or polynucleotide sequence |
|---|---|---|
| Human ANGPTL4 amino acid sequence (NCBI Reference Sequence: NP_647475.1) | 1 | MSGAPTAGAALMLCAATAVLLSAQGGPVQSKSPRFASWDEMN VLAHGLLQLGQGLREHAERTRSQLSALERRLSACGSACQGTE GSTDLPLAPESRVDPEVLHSLQTQLKAQNSRIQQLFHKVAQQ QRHLEKQHLRIQHLQSQFGLLDHKHLDHEVAKPARRKRLPEM AQPVDPAHNVSRLHRLPRDCQELFQVGERQSGLFEIQPQGSP PFLVNCKMTSDGGWTVIQRRHDGSVDFNRPWEAYKAGFGDPH GEFWLGLEKVHSITGDRNSRLAVQLRDWDGNAELLQFSVHLG GEDTAYSLQLTAPVAGQLGATTVPPSGLSVPFSTWDQDHDLR RDKNCAKSLSGGWWFGTCSHSNLNGQYFRSIPQQRQKLKKGI FWKTWRGRYYPLQATTMLIQPMAAEAAS |
| Human ANGPTL4 nucleic acid sequence (NCBI Reference NM_139314.2) | 2 | ATGAGCGGTGCTCCGACGGCCGGGGCAGCCCTGATGCTCTGC GCCGCCACCGCCGTGCTACTGAGCGCTCAGGGCGGACCCGTG CAGTCCAAGTCGCCGCGCTTTGCGTCCTGGGACGAGATGAAT GTCCTGGCGCACGGACTCCTGCAGCTCGGCCAGGGGCTGCGC GAACACGCGGAGCGCACCCGCAGTCAGCTGAGCGCGCTGGAG CGGCGCCTGAGCGCGTGCGGGTCCGCCTGTCAGGGAACCGAG GGGTCCACCGACCTCCCGTTAGCCCCTGAGAGCCGGGTGGAC CCTGAGGTCCTTCACAGCCTGCAGACACAACTCAAGGCTCAG AACAGCAGGATCCAGCAACTCTTCCACAAGGTGGCCCAGCAG CAGCGGCACCTGGAGAAGCAGCACCTGCGAATTCAGCATCTG CAAAGCCAGTTTGGCCTCCTGGACCACAAGCACCTAGACCAT GAGGTGGCCAAGCCTGCCCGAAGAAAGAGGCTGCCCGAGATG GCCCAGCCAGTTGACCCGGCTCACAATGTCAGCCGCCTGCAC CGGCTGCCCAGGGATTGCCAGGAGCTGTTCCAGGTTGGGGAG AGGCAGAGTGGACTATTTGAAATCCAGCCTCAGGGGTCTCCG CCATTTTTGGTGAACTGCAAGATGACCTCAGATGGAGGCTGG ACAGTAATTCAGAGGCGCCACGATGGCTCAGTGGACTTCAAC CGGCCCTGGGAAGCCTACAAGGCGGGGTTTGGGGATCCCCAC GGCGAGTTCTGGCTGGGTCTGGAGAAGGTGCATAGCATCACG GGGGACCGCAACAGCCGCCTGGCCGTGCAGCTGCGGGACTGG GATGGCAACGCCGAGTTGCTGCAGTTCTCCGTGCACCTGGGT |

TABLE 1-continued

Examples of ANGPTL4 Antibodies, Fabs and ANGPTL4 Proteins

| Sequence Description | Sequence Identifier (SEQ ID NO.) | Amino acid or polynucleotide sequence |
|---|---|---|
| | | GGCGAGGACACGGCCTATAGCCTGCAGCTCACTGCACCCGTG<br>GCCGGCCAGCTGGGCGCCACCACCGTCCCACCCAGCGGCCTC<br>TCCGTACCCTTCTCCACTTGGGACCAGGATCACGACCTCCGC<br>AGGGACAAGAACTGCGCCAAGAGCCTCTCTGGAGGCTGGTGG<br>TTTGGCACCTGCAGCCATTCCAACCTCAACGGCCAGTACTTC<br>CGCTCCATCCCACAGCAGCGGCAGAAGCTTAAGAAGGGAATC<br>TTCTGGAAGACCTGGCGGGGCCGCTACTACCCGCTGCAGGCC<br>ACCACCATGTTGATCCAGCCCATGGCAGCAGAGGCAGCCTCC<br>TAGCGTC |
| Cyno ANGPTL4 (amino acid sequence) | 3 | MRGAPTAGAALMLCVATAVLLRAQGGPVQSKSPRFASWDEMN<br>VLAHGLLQLGQGLREHAERTRSQLNALERRLSACGSACQGTE<br>GSTALPLAPESRVDPEVLHSLQTQLKAQNSRIQQLFHKVAQQ<br>QRHLEKQHLRIQRLQSQVGLLDPKHLDHEVAKPARRKRRPEM<br>AQPVDSAHNASRLHRLPRDCQELFEDGERQSGLFEIQPQGSP<br>PFLVNCKMTSDGGWTVIQRRHDGSVDFNRPWEAYKAGFGDPQ<br>GEFWLGLEKVHSITGDRNSRLAVQLQDWDGNAESLQFSVHLG<br>GEDTAYSLQLTEPVASQLGATTVPPSGLSVPFSTWDQDHDLR<br>RDKNCAKSLSGGWWFGTCSHSNLNGQYFRSIPQQRQELKKGI<br>FWKTWRGRYYPLQATTMLIQPTAAEEAAS |
| Cyno ANGPTL4 (nucleic acid sequence) | 4 | ATGCGCGGTGCTCCGACGGCCGGAGCAGCCCTGATGCTCTGC<br>GTCGCCACGGCCGTGCTGCTGAGAGCTCAGGGCGGCCCCGTG<br>CAGTCCAAGTCTCCGCGCTTTGCGTCCTGGGACGAGATGAAT<br>GTCCTGGCGCACGGACTCCTGCAGCTAGGCCAGGGGCTGCGC<br>GAACACGCGGAGCGCACCCGCAGTCAGCTGAACGCGCTGGAG<br>CGGCGCCTCAGCGCTTGCGGGTCTGCCTGCCAGGGAACCGAG<br>GGGTCCACCGCCCTCCCGTTAGCCCCTGAGAGCCGGGTGGAC<br>CCTGAGGTCCTTCACAGCCTGCAGACACAACTCAAGGCTCAG<br>AACAGCAGGATCCAGCAACTCTTCCACAAGGTGGCCCAGCAG<br>CAGCGGCACCTGGAGAAGCAGCACCTGCGAATTCAGCGTCTG<br>CAAAGCCAGGTTGGCCTCCTGGACCCCAAGCACCTAGACCAT<br>GAGGTGGCCAAGCCTGCCCGAAGAAAGAGGCGGCCCGAGATG<br>GCCCAGCCAGTTGACTCGGCTCACAATGCCAGCCGCCTGCAC<br>CGGCTGCCCAGGGATTGCCAGGAGCTGTTTGAAGATGGGGAG<br>AGGCAGAGTGGACTATTTGAGATCCAGCCTCAGGGGTCTCCG<br>CCATTTTTGGTGAACTGCAAGATGACCTCAGATGGAGGCTGG<br>ACAGTAATTCAGAGGCGCCACGATGGCTCTGTGGACTTCAAC<br>CGGCCCTGGGAAGCCTACAAGGCGGGGTTTGGGGATCCCCAA<br>GGCGAGTTCTGGCTGGGCCTGGAGAAGGTGCATAGCATCACA<br>GGGGACCGCAACAGCCGCCTGGCCGTGCAGCTGCAGGACTGG<br>GATGGCAACGCCGAGTCGCTGCAGTTCTCTGTGCACCTGGGT<br>GGCGAGGACACGGCTTACAGCCTGCAGCTCACCGAGCCCGTG<br>GCCAGCCAGTTGGGTGCCACCACCGTCCCGCCTAGCGGCCTC<br>TCCGTACCCTTCTCCACTTGGGACCAGGATCACGACCTCCGC<br>AGGGACAAGAACTGCGCCAAGAGCCTCTCTGGAGGCTGGTGG<br>TTTGGCACCTGCAGCCATTCCAACCTCAATGGCCAGTACTTC<br>CGCTCCATCCCACAGCAGCGGCAGGAGCTTAAGAAAGGAATC<br>TTCTGGAAGACCTGGCGGGGCCGCTACTACCCGCTGCAGGCC<br>ACCACCATGTTGATCCAGCCCACGGCGGCAGAGGCAGCCTCC<br>TAG |
| Human ANGPTL3 amino acid sequence (NCBI Reference NM_014495.3) | 5 | MFTIKLLLFIVPLVISSRIDQDNSSFDSLSPEPKSRFAMLDD<br>VKILANGLLQLGHGLKDFVHKTKGQINDIFQKLNIFDQSFYD<br>LSLQTSEIKEEEKELRRTTYKLQVKNEEVKNMSLELNSKLES<br>LLEEKILLQQKVKYLEEQLTNLIQNQPETPEHPEVTSLKTFV<br>EKQDNSIKDLLQTVEDQYKQLNQQHSQIKEIENQLRRTSIQE<br>PTEISLSSKPRAPRTTPFLQLNEIRNVKHDGIPAECTTIYNR<br>GEHTSGMYAIRPSNSQVFHVYCDVISGSPWTLIQHRIDGSQN<br>FNETWENYKYGFGRLDGEFWLGLEKIYSIVKQSNYVLRIELE<br>DWKDNKHYIEYSFYLGNHETNYTLHLVAITGNVPNAIPENKD<br>LVFSTWDHKAKGHFNCPEGYSGGWWWHDECGENNLNGKYNKP<br>RAKSKPERRRGLSWKSQNGRLYSIKSTKMLIHPTDSESFE |
| Human ANGPTL3 nucleic acid sequence (NCBI Reference NM_014495.3) | 6 | ATGTTCACAATTAAGCTCCTTCTTTTTATTGTTCCTCTAGTT<br>ATTTCCTCCAGAATTGATCAAGACAATTCATCATTTGATTCT<br>CTATCTCCAGAGCCAAAATCAAGATTTGCTATGTTAGACGAT<br>GTAAAAATTTTAGCCAATGGCCTCCTTCAGTTGGGACATGGT<br>CTTAAAGACTTTGTCCATAAGACGAAGGGCCAAATTAATGAC<br>ATATTTCAAAAACTCAACATATTTGATCAGTCTTTTTATGAT<br>CTATCGCTGCAAACCAGTGAAATCAAGAAGAAGAAAAGGAA<br>CTGAGAAGAACTACATATAAACTACAAGTCAAAAATGAAGAG<br>GTAAAGAATATGTCACTTGAACTCAACTCAAAACTTGAAAGC<br>CTCCTAGAAGAAAAAATTCTACTTCAACAAAAAGTGAAATAT |

TABLE 1-continued

Examples of ANGPTL4 Antibodies, Fabs and ANGPTL4 Proteins

| Sequence Description | Sequence Identifier (SEQ ID NO.) | Amino acid or polynucleotide sequence |
|---|---|---|
| | | TTAGAAGAGCAACTAACTAACTTAATTCAAAATCAACCTGAA<br>ACTCCAGAACACCCAGAAGTAACTTCACTTAAAACTTTTGTA<br>GAAAAACAAGATAATAGCATCAAAGACCTTCTCCAGACCGTG<br>GAAGACCAATATAAACAATTAAACCAACAGCATAGTCAAATA<br>AAAGAAATAGAAAATCAGCTCAGAAGGACTAGTATTCAAGAA<br>CCCACAGAAATTTCTCTATCTTCCAAGCCAAGAGCACCAAGA<br>ACTACTCCCTTTCTTCAGTTGAATGAAATAAGAAATGTAAAA<br>CATGATGGCATTCCTGCTGAATGTACCACCATTTATAACAGA<br>GGTGAACATACAAGTGGCATGTATGCCATCAGACCCAGCAAC<br>TCTCAAGTTTTTCATGTCTACTGTGATGTTATATCAGGTAGT<br>CCATGGACATTAATTCAACATCGAATAGATGGATCACAAAAC<br>TTCAATGAAACGTGGGAGAACTACAAATATGGTTTTGGGAGG<br>CTTGATGGAGAATTTTGGTTGGGCCTAGAGAAGATATACTCC<br>ATAGTGAAGCAATCTAATTATGTTTTACGAATTGAGTTGGAA<br>GACTGGAAAGACAACAAACATTATATTGAATATTCTTTTTAC<br>TTGGGAAATCACGAAACCAACTATACGCTACATCTAGTTGCG<br>ATTACTGGCAATGTCCCCAATGCAATCCCGGAAAACAAAGAT<br>TTGGTGTTTTCTACTTGGGATCACAAAGCAAAGGACACTTC<br>AACTGTCCAGAGGGTTATTCAGGAGGCTGGTGGTGGCATGAT<br>GAGTGTGGAGAAAACAACCTAAATGGTAAATATAACAAACCA<br>AGAGCAAAATCTAAGCCAGAGAGGAGAAGAGGATTATCTTGG<br>AAGTCTCAAATGGAAGGTTATACTCTATAAAATCAACCAAA<br>ATGTTGATCCATCCAACAGATTCAGAAAGCTTTGAA |
| NEG276 | | |
| HCDR1 (Kabat) | 7 | SSWMQ |
| HCDR2 (Kabat) | 8 | EIDPSDNYANYNQKFQG |
| HCDR3 (Kabat) | 9 | GSYFSNFFDY |
| HCDR1 (Chothia) | 10 | AYTFTSS |
| HCDR2 (Chothia) | 11 | DPSDNY |
| HCDR3 (Chothia) | 12 | GSYFSNFFDY |
| VH | 13 | QVQLVQSGAEVKKPGASVKVSCKASAYTFTSSWMQWVRQAPG<br>QGLEWMGEIDPSDNYANYNQKFQGRVTLTVDTSTSTAYMELS<br>SLRSEDTAVYYCASGSYFSNFFDYWGQGTLVTVSS |
| DNA Encoding VH | 14 | CAGGTGCAGCTGGTGCAGTCTGGCGCCGAAGTGAAGAAACCA<br>GGCGCCAGCGTGAAGGTGTCCTGCAAGGCCAGCGCCTACACC<br>TTTACCAGCAGCTGGATGCAGTGGGTGCGCCAGGCTCCTGGA<br>CAGGGCCTGGAATGGATGGGCGAGATCGACCCCAGCGACAAC<br>TACGCCAACTACAACCAGAAATTCCAGGGCAGAGTGACCCTG<br>ACCGTGGACACCAGCACCTCCACCGCCTACATGGAACTGAGC<br>AGCCTGCGGAGCGAGGACACCGCCGTGTACTATTGTGCCAGC<br>GGCAGCTACTTCAGCAACTTCTTCGACTACTGGGGCCAGGGC<br>ACCCTCGTGACCGTGTCATCT |
| Heavy Chain | 15 | QVQLVQSGAEVKKPGASVKVSCKASAYTFTSSWMQWVRQAPG<br>QGLEWMGEIDPSDNYANYNQKFQGRVTLTVDTSTSTAYMELS<br>SLRSEDTAVYYCASGSYFSNFFDYWGQGTLVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKRVEPKSCDKTHTCPPCPAPELLGGPSVFLFPPKPKDT<br>LMISRTPEVTCVVVDVSHEDPEVKFNWYVDGVEVHNAKTKPR<br>EEQYNSTYRVVSVLTVLHQDWLNGKEYKCKVSNKALPAPIEK<br>TISKAKGQPREPQVYTLPPSREEMTKNQVSLTCLVKGFYPSD<br>IAVEWESNGQPENNYKTTPPVLDSDGSFFLYSKLTVDKSRWQ<br>QGNVFSCSVMHEALHNHYTQKSLSLSPGK |
| DNA Encoding Heavy Chain | 16 | CAGGTGCAGCTGGTGCAGTCTGGCGCCGAAGTGAAGAAACCA<br>GGCGCCAGCGTGAAGGTGTCCTGCAAGGCCAGCGCCTACACC<br>TTTACCAGCAGCTGGATGCAGTGGGTGCGCCAGGCTCCTGGA<br>CAGGGCCTGGAATGGATGGGCGAGATCGACCCCAGCGACAAC<br>TACGCCAACTACAACCAGAAATTCCAGGGCAGAGTGACCCTG<br>ACCGTGGACACCAGCACCTCCACCGCCTACATGGAACTGAGC<br>AGCCTGCGGAGCGAGGACACCGCCGTGTACTATTGTGCCAGC<br>GGCAGCTACTTCAGCAACTTCTTCGACTACTGGGGCCAGGGC<br>ACCCTCGTGACCGTGTCATCTGCTAGCACCAAGGGCCCCAGC<br>GTGTTCCCCCTGGCCCCCAGCAGCAAGAGCACCAGCGGCGGC |

TABLE 1-continued

Examples of ANGPTL4 Antibodies, Fabs and ANGPTL4 Proteins

| Sequence Description | Sequence Identifier (SEQ ID NO.) | Amino acid or polynucleotide sequence |
|---|---|---|
| | | ACAGCCGCCCTGGGCTGCCTGGTGAAGGACTACTTCCCCGAG<br>CCCGTGACCGTGTCCTGGAACAGCGGAGCCCTGACCTCCGGC<br>GTGCACACCTTCCCCGCCGTGCTGCAGAGCAGCGGCCTGTAC<br>AGCCTGTCCAGCGTGGTGACAGTGCCCAGCAGCAGCCTGGGC<br>ACCCAGACCTACATCTGCAACGTGAACCACAAGCCCAGCAAC<br>ACCAAGGTGGACAAGAGAGTGGAGCCCAAGAGCTGCGACAAG<br>ACCCACACCTGCCCCCCCTGCCCAGCCCCAGAGCTGCTGGGC<br>GGACCCTCCGTGTTCCTGTTCCCCCCCAAGCCCAAGGACACC<br>CTGATGATCAGCAGGACCCCCGAGGTGACCTGCGTGGTGGTG<br>GACGTGAGCCACGAGGACCCAGAGGTGAAGTTCAACTGGTAC<br>GTGGACGGCGTGGAGGTGCACAACGCCAAGACCAAGCCCAGA<br>GAGGAGCAGTACAACAGCACCTACAGGGTGGTGTCCGTGCTG<br>ACCGTGCTGCACCAGGACTGGCTGAACGGCAAGGAATACAAG<br>TGCAAGGTCTCCAACAAGGCCCTGCCAGCCCCCATCGAAAAG<br>ACCATCAGCAAGGCCAAGGGCCAGCCACGGGAGCCCCAGGTG<br>TACACCCTGCCCCCCTCCCGGGAGGAGATGACCAAGAACCAG<br>GTGTCCCTGACCTGTCTGGTGAAGGGCTTCTACCCCAGCGAC<br>ATCGCCGTGGAGTGGGAGAGCAACGGCCAGCCCGAGAACAAC<br>TACAAGACCACCCCCCCAGTGCTGGACAGCGACGGCAGCTTC<br>TTCCTGTACAGCAAGCTGACCGTGGACAAGTCCAGGTGGCAG<br>CAGGGCAACGTGTTCAGCTGCAGCGTGATGCACGAGGCCCTG<br>CACAACCACTACACCCAGAAGAGCCTGAGCCTGTCCCCCGGC<br>AAG |
| LCDR1 (Kabat) | 17 | KASQDIGSNLN |
| LCDR2 (Kabat) | 18 | AVSNRGP |
| LCDR3 (Kabat) | 19 | LQYASSPWT |
| LCDR1 (Chothia) | 20 | SQDIGSN |
| LCDR2 (Chothia) | 21 | AVS |
| LCDR3 (Chothia) | 22 | YASSPW |
| VL | 23 | EIVMTQSPATLSVSPGERATLSCKASQDIGSNLNWLQQKPGQ<br>APRRLIYAVSNRGPGIPARFSGSRSGSEYTLTISSLQSEDFA<br>VYYCLQYASSPWTFGQGTKVEIK |
| DNA Encoding VL | 24 | GAGATCGTGATGACACAGAGCCCCGCCACCCTGTCCGTGTCT<br>CCAGGCGAAAGAGCCACCCTGAGCTGCAAAGCCAGCCAGGAC<br>ATCGGCAGCAACCTGAACTGGCTGCAGCAGAAACCAGGCCAG<br>GCCCCCAGAAGGCTGATCTACGCTGTTTCCAACCGTGGTCCT<br>GGCATCCCCGCCAGATTTTCCGGCAGCAGATCCGGCAGCGAG<br>TACACCCTGACCATCAGCAGCCTGCAGAGCGAGGACTTCGCC<br>GTGTACTACTGCCTGCAGTACGCCAGCAGCCCCTGGACATTT<br>GGCCAGGGCACCAAGGTGGAAATCAAG |
| Light Chain | 25 | EIVMTQSPATLSVSPGERATLSCKASQDIGSNLNWLQQKPGQ<br>APRRLIYAVSNRGPGIPARFSGSRSGSEYTLTISSLQSEDFA<br>VYYCLQYASSPWTFGQGTKVEIKRTVAAPSVFIFPPSDEQLK<br>SGTASVVCLLNNFYPREAKVQWKVDNALQSGNSQESVTEQDS<br>KDSTYSLSSTLTLSKADYEKHKVYACEVTHQGLSSPVTKSFN<br>RGEC |
| DNA encoding Light Chain | 26 | GAGATCGTGATGACACAGAGCCCCGCCACCCTGTCCGTGTCT<br>CCAGGCGAAAGAGCCACCCTGAGCTGCAAAGCCAGCCAGGAC<br>ATCGGCAGCAACCTGAACTGGCTGCAGCAGAAACCAGGCCAG<br>GCCCCCAGAAGGCTGATCTACGCTGTTTCCAACCGTGGTCCT<br>GGCATCCCCGCCAGATTTTCCGGCAGCAGATCCGGCAGCGAG<br>TACACCCTGACCATCAGCAGCCTGCAGAGCGAGGACTTCGCC<br>GTGTACTACTGCCTGCAGTACGCCAGCAGCCCCTGGACATTT<br>GGCCAGGGCACCAAGGTGGAAATCAAGCGTACGGTGGCCGCT<br>CCCAGCGTGTTCATCTTCCCCCCCAGCGACGAGCAGCTGAAG<br>AGCGGCACCGCCAGCGTGGTGCCTGCTGAACAACTTCTAC<br>CCCCGGGAGGCCAAGGTGCAGTGGAAGGTGGACAACGCCCTG<br>CAGAGCGGCAACAGCCAGGAGAGCGTCACCGAGCAGGACAGC<br>AAGGACTCCACCTACAGCCTGAGCAGCACCCTGACCCTGAGC<br>AAGGCCGACTACGAGAAGCATAAGGTGTACGCCTGCGAGGTG<br>ACCCACCAGGGCCTGTCCAGCCCCGTGACCAAGAGCTTCAAC<br>AGGGGCGAGTGC |

TABLE 1-continued

Examples of ANGPTL4 Antibodies, Fabs and ANGPTL4 Proteins

| Sequence Description | Sequence Identifier (SEQ ID NO.) | Amino acid or polynucleotide sequence |
|---|---|---|
| NEG276-LALA | | |
| HCDR1 (Kabat) | 7 | SSWMQ |
| HCDR2 (Kabat) | 8 | EIDPSDNYANYNQKFQG |
| HCDR3 (Kabat) | 9 | GSYFSNFFDY |
| HCDR1 (Chothia) | 10 | AYTFTSS |
| HCDR2 (Chothia) | 11 | DPSDNY |
| HCDR3 (Chothia) | 12 | GSYFSNFFDY |
| VH | 13 | QVQLVQSGAEVKKPGASVKVSCKASAYTFTSSWMQWVRQAPG QGLEWMGEIDPSDNYANYNQKFQGRVTLTVDTSTSTAYMELS SLRSEDTAVYYCASGSYFSNFFDYWGQGTLVTVSS |
| DNA Encoding VH | 27 | CAGGTGCAGCTGGTGCAGTCAGGCGCCGAAGTGAAGAAACCC GGCGCTAGTGTGAAAGTCAGCTGTAAAGCTAGTGCCTACACC TTCACCTCTAGCTGGATGCAGTGGGTCAGACAGGCCCCAGGT CAGGGCCTGGAGTGGATGGGCGAGATCGACCCTAGCGATAAC TACGCTAACTATAATCAGAAGTTTCAGGGTAGAGTCACCCTG ACCGTGGACACTAGCACTAGCACCGCCTATATGGAACTGTCT AGCCTGAGATCAGAGGACACCGCCGTCTACTACTGCGCTAGT GGTAGCTACTTCTCTAACTTCTTCGACTACTGGGGTCAGGGC ACCCTGGTCACCGTGTCTAGC |
| Heavy Chain | 28 | QVQLVQSGAEVKKPGASVKVSCKASAYTFTSSWMQWVRQAPG QGLEWMGEIDPSDNYANYNQKFQGRVTLTVDTSTSTAYMELS SLRSEDTAVYYCASGSYFSNFFDYWGQGTLVTVSSASTKGPS VFPLAPSSKSTSGGTAALGCLVKDYFPEPVTVSWNSGALTSG VHTFPAVLQSSGLYSLSSVVTVPSSSLGTQTYICNVNHKPSN TKVDKRVEPKSCDKTHTCPPCPAPEAAGGPSVFLFPPKPKDT LMISRTPEVTCVVVDVSHEDPEVKFNWYVDGVEVHNAKTKPR EEQYNSTYRVVSVLTVLHQDWLNGKEYKCKVSNKALPAPIEK TISKAKGQPREPQVYTLPPSREEMTKNQVSLTCLVKGFYPSD IAVEWESNGQPENNYKTTPPVLDSDGSFFLYSKLTVDKSRWQ QGNVFSCSVMHEALHNHYTQKSLSLSPGK |
| DNA Encoding Heavy Chain | 29 | CAGGTGCAGCTGGTGCAGTCAGGCGCCGAAGTGAAGAAACCC GGCGCTAGTGTGAAAGTCAGCTGTAAAGCTAGTGCCTACACC TTCACCTCTAGCTGGATGCAGTGGGTCAGACAGGCCCCAGGT CAGGGCCTGGAGTGGATGGGCGAGATCGACCCTAGCGATAAC TACGCTAACTATAATCAGAAGTTTCAGGGTAGAGTCACCCTG ACCGTGGACACTAGCACTAGCACCGCCTATATGGAACTGTCT AGCCTGAGATCAGAGGACACCGCCGTCTACTACTGCGCTAGT GGTAGCTACTTCTCTAACTTCTTCGACTACTGGGGTCAGGGC ACCCTGGTCACCGTGTCTAGCGCTAGCACTAAGGGCCCCTCC GTGTTCCCTCTGGCCCCTTCCAGCAAGTCTACCTCCGGCGGC ACAGCTGCTCTGGGCTGCCTGGTCAAGGACTACTTCCCTGAG CCTGTGACAGTGTCCTGGAACTCTGGCGCCCTGACCTCTGGC GTGCACACCTTCCCTGCCGTGCTGCAGTCCTCCGGCCTGTAC TCCCTGTCCTCCGTGGTCACAGTGCCTTCAAGCAGCCTGGGC ACCCAGACCTATATCTGCAACGTGAACCACAAGCCTTCCAAC ACCAAGGTGGACAAGCGGGTGGAGCCTAAGTCCTGCGACAAG ACCCACACCTGTCCTCCCTGCCCTGCTCCTGAAGCTGCTGGC GGCCCTTCTGTGTTCCTGTTCCCTCCAAAGCCCAAGGACACC CTGATGATCTCCCGGACCCCTGAAGTGACCTGCGTGGTGGTG GACGTGTCCCACGAGGATCCTGAAGTGAAGTTCAATTGGTAC GTGGACGGCGTGGAGGTGCACAACGCCAAGACCAAGCCTCGG GAGGAACAGTACAACTCCACCTACCGGGTGGTGTCCGTGCTG ACCGTGCTGCACCAGGACTGGCTGAACGGCAAAGAGTACAAG TGCAAAGTCTCCAACAAGGCCCTGCCTGCCCCTATCGAAAAG ACAATCTCCAAGGCCAAGGGCCAGCCTAGGGAACCCCAGGTG TACACCCTGCCACCCAGCCGGGAGGAAATGACCAAGAACCAG GTGTCCCTGACCTGTCTGGTCAAGGGCTTCTACCCTTCCGAT ATCGCCGTGGAGTGGGAGTCTAACGGCCAGCCTGAGAACAAC TACAAGACCACCCCTCCTGTGCTGGACTCCGACGGCTCCTTC TTCCTGTACTCCAAACTGACCGTGGACAAGTCCCGGTGGCAG CAGGGCAACGTGTTCTCCTGCTCCGTGATGCACGAGGCCCTG CACAACCACTACACCCAGAAGTCCCTGTCCCTGTCTCCCGGC AAG |

TABLE 1-continued

Examples of ANGPTL4 Antibodies, Fabs and ANGPTL4 Proteins

| Sequence Description | Sequence Identifier (SEQ ID NO.) | Amino acid or polynucleotide sequence |
|---|---|---|
| LCDR1 (Kabat) | 17 | KASQDIGSNLN |
| LCDR2 (Kabat) | 18 | AVSNRGP |
| LCDR3 (Kabat) | 19 | LQYASSPWT |
| LCDR1 (Chothia) | 20 | SQDIGSN |
| LCDR2 (Chothia) | 21 | AVS |
| LCDR3 (Chothia) | 22 | YASSPW |
| VL | 23 | EIVMTQSPATLSVSPGERATLSCKASQDIGSNLNWLQQKPGQ APRRLIYAVSNRGPGIPARFSGSRSGSEYTLTISSLQSEDFA VYYCLQYASSPWTFGQGTKVEIK |
| DNA Encoding VL | 30 | GAGATCGTGATGACTCAGTCACCCGCTACCCTGAGCGTCAGC CCTGGCGAGCGGGCTACACTGAGCTGTAAAGCCTCTCAGGAT ATCGGCTCTAACCTGAACTGGCTGCAGCAGAAGCCCGGTCAG GCCCCTAGACGGCTGATCTACGCCGTGTCTAATAGAGGCCCC GGAATCCCCGCTAGGTTTAGCGGCTCTAGGTCAGGTTCAGAG TACACCCTGACTATCTCTAGCCTGCAGTCAGAGGACTTCGCC GTCTACTACTGCCTGCAGTACGCCTCTAGCCCCTGGACCTTC GGTCAGGGCACTAAGGTCGAGATTAAG |
| Light Chain | 25 | EIVMTQSPATLSVSPGERATLSCKASQDIGSNLNWLQQKPGQ APRRLIYAVSNRGPGIPARFSGSRSGSEYTLTISSLQSEDFA VYYCLQYASSPWTFGQGTKVEIKRTVAAPSVFIFPPSDEQLK SGTASVVCLLNNFYPREAKVQWKVDNALQSGNSQESVTEQDS KDSTYSLSSTLTLSKADYEKHKVYACEVTHQGLSSPVTKSFN RGEC |
| DNA Encoding Light Chain | 31 | GAGATCGTGATGACTCAGTCACCCGCTACCCTGAGCGTCAGC CCTGGCGAGCGGGCTACACTGAGCTGTAAAGCCTCTCAGGAT ATCGGCTCTAACCTGAACTGGCTGCAGCAGAAGCCCGGTCAG GCCCCTAGACGGCTGATCTACGCCGTGTCTAATAGAGGCCCC GGAATCCCCGCTAGGTTTAGCGGCTCTAGGTCAGGTTCAGAG TACACCCTGACTATCTCTAGCCTGCAGTCAGAGGACTTCGCC GTCTACTACTGCCTGCAGTACGCCTCTAGCCCCTGGACCTTC GGTCAGGGCACTAAGGTCGAGATTAAGCGTACGGTGGCCGCT CCCAGCGTGTTCATCTTCCCCCCCAGCGACGAGCAGCTGAAG AGCGGCACCGCCAGCGTGGTGTGCCTGCTGAACAACTTCTAC CCCCGGGAGGCCAAGGTGCAGTGGAAGGTGGACAACGCCCTG CAGAGCGGCAACAGCCAGGAGAGCGTCACCGAGCAGGACAGC AAGGACTCCACCTACAGCCTGAGCAGCACCCTGACCCTGAGC AAGGCCGACTACGAGAAGCATAAGGTGTACGCCTGCGAGGTG ACCCACCAGGGCCTGTCCAGCCCCGTGACCAAGAGCTTCAAC AGGGGCGAGTGC |
| NEG278 | | |
| HCDR1 (Kabat) | 32 | SSWMQ |
| HCDR2 (Kabat) | 33 | EIDPSDNYANYNQKFQG |
| HCDR3 (Kabat) | 34 | GSYFSNFFDY |
| HCDR1 (Chothia) | 35 | AYTFTSS |
| HCDR2 (Chothia) | 36 | DPSDNY |
| HCDR3 (Chothia) | 37 | GSYFSNFFDY |
| VH | 38 | QVQLVQSGAEVKKPGASVKVSCKASAYTFTSSWMQWVRQAPG QGLEWMGEIDPSDNYANYNQKFQGRVTLTVDTSTSTAYMELS SLRSEDTAVYYCASGSYFSNFFDYWGQGTLVTVSS |
| DNA Encoding VH | 39 | CAGGTGCAGCTGGTGCAGTCTGGCGCCGAAGTGAAGAAACCA GGCGCCAGCGTGAAGGTGTCCTGCAAGGCCAGCGCCTACACC TTTACCAGCAGCTGGATGCAGTGGGTGCGCCAGGCTCCTGGA CAGGGGCCTGGAATGGATGGGCGAGATCGACCCCAGCGACAAC TACGCCAACTACAACCAGAAATTCCAGGGCAGAGTGACCCTG ACCGTGGACACCAGCACCTCCACCGCCTACATGGAACTGAGC |

TABLE 1-continued

Examples of ANGPTL4 Antibodies, Fabs and ANGPTL4 Proteins

| Sequence Description | Sequence Identifier (SEQ ID NO.) | Amino acid or polynucleotide sequence |
|---|---|---|
| | | AGCCTGCGGAGCGAGGACACCGCCGTGTACTATTGTGCCAGC GGCAGCTACTTCAGCAACTTCTTCGACTACGGGGCCAGGGC ACCCTCGTGACCGTGTCATCT |
| Heavy Chain | 40 | QVQLVQSGAEVKKPGASVKVSCKASAYTFTSSWMQWVRQAPG QGLEWMGEIDPSDNYANYNQKFQGRVTLTVDTSTSTAYMELS SLRSEDTAVYYCASGSYFSNFFDYWGQGTLVTVSSASTKGPS VFPLAPSSKSTSGGTAALGCLVKDYFPEPVTVSWNSGALTSG VHTFPAVLQSSGLYSLSSVVTVPSSSLGTQTYICNVNHKPSN TKVDKRVEPKSCDKTHTCPPCPAPELLGGPSVFLFPPKPKDT LMISRTPEVTCVVVDVSHEDPEVKFNWYVDGVEVHNAKTKPR EEQYNSTYRVVSVLTVLHQDWLNGKEYKCKVSNKALPAPIEK TISKAKGQPREPQVYTLPPSREEMTKNQVSLTCLVKGFYPSD IAVEWESNGQPENNYKTTPPVLDSDGSFFLYSKLTVDKSRWQ QGNVFSCSVMHEALHNHYTQKSLSLSPGK |
| DNA Encoding Heavy Chain | 41 | CAGGTGCAGCTGGTGCAGTCTGGCGCCGAAGTGAAGAAACCA GGCGCCAGCGTGAAGGTGTCCTGCAAGGCCAGCGCCTACACC TTTACCAGCAGCTGGATGCAGTGGGTGCGCCAGGCTCCTGGA CAGGGCCTGGAATGGATGGGCGAGATCGACCCCAGCGACAAC TACGCCAACTACAACCAGAAATTCCAGGGCAGAGTGACCCTG ACCGTGGACACCAGCACCTCCACCGCCTACATGGAACTGAGC AGCCTGCGGAGCGAGGACACCGCCGTGTACTATTGTGCCAGC GGCAGCTACTTCAGCAACTTCTTCGACTACGGGGCCAGGGC ACCCTCGTGACCGTGTCATCTGCTAGCACCAAGGGCCCCAGC GTGTTCCCCCTGGCCCCCAGCAGCAAGAGCACCAGCGGCGGC ACAGCCGCCCTGGGCTGCCTGGTGAAGGACTACTTCCCCGAG CCCGTGACCGTGTCCTGGAACAGCGGAGCCCTGACCTCCGGC GTGCACACCTTCCCCGCCGTGCTGCAGAGCAGCGGCCTGTAC AGCCTGTCCAGCGTGGTGACAGTGCCCAGCAGCAGCCTGGGC ACCCAGACCTACATCTGCAACGTGAACCACAAGCCCAGCAAC ACCAAGGTGGACAAGAGAGTGGAGCCCAAGAGCTGCGACAAG ACCCACACCTGCCCCCCCTGCCCAGCCCCAGAGCTGCTGGGC GGACCCTCCGTGTTCCTGTTCCCCCCCAAGCCCAAGGACACC CTGATGATCAGCAGGACCCCCGAGGTGACCTGCGTGGTGGTG GACGTGAGCCACGAGGACCCAGAGGTGAAGTTCAACTGGTAC GTGGACGGCGTGGAGGTGCACAACGCCAAGACCAAGCCCAGA GAGGAGCAGTACAACAGCACCTACAGGGTGGTGTCCGTGCTG ACCGTGCTGCACCAGGACTGGCTGAACGGCAAGGAATACAAG TGCAAGGTCTCCAACAAGGCCCTGCCAGCCCCCATCGAAAAG ACCATCAGCAAGGCCAAGGGCCAGCCACGGGAGCCCCAGGTG TACACCCTGCCCCCCTCCCGGGAGGAGATGACCAAGAACCAG GTGTCCCTGACCTGTCTGGTGAAGGGCTTCTACCCCAGCGAC ATCGCCGTGGAGTGGGAGAGCAACGGCCAGCCCGAGAACAAC TACAAGACCACCCCCCCAGTGCTGGACAGCGACGGCAGCTTC TTCCTGTACAGCAAGCTGACCGTGGACAAGTCCAGGTGGCAG CAGGGCAACGTGTTCAGCTGCAGCGTGATGCACGAGGCCCTG CACAACCACTACACCCAGAAGAGCCTGAGCCTGTCCCCCGGC AAG |
| LCDR1 (Kabat) | 42 | KASQDIGSNLN |
| LCDR2 (Kabat) | 43 | AASVREP |
| LCDR3 (Kabat) | 44 | LQYASSPWT |
| LCDR1 (Chothia) | 45 | SQDIGSN |
| LCDR2 (Chothia) | 46 | AAS |
| LCDR3 (Chothia) | 47 | YASSPW |
| VL | 48 | EIVMTQSPATLSVSPGERATLSCKASQDIGSNLNWLQQKPGQ APRRLIYAASVREPGIPARFSGSRSGSEYTLTISSLQSEDFA VYYCLQYASSPWTFGQGTKVEIK |
| DNA Encoding VL | 49 | GAGATCGTGATGACACAGAGCCCCGCCACCCTGTCCGTGTCT CCAGGCGAAAGAGCCACCCTGAGCTGCAAAGCCAGCCAGGAC ATCGGCAGCAACCTGAACTGGCTGCAGCAGAAACCAGGCCAG GCCCCCAGAAGGCTGATCTACGCTGCTTCCGTCCGTGAGCCT GGCATCCCCGCCAGATTTTCCGGCAGCAGATCCGGCAGCGAG TACACCCTGACCATCAGCAGCCTGCAGAGCGAGGACTTCGCC GTGTACTACTGCCTGCAGTACGCCAGCAGCCCCTGGACATTT GGCCAGGGCACCAAGGTGGAAATCAAG |

TABLE 1-continued

Examples of ANGPTL4 Antibodies, Fabs and ANGPTL4 Proteins

| Sequence Description | Sequence Identifier (SEQ ID NO.) | Amino acid or polynucleotide sequence |
|---|---|---|
| Light Chain | 50 | EIVMTQSPATLSVSPGERATLSCKASQDIGSNLNWLQQKPGQ APRRLIYAASVREPGIPARFSGSRSGSEYTLTISSLQSEDFA VYYCLQYASSPWTFGQGTKVEIKRTVAAPSVFIFPPSDEQLK SGTASVVCLLNNFYPREAKVQWKVDNALQSGNSQESVTEQDS KDSTYSLSSTLTLSKADYEKHKVYACEVTHQGLSSPVTKSFN RGEC |
| DNA Encoding Light Chain | 51 | GAGATCGTGATGACACAGAGCCCCGCCACCCTGTCCGTGTCT CCAGGCGAAAGAGCCACCCTGAGCTGCAAAGCCAGCCAGGAC ATCGGCAGCAACCTGAACTGGCTGCAGCAGAAACCAGGCCAG GCCCCCAGAAGGCTGATCTACGCTGCTTCCGTCCGTGAGCCT GGCATCCCCGCCAGATTTTCCGGCAGCAGATCCGGCAGCGAG TACACCCTGACCATCAGCAGCCTGCAGAGCGAGGACTTCGCC GTGTACTACTGCCTGCAGTACGCCAGCAGCCCCTGGACATTT GGCCAGGGCACCAAGGTGGAAATCAAGCGTACGGTGGCCGCT CCCAGCGTGTTCATCTTCCCCCCCAGCGACGAGCAGCTGAAG AGCGGCACCGCCAGCGTGGTGTGCCTGCTGAACAACTTCTAC CCCCGGGAGGCCAAGGTGCAGTGGAAGGTGGACAACGCCCTG CAGAGCGGCAACAGCCAGGAGAGCGTCACCGAGCAGGACAGC AAGGACTCCACCTACAGCCTGAGCAGCACCCTGACCCTGAGC AAGGCCGACTACGAGAAGCATAAGGTGTACGCCTGCGAGGTG ACCCACCAGGGCCTGTCCAGCCCCGTGACCAAGAGCTTCAAC AGGGGCGAGTGC |
| NEG310 | | |
| HCDR1 (Kabat) | 52 | SYTMH |
| HCDR2 (Kabat) | 53 | YINPSSGYTKYNQKFQG |
| HCDR3 (Kabat) | 54 | GWLLLAMDY |
| HCDR1 (Chothia) | 55 | GYTFTSY |
| HCDR2 (Chothia) | 56 | NPSSGY |
| HCDR3 (Chothia) | 57 | GWLLLAMDY |
| VH | 58 | QVQLVQSGAEVKKPGASVKVSCKASGYTFTSYTMHWVRQAPG QGLEWMGYINPSSGYTKYNQKFQGRVTMTADKSTSTAYMELS SLRSEDTAVYYCAEGWLLLAMDYWGQGTLVTVSS |
| DNA Encoding VH | 59 | CAGGTGCAGCTGGTGCAGTCTGGCGCCGAAGTGAAGAAACCA GGCGCCAGCGTGAAGGTGTCCTGCAAGGCCAGCGGCTACACC TTTACCAGCTACACCATGCACTGGGTGCGCCAGGCTCCAGGC CAGGGACTGGAATGGATGGGCTACATCAACCCCAGCAGCGGC TATACCAAGTACAACCAGAAATTCCAGGGCCGCGTGACCATG ACCGCCGACAAGAGCACAAGCACCGCCTACATGGAACTGAGC AGCCTGCGGAGCGAGGACACCGCCGTGTACTATTGTGCCGAG GGCTGGCTGCTGCTGGCCATGGATTATTGGGGCCAGGGCACC CTCGTGACCGTGTCTAGT |
| Heavy Chain | 60 | QVQLVQSGAEVKKPGASVKVSCKASGYTFTSYTMHWVRQAPG QGLEWMGYINPSSGYTKYNQKFQGRVTMTADKSTSTAYMELS SLRSEDTAVYYCAEGWLLLAMDYWGQGTLVTVSSASTKGPSV FPLAPSSKSTSGGTAALGCLVKDYFPEPVTVSWNSGALTSGV HTFPAVLQSSGLYSLSSVVTVPSSSLGTQTYICNVNHKPSNT KVDKRVEPKSCDKTHTCPPCPAPELLGGPSVFLFPPKPKDTL MISRTPEVTCVVVDVSHEDPEVKFNWYVDGVEVHNAKTKPRE EQYNSTYRVVSVLTVLHQDWLNGKEYKCKVSNKALPAPIEKT ISKAKGQPREPQVYTLPPSREEMTKNQVSLTCLVKGFYPSDI AVEWESNGQPENNYKTTPPVLDSDGSFFLYSKLTVDKSRWQQ GNVFSCSVMHEALHNHYTQKSLSLSPGK |
| DNA Encoding Heavy Chain | 61 | CAGGTGCAGCTGGTGCAGTCTGGCGCCGAAGTGAAGAAACCA GGCGCCAGCGTGAAGGTGTCCTGCAAGGCCAGCGGCTACACC TTTACCAGCTACACCATGCACTGGGTGCGCCAGGCTCCAGGC CAGGGACTGGAATGGATGGGCTACATCAACCCCAGCAGCGGC TATACCAAGTACAACCAGAAATTCCAGGGCCGCGTGACCATG ACCGCCGACAAGAGCACAAGCACCGCCTACATGGAACTGAGC AGCCTGCGGAGCGAGGACACCGCCGTGTACTATTGTGCCGAG GGCTGGCTGCTGCTGGCCATGGATTATTGGGGCCAGGGCACC CTCGTGACCGTGTCTAGTGCTAGCACCAAGGGCCCCAGCGTG |

TABLE 1-continued

Examples of ANGPTL4 Antibodies, Fabs and ANGPTL4 Proteins

| Sequence Description | Sequence Identifier (SEQ ID NO.) | Amino acid or polynucleotide sequence |
|---|---|---|
| | | TTCCCCCTGGCCCCCAGCAGCAAGAGCACCAGCGGCGGCACA GCCGCCCTGGGCTGCTGGTGAAGGACTACTTCCCCGAGCCC GTGACCGTGTCCTGGAACAGCGGAGCCCTGACCTCCGGCGTG CACACCTTCCCCGCCGTGCTGCAGAGCAGCGGCCTGTACAGC CTGTCCAGCGTGGTGACAGTGCCCAGCAGCAGCCTGGGCACC CAGACCTACATCTGCAACGTGAACCACAAGCCCAGCAACACC AAGGTGGACAAGAGAGTGGAGCCCAAGAGCTGCGACAAGACC CACACCTGCCCCCCCTGCCCAGCCCCAGAGCTGCTGGGCGGA CCCTCCGTGTTCCTGTTCCCCCCCAAGCCCAAGGACACCCTG ATGATCAGCAGGACCCCCGAGGTGACCTGCGTGGTGGTGGAC GTGAGCCACGAGGACCCAGAGGTGAAGTTCAACTGGTACGTG GACGGCGTGGAGGTGCACAACGCCAAGACCAAGCCCAGAGAG GAGCAGTACAACAGCACCTACAGGGTGGTGTCCGTGCTGACC GTGCTGCACCAGGACTGGCTGAACGGCAAGGAATACAAGTGC AAGGTCTCCAACAAGGCCCTGCCAGCCCCCATCGAAAAGACC ATCAGCAAGGCCAAGGGCCAGCCACGGGAGCCCCAGGTGTAC ACCCTGCCCCCCTCCCGGGAGGAGATGACCAAGAACCAGGTG TCCCTGACCTGTCTGGTGAAGGGCTTCTACCCCAGCGACATC GCCGTGGAGTGGGAGAGCAACGGCCAGCCCGAGAACAACTAC AAGACCACCCCCCCAGTGCTGGACAGCGACGGCAGCTTCTTC CTGTACAGCAAGCTGACCGTGGACAAGTCCAGGTGGCAGCAG GGCAACGTGTTCAGCTGCAGCGTGATGCACGAGGCCCTGCAC AACCACTACACCCAGAAGAGCCTGAGCCTGTCCCCCGGCAAG |
| LCDR1 (Kabat) | 62 | RSSTGAVTTSNYAI |
| LCDR2 (Kabat) | 63 | GTNNRAP |
| LCDR3 (Kabat) | 64 | ALWYSDHWV |
| LCDR1 (Chothia) | 65 | STGAVTTSNY |
| LCDR2 (Chothia) | 66 | GTN |
| LCDR3 (Chothia) | 67 | WYSDHW |
| VL | 68 | EAVVTQSPATLSLSPGERATLSCRSSTGAVTTSNYAIWVQEK PGQAPRGLIGGTNNRAPGIPARFSGSLSGDDATLTISSLQPE DFAVYFCALWYSDHWVFGQGTKVEIK |
| DNA Encoding VL | 69 | GAAGCCGTCGTGACACAGAGCCCTGCCACCCTGTCACTGAGC CCTGGCGAAAGAGCCACCCTGAGCTGCAGATCTAGCACCGGC GCTGTGACCACCAGCAACTACGCCATCTGGGTGCAGGAAAAG CCCGGCCAGGCTCCCAGAGGACTGATCGGCGGCACCAACAAT AGAGCCCCTGGCATCCCCGCCAGATTCAGCGGATCTCTGTCT GGCGACGACGCCACACTGACCATCAGCAGCCTGCAGCCCGAG GACTTCGCCGTGTACTTCTGCGCCCTGTGGTACAGCGACCAC TGGGTGTTCGGCCAGGGCACCAAGGTGGAAATCAAG |
| Light Chain | 70 | EAVVTQSPATLSLSPGERATLSCRSSTGAVTTSNYAIWVQEK PGQAPRGLIGGTNNRAPGIPARFSGSLSGDDATLTISSLQPE DFAVYFCALWYSDHWVFGQGTKVEIKRTVAAPSVFIFPPSDE QLKSGTASVVCLLNNFYPREAKVQWKVDNALQSGNSQESVTE QDSKDSTYSLSSTLTLSKADYEKHKVYACEVTHQGLSSPVTK SFNRGEC |
| DNA Encoding Light Chain | 71 | GAAGCCGTCGTGACACAGAGCCCTGCCACCCTGTCACTGAGC CCTGGCGAAAGAGCCACCCTGAGCTGCAGATCTAGCACCGGC GCTGTGACCACCAGCAACTACGCCATCTGGGTGCAGGAAAAG CCCGGCCAGGCTCCCAGAGGACTGATCGGCGGCACCAACAAT AGAGCCCCTGGCATCCCCGCCAGATTCAGCGGATCTCTGTCT GGCGACGACGCCACACTGACCATCAGCAGCCTGCAGCCCGAG GACTTCGCCGTGTACTTCTGCGCCCTGTGGTACAGCGACCAC TGGGTGTTCGGCCAGGGCACCAAGGTGGAAATCAAGCGTACG GTGGCCGCTCCCAGCGTGTTCATCTTCCCCCCCAGCGACGAG CAGCTGAAGAGCGGCACCGCCAGCGTGGTGTGCCTGCTGAAC AACTTCTACCCCGGGAGGCCAAGGTGCAGTGGAAGGTGGAC AACGCCCTGCAGAGCGGCAACAGCCAGGAGAGCGTCACCGAG CAGGACAGCAAGGACTCCACCTACAGCCTGAGCAGCACCCTG ACCCTGAGCAAGGCCGACTACGAGAAGCATAAGGTGTACGCC TGCGAGGTGACCCACCAGGGCCTGTCCAGCCCCGTGACCAAG AGCTTCAACAGGGGCGAGTGC |

TABLE 1-continued

Examples of ANGPTL4 Antibodies, Fabs and ANGPTL4 Proteins

| Sequence Description | Sequence Identifier (SEQ ID NO.) | Amino acid or polynucleotide sequence |
|---|---|---|
| NEG313 | | |
| HCDR1 (Kabat) | 72 | NYWIT |
| HCDR2 (Kabat) | 73 | DFYPGGGSTNYNAKLQG |
| HCDR3 (Kabat) | 74 | SPPQVAPFDY |
| HCDR1 (Chothia) | 75 | GYTFNNY |
| HCDR2 (Chothia) | 76 | YPGGGS |
| HCDR3 (Chothia) | 77 | SPPQVAPFDY |
| VH | 78 | QVQLVQSGAEVKKPGASVKVSCKASGYTFNNYWITWVRQAPG QGLEWMGDFYPGGGSTNYNAKLQGRVTLTVDTSTSTAYMELR SLRSDDTAVYYCARSPPQVAPFDYWGQGTLVTVSS |
| DNA encoding VH | 79 | CAGGTGCAGCTGGTGCAGTCTGGCGCCGAAGTGAAGAAACCA GGCGCCAGCGTGAAGGTGTCCTGCAAGGCCAGCGGCTACACC TTTAACAACTACTGGATCACCTGGGTGCGCCAGGCCCCTGGA CAGGGACTGGAATGGATGGGCGACTTCTACCCTGGCGGCGGC AGCACCAACTACAACGCCAAGCTGCAGGGCAGAGTGACCCTG ACCGTGGACACCAGCACCTCCACCGCCTACATGGAACTGCGG AGCCTGAGAAGCGACGACACCGCCGTGTATTACTGCGCTAGA AGCCCTCCTCAGGTGGCCCCCTTCGATTATTGGGGCCAGGGC ACACTCGTGACCGTGTCCTCT |
| Heavy Chain | 80 | QVQLVQSGAEVKKPGASVKVSCKASGYTFNNYWITWVRQAPG QGLEWMGDFYPGGGSTNYNAKLQGRVTLTVDTSTSTAYMELR SLRSDDTAVYYCARSPPQVAPFDYWGQGTLVTVSSASTKGPS VFPLAPSSKSTSGGTAALGCLVKDYFPEPVTVSWNSGALTSG VHTFPAVLQSSGLYSLSSVVTVPSSSLGTQTYICNVNHKPSN TKVDKRVEPKSCDKTHTCPPCPAPELLGGPSVFLFPPKPKDT LMISRTPEVTCVVVDVSHEDPEVKFNWYVDGVEVHNAKTKPR EEQYNSTYRVVSVLTVLHQDWLNGKEYKCKVSNKALPAPIEK TISKAKGQPREPQVYTLPPSREEMTKNQVSLTCLVKGFYPSD IAVEWESNGQPENNYKTTPPVLDSDGSFFLYSKLTVDKSRWQ QGNVFSCSVMHEALHNHYTQKSLSLSPGK |
| DNA Encoding Heavy Chain | 81 | CAGGTGCAGCTGGTGCAGTCTGGCGCCGAAGTGAAGAAACCA GGCGCCAGCGTGAAGGTGTCCTGCAAGGCCAGCGGCTACACC TTTAACAACTACTGGATCACCTGGGTGCGCCAGGCCCCTGGA CAGGGACTGGAATGGATGGGCGACTTCTACCCTGGCGGCGGC AGCACCAACTACAACGCCAAGCTGCAGGGCAGAGTGACCCTG ACCGTGGACACCAGCACCTCCACCGCCTACATGGAACTGCGG AGCCTGAGAAGCGACGACACCGCCGTGTATTACTGCGCTAGA AGCCCTCCTCAGGTGGCCCCCTTCGATTATTGGGGCCAGGGC ACACTCGTGACCGTGTCCTCTGCTAGCACCAAGGGCCCCAGC GTGTTCCCCCTGGCCCCCAGCAGCAAGAGCACCAGCGGCGGC ACAGCCGCCCTGGGCTGCCTGGTGAAGGACTACTTCCCCGAG CCCGTGACCGTGTCCTGGAACAGCGGAGCCCTGACCTCCGGC GTGCACACCTTCCCCGCCGTGCTGCAGAGCAGCGGCCTGTAC AGCCTGTCCAGCGTGGTGACAGTGCCCAGCAGCAGCCTGGGC ACCCAGACCTACATCTGCAACGTGAACCACAAGCCCAGCAAC ACCAAGGTGGACAAGAGAGTGGAGCCCAAGAGCTGCGACAAG ACCCACACCTGCCCCCCCTGCCCAGCCCCAGAGCTGCTGGGC GGACCCTCCGTGTTCCTGTTCCCCCCCAAGCCCAAGGACACC CTGATGATCAGCAGGACCCCCGAGGTGACCTGCGTGGTGGTG GACGTGAGCCACGAGGACCCAGAGGTGAAGTTCAACTGGTAC GTGGACGGCGTGGAGGTGCACAACGCCAAGACCAAGCCCAGA GAGGAGCAGTACAACAGCACCTACAGGGTGGTGTCCGTGCTG ACCGTGCTGCACCAGGACTGGCTGAACGGCAAGGAATACAAG TGCAAGGTCTCCAACAAGGCCCTGCCAGCCCCATCGAAAAG ACCATCAGCAAGGCCAAGGGCCAGCCACGGGAGCCCCAGGTG TACACCCTGCCCCCCTCCCGGGAGGAGATGACCAAGAACCAG GTGTCCCTGACCTGTCTGGTGAAGGGCTTCTACCCCAGCGAC ATCGCCGTGGAGTGGGAGAGCAACGGCCAGCCCGAGAACAAC TACAAGACCACCCCCCCAGTGCTGGACAGCGACGGCAGCTTC TTCCTGTACAGCAAGCTGACCGTGGACAAGTCCAGGTGGCAG CAGGGCAACGTGTTCAGCTGCAGCGTGATGCACGAGGCCCTG CACAACCACTACACCCAGAAGAGCCTGAGCCTGTCCCCCGGC AAG |

TABLE 1-continued

Examples of ANGPTL4 Antibodies, Fabs and ANGPTL4 Proteins

| Sequence Description | Sequence Identifier (SEQ ID NO.) | Amino acid or polynucleotide sequence |
| --- | --- | --- |
| LCDR1 (Kabat) | 82 | QASDYIYHWLG |
| LCDR2 (Kabat) | 83 | GASGLET |
| LCDR3 (Kabat) | 84 | QQYWSTPWT |
| LCDR1 (Chothia) | 85 | SDYIYHW |
| LCDR2 (Chothia) | 86 | GAS |
| LCDR3 (Chothia) | 87 | YWSTPW |
| VL | 88 | DIQMTQSPSSLSASVGDRVTITCQASDYIYHWLGWYQQKPGK APKLLISGASGLETGVPSRFSGSGSGKDYTFTISSLQPEDIA TYYCQQYWSTPWTFGQGTKLEIK |
| DNA Encoding VL | 89 | GACATCCAGATGACCCAGAGCCCCAGCAGCCTGTCTGCCAGC GTGGGCGACAGGGTGACCATCACCTGTCAGGCCAGCGACTAC ATCTACCACTGGCTGGGCTGGTATCAGCAGAAGCCCGGCAAG GCCCCCAAGCTGCTGATTAGCGGAGCCTCCGGTCTGGAAACC GGCGTGCCAAGCAGATTTTCCGGCAGCGGCTCCGGCAAGGAC TACACCTTCACCATCAGCTCCCTGCAGCCCGAGGATATCGCC ACCTACTACTGCCAGCAGTACTGGTCCACCCCCTGGACCTTT GGCCAGGGCACCAAGCTGGAAATCAAG |
| Light Chain | 90 | DIQMTQSPSSLSASVGDRVTITCQASDYIYHWLGWYQQKPGK APKLLISGASGLETGVPSRFSGSGSGKDYTFTISSLQPEDIA TYYCQQYWSTPWTFGQGTKLEIKRTVAAPSVFIFPPSDEQLK SGTASVVCLLNNFYPREAKVQWKVDNALQSGNSQESVTEQDS KDSTYSLSSTLTLSKADYEKHKVYACEVTHQGLSSPVTKSFN RGEC |
| DNA Encoding Light Chain | 91 | GACATCCAGATGACCCAGAGCCCCAGCAGCCTGTCTGCCAGC GTGGGCGACAGGGTGACCATCACCTGTCAGGCCAGCGACTAC ATCTACCACTGGCTGGGCTGGTATCAGCAGAAGCCCGGCAAG GCCCCCAAGCTGCTGATTAGCGGAGCCTCCGGTCTGGAAACC GGCGTGCCAAGCAGATTTTCCGGCAGCGGCTCCGGCAAGGAC TACACCTTCACCATCAGCTCCCTGCAGCCCGAGGATATCGCC ACCTACTACTGCCAGCAGTACTGGTCCACCCCCTGGACCTTT GGCCAGGGCACCAAGCTGGAAATCAAGCGTACGGTGGCCGCT CCCAGCGTGTTCATCTTCCCCCCCAGCGACGAGCAGCTGAAG AGCGGCACCGCCAGCGTGGTGTGCCTGCTGAACAACTTCTAC CCCCGGGAGGCCAAGGTGCAGTGGAAGGTGGACAACGCCCTG CAGAGCGGCAACAGCCAGGAGAGCGTCACCGAGCAGGACAGC AAGGACTCCACCTACAGCCTGAGCAGCACCCTGACCCTGAGC AAGGCCGACTACGAGAAGCATAAGGTGTACGCCTGCGAGGTG ACCCACCAGGGCCTGTCCAGCCCCGTGACCAAGAGCTTCAAC AGGGGCGAGTGC |
| NEG315 | | |
| HCDR1 (Kabat) | 92 | NYWIT |
| HCDR2 (Kabat) | 93 | DFYPGGGNTNYNAKLQG |
| HCDR3 (Kabat) | 94 | SPPQVAPFDY |
| HCDR1 (Chothia) | 95 | GYTFTNY |
| HCDR2 (Chothia) | 96 | YPGGGN |
| HCDR3 (Chothia) | 97 | SPPQVAPFDY |
| VH | 98 | QVQLVQSGAEVKKPGASVKVSCKASGYTFTNYWITWVRQAPG QGLEWMGDFYPGGGNTNYNAKLQGRVTLTVDTSTSTAYMELR SLRSDDTAVYYCARSPPQVAPFDYWGQGTLVTVSS |
| DNA Encoding VH | 99 | CAGGTGCAGCTGGTGCAGTCTGGCGCCGAAGTGAAGAAACCA GGCGCCAGCGTGAAGGTGTCCTGCAAGGCCAGCGGCTACACC TTTACCAACTACTGGATCACCTGGGTGCGCCAGGCCCCTGGA CAGGGACTGGAATGGATGGGCGACTTCTACCCTGGCGGCGGC AACACCAACTACAACGCCAAGCTGCAGGGCAGAGTGACCCTG ACCGTGGACACCAGCACCTCCACCGCCTACATGGAACTGCGG |

TABLE 1-continued

Examples of ANGPTL4 Antibodies, Fabs and ANGPTL4 Proteins

| Sequence Description | Sequence Identifier (SEQ ID NO.) | Amino acid or polynucleotide sequence |
|---|---|---|
| | | AGCCTGAGAAGCGACGACACCGCCGTGTATTACTGCGCTAGA<br>AGCCCTCCTCAGGTGGCCCCCTTCGATTATTGGGGCCAGGGC<br>ACACTCGTGACCGTGTCCTCT |
| Heavy Chain | 100 | QVQLVQSGAEVKKPGASVKVSCKASGYTFTNYWITWVRQAPG<br>QGLEWMGDFYPGGGNTNYNAKLQGRVTLTVDTSTSTAYMELR<br>SLRSDDTAVYYCARSPPQVAPFDYWGQGTLVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKRVEPKSCDKTHTCPPCPAPELLGGPSVFLFPPKPKDT<br>LMISRTPEVTCVVVDVSHEDPEVKFNWYVDGVEVHNAKTKPR<br>EEQYNSTYRVVSVLTVLHQDWLNGKEYKCKVSNKALPAPIEK<br>TISKAKGQPREPQVYTLPPSREEMTKNQVSLTCLVKGFYPSD<br>IAVEWESNGQPENNYKTTPPVLDSDGSFFLYSKLTVDKSRWQ<br>QGNVFSCSVMHEALHNHYTQKSLSLSPGK |
| DNA Encoding Heavy Chain | 101 | CAGGTGCAGCTGGTGCAGTCTGGCGCCGAAGTGAAGAAACCA<br>GGCGCCAGCGTGAAGGTGTCCTGCAAGGCCAGCGGCTACACC<br>TTTACCAACTACTGGATCACCTGGGTGCGCCAGGCCCCTGGA<br>CAGGGACTGGAATGGATGGGCGACTTCTACCCTGGCGGCGGC<br>AACACCAACTACAACGCCAAGCTGCAGGGCAGAGTGACCCTG<br>ACCGTGGACACCAGCACCTCCACCGCCTACATGGAACTGCGG<br>AGCCTGAGAAGCGACGACACCGCCGTGTATTACTGCGCTAGA<br>AGCCCTCCTCAGGTGGCCCCCTTCGATTATTGGGGCCAGGGC<br>ACACTCGTGACCGTGTCCTCTGCTAGCACCAAGGGCCCCAGC<br>GTGTTCCCCCTGGCCCCCAGCAGCAAGAGCACCAGCGGCGGC<br>ACAGCCGCCCTGGGCTGCCTGGTGAAGGACTACTTCCCCGAG<br>CCCGTGACCGTGTCCTGGAACAGCGGAGCCCTGACCTCCGGC<br>GTGCACACCTTCCCCGCCGTGCTGCAGAGCAGCGGCCTGTAC<br>AGCCTGTCCAGCGTGGTGACAGTGCCCAGCAGCAGCCTGGGC<br>ACCCAGACCTACATCTGCAACGTGAACCACAAGCCCAGCAAC<br>ACCAAGGTGGACAAGAGAGTGGAGCCCAAGAGCTGCGACAAG<br>ACCCACACCTGCCCCCCCTGCCCAGCCCCAGAGCTGCTGGGC<br>GGACCCTCCGTGTTCCTGTTCCCCCCCAAGCCCAAGGACACC<br>CTGATGATCAGCAGGACCCCCGAGGTGACCTGCGTGGTGGTG<br>GACGTGAGCCACGAGGACCCAGAGGTGAAGTTCAACTGGTAC<br>GTGGACGGCGTGGAGGTGCACAACGCCAAGACCAAGCCCAGA<br>GAGGAGCAGTACAACAGCACCTACAGGGTGGTGTCCGTGCTG<br>ACCGTGCTGCACCAGGACTGGCTGAACGGCAAGGAATACAAG<br>TGCAAGGTCTCCAACAAGGCCCTGCCAGCCCCCATCGAAAAG<br>ACCATCAGCAAGGCCAAGGGCCAGCCACGGGAGCCCCAGGTG<br>TACACCCTGCCCCCCTCCCGGGAGGAGATGACCAAGAACCAG<br>GTGTCCCTGACCTGTCTGGTGAAGGGCTTCTACCCCAGCGAC<br>ATCGCCGTGGAGTGGGAGAGCAACGGCCAGCCCGAGAACAAC<br>TACAAGACCACCCCCCCAGTGCTGGACAGCGACGGCAGCTTC<br>TTCCTGTACAGCAAGCTGACCGTGGACAAGTCCAGGTGGCAG<br>CAGGGCAACGTGTTCAGCTGCAGCGTGATGCACGAGGCCCTG<br>CACAACCACTACACCCAGAAGAGCCTGAGCCTGTCCCCCGGC<br>AAG |
| LCDR1 (Kabat) | 102 | QASEYIYNWLG |
| LCDR2 (Kabat) | 103 | GASGLET |
| LCDR3 (Kabat) | 104 | QQYWSTPWT |
| LCDR1 (Chothia) | 105 | SEYIYNW |
| LCDR2 (Chothia) | 106 | GAS |
| LCDR3 (Chothia) | 107 | YWSTPW |
| VL | 108 | DIQMTQSPSSLSASVGDRVTITCQASEYIYNWLGWYQQKPGK<br>APKLLISGASGLETGVPSRFSGSGSGKDYTFTISSLQPEDIA<br>TYYCQQYWSTPWTFGQGTKLEIK |
| DNA Encoding VL | 109 | GACATCCAGATGACCCAGAGCCCCAGCAGCCTGTCTGCCAGC<br>GTGGGCGACAGGGTGACCATCACCTGTCAGGCCAGCGAATAC<br>ATCTACAACTGGCTGGGCTGGTATCAGCAGAAGCCCGGCAAG<br>GCCCCCAAGCTGCTGATTAGCGGAGCCTCCGGTCTGGAAACC<br>GGCGTGCCAAGCAGATTTTCCGGCAGCGGCTCCGGCAAGGAC<br>TACACCTTCACCATCAGCTCCCTGCAGCCCGAGGATATCGCC<br>ACCTACTACTGCCAGCAGTACTGGTCCACCCCCTGGACCTTT<br>GGCCAGGGCACCAAGCTGGAAATCAAG |

TABLE 1-continued

Examples of ANGPTL4 Antibodies, Fabs and ANGPTL4 Proteins

| Sequence Description | Sequence Identifier (SEQ ID NO.) | Amino acid or polynucleotide sequence |
|---|---|---|
| Light Chain | 110 | DIQMTQSPSSLSASVGDRVTITCQASEYIYNWLGWYQQKPGK APKLLISGASGLETGVPSRFSGSGSGKDYTFTISSLQPEDIA TYYCQQYWSTPWTFGQGTKLEIKRTVAAPSVFIFPPSDEQLK SGTASVVCLLNNFYPREAKVQWKVDNALQSGNSQESVTEQDS KDSTYSLSSTLTLSKADYEKHKVYACEVTHQGLSSPVTKSFN RGEC |
| DNA Encoding Light Chain | 111 | GACATCCAGATGACCCAGAGCCCCAGCAGCCTGTCTGCCAGC GTGGGCGACAGGGTGACCATCACCTGTCAGGCCAGCGAATAC ATCTACAACTGGCTGGGCTGGTATCAGCAGAAGCCCGGCAAG GCCCCCAAGCTGCTGATTAGCGGAGCCTCCGGTCTGGAAACC GGCGTGCCAAGCAGATTTTCCGGCAGCGGCTCCGGCAAGGAC TACACCTTCACCATCAGCTCCCTGCAGCCCGAGGATATCGCC ACCTACTACTGCCAGCAGTACTGGTCCACCCCCTGGACCTTT GGCCAGGGCACCAAGCTGGAAATCAAGCGTACGGTGGCCGCT CCCAGCGTGTTCATCTTCCCCCCCAGCGACGAGCAGCTGAAG AGCGGCACCGCCAGCGTGGTGTGCCTGCTGAACAACTTCTAC CCCCGGGAGGCCAAGGTGCAGTGGAAGGTGGACAACGCCCTG CAGAGCGGCAACAGCCAGGAGAGCGTCACCGAGCAGGACAGC AAGGACTCCACCTACAGCCTGAGCAGCACCCTGACCCTGAGC AAGGCCGACTACGAGAAGCATAAGGTGTACGCCTGCGAGGTG ACCCACCAGGGCCTGTCCAGCCCCGTGACCAAGAGCTTCAAC AGGGGCGAGTGC |

NEG318

| HCDR1 (Kabat) | 112 | SFWIT |
| HCDR2 (Kabat) | 113 | DIYPGGATTNYNEKLQG |
| HCDR3 (Kabat) | 114 | SPPQVGPFDY |
| HCDR1 (Chothia) | 115 | GYTFTSF |
| HCDR2 (Chothia) | 116 | YPGGAT |
| HCDR3 (Chothia) | 117 | SPPQVGPFDY |
| VH | 118 | QVQLVQSGAEVKKPGASVKVSCKASGYTFTSFWITWVRQAPG QGLEWMGDIYPGGATTNYNEKLQGRVTLTVDTSTSTAYMELR SLRSDDTAVYYCARSPPQVGPFDYWGQGTLVTVSS |
| DNA Encoding VH | 119 | CAGGTGCAGCTGGTGCAGTCTGGCGCCGAAGTGAAGAAACCA GGCGCCAGCGTGAAGGTGTCCTGCAAGGCCAGCGGCTATACC TTCACCAGCTTTTGGATCACCTGGGTGCGCCAGGCCCCTGGA CAGGGACTGGAATGGATGGGCGACATCTACCCTGGCGGCGCC ACCACCAACTACAACGAGAAGCTGCAGGGCAGAGTGACCCTG ACCGTGGACACCAGCACCTCCACCGCCTACATGGAACTGCGG AGCCTGAGAAGCGACGACACCGCCGTGTACTACTGCGCTAGA AGCCCTCCTCAGGTGGGCCCCTTCGATTATTGGGGCCAGGGC ACACTCGTGACCGTGTCCTCT |
| Heavy Chain | 120 | QVQLVQSGAEVKKPGASVKVSCKASGYTFTSFWITWVRQAPG QGLEWMGDIYPGGATTNYNEKLQGRVTLTVDTSTSTAYMELR SLRSDDTAVYYCARSPPQVGPFDYWGQGTLVTVSSASTKGPS VFPLAPSSKSTSGGTAALGCLVKDYFPEPVTVSWNSGALTSG VHTFPAVLQSSGLYSLSSVVTVPSSSLGTQTYICNVNHKPSN TKVDKRVEPKSCDKTHTCPPCPAPELLGGPSVFLFPPKPKDT LMISRTPEVTCVVVDVSHEDPEVKFNWYVDGVEVHNAKTKPR EEQYNSTYRVVSVLTVLHQDWLNGKEYKCKVSNKALPAPIEK TISKAKGQPREPQVYTLPPSREEMTKNQVSLTCLVKGFYPSD IAVEWESNGQPENNYKTTPPVLDSDGSFFLYSKLTVDKSRWQ QGNVFSCSVMHEALHNHYTQKSLSLSPGK |
| DNA Encoding Heavy Chain | 121 | CAGGTGCAGCTGGTGCAGTCTGGCGCCGAAGTGAAGAAACCA GGCGCCAGCGTGAAGGTGTCCTGCAAGGCCAGCGGCTATACC TTCACCAGCTTTTGGATCACCTGGGTGCGCCAGGCCCCTGGA CAGGGACTGGAATGGATGGGCGACATCTACCCTGGCGGCGCC ACCACCAACTACAACGAGAAGCTGCAGGGCAGAGTGACCCTG ACCGTGGACACCAGCACCTCCACCGCCTACATGGAACTGCGG AGCCTGAGAAGCGACGACACCGCCGTGTACTACTGCGCTAGA AGCCCTCCTCAGGTGGGCCCCTTCGATTATTGGGGCCAGGGC ACACTCGTGACCGTGTCCTCTGCTAGCACCAAGGGCCCCAGC |

TABLE 1-continued

Examples of ANGPTL4 Antibodies, Fabs and ANGPTL4 Proteins

| Sequence Description | Sequence Identifier (SEQ ID NO.) | Amino acid or polynucleotide sequence |
|---|---|---|
| | | GTGTTCCCCCTGGCCCCCAGCAGCAAGAGCACCAGCGGCGGC ACAGCCGCCCTGGGCTGCCTGGTGAAGGACTACTTCCCCGAG CCCGTGACCGTGTCCTGGAACAGCGGAGCCCTGACCTCCGGC GTGCACACCTTCCCCGCCGTGCTGCAGAGCAGCGGCCTGTAC AGCCTGTCCAGCGTGGTGACAGTGCCCAGCAGCAGCCTGGGC ACCCAGACCTACATCTGCAACGTGAACCACAAGCCCAGCAAC ACCAAGGTGGACAAGAGAGTGGAGCCCAAGAGCTGCGACAAG ACCCACACCTGCCCCCCCTGCCCAGCCCCAGAGCTGCTGGGC GGACCCTCCGTGTTCCTGTTCCCCCCCAAGCCCAAGGACACC CTGATGATCAGCAGGACCCCCGAGGTGACCTGCGTGGTGGTG GACGTGAGCCACGAGGACCCAGAGGTGAAGTTCAACTGGTAC GTGGACGGCGTGGAGGTGCACAACGCCAAGACCAAGCCCAGA GAGGAGCAGTACAACAGCACCTACAGGGTGGTGTCCGTGCTG ACCGTGCTGCACCAGGACTGGCTGAACGGCAAGGAATACAAG TGCAAGGTCTCCAACAAGGCCCTGCCAGCCCCCATCGAAAAG ACCATCAGCAAGGCCAAGGGCCAGCCACGGGAGCCCCAGGTG TACACCCTGCCCCCCTCCCGGGAGGAGATGACCAAGAACCAG GTGTCCCTGACCTGTCTGGTGAAGGGCTTCTACCCCAGCGAC ATCGCCGTGGAGTGGGAGAGCAACGGCCAGCCCGAGAACAAC TACAAGACCACCCCCCCAGTGCTGGACAGCGACGGCAGCTTC TTCCTGTACAGCAAGCTGACCGTGGACAAGTCCAGGTGGCAG CAGGGCAACGTGTTCAGCTGCAGCGTGATGCACGAGGCCCTG CACAACCACTACACCCAGAAGAGCCTGAGCCTGTCCCCCGGC AAG |
| LCDR1 (Kabat) | 122 | QASDYIYHWLA |
| LCDR2 (Kabat) | 123 | GASSLET |
| LCDR3 (Kabat) | 124 | QQYWSIPWT |
| LCDR1 (Chothia) | 125 | SDYIYHW |
| LCDR2 (Chothia) | 126 | GAS |
| LCDR3 (Chothia) | 127 | YWSIPW |
| VL | 128 | DIQMTQSPSSLSASVGDRVTITCQASDYIYHWLAWYQQKPGK APKLLISGASSLETGVPSRFSGSGSGKDYTFTISSLQPEDIA TYYCQQYWSIPWTFGQGTKLEIK |
| DNA Encoding VL | 129 | GACATCCAGATGACCCAGAGCCCCAGCAGCCTGTCTGCCAGC GTGGGCGACAGAGTGACCATCACCTGTCAGGCCAGCGACTAC ATCTACCACTGGCTGGCCTGGTATCAGCAGAAGCCCGGCAAG GCCCCCAAGCTGCTGATTAGCGGAGCCTCCAGTCTGGAAACC GGCGTGCCAAGCAGATTTTCCGGCAGCGGCTCCGGCAAGGAC TACACCTTCACCATCAGCTCCCTGCAGCCCGAGGATATCGCC ACCTACTACTGCCAGCAGTACTGGTCCATCCCCTGGACCTTT GGCCAGGGCACCAAGCTGGAAATCAAG |
| Light Chain | 130 | DIQMTQSPSSLSASVGDRVTITCQASDYIYHWLAWYQQKPGK APKLLISGASSLETGVPSRFSGSGSGKDYTFTISSLQPEDIA TYYCQQYWSIPWTFGQGTKLEIKRTVAAPSVFIFPPSDEQLK SGTASVVCLLNNFYPREAKVQWKVDNALQSGNSQESVTEQDS KDSTYSLSSTLTLSKADYEKHKVYACEVTHQGLSSPVTKSFN RGEC |
| DNA Encoding Light Chain | 131 | GACATCCAGATGACCCAGAGCCCCAGCAGCCTGTCTGCCAGC GTGGGCGACAGAGTGACCATCACCTGTCAGGCCAGCGACTAC ATCTACCACTGGCTGGCCTGGTATCAGCAGAAGCCCGGCAAG GCCCCCAAGCTGCTGATTAGCGGAGCCTCCAGTCTGGAAACC GGCGTGCCAAGCAGATTTTCCGGCAGCGGCTCCGGCAAGGAC TACACCTTCACCATCAGCTCCCTGCAGCCCGAGGATATCGCC ACCTACTACTGCCAGCAGTACTGGTCCATCCCCTGGACCTTT GGCCAGGGCACCAAGCTGGAAATCAAGCGTACGGTGGCCGCT CCCAGCGTGTTCATCTTCCCCCCCAGCGACGAGCAGCTGAAG AGCGGCACCGCCAGCGTGGTGTGCCTGCTGAACAACTTCTAC CCCCGGGAGGCCAAGGTGCAGTGGAAGGTGGACAACGCCCTG CAGAGCGGCAACAGCCAGGAGAGCGTCACCGAGCAGGACAGC AAGGACTCCACCTACAGCCTGAGCAGCACCCTGACCCTGAGC AAGGCCGACTACGAGAAGCATAAGGTGTACGCCTGCGAGGTG ACCCACCAGGGCCTGTCCAGCCCCGTGACCAAGAGCTTCAAC AGGGGCGAGTGC |

TABLE 1-continued

Examples of ANGPTL4 Antibodies, Fabs and ANGPTL4 Proteins

| Sequence Description | Sequence Identifier (SEQ ID NO.) | Amino acid or polynucleotide sequence |
|---|---|---|
| NEG319 | | |
| HCDR1 (Kabat) | 132 | SFWIT |
| HCDR2 (Kabat) | 133 | DIYPGGANTNYNEKLQG |
| HCDR3 (Kabat) | 134 | SPPQVGPFDY |
| HCDR1 (Chothia) | 135 | GYTFTSF |
| HCDR2 (Chothia) | 136 | YPGGAN |
| HCDR3 (Chothia) | 137 | SPPQVGPFDY |
| VH | 138 | QVQLVQSGAEVKKPGASVKVSCKASGYTFTSFWITWVRQAPG QGLEWMGDIYPGGANTNYNEKLQGRVTLTVDTSTSTAYMELR SLRSDDTAVYYCARSPPQVGPFDYWGQGTLVTVSS |
| DNA Encoding VH | 139 | CAGGTGCAGCTGGTGCAGTCTGGCGCCGAAGTGAAGAAACCA GGCGCCAGCGTGAAGGTGTCCTGCAAGGCCAGCGGCTATACC TTCACCAGCTTTTGGATCACCTGGGTGCGCCAGGCCCCTGGA CAGGGACTGGAATGGATGGGCGACATCTACCCTGGCGGCGCC AACACCAACTACAACGAGAAGCTGCAGGGCAGAGTGACCCTG ACCGTGGACACCAGCACCTCCACCGCCTACATGGAACTGCGG AGCCTGAGAAGCGACGACACCGCCGTGTACTACTGCGCTAGA AGCCCTCCTCAGGTGGGCCCCTTCGATTATTGGGGCCAGGGC ACACTCGTGACCGTGTCCTCT |
| Heavy Chain | 140 | QVQLVQSGAEVKKPGASVKVSCKASGYTFTSFWITWVRQAPG QGLEWMGDIYPGGANTNYNEKLQGRVTLTVDTSTSTAYMELR SLRSDDTAVYYCARSPPQVGPFDYWGQGTLVTVSSASTKGPS VFPLAPSSKSTSGGTAALGCLVKDYFPEPVTVSWNSGALTSG VHTFPAVLQSSGLYSLSSVVTVPSSSLGTQTYICNVNHKPSN TKVDKRVEPKSCDKTHTCPPCPAPELLGGPSVFLFPPKPKDT LMISRTPEVTCVVVDVSHEDPEVKFNWYVDGVEVHNAKTKPR EEQYNSTYRVVSVLTVLHQDWLNGKEYKCKVSNKALPAPIEK TISKAKGQPREPQVYTLPPSREEMTKNQVSLTCLVKGFYPSD IAVEWESNGQPENNYKTTPPVLDSDGSFFLYSKLTVDKSRWQ QGNVFSCSVMHEALHNHYTQKSLSLSPGK |
| DNA Encoding Heavy Chain | 141 | CAGGTGCAGCTGGTGCAGTCTGGCGCCGAAGTGAAGAAACCA GGCGCCAGCGTGAAGGTGTCCTGCAAGGCCAGCGGCTATACC TTCACCAGCTTTTGGATCACCTGGGTGCGCCAGGCCCCTGGA CAGGGACTGGAATGGATGGGCGACATCTACCCTGGCGGCGCC AACACCAACTACAACGAGAAGCTGCAGGGCAGAGTGACCCTG ACCGTGGACACCAGCACCTCCACCGCCTACATGGAACTGCGG AGCCTGAGAAGCGACGACACCGCCGTGTACTACTGCGCTAGA AGCCCTCCTCAGGTGGGCCCCTTCGATTATTGGGGCCAGGGC ACACTCGTGACCGTGTCCTCTGCTAGCACCAAGGGCCCCAGC GTGTTCCCCCTGGCCCCCAGCAGCAAGAGCACCAGCGGCGGC ACAGCCGCCCTGGGCTGCCTGGTGAAGGACTACTTCCCCGAG CCCGTGACCGTGTCCTGGAACAGCGGAGCCCTGACCTCCGGC GTGCACACCTTCCCCGCCGTGCTGCAGAGCAGCGGCCTGTAC AGCCTGTCCAGCGTGGTGACAGTGCCCAGCAGCAGCCTGGGC ACCCAGACCTACATCTGCAACGTGAACCACAAGCCCAGCAAC ACCAAGGTGGACAAGAGAGTGGAGCCCAAGAGCTGCGACAAG ACCCACACCTGCCCCCCCTGCCCAGCCCCAGAGCTGCTGGGC GGACCCTCCGTGTTCCTGTTCCCCCCCAAGCCCAAGGACACC CTGATGATCAGCAGGACCCCCGAGGTGACCTGCGTGGTGGTG GACGTGAGCCACGAGGACCCAGAGGTGAAGTTCAACTGGTAC GTGGACGGCGTGGAGGTGCACAACGCCAAGACCAAGCCCAGA GAGGAGCAGTACAACAGCACCTACAGGGTGGTGTCCGTGCTG ACCGTGCTGCACCAGGACTGGCTGAACGGCAAGGAATACAAG TGCAAGGTCTCCAACAAGGCCCTGCCAGCCCCCATCGAAAAG ACCATCAGCAAGGCCAAGGGCCAGCCACGGGAGCCCCAGGTG TACACCCTGCCCCCCTCCCGGGAGGAGATGACCAAGAACCAG GTGTCCCTGACCTGTCTGGTGAAGGGCTTCTACCCCAGCGAC ATCGCCGTGGAGTGGGAGAGCAACGGCCAGCCCGAGAACAAC TACAAGACCACCCCCCCAGTGCTGGACAGCGACGGCAGCTTC TTCCTGTACAGCAAGCTGACCGTGGACAAGTCCAGGTGGCAG CAGGGCAACGTGTTCAGCTGCAGCGTGATGCACGAGGGCCTG CACAACCACTACACCCAGAAGAGCCTGAGCCTGTCCCCCGGC AAG |

TABLE 1-continued

Examples of ANGPTL4 Antibodies, Fabs and ANGPTL4 Proteins

| Sequence Description | Sequence Identifier (SEQ ID NO.) | Amino acid or polynucleotide sequence |
|---|---|---|
| LCDR1 (Kabat) | 142 | QASEYIINWLA |
| LCDR2 (Kabat) | 143 | GATGLET |
| LCDR3 (Kabat) | 144 | QQYWSIPWT |
| LCDR1 (Chothia) | 145 | SEYIINW |
| LCDR2 (Chothia) | 146 | GAT |
| LCDR3 (Chothia) | 147 | YWSIPW |
| VL | 148 | DIQMTQSPSSLSASVGDRVTITCQASEYIINWLAWYQQKPGK APKLLISGATGLETGVPSRFSGSGSGKDYTFTISSLQPEDIA TYYCQQYWSIPWTFGQGTKLEIK |
| DNA Encoding VL | 149 | GACATCCAGATGACCCAGAGCCCCAGCAGCCTGTCTGCCAGC GTGGGCGACAGAGTGACCATCACCTGTCAGGCCAGCGAATAC ATCATAAACTGGCTGGCCTGGTATCAGCAGAAGCCCGGCAAG GCCCCCAAGCTGCTGATTAGCGGAGCCACCGGTCTGGAAACC GGCGTGCCAAGCAGATTTTCCGGCAGCGGCTCCGGCAAGGAC TACACCTTCACCATCAGCTCCCTGCAGCCCGAGGATATCGCC ACCTACTACTGCCAGCAGTACTGGTCCATCCCCTGGACCTTT GGCCAGGGCACCAAGCTGGAAATCAAG |
| Light Chain | 150 | DIQMTQSPSSLSASVGDRVTITCQASEYIINWLAWYQQKPGK APKLLISGATGLETGVPSRFSGSGSGKDYTFTISSLQPEDIA TYYCQQYWSIPWTFGQGTKLEIKRTVAAPSVFIFPPSDEQLK SGTASVVCLLNNFYPREAKVQWKVDNALQSGNSQESVTEQDS KDSTYSLSSTLTLSKADYEKHKVYACEVTHQGLSSPVTKSFN RGEC |
| DNA Encoding Light Chain | 151 | GACATCCAGATGACCCAGAGCCCCAGCAGCCTGTCTGCCAGC GTGGGCGACAGAGTGACCATCACCTGTCAGGCCAGCGAATAC ATCATAAACTGGCTGGCCTGGTATCAGCAGAAGCCCGGCAAG GCCCCCAAGCTGCTGATTAGCGGAGCCACCGGTCTGGAAACC GGCGTGCCAAGCAGATTTTCCGGCAGCGGCTCCGGCAAGGAC TACACCTTCACCATCAGCTCCCTGCAGCCCGAGGATATCGCC ACCTACTACTGCCAGCAGTACTGGTCCATCCCCTGGACCTTT GGCCAGGGCACCAAGCTGGAAATCAAGCGTACGGTGGCCGCT CCCAGCGTGTTCATCTTCCCCCCCAGCGACGAGCAGCTGAAG AGCGGCACCGCCAGCGTGGTGTGCCTGCTGAACAACTTCTAC CCCCGGGAGGCCAAGGTGCAGTGGAAGGTGGACAACGCCCTG CAGAGCGGCAACAGCCAGGAGAGCGTCACCGAGCAGGACAGC AAGGACTCCACCTACAGCCTGAGCAGCACCCTGACCCTGAGC AAGGCCGACTACGAGAAGCATAAGGTGTACGCCTGCGAGGTG ACCCACCAGGGCCTGTCCAGCCCCGTGACCAAGAGCTTCAAC AGGGGCGAGTGC |

Other antibodies of the invention include those where the amino acids or nucleic acids encoding the amino acids have been mutated, yet have at least 60, 65, 70, 75, 80, 85, 90, or 95 percent identity to the sequences described in Table 1. Some embodiments include mutant amino acid sequences wherein no more than 1, 2, 3, 4 or 5 amino acids have been mutated in the variable regions when compared with the variable regions depicted in the sequence described in Table 1, while retaining substantially the same antigen binding activity.

Since each of these antibodies can bind to ANGPTL4, the VH, VL, full-length light chain, and full-length heavy chain sequences (amino acid sequences and the nucleotide sequences encoding the amino acid sequences) can be "mixed and matched" to create other ANGPTL4-binding antibodies of the invention. Such "mixed and matched" ANGPTL4-binding antibodies can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full-length heavy chain sequence from a particular full-length heavy chain/full length light chain pairing should be replaced with a structurally similar full-length heavy chain sequence. Likewise, a VL sequence from a particular VH/VL pairing should be replaced with a structurally similar VL sequence. Likewise a full-length light chain sequence from a particular full-length heavy chain/full-length light chain pairing should be replaced with a structurally similar full-length light chain sequence.

Accordingly, in one aspect, the invention provides an isolated antibody or antigen binding region thereof having: a heavy chain variable domain comprising an amino acid sequence selected from the group consisting of SEQ ID NOs: 13, 38, 58, 78, 98, 118, and 138, and a light chain variable domain comprising an amino acid sequence selected from the group consisting of SEQ ID NOs: 23, 48, 68, 88, 108, 128, and 148, wherein the antibody specifically binds to ANGPTL4 (e.g., human ANGPTL4).

More specifically, in certain aspects, the invention provides an isolated antibody or antigen binding region thereof having a heavy chain variable domain and a light chain variable domain comprising amino acid sequences selected from SEQ ID NOs: 13 and 23; 38 and 48; 58 and 68; 78 and 88; 98 and 108, 118 and 128, or 138 and 148, respectively.

In another aspect, the invention provides (i) an isolated antibody having: a full-length heavy chain comprising an amino acid sequence that has been optimized for expression in a mammalian cell selected from the group consisting of SEQ ID NOs: 15, 28, 40, 60, 80, 100, 120, and 140, and a full-length light chain comprising an amino acid sequence that has been optimized for expression in a mammalian cell selected from the group consisting of SEQ ID NOs: 25, 50, 70, 90, 110, 130, and 150; or (ii) a functional protein comprising an antigen binding portion thereof. More specifically, in certain aspects, the invention provides an isolated antibody or antigen binding region thereof having a heavy chain and a light chain comprising amino acid sequences selected from SEQ ID NOs: 15 and 25; 28 and 25; 40 and 50; 60 and 70; 80 and 90; 100 and 110; 120 and 130; or 140 and 150, respectively.

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme).

For example, under Kabat, the CDR amino acid residues of antibody FF1 in the heavy chain variable domain (VH) are numbered 31-35 (HCDR1), 50-66 (HCDR2), and 99-104 (HCDR3); and the CDR amino acid residues in the light chain variable domain (VL) are numbered 24-34 (LCDR1), 50-55 (LCDR2), and 89-97 (LCDR3). Under Chothia the CDR amino acids in the VH are numbered 26-32 (HCDR1), 52-57 (HCDR2), and 99-104 (HCDR3); and the amino acid residues in VL are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-66 (HCDR2), and 90-104 (HCDR3) in human VH and amino acid residues 24-34 (LCDR1), 50-55 (LCDR2), and 89-97 (LCDR3) in human VL.

In another aspect, the present invention provides ANGPTL4 binding antibodies that comprise the heavy chain and light chain CDR1s, CDR2s, and CDR3s as described in Table 1, or combinations thereof. The amino acid sequences of the VH CDR1s of the antibodies are shown in SEQ ID NOs: 7, 32, 52, 72, 92, 112, and 132. The amino acid sequences of the VH CDR2s of the antibodies and are shown in SEQ ID NOs: 8, 33, 53, 73, 93, 113, and 133. The amino acid sequences of the VH CDR3s of the antibodies are shown in SEQ ID NOs: 9, 34, 54, 74, 94, 114, and 134. The amino acid sequences of the VL CDR1s of the antibodies are shown in SEQ ID NOs: 17, 42, 62, 82, 102, 122, and 142. The amino acid sequences of the VL CDR2s of the antibodies are shown in SEQ ID NOs: 18, 43, 63, 83, 103, 123, and 143. The amino acid sequences of the VL CDR3s of the antibodies are shown in SEQ ID NOs: 19, 44, 64, 84, 104, 124, and 144. These CDR regions are delineated using the Kabat system.

Alternatively, as defined using the Chothia system (Al-Lazikani et al., (1997) JMB 273, 927-948), the amino acid sequences of the VH CDR1s of the antibodies are shown in SEQ ID NOs: 10, 35, 55, 75, 95, 115, and 135. The amino acid sequences of the VH CDR2s of the antibodies and are shown in SEQ ID NOs: 11, 36, 56, 76, 96, 116, and 136. The amino acid sequences of the VH CDR3s of the antibodies are shown in SEQ ID NOs: 12, 37, 57, 77, 97, 117, 117, and 137. The amino acid sequences of the VL CDR1s of the antibodies are shown in SEQ ID NOs: 20, 45, 65, 85, 105, 125, and 145. The amino acid sequences of the VL CDR2s of the antibodies are shown in SEQ ID NOs: 21, 46, 66, 86, 106, 126, and 146. The amino acid sequences of the VL CDR3s of the antibodies are shown in SEQ ID NOs: 22, 47, 67, 87, 107, 127, and 147.

Given that each of these antibodies can bind to ANGPTL4 and that antigen-binding specificity is provided primarily by the CDR1, 2 and 3 regions, the VH CDR1, 2 and 3 sequences and VL CDR1, 2 and 3 sequences can be "mixed and matched" (i.e., CDRs from different antibodies can be mixed and matched, although each antibody preferably contains a VH CDR1, 2 and 3 and a VL CDR1, 2 and 3 to create other ANGPTL4 binding molecules of the invention. Such "mixed and matched" ANGPTL4 binding antibodies can be tested using the binding assays known in the art and those described in the Examples (e.g., ELISAs, SET, Biacore). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences shown herein for monoclonal antibodies of the present invention. In addition to the foregoing, in one embodiment, the antigen binding fragments of the antibodies described herein can comprise a VH CDR1, 2, and 3, or a VL CDR 1, 2, and 3, wherein the fragment binds to ANGPTL4 as a single variable domain.

In certain embodiments of the invention, the antibodies or antigen binding fragments thereof may have the heavy and light chain sequences of the Humanized antibodies described in Table 1. More specifically, the antibody or antigen binding fragments thereof may have the heavy and light sequence of NEG276, NEG276-LALA, NEG278, NEG310, NEG313, NEG315, NEG318, and NEG319.

In other embodiments of the invention the antibody or antigen binding fragment in that specifically binds ANGPTL4 comprises a heavy chain variable region CDR1, a heavy chain variable region CDR2, a heavy chain variable region CDR3, a light chain variable region CDR1, a light chain variable region CDR2, and a light chain variable region CDR3 as defined by Kabat and described in Table 1. In still other embodiments of the invention the antibody or antigen binding fragment in that specifically binds ANGPTL4 comprises a heavy chain variable region CDR1, a heavy chain variable region CDR2, a heavy chain variable region CDR3, a light chain variable region CDR1, a light chain variable region CDR2, and a light chain variable region CDR3 as defined by Chothia and described in Table 1.

In a specific embodiment, the invention includes an antibody that specifically binds to ANGPTL4 comprising a heavy chain variable region CDR1 of SEQ ID NO: 7; a heavy chain variable region CDR2 of SEQ ID NO: 8; a heavy chain variable region CDR3 of SEQ ID NO: 9; a light chain variable region CDR1 of SEQ ID NO: 17; a light chain variable region CDR2 of SEQ ID NO: 18; and a light chain variable region CDR3 of SEQ ID NO: 19.

In another specific embodiment, the invention includes an antibody that specifically binds to ANGPTL4 comprising a heavy chain variable region CDR1 of SEQ ID NO: 32; a heavy chain variable region CDR2 of SEQ ID NO: 33; a heavy chain variable region CDR3 of SEQ ID NO: 34; a light chain variable region CDR1 of SEQ ID NO: 42; a light chain variable region CDR2 of SEQ ID NO: 43; and a light chain variable region CDR3 of SEQ ID NO: 44.

In another specific embodiment, the invention includes an antibody that specifically binds to ANGPTL4 comprising a heavy chain variable region CDR1 of SEQ ID NO: 52; a heavy chain variable region CDR2 of SEQ ID NO: 53; a heavy chain variable region CDR3 of SEQ ID NO: 54; a light chain variable region CDR1 of SEQ ID NO: 62; a light chain variable region CDR2 of SEQ ID NO: 63; and a light chain variable region CDR3 of SEQ ID NO: 64.

In another specific embodiment, the invention includes an antibody that specifically binds to ANGPTL4 comprising a heavy chain variable region CDR1 of SEQ ID NO: 72; a heavy chain variable region CDR2 of SEQ ID NO: 73; a heavy chain variable region CDR3 of SEQ ID NO: 74; a light chain variable region CDR1 of SEQ ID NO: 82; a light chain variable region CDR2 of SEQ ID NO: 83; and a light chain variable region CDR3 of SEQ ID NO: 84.

In another specific embodiment, the invention includes an antibody that specifically binds to ANGPTL4 comprising a heavy chain variable region CDR1 of SEQ ID NO: 92; a heavy chain variable region CDR2 of SEQ ID NO: 93; a heavy chain variable region CDR3 of SEQ ID NO: 94; a light chain variable region CDR1 of SEQ ID NO: 102; a light chain variable region CDR2 of SEQ ID NO: 103; and a light chain variable region CDR3 of SEQ ID NO: 104.

In another specific embodiment, the invention includes an antibody that specifically binds to ANGPTL4 comprising a heavy chain variable region CDR1 of SEQ ID NO: 112; a heavy chain variable region CDR2 of SEQ ID NO: 113; a heavy chain variable region CDR3 of SEQ ID NO: 114; a light chain variable region CDR1 of SEQ ID NO: 122; a light chain variable region CDR2 of SEQ ID NO: 123; and a light chain variable region CDR3 of SEQ ID NO: 124.

In another specific embodiment, the invention includes an antibody that specifically binds to ANGPTL4 comprising a heavy chain variable region CDR1 of SEQ ID NO: 132; a heavy chain variable region CDR2 of SEQ ID NO: 133; a heavy chain variable region CDR3 of SEQ ID NO: 134; a light chain variable region CDR1 of SEQ ID NO: 142; a light chain variable region CDR2 of SEQ ID NO: 143; and a light chain variable region CDR3 of SEQ ID NO: 144.

In another specific embodiment, the invention includes an antibody that specifically binds to ANGPTL4 comprising a heavy chain variable region CDR1 of SEQ ID NO: 10; a heavy chain variable region CDR2 of SEQ ID NO: 11; a heavy chain variable region CDR3 of SEQ ID NO: 12; a light chain variable region CDR1 of SEQ ID NO: 20; a light chain variable region CDR2 of SEQ ID NO: 21; and a light chain variable region CDR3 of SEQ ID NO: 22.

In another specific embodiment, the invention includes an antibody that specifically binds to ANGPTL4 comprising a heavy chain variable region CDR1 of SEQ ID NO: 35; a heavy chain variable region CDR2 of SEQ ID NO: 36; a heavy chain variable region CDR3 of SEQ ID NO: 37; a light chain variable region CDR1 of SEQ ID NO: 45; a light chain variable region CDR2 of SEQ ID NO: 46; and a light chain variable region CDR3 of SEQ ID NO: 47.

In another specific embodiment, the invention includes an antibody that specifically binds to ANGPTL4 comprising a heavy chain variable region CDR1 of SEQ ID NO: 55; a heavy chain variable region CDR2 of SEQ ID NO: 56; a heavy chain variable region CDR3 of SEQ ID NO: 57; a light chain variable region CDR1 of SEQ ID NO: 65; a light chain variable region CDR2 of SEQ ID NO: 66; and a light chain variable region CDR3 of SEQ ID NO: 67.

In another specific embodiment, the invention includes an antibody that specifically binds to ANGPTL4 comprising a heavy chain variable region CDR1 of SEQ ID NO: 75; a heavy chain variable region CDR2 of SEQ ID NO: 76; a heavy chain variable region CDR3 of SEQ ID NO: 77; a light chain variable region CDR1 of SEQ ID NO: 85; a light chain variable region CDR2 of SEQ ID NO: 86; and a light chain variable region CDR3 of SEQ ID NO: 87.

In another specific embodiment, the invention includes an antibody that specifically binds to ANGPTL4 comprising a heavy chain variable region CDR1 of SEQ ID NO: 95; a heavy chain variable region CDR2 of SEQ ID NO: 96; a heavy chain variable region CDR3 of SEQ ID NO: 97; a light chain variable region CDR1 of SEQ ID NO: 105; a light chain variable region CDR2 of SEQ ID NO: 106; and a light chain variable region CDR3 of SEQ ID NO: 107.

In another specific embodiment, the invention includes an antibody that specifically binds to ANGPTL4 comprising a heavy chain variable region CDR1 of SEQ ID NO: 115; a heavy chain variable region CDR2 of SEQ ID NO: 116; a heavy chain variable region CDR3 of SEQ ID NO: 117; a light chain variable region CDR1 of SEQ ID NO: 125; a light chain variable region CDR2 of SEQ ID NO: 126; and a light chain variable region CDR3 of SEQ ID NO: 127.

In another specific embodiment, the invention includes an antibody that specifically binds to ANGPTL4 comprising a heavy chain variable region CDR1 of SEQ ID NO: 135; a heavy chain variable region CDR2 of SEQ ID NO: 136; a heavy chain variable region CDR3 of SEQ ID NO: 137; a light chain variable region CDR1 of SEQ ID NO: 145; a light chain variable region CDR2 of SEQ ID NO: 146; and a light chain variable region CDR3 of SEQ ID NO: 147.

In certain embodiments, the invention includes antibodies or antigen binding fragments that specifically bind to ANGPTL4 as described in Table 1. In a preferred embodiment, the antibody, or antigen binding fragment, that binds ANGPTL4 is NEG276, NEG276-LALA, NEG278, NEG310, NEG313, NEG315, NEG318, NEG319.

Homologous Antibodies

In yet another embodiment, the present invention provides an antibody, or an antigen binding fragment thereof, comprising amino acid sequences that are homologous to the sequences described in Table 1, and the antibody binds to a ANGPTL4 protein (e.g., human and cynomolgus monkey ANGPTL4), and retains the desired functional properties of those antibodies described in Table 1.

For example, the invention provides an isolated antibody, or a functional antigen binding fragment thereof, comprising a heavy chain variable domain and a light chain variable domain, wherein the heavy chain variable domain comprises an amino acid sequence that is at least 80%, at least 90%, or at least 95% identical to an amino acid sequence selected from the group consisting of SEQ ID NOs: 13, 38, 58, 78, 98, 118, and 138; the light chain variable domain comprises an amino acid sequence that is at least 80%, at least 90%, or at least 95% identical to an amino acid sequence selected from the group consisting of SEQ ID NOs: 23, 23, 48, 68, 88, 108, 128, 148; and the antibody specifically binds to ANGPTL4 (e.g., human and cynomolgus monkey ANGPTL4). In certain aspects of the invention the heavy and light chain sequences further comprise HCDR1, HCDR2, HCDR3, LCDR1, LCDR2, and LCDR3 sequences as defined by Kabat, for example SEQ ID NOs: 7, 8, 9, 17, 18, and 19, respectively. In certain other aspects of the invention the heavy and light chain sequences further comprise HCDR1, HCDR2, HCDR3, LCDR1, LCDR2, and LCDR3 sequences as defined by Chothia, for example SEQ ID NOs: 10, 11, 12, 20, 21, and 22, respectively.

In other embodiments, the VH and/or VL amino acid sequences may be 50%, 60%, 70%, 80%, 90%, 95%, 96%, 97%, 98% or 99% identical to the sequences set forth in Table 1. In other embodiments, the VH and/or VL amino acid sequences may be identical except for an amino acid substitution in no more than 1, 2, 3, 4 or 5 amino acid positions. An antibody having VH and VL regions having high (i.e., 80% or greater) identity to the VH and VL regions of those described in Table 1 can be obtained by mutagenesis (e.g., site-directed or PCR-mediated mutagenesis) of nucleic acid molecules encoding SEQ ID NOs: 13, 38, 58, 78, 98, 118, 118, or 138 and SEQ ID NOs: 23, 48, 68, 88, 108, 128, or 148, respectively, followed by testing of the encoded altered antibody for retained function using the functional assays described herein.

In other embodiments, the full-length heavy chain and/or full-length light chain amino acid sequences may be 50% 60%, 70%, 80%, 90%, 95%, 96%, 97%, 98% or 99% identical to the sequences set forth in Table 1. An antibody having a full-length heavy chain and full-length light chain having high (i.e., 80% or greater) identity to the full-length heavy chains of any of SEQ ID NOs: 15, 28, 40, 60, 80, 100, 120, or 140, and full-length light chains of any of SEQ ID NOs: 25, 25, 50, 70, 90, 110, 130, or 150, can be obtained by mutagenesis (e.g., site-directed or PCR-mediated mutagenesis) of nucleic acid molecules encoding such polypeptides, followed by testing of the encoded altered antibody for retained function using the functional assays described herein.

In other embodiments, the full-length heavy chain and/or full-length light chain nucleotide sequences may be 60%, 70%, 80%, 90%, 95%, 96%, 97%, 98% or 99% identical to the sequences set forth in Table 1.

In other embodiments, the variable regions of heavy chain and/or the variable regions of light chain nucleotide sequences may be 60%, 70%, 80%, 90%, 95%, 96%, 97%, 98% or 99% identical to the sequences set forth in Table 1.

As used herein, the percent identity between the two sequences is a function of the number of identical positions shared by the sequences (i.e., % identity equals number of identical positions/total number of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

Additionally or alternatively, the protein sequences of the present invention can further be used as a "query sequence" to perform a search against public databases to, for example, identify related sequences. For example, such searches can be performed using the BLAST program (version 2.0) of Altschul, et al., 1990 J. Mol. Biol. 215:403-10.

Antibodies with Conservative Modifications

In certain embodiments, an antibody of the invention has a heavy chain variable region comprising CDR1, CDR2, and CDR3 sequences and a light chain variable region comprising CDR1, CDR2, and CDR3 sequences, wherein one or more of these CDR sequences have specified amino acid sequences based on the antibodies described herein or conservative modifications thereof, and wherein the antibodies retain the desired functional properties of the ANGPTL4-binding antibodies of the invention.

Accordingly, the invention provides an isolated antibody, or a antigen binding fragment thereof, consisting of a heavy chain variable region comprising CDR1, CDR2, and CDR3 sequences and a light chain variable region comprising CDR1, CDR2, and CDR3 sequences, wherein: the heavy chain variable region CDR1 amino acid sequences are selected from the group consisting of SEQ ID NOs: 7, 32, 52, 72, 92, 112, and 132, and conservative modifications thereof; the heavy chain variable region CDR2 amino acid sequences are selected from the group consisting of SEQ ID NOs: 8, 33, 53, 73, 93, 113, and 133, and conservative modifications thereof; the heavy chain variable region CDR3 amino acid sequences are selected from the group consisting of SEQ ID NOs: 9, 34, 54, 74, 94, 114, and 134, and conservative modifications thereof; the light chain variable regions CDR1 amino acid sequences are selected from the group consisting of SEQ ID NOs: 17, 42, 62, 82, 102, 122, and 142, and conservative modifications thereof; the light chain variable regions CDR2 amino acid sequences are selected from the group consisting of SEQ ID NOs: 18, 43, 63, 83, 103, 123, and 143, and conservative modifications thereof; the light chain variable regions of CDR3 amino acid sequences are selected from the group consisting of SEQ ID NOs: 19, 44, 64, 84, 104, 124, and 144, and conservative modifications thereof; and the antibody or antigen binding fragments thereof specifically binds to ANGPTL4.

In other embodiments, the antibody of the invention is optimized for expression in a mammalian cell has a full length heavy chain sequence and a full length light chain sequence, wherein one or more of these sequences have specified amino acid sequences based on the antibodies described herein or conservative modifications thereof, and wherein the antibodies retain the desired functional properties of the ANGPTL4 binding antibodies of the invention. Accordingly, the invention provides an isolated antibody optimized for expression in a mammalian cell consisting of a full-length heavy chain and a full-length light chain wherein the full length heavy chain has amino acid sequences selected from the group of SEQ ID NOs: 15, 28, 40, 60, 80, 100, 120, and 140, and conservative modifications thereof; and the full length light chain has amino acid sequences selected from the group of SEQ ID NOs: 25, 50, 70, 90, 110, 130, and 150, and conservative modifications thereof; and the antibody specifically binds to ANGPTL4 (e.g., human and cynomolgus monkey ANGPTL4).

Antibodies that Bind to the Same Epitope

The present invention provides antibodies that bind to the same epitope as the ANGPTL4 binding antibodies described in Table 1. Additional antibodies can therefore be identified based on their ability to compete (e.g., to competitively inhibit the binding of, in a statistically significant manner) with other antibodies of the invention in ANGPTL4 binding assays (such as those described in the Examples). The ability of a test antibody to inhibit the binding of antibodies of the present invention to a ANGPTL4 protein demonstrates that the test antibody can compete with that antibody for binding to ANGPTL4; such an antibody may, according to non-limiting theory, bind to the same or a related (e.g., a structurally similar or spatially proximal) epitope on the ANGPTL4 protein as the antibody with which it competes. In a certain embodiment, the antibody that binds to the same epitope on ANGPTL4 as the antibodies of the present invention is a humanized antibody. Such humanized antibodies can be prepared and isolated as described herein. As used herein, an antibody "competes" for binding when the competing antibody inhibits ANGPTL4 binding of an antibody or antigen binding fragment of the invention by more than 50% (for example, 80%, 85%, 90%, 95%, 98% or 99%) in the presence of an equimolar concentration of competing antibody.

In other embodiments the antibodies or antigen binding fragments of the invention bind to one or more epitopes of ANGPTL4. In some embodiments, the epitopes to which the present antibodies or antigen binding fragments bind are linear eptiopes. In other embodiments, the epitopes to which the present antibodies or antigen binding fragments bind are non-linear, conformational eptiopes.

Engineered and Modified Antibodies

An antibody of the invention further can be prepared using an antibody having one or more of the VH and/or VL sequences shown herein as starting material to engineer a modified antibody, which modified antibody may have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad., U.S.A. 86:10029-10033; U.S. Pat. No. 5,225,539 to Winter, and U.S. Pat. Nos. 5,530,101; 5,585,089; 5,693,762 and 6,180,370 to Queen et al.).

Accordingly, another embodiment of the invention pertains to an isolated antibody, or an antigen binding fragment thereof, comprising a heavy chain variable region comprising CDR1 sequences having an amino acid sequence selected from the group consisting of SEQ ID NOs: 7, 32, 52, 72, 92, 112, and 132; CDR2 sequences having an amino acid sequence selected from the group consisting of SEQ ID NOs: 8, 33, 53, 73, 93, 113, and 133; CDR3 sequences having an amino acid sequence selected from the group consisting of SEQ ID NOs: 9, 34, 54, 74, 94, 114, and 134, respectively; and a light chain variable region having CDR1 sequences having an amino acid sequence selected from the group consisting of SEQ ID NOs: 17, 42, 62, 82, 102, 122, and 142; CDR2 sequences having an amino acid sequence selected from the group consisting of SEQ ID NOs: 18, 43, 63, 83, 103, 123, and 143; and CDR3 sequences consisting of an amino acid sequence selected from the group consisting of SEQ ID NOs: 19, 44, 64, 84, 104, 124, and 144, respectively. Thus, such antibodies contain the VH and VL CDR sequences of monoclonal antibodies, yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the world wide web at mrc-cpe.cam.ac.uk/vbase), as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. Mol. Biol. 227:776-798; and Cox, J. P. L. et al., 1994 Eur. J Immunol. 24:827-836; the contents of each of which are expressly incorporated herein by reference.

An example of framework sequences for use in the antibodies of the invention are those that are structurally similar to the framework sequences used by selected antibodies of the invention, e.g., consensus sequences and/or framework sequences used by monoclonal antibodies of the invention. The VH CDR1, 2 and 3 sequences, and the VL CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al). Frameworks that can be utilized as scaffolds on which to build the antibodies and antigen binding fragments described herein include, but are not limited to VH1A, VH1B, VH3, Vk1, VI2, and Vk2. Additional frameworks are known in the art and may be found, for example, in the vBase data base on the world wide web at vbase.mrc-cpe.cam.ac.uk/index.php?&MMN_position=1:1.

Accordingly, an embodiment of the invention relates to isolated ANGPTL4 binding antibodies, or antigen binding fragments thereof, comprising a heavy chain variable region comprising an amino acid sequence selected from the group consisting of SEQ ID NOs: 13, 38, 58, 78, 98, 118, and 138, or an amino acid sequence having one, two, three, four or five amino acid substitutions, deletions or additions in the framework region of such sequences, and further comprising a light chain variable region having an amino acid sequence selected from the group consisting of SEQ ID NOs: 23, 48, 68, 88, 108, 128, and 148, or an amino acid sequence having one, two, three, four or five amino acid substitutions, deletions or additions in the framework region of such sequences.

Another type of variable region modification is to mutate amino acid residues within the VH and/or VL CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications (as discussed above)

can be introduced. The mutations may be amino acid substitutions, additions or deletions. Moreover, typically no more than one, two, three, four or five residues within a CDR region are altered.

Accordingly, in another embodiment, the invention provides isolated ANGPTL4-binding antibodies, or antigen binding fragments thereof, consisting of a heavy chain variable region having a VH CDR1 region consisting of an amino acid sequence selected from the group having SEQ ID NOs: 7, 32, 52, 72, 92, 112, and 132, or an amino acid sequence having one, two, three, four or five amino acid substitutions, deletions or additions as compared to SEQ ID NOs: 7, 32, 52, 72, 92, 112, 112, and 132; a VH CDR2 region having an amino acid sequence selected from the group consisting of SEQ ID NOs: 8, 33, 53, 73, 93, 113, and 133, or an amino acid sequence having one, two, three, four or five amino acid substitutions, deletions or additions as compared to SEQ ID NOs: 8, 33, 53, 73, 93, 113, and 133; a VH CDR3 region having an amino acid sequence selected from the group consisting of SEQ ID NOs: 9, 34, 54, 74, 94, 114, 114, and 134, or an amino acid sequence having one, two, three, four or five amino acid substitutions, deletions or additions as compared to SEQ ID NOs: 9, 34, 54, 74, 94, 114, and 134; a VL CDR1 region having an amino acid sequence selected from the group consisting of SEQ ID NOs:17, 42, 62, 82, 102, 122, and 142, or an amino acid sequence having one, two, three, four or five amino acid substitutions, deletions or additions as compared to SEQ ID NOs: 17, 42, 62, 82, 102, 122, and 142; a VL CDR2 region having an amino acid sequence selected from the group consisting of SEQ ID NOs: 18, 43, 63, 83, 103, 123, and 143, or an amino acid sequence having one, two, three, four or five amino acid substitutions, deletions or additions as compared to SEQ ID NOs: 18, 43, 63, 83, 103, 123, and 143; and a VL CDR3 region having an amino acid sequence selected from the group consisting of SEQ ID NOs: 19, 44, 64, 84, 104, 124, and 144, or an amino acid sequence having one, two, three, four or five amino acid substitutions, deletions or additions as compared to SEQ ID NOs: 19, 44, 64, 84, 104, 124, and 144.

Accordingly, in another embodiment, the invention provides isolated ANGPTL4-binding antibodies, or antigen binding fragments thereof, consisting of a heavy chain variable region having a VH CDR1 region consisting of an amino acid sequence selected from the group having SEQ ID NOs: 10, 35, 55, 75, 95, 115, and 135 or an amino acid sequence having one, two, three, four or five amino acid substitutions, deletions or additions as compared to SEQ ID NOs: 10, 35, 55, 75, 95, 115, and 135; a VH CDR2 region having an amino acid sequence selected from the group consisting of SEQ ID NOs: 11, 36, 56, 76, 96, 116, and 136 or an amino acid sequence having one, two, three, four or five amino acid substitutions, deletions or additions as compared to SEQ ID NOs: 11, 36, 56, 76, 96, 116, and 136; a VH CDR3 region having an amino acid sequence selected from the group consisting of SEQ ID NOs: 12, 37, 57, 77, 97, 117, and 137, or an amino acid sequence having one, two, three, four or five amino acid substitutions, deletions or additions as compared to SEQ ID NOs: 12, 37, 57, 77, 97, 117, and 137; a VL CDR1 region having an amino acid sequence selected from the group consisting of SEQ ID NOs: 20, 45, 65, 85, 105, 125, and 145, or an amino acid sequence having one, two, three, four or five amino acid substitutions, deletions or additions as compared to SEQ ID NOs: 20, 45, 65, 85, 105, 125, and 145; a VL CDR2 region having an amino acid sequence selected from the group consisting of SEQ ID NOs: 21, 46, 66, 86, 106, 126, and 146, or an amino acid sequence having one, two, three, four or five amino acid substitutions, deletions or additions as compared to SEQ ID NOs: 21, 46, 66, 86, 106, 126, and 146; and a VL CDR3 region having an amino acid sequence selected from the group consisting of SEQ ID NOs: 22, 47, 67, 87, 107, 127, and 147, or an amino acid sequence having one, two, three, four or five amino acid substitutions, deletions or additions as compared to SEQ ID NOs: 22, 47, 67, 87, 107, 127, and 147.

Grafting Antigen-binding Domains into Alternative Frameworks or Scaffolds

A wide variety of antibody/immunoglobulin frameworks or scaffolds can be employed so long as the resulting polypeptide includes at least one binding region which specifically binds to ANGPTL4. Such frameworks or scaffolds include the 5 main idiotypes of human immunoglobulins, or fragments thereof, and include immunoglobulins of other animal species, preferably having humanized aspects. Single heavy-chain antibodies such as those identified in camelids are of particular interest in this regard. Novel frameworks, scaffolds and fragments continue to be discovered and developed by those skilled in the art.

In one aspect, the invention pertains to generating non-immunoglobulin based antibodies using non-immunoglobulin scaffolds onto which CDRs of the invention can be grafted. Known or future non-immunoglobulin frameworks and scaffolds may be employed, as long as they comprise a binding region specific for the target ANGPTL4 protein. Known non-immunoglobulin frameworks or scaffolds include, but are not limited to, fibronectin (Compound Therapeutics, Inc., Waltham, Mass.), ankyrin (Molecular Partners AG, Zurich, Switzerland), domain antibodies (Domantis, Ltd., Cambridge, Mass., and Ablynx nv, Zwijnaarde, Belgium), lipocalin (*Pieris* Proteolab AG, Freising, Germany), small modular immuno-pharmaceuticals (Trubion Pharmaceuticals Inc., Seattle, Wash.), maxybodies (Avidia, Inc., Mountain View, Calif.), Protein A (Affibody AG, Sweden), and affilin (gamma-crystallin or ubiquitin) (Scil Proteins GmbH, Halle, Germany).

The fibronectin scaffolds are based on fibronectin type III domain (e.g., the tenth module of the fibronectin type III (10 Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (see U.S. Pat. No. 6,818,418). These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the invention using standard cloning techniques.

The ankyrin technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, U.S. Patent Application Publication Nos. 20040175756; 20050053973; 20050048512; and 20060008844.

Affibody affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate affibody libraries with a large number of ligand variants (See e.g., U.S. Pat. No. 5,831,012). Affibody molecules mimic antibodies, they have a molecular weight of 6 kDa, compared to the molecular weight of antibodies, which is 150 kDa. In spite of its small size, the binding site of affibody molecules is similar to that of an antibody.

Anticalins are products developed by the company *Pieris ProteoLab AG*. They are derived from lipocalins, a widespread group of small and robust proteins that are usually involved in the physiological transport or storage of chemically sensitive or insoluble compounds. Several natural lipocalins occur in human tissues or body liquids. The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain. The set of four loops, which makes up the binding pocket, shows pronounced structural plasticity and tolerates a variety of side chains. The binding site can thus be reshaped in a proprietary process in order to recognize prescribed target molecules of different shape with high affinity and specificity. One protein of lipocalin family, the bilin-binding protein (BBP) of *Pieris Brassicae* has been used to develop anticalins by mutagenizing the set of four loops. One example of a patent application describing anticalins is in PCT Publication No. WO 199916873.

Affilin molecules are small non-immunoglobulin proteins which are designed for specific affinities towards proteins and small molecules. New affilin molecules can be very quickly selected from two libraries, each of which is based on a different human derived scaffold protein. Affilin molecules do not show any structural homology to immunoglobulin proteins. Currently, two affilin scaffolds are employed, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368.

Protein epitope mimetics (PEM) are medium-sized, cyclic, peptide-like molecules (MW 1-2 kDa) mimicking beta-hairpin secondary structures of proteins, the major secondary structure involved in protein-protein interactions.

The present invention provides fully human antibodies that specifically bind to a ANGPTL4 protein. Compared to the chimeric or humanized antibodies, the human ANGPTL4-binding antibodies of the invention have further reduced antigenicity when administered to human subjects.

Camelid Antibodies

Antibody proteins obtained from members of the camel and dromedary (*Camelus bactrianus* and *Calelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994).

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J 17: 3512-3520. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitated drug transport across the blood brain barrier. See U.S. patent application 20040161738 published Aug. 19, 2004. These features combined with the low antigenicity to humans indicate great therapeutic potential. Further, these molecules can be fully expressed in prokaryotic cells such as *E. coli* and are expressed as fusion proteins with bacteriophage and are functional.

Accordingly, a feature of the present invention is a camelid antibody or nanobody having high affinity for ANGPTL4. In certain embodiments herein, the camelid antibody or nanobody is naturally produced in the camelid animal, i.e., is produced by the camelid following immunization with ANGPTL4 or a peptide fragment thereof, using techniques described herein for other antibodies. Alternatively, the ANGPTL4-binding camelid nanobody is engineered, i.e., produced by selection for example from a library of phage displaying appropriately mutagenized camelid nanobody proteins using panning procedures with ANGPTL4 as a target as described in the examples herein. Engineered nanobodies can further be customized by genetic engineering to have a half life in a recipient subject of from 45 minutes to two weeks. In a specific embodiment, the camelid antibody or nanobody is obtained by grafting the CDRs sequences of the heavy or light chain of the human antibodies of the invention into nanobody or single domain antibody framework sequences, as described for example in PCT/EP93/02214.

Bispecific Molecules and Multivalent Antibodies

In another aspect, the present invention features bispecific or multispecific molecules comprising a ANGPTL4-binding antibody, or a fragment thereof, of the invention. An antibody of the invention, or antigen-binding regions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multi-specific molecules that bind to more than two different binding sites and/or target molecules; such multi-specific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for ANGPTL4 and a second binding specificity for a second target epitope. For example, the second target epitope is another epitope of ANGPTL4 different from the first target epitope.

Additionally, for the invention in which the bispecific molecule is multi-specific, the molecule can further include a third binding specificity, in addition to the first and second target epitope.

In one embodiment, the bispecific molecules of the invention comprise as a binding specificity at least one antibody, or an antibody fragment thereof, including, e.g., a Fab, Fab', F(ab')2, Fv, or a single chain Fv. The antibody may also be a light chain or heavy chain dimer, or any minimal fragment thereof such as a Fv or a single chain construct as described in Ladner et al. U.S. Pat. No. 4,946,778.

Diabodies are bivalent, bispecific molecules in which VH and VL domains are expressed on a single polypeptide chain, connected by a linker that is too short to allow for pairing between the two domains on the same chain. The VH and VL domains pair with complementary domains of another chain, thereby creating two antigen binding sites (see e.g., Holliger et al., 1993 Proc. Natl. Acad. Sci. USA 90:6444-6448; Poljak et al., 1994 Structure 2:1121-1123). Diabodies can be produced by expressing two polypeptide chains with either the structure VHA-VLB and VHB-VLA (VH-VL configuration), or VLA-VHB and VLB-VHA (VL-VH configuration) within the same cell. Most of them can be expressed in soluble form in bacteria. Single chain diabodies (scDb) are produced by connecting the two diabody-forming polypeptide chains with linker of approximately 15 amino acid residues (see Holliger and Winter, 1997 Cancer Immunol. Immunother., 45(3-4):128-30; Wu et al., 1996 Immunotechnology, 2(1):21-36). scDb can be expressed in bacteria in soluble, active monomeric form (see Holliger and Winter, 1997 Cancer Immunol. Immunother., 45(34): 128-30; Wu et al., 1996 Immunotechnology, 2(1):21-36; Pluckthun and Pack, 1997 Immunotechnology, 3(2): 83-105; Ridgway et al., 1996 Protein Eng., 9(7):617-21). A diabody can be fused to Fc to generate a "di-diabody" (see Lu et al., 2004 J. Biol. Chem., 279(4):2856-65).

Other antibodies which can be employed in the bispecific molecules of the invention are murine, chimeric and humanized monoclonal antibodies.

Bispecific molecules can be prepared by conjugating the constituent binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-I-carboxylate (sulfo-SMCC) (see e.g., Karpovsky et al., 1984 J. Exp. Med. 160:1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')2 or ligand×Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

In another aspect, the present invention provides multivalent compounds comprising at least two identical or different antigen-binding portions of the antibodies of the invention binding to ANGPTL4. The antigen-binding portions can be linked together via protein fusion or covalent or non covalent linkage. Alternatively, methods of linkage have been described for the bispecific molecules. Tetravalent compounds can be obtained for example by cross-linking antibodies of the antibodies of the invention with an antibody that binds to the constant regions of the antibodies of the invention, for example the Fc or hinge region.

Trimerizing domain are described for example in Borean patent EP 1 012 28061. Pentamerizing modules are described for example in PCT/EP97/05897.

Antibodies with Extended Half Life

The present invention provides for antibodies that specifically bind to ANGPTL4 protein which have an extended half-life in vivo.

Many factors may affect a protein's half life in vivo. For examples, kidney filtration, metabolism in the liver, degradation by proteolytic enzymes (proteases), and immunogenic responses (e.g., protein neutralization by antibodies and uptake by macrophages and dendritic cells). A variety of strategies can be used to extend the half life of the antibodies of the present invention. For example, by chemical linkage to polyethyleneglycol (PEG), reCODE PEG, antibody scaffold, polysialic acid (PSA), hydroxyethyl starch (HES), albumin-binding ligands, and carbohydrate shields; by genetic fusion to proteins binding to serum proteins, such as albumin, IgG, FcRn, and transferring; by coupling (genetically or chemically) to other binding moieties that bind to serum proteins, such as nanobodies, Fabs, DARPins, avimers, affibodies, and anticalins; by genetic fusion to rPEG, albumin, domain of albumin, albumin-binding proteins, and Fc; or by incorporation into nanocarriers, slow release formulations, or medical devices.

To prolong the serum circulation of antibodies in vivo, inert polymer molecules such as high molecular weight PEG can be attached to the antibodies or a fragment thereof with or without a multifunctional linker either through site-specific conjugation of the PEG to the N- or C-terminus of the antibodies or via epsilon-amino groups present on lysine residues. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods well-known to those of skill in the art, for example, by immunoassays described herein. Methods for pegylating proteins are known in the art and can be applied to the antibodies of the invention. See for example, EP 0 154 316 by Nishimura et al. and EP 0 401 384 by Ishikawa et al.

Other modified pegylation technologies include reconstituting chemically orthogonal directed engineering technology (ReCODE PEG), which incorporates chemically specified side chains into biosynthetic proteins via a reconstituted system that includes tRNA synthetase and tRNA. This technology enables incorporation of more than 30 new amino acids into biosynthetic proteins in E. coli, yeast, and mammalian cells. The tRNA incorporates a nonnative amino acid any place an amber codon is positioned, converting the amber from a stop codon to one that signals incorporation of the chemically specified amino acid.

Recombinant pegylation technology (rPEG) can also be used for serum halflife extension. This technology involves genetically fusing a 300-600 amino acid unstructured protein tail to an existing pharmaceutical protein. Because the apparent molecular weight of such an unstructured protein chain is about 15-fold larger than its actual molecular weight, the serum halflife of the protein is greatly increased. In contrast to traditional PEGylation, which requires chemical conjugation and repurification, the manufacturing process is greatly simplified and the product is homogeneous.

Polysialytion is another technology, which uses the natural polymer polysialic acid (PSA) to prolong the active life and improve the stability of therapeutic peptides and proteins. PSA is a polymer of sialic acid (a sugar). When used for protein and therapeutic peptide drug delivery, polysialic acid provides a protective microenvironment on conjugation. This increases the active life of the therapeutic protein in the circulation and prevents it from being recognized by the immune system. The PSA polymer is naturally found in the human body. It was adopted by certain bacteria which evolved over millions of years to coat their walls with it. These naturally polysialylated bacteria were then able, by virtue of molecular mimicry, to foil the body's defense system. PSA, nature's ultimate stealth technology, can be easily produced from such bacteria in large quantities and with predetermined physical characteristics. Bacterial PSA is completely non-immunogenic, even when coupled to proteins, as it is chemically identical to PSA in the human body.

Another technology includes the use of hydroxyethyl starch ("HES") derivatives linked to antibodies. HES is a modified natural polymer derived from waxy maize starch and can be metabolized by the body's enzymes. HES solutions are usually administered to substitute deficient blood volume and to improve the rheological properties of the blood. Hesylation of an antibody enables the prolongation of the circulation half-life by increasing the stability of the molecule, as well as by reducing renal clearance, resulting in an increased biological activity. By varying different parameters, such as the molecular weight of HES, a wide range of HES antibody conjugates can be customized.

Antibodies having an increased half-life in vivo can also be generated introducing one or more amino acid modifications (i.e., substitutions, insertions or deletions) into an IgG constant domain, or FcRn binding fragment thereof (preferably a Fc or hinge Fc domain fragment). See, e.g., International Publication No. WO 98/23289; International Publication No. WO 97/34631; and U.S. Pat. No. 6,277,375.

Further, antibodies can be conjugated to albumin (e.g., human serum albumin; HSA) in order to make the antibody or antibody fragment more stable in vivo or have a longer half life in vivo. The techniques are well-known in the art, see, e.g., International Publication Nos. WO 93/15199, WO 93/15200, and WO 01/77137; and European Patent No. EP 413,622. In addition, in the context of a bispecific antibody as described above, the specificities of the antibody can be designed such that one binding domain of the antibody binds to ANGPTL4 while a second binding domain of the antibody binds to serum albumin, preferably HSA.

The strategies for increasing half life is especially useful in nanobodies, fibronectin-based binders, and other antibodies or proteins for which increased in vivo half life is desired.

Antibody Conjugates

The present invention provides antibodies or fragments thereof that specifically bind to a ANGPTL4 protein recombinantly fused or chemically conjugated (including both covalent and non-covalent conjugations) to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. In particular, the invention provides fusion proteins comprising an antigen-binding fragment of an antibody described herein (e.g., a Fab fragment, Fd fragment, Fv fragment, F(ab)2 fragment, a VH domain, a VH CDR, a VL domain or a VL CDR) and a heterologous protein, polypeptide, or peptide. Methods for fusing or conjugating proteins, polypeptides, or peptides to an antibody or an antibody fragment are known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International Publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson, et al., 1999, J. Mol. Biol. 287:265-76; and Lorenzo and Blasco, 1998, Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. A polynucleotide encoding an antibody or fragment thereof that specifically binds to a ANGPTL4 protein may be recombined with one or more components, motifs, sections, parts, domains, fragments, etc. of one or more heterologous molecules.

Moreover, the antibodies or fragments thereof can be fused to marker sequences, such as a peptide to facilitate purification. In preferred embodiments, the marker amino acid sequence is a hexa-histidine peptide (SEQ ID NO: 154), such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexa-histidine (SEQ ID NO: 154) provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "flag" tag.

In other embodiments, antibodies of the present invention or fragments thereof conjugated to a diagnostic or detectable agent. Such antibodies can be useful for monitoring or prognosing the onset, development, progression and/or severity of a disease or disorder as part of a clinical testing procedure, such as determining the efficacy of a particular therapy. Such diagnosis and detection can accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidinlbiotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine (131I, 125I, 123I, and 121I), carbon (14C), sulfur (35S), tritium (3H), indium (115In, 113In, 112In, and 111In), technetium (99Tc), thallium (201Ti), gallium (68Ga, 67Ga), palladium (103Pd), molybdenum (99Mo), xenon (133Xe), fluorine (18F), 153Sm, 177Lu, 159Gd, 149Pm, 140La, 175Yb, 166Ho, 90Y, 47Sc, 186Re, 188Re, 142 Pr, 105Rh, 97Ru, 68Ge, 57Co, 65Zn, 85Sr, 32P, 153Gd, 169Yb, 51Cr, 54Mn, 75Se, 113Sn, and 117Tin; and positron emitting metals using various positron emission tomographies, and noradioactive paramagnetic metal ions.

The present invention further encompasses uses of antibodies or fragments thereof conjugated to a therapeutic moiety. An antibody or fragment thereof may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells.

Further, an antibody or fragment thereof may be conjugated to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, *pseudomonas* exotoxin, cholera toxin, or diphtheria toxin; a protein such as tumor necrosis factor, α-interferon, β-interferon, nerve growth factor, platelet derived growth factor, tissue plasminogen activator, an apoptotic agent, an anti-angiogenic agent; or, a biological response modifier such as, for example, a lymphokine.

Moreover, an antibody can be conjugated to therapeutic moieties such as a radioactive metal ion, such as alph-emiters such as 213Bi or macrocyclic chelators useful for conjugating radiometal ions, including but not limited to, 131In, 131LU, 131Y, 131Ho, 131Sm, to polypeptides. In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4(10):2483-90; Peterson et al., 1999, Bioconjug. Chem. 10(4):553-7; and Zimmerman et al., 1999, Nucl. Med. Biol. 26(8):943-50, each incorporated by reference in their entireties.

Techniques for conjugating therapeutic moieties to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119-58.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Methods of Producing Antibodies of the Invention

Nucleic Acids Encoding the Antibodies

The invention provides substantially purified nucleic acid molecules which encode polypeptides comprising segments or domains of the ANGPTL4-binding antibody chains described above. Some of the nucleic acids of the invention comprise the nucleotide sequence encoding the heavy chain variable region shown in SEQ ID NO: 13, 38, 58, 78, 98, 118, or 138, and/or the nucleotide sequence encoding the light chain variable region shown in SEQ ID NO: 23, 48, 68, 88, 108, 128, or 148. In a specific embodiment, the nucleic acid molecules are those identified in Table 1. Some other nucleic acid molecules of the invention comprise nucleotide sequences that are substantially identical (e.g., at least 65, 80%, 95%, or 99%) to the nucleotide sequences of those identified in Table 1. When expressed from appropriate expression vectors, polypeptides encoded by these polynucleotides are capable of exhibiting ANGPTL4 antigen binding capacity.

Also provided in the invention are polynucleotides which encode at least one CDR region and usually all three CDR regions from the heavy or light chain of the ANGPTL4-binding antibody set forth above. Some other polynucleotides encode all or substantially all of the variable region sequence of the heavy chain and/or the light chain of the ANGPTL4-binding antibody set forth above. Because of the degeneracy of the code, a variety of nucleic acid sequences will encode each of the immunoglobulin amino acid sequences.

The nucleic acid molecules of the invention can encode both a variable region and a constant region of the antibody. Some of nucleic acid sequences of the invention comprise nucleotides encoding a heavy chain sequence that is substantially identical (e.g., at least 80%, 90%, or 99%) to the heavy chain sequence set forth in SEQ ID NO: 15, 28, 40, 60, 80, 100, 120, and 140. Some other nucleic acid sequences comprising nucleotide encoding a light chain sequence that is substantially identical (e.g., at least 80%, 90%, or 99%) to the light chain sequence set forth in SEQ ID NO: 25, 50, 70, 90, 110, 130, and 150.

The polynucleotide sequences can be produced by de novo solid-phase DNA synthesis or by PCR mutagenesis of an existing sequence (e.g., sequences as described in the Examples below) encoding a ANGPTL4-binding antibody or its binding fragment. Direct chemical synthesis of nucleic acids can be accomplished by methods known in the art, such as the phosphotriester method of Narang et al., 1979, Meth. Enzymol. 68:90; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Mattila et al., Nucleic Acids Res. 19:967, 1991; and Eckert et al., PCR Methods and Applications 1:17, 1991.

Also provided in the invention are expression vectors and host cells for producing the ANGPTL4-binding antibodies described above. Various expression vectors can be employed to express the polynucleotides encoding the ANGPTL4-binding antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of the ANGPTL4-binding polynucleotides and polypeptides in mammalian (e.g., human) cells include pThioHis A, B & C, pcDNA3.1/His, pEBVHis A, B & C, (Invitrogen, San Diego, Calif.), MPSV vectors, and numerous other vectors known in the art for expressing other proteins. Useful viral vectors include vectors based on retroviruses, adenoviruses, adeno-associated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding a ANGPTL4-binding antibody chain or fragment. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of a ANGPTL4-binding antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted ANGPTL4-binding antibody sequences. More often, the inserted ANGPTL4-binding antibody sequences are linked to a signal sequences before inclusion in the vector. Vectors to be used to receive sequences encoding ANGPTL4-binding antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the ANGPTL4-binding antibody chains can be either prokaryotic or eukaryotic. *E. coli* is one prokaryotic host useful for cloning and expressing the polynucleotides of the present invention. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express ANGPTL4-binding polypeptides of the invention. Insect cells in combination with baculovirus vectors can also be used.

In some preferred embodiments, mammalian host cells are used to express and produce the ANGPTL4-binding polypeptides of the present invention. For example, they can be either a hybridoma cell line expressing endogenous immunoglobulin genes (e.g., the 1D6.C9 myeloma hybridoma clone as described in the Examples) or a mammalian cell line harboring an exogenous expression vector (e.g., the SP2/0 myeloma cells exemplified below). These include any normal mortal or normal or abnormal immortal animal or human cell. For example, a number of suitable host cell lines capable of secreting intact immunoglobulins have been developed including the CHO cell lines, various Cos cell lines, HeLa cells, myeloma cell lines, transformed B-cells and hybridomas. The use of mammalian tissue cell culture to express polypeptides is discussed generally in, e.g., Winnacker, FROM GENES TO CLONES, VCH Publishers, N.Y., N.Y., 1987. Expression vectors for mammalian host cells can include expression control sequences, such as an origin of replication, a promoter, and an enhancer (see, e.g., Queen, et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express ANGPTL4-binding antibody chains or binding fragments can be prepared using expression vectors of the invention which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Generation of Monoclonal Antibodies of the Invention

Monoclonal antibodies (mAbs) can be produced by a variety of techniques, including conventional monoclonal antibody methodology e.g., the standard somatic cell hybridization technique of Kohler and Milstein, 1975 Nature 256: 495. Many techniques for producing monoclonal antibody can be employed e.g., viral or oncogenic transformation of B lymphocytes.

Animal systems for preparing hybridomas include the murine, rat and rabbit systems. Hybridoma production in the mouse is a well established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art. See e.g., U.S. Pat. No. 5,225,539 to Winter, and U.S. Pat. Nos. 5,530,101; 5,585,089; 5,693,762 and 6,180,370 to Queen et al.

In a certain embodiment, the antibodies of the invention are humanized antibodies. Such humanized antibodies directed against ANGPTL4 can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode un-rearranged human heavy (μ and γ) and κ light chain immunoglobulin sequences, together with targeted mutations that inactivate the endogenous p and K chain loci (see e.g., Lonberg, et al., 1994 Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al., 1994 supra; reviewed in Lonberg, N., 1994 Handbook of Experimental Pharmacology 113:49-101; Lonberg, N. and Huszar, D., 1995 Intern. Rev. Immunol. 13: 65-93, and Harding, F. and Lonberg, N., 1995 Ann. N. Y. Acad. Sci. 764:536-546). The preparation and use of HuMAb mice, and the genomic modifications carried by such mice, is further described in Taylor, L. et al., 1992 Nucleic Acids Research 20:6287-6295; Chen, J. et at., 1993 International Immunology 5: 647-656; Tuaillon et al., 1993 Proc. Natl. Acad. Sci. USA 94:3720-3724; Choi et al., 1993 Nature Genetics 4:117-123; Chen, J. et al., 1993 EMBO J. 12: 821-830; Tuaillon et al., 1994 J. Immunol. 152:2912-2920; Taylor, L. et al., 1994 International Immunology 579-591; and Fishwild, D. et al., 1996 Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92103918, WO 93/12227, WO 94/25585, WO 97113852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchomosomes such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise ANGPTL4-binding antibodies of the invention. For example, an alternative transgenic system referred to as the Xenomouse (Abgenix, Inc.) can be used. Such mice are described in, e.g., U.S. Pat. Nos. 5,939,598; 6,075,181; 6,114,598; 6, 150,584 and 6,162,963 to Kucherlapati et al.

Moreover, alternative transchromosomic animal systems expressing human immunoglobulin genes are available in the art and can be used to raise ANGPTL4-binding antibodies of the invention. For example, mice carrying both a human heavy chain transchromosome and a human light chain tranchromosome, referred to as "TC mice" can be used; such mice are described in Tomizuka et al., 2000 Proc. Natl. Acad. Sci. USA 97:722-727. Furthermore, cows carrying human heavy and light chain transchromosomes have been described in the art (Kuroiwa et al., 2002 Nature Biotechnology 20:889-894) and can be used to raise ANGPTL4-binding antibodies of the invention.

Humanized antibodies of the invention can also be prepared using phage display methods for screening libraries of human immunoglobulin genes. Such phage display methods for isolating human antibodies are established in the art or described in the examples below. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Humanized antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Framework or Fc Engineering

Engineered antibodies of the invention include those in which modifications have been made to framework residues within VH and/or VL, e.g., to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis. Such "backmutated" antibodies are also intended to be encompassed by the invention.

Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al., 2001 J. Biol. Chem. 276:6591-6604).

In still another embodiment, the glycosylation of an antibody is modified. For example, an aglycoslated antibody can be made (i.e., the antibody lacks glycosylation). Glycosylation can be altered to, for example, increase the affinity of the antibody for "antigen". Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta(1, 4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180).

Methods of Engineering Altered Antibodies

As discussed above, the ANGPTL4-binding antibodies having VH and VL sequences or full length heavy and light chain sequences shown herein can be used to create new ANGPTL4-binding antibodies by modifying full length heavy chain and/or light chain sequences, VH and/or VL sequences, or the constant region(s) attached thereto. Thus, in another aspect of the invention, the structural features of a ANGPTL4-binding antibody of the invention are used to create structurally related ANGPTL4-binding antibodies that retain at least one functional property of the antibodies of the invention, such as binding to human ANGPTL4 and also inhibiting one or more functional properties of ANGPTL4 (e.g., inhibit ANGPTL4 binding to the ANGPTL4 receptor, inhibit ANGPTL4-dependent cell proliferation).

For example, one or more CDR regions of the antibodies of the present invention, or mutations thereof, can be combined recombinantly with known framework regions and/or other CDRs to create additional, recombinantly-engineered, ANGPTL4-binding antibodies of the invention, as discussed above. Other types of modifications include those described in the previous section. The starting material for the engineering method is one or more of the VH and/or VL sequences provided herein, or one or more CDR regions thereof. To create the engineered antibody, it is not necessary to actually prepare (i.e., express as a protein) an antibody having one or more of the VH and/or VL sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing a ANGPTL4-binding antibody consisting of a heavy chain variable region antibody sequence having a CDR1 sequence selected from the group consisting of SEQ ID NOs: 7, 32, 52, 72, 92, 112, and 132, a CDR2 sequence selected from the group consisting of SEQ ID NOs: 8, 33, 53, 73, 93, 113, and 133, and/or a CDR3 sequence selected from the group consisting of SEQ ID NOs: 9, 34, 54, 74, 94, 114, and 134; and a light chain variable region antibody sequence having a CDR1 sequence selected from the group consisting of SEQ ID NOs: 17, 42, 62, 82, 102, 122, and 142, a CDR2 sequence selected from the group consisting of SEQ ID NOs: 18, 43, 63, 83, 103, 123, and 143, and/or a CDR3 sequence selected from the group consisting of SEQ ID NOs: 19, 44, 64, 84, 104, 124, and 144; altering at least one amino acid residue within the heavy chain variable region antibody sequence and/or the light chain variable region antibody sequence to create at least one altered antibody sequence; and expressing the altered antibody sequence as a protein.

Accordingly, in another embodiment, the invention provides a method for preparing a ANGPTL4-binding antibody consisting of a heavy chain variable region antibody sequence having a CDR1 sequence selected from the group consisting of SEQ ID NOs: 10, 35, 55, 75, 95, 115, and 135, a CDR2 sequence selected from the group consisting of SEQ ID NOs: 11, 36, 56, 76, 96, 116, and 136, and/or a CDR3 sequence selected from the group consisting of SEQ ID NOs: 12, 37, 57, 77, 97, 117, and 137; and a light chain variable region antibody sequence having a CDR1 sequence selected from the group consisting of SEQ ID NOs: 20, 45, 65, 85, 105, 125, and 145, a CDR2 sequence selected from the group consisting of SEQ ID NOs: 21, 46, 66, 86, 106, 126, and 146, and/or a CDR3 sequence selected from the group consisting of SEQ ID NOs: 22, 47, 67, 87, 107, 127, and 147; altering at least one amino acid residue within the heavy chain variable region antibody sequence and/or the light chain variable region antibody sequence to create at least one altered antibody sequence; and expressing the altered antibody sequence as a protein.

Accordingly, in another embodiment, the invention provides a method for preparing a ANGPTL4-binding antibody optimized for expression in a mammalian cell consisting of: a full-length heavy chain antibody sequence having a sequence selected from the group of SEQ ID NOs: 15, 28, 40, 60, 80, 100, 120, and 140; and a full length light chain antibody sequence having a sequence selected from the group of 25, 50, 70, 90, 110, 130, and 150; altering at least one amino acid residue within the full length heavy chain antibody sequence and/or the full length light chain antibody sequence to create at least one altered antibody sequence; and expressing the altered antibody sequence as a protein. In one embodiment, the alteration of the heavy or light chain is in the framework region of the heavy or light chain.

The altered antibody sequence can also be prepared by screening antibody libraries having fixed CDR3 sequences or minimal essential binding determinants as described in US2005/0255552 and diversity on CDR1 and CDR2 sequences. The screening can be performed according to any screening technology appropriate for screening antibodies from antibody libraries, such as phage display technology.

Standard molecular biology techniques can be used to prepare and express the altered antibody sequence. The antibody encoded by the altered antibody sequence(s) is one that retains one, some or all of the functional properties of the ANGPTL4-binding antibodies described herein, which functional properties include, but are not limited to, specifically binding to human, cynomolgus, rat, and/or mouse ANGPTL4; and the antibody inhibit ANGPTL4-dependent cell proliferation in a F36E and/or Ba/F3-ANGPTL4R cell proliferation assay.

In certain embodiments of the methods of engineering antibodies of the invention, mutations can be introduced randomly or selectively along all or part of an ANGPTL4-binding antibody coding sequence and the resulting modified ANGPTL4-binding antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

In certain embodiments of the invention antibodies have been engineered to remove sites of deamidation. Deamidation is known to cause structural and functional changes in a peptide or protein. Deamidation can result in decreased bioactivity, as well as alterations in pharmacokinetics and antigenicity of the protein pharmaceutical. (*Anal Chem.* 2005 Mar. 1; 77(5):1432-9).

In certain embodiments of the invention the antibodies have been engineered to increase pI and inprove their drug-like properties. The pI of a protein is a key determinant of the overall biophysical properties of a molecule. Antibodies that have low pIs have been known to be less soluble, less stable, and prone to aggregation. Further, the purification of antibodies with low pI is challenging and can be problematic especially during scale-up for clinical use. Increasing the pI of the anti-ANGPTL4 antibodies, or Fabs, of the invention improved their solubility, enabling the antibodies to be formulated at higher concentrations (>100 mg/ml). Formulation of the antibodies at high concentrations (e.g. >100 mg/ml) offers the advantage of being able to administer higher doses of the antibodies into eyes of patients via intravitreal injections, which in turn may enable reduced dosing frequency, a significant advantage for treatment of chronic diseases including cardiovascular disorders. Higher pIs may also increase the FcRn-mediated recycling of the IgG version of the antibody thus enabling the drug to persist in the body for a longer duration, requiring fewer injections. Finally, the overall stability of the antibodies is significantly improved due to the higher pI resulting in longer shelf-life and bioactivity in vivo. Preferably, the pI is greater than or equal to 8.2.

The functional properties of the altered antibodies can be assessed using standard assays available in the art and/or described herein, such as those set forth in the Examples (e.g., ELISAs).

Prophylactic and Therapeutic Uses

Antibodies that binds ANGPTL4 as described herein, can be used at a therapeutically useful concentration for the treatment of a disease or disorder associated with increased ANGPTL4 levels and/or activity by administering to a subject in need thereof an effective amount of the antibodies or antigen binding fragments of the invention. The present invention provides a method of treating ANGPTL4-associated cardiovascular disorders by administering to a subject in need thereof an effective amount of the antibodies of the invention. The present invention provides a method of treating ANGPTL4-associated cardiovascular disorders by administering to a subject in need thereof an effective amount of the antibodies of the invention.

The antibodies of the invention can be used, inter alia, to prevent treat, prevent, and improve ANGPTL4 associated conditions or disorders, including but not limited to any number of conditions or diseases in which the ANGPTL4 protein levels are aberrantly high and/or in which a reduction of ANGPTL4 protein levels is sought. These conditions include but are not limited to those involving lipid metabolism, such as hyperlipidemia, hyperlipoproteinemia and dyslipidemia, including atherogenic dyslipidemia, diabetic dyslipidemia, hypertriglyceridemia (e.g., severe hypertriglyceridemia (e.g., with TG>1000 mg/dL), hypertriglyceridemia associated with obesity, and Type V hypertriglyceridemia) hypercholesterolemia, chylomicronemia, mixed dyslipidemia (obesity, metabolic syndrome, diabetes, etc.), lipodystrophy, lipoatrophy, and other conditions caused by, e.g., decreased LPL activity and/or LPL deficiency, decreased LDL receptor activity and/or LDL receptor deficiency, altered ApoC2, ApoE deficiency, increased ApoB, increased production and/or decreased elimination of very low-density lipoprotein (VLDL), certain drug treatment (e.g., glucocorticoid treatment-induced dyslipidemia), any genetic predisposition, diet, life style, and the like.

Other ANGPTL4-associated diseases or disorders associated with or resulting from hyperlipidemia, hyperlipoproteinemia, and/or dyslipidemia, include, but are not limited to, cardiovascular diseases or disorders, such as atherosclerosis, aneurysm, hypertension, angina, stroke, cerebrovascular diseases, congestive heart failure, coronary artery diseases, myocardial infarction, peripheral vascular diseases, and the like; acute pancreatitis; nonalcoholic steatohepatitis (NASH); blood sugar disorders, such as diabetes; obesity, and the like.

The antibodies of the invention can also be used in combination with other agents for the prevention, treatment, or improvement of ANGPTL4 associated disorders. For example, statin therapies may be used in combination with the ANGPTL4 antibodies and antigen binding fragments of the invention for the treatment of patients with triglyceride-related disorders.

Pharmaceutical Compositions

The invention provides pharmaceutical compositions comprising the ANGPTL4-binding antibodies (intact or binding fragments) formulated together with a pharmaceutically acceptable carrier. The compositions can additionally contain one or more other therapeutic agents that are suitable for treating or preventing, for example, cardiovascular disorders. Pharmaceutically acceptable carriers enhance or stabilize the composition, or can be used to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the present invention can be administered by a variety of methods known in the art. The route and/or mode of administration vary depending upon the desired results. It is preferred that administration be intravitreal, intravenous, intramuscular, intraperitoneal, or subcutaneous, or administered proximal to the site of the target. The pharmaceutically acceptable carrier should be suitable for intravitreal, intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

The composition should be sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions of the invention can be prepared in accordance with methods well known and routinely practiced in the art. See, e.g., Remington: The Science and Practice of Pharmacy, Mack Publishing Co., 20th ed., 2000; and Sustained and Controlled Release Drug Delivery Systems, J. R. Robinson, ed., Marcel Dekker, Inc., New York, 1978. Pharmaceutical compositions are preferably manufactured under GMP conditions. Typically, a therapeutically effective dose or efficacious dose of the ANGPTL4-binding antibody is employed in the pharmaceutical compositions of the invention. The ANGPTL4-binding antibodies are formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

A physician or veterinarian can start doses of the antibodies of the invention employed in the pharmaceutical composition at levels lower than that required to achieve the desired therapeutic effect and gradually increase the dosage until the desired effect is achieved. In general, effective doses of the compositions of the present invention, for the treatment of a cardiovascular disorders described herein vary depending upon many different factors, including means of administration, target site, physiological state of the patient, whether the patient is human or an animal, other medications administered, and whether treatment is prophylactic or therapeutic. Treatment dosages need to be titrated to optimize safety and efficacy. For systemic administration with an antibody, the dosage ranges from about 0.0001 to 100 mg/kg, and more usually 0.01 to 15 mg/kg, of the host body weight. For intravitreal administration with an antibody, the dosage may range from 0.1 mg/eye to 5 mg/eye. For example, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml, 2.1 mg/ml, 2.2 mg/ml, 2.3 mg/ml, 2.4 mg/ml, 2.5 mg/ml, 2.6 mg/ml, 2.7 mg/ml, 2.8 mg/ml, 2.9 mg/ml, 3.0 mg/ml, 3.1 mg/ml, 3.2 mg/ml, 3.3 mg/ml, 3.4 mg/ml, 3.5 mg/ml, 3.6 mg/ml, 3.7 mg/ml, 3.8 mg/ml, 3.9 mg/ml, 4.0 mg/ml, 4.1 mg/ml, 4.2 mg/ml, 4.3 mg/ml, 4.4 mg/ml, 4.5 mg/ml, 4.6 mg/ml, 4.7 mg/ml, 4.8 mg/ml, 4.9 mg/ml, or 5.0 mg/ml. An exemplary treatment regime entails systemic administration once per every two weeks or once a month or once every 3 to 6 months. An exemplary treatment regime entails systemic administration once per every two weeks or once a month or once every 3 to 6 months, or as needed (PRN).

Antibody is usually administered on multiple occasions. Intervals between single dosages can be weekly, monthly or yearly. Intervals can also be irregular as indicated by measuring blood levels of ANGPTL4-binding antibody in the patient. In addition alternative dosing intervals can be determined by a physician and administered monthly or as necessary to be efficacious. In some methods of systemic administration, dosage is adjusted to achieve a plasma antibody concentration of 1-1000 µg/ml and in some methods 25-500 µg/ml. Alternatively, antibody can be administered as a sustained release formulation, in which case less frequent administration is required. Dosage and frequency vary depending on the half-life of the antibody in the patient. In general, humanized antibodies show longer half life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

EXAMPLES

The following examples are provided to further illustrate the invention but not to limit its scope. Other variants of the invention will be readily apparent to one of ordinary skill in the art and are encompassed by the appended claims.

Example 1: Preparation of Purified Recombinant Human ANGPTL4 for use as Antigen and in Antibody Characterization Experiments A nucleic acid sequence encoding full-length human ANGPTL4 polypeptide (amino acids 26-406, matching NCBI sequence NM_139314.2) with N-terminal signal peptide from human IgG-kappa (MKTFILLLWVLLLWVIFLL-PGATA) (SEQ ID NO: 152), and C-terminal FLAG epitope (DYKDDDDKH) (SEQ ID NO: 153), hexahistidine purification tag (HHHHHH) (SEQ ID NO: 154), and Avi tag (i.e., BirA biotinylation sequence GGGLNDIFEAQKIEWHE) (SEQ ID NO: 155) was subcloned into the mammalian cell expression vector pRS5a to generate the plasmid pRS-Ikk-hANGPTL4(26-406)-FLAG-6HIS-Avi ('6HIS' disclosed as SEQ ID NO: 154) containing a 20 amino acid IKK signal sequence followed by amino acids 26-406 of human ANGPTL4 with carboxyl-terminal Flag, 6HIS (SEQ ID NO: 154), and Avi tags (Table 2, SEQ ID NO: 156).

For some preparations, the following procedures were used to express, purify, and biotinylate human ANGPTL4 protein (Method 1): Suspension adapted HEK293T cells were cultured in serum-free FreeStyle 293 expression medium (Life Technologies, catalog number 12338-018) and transfected with the plasmid pRS-Ikk-hANGPTL4(26-406)-FLAG-His6-Avi ('His6' disclosed as SEQ ID NO: 154) using polyethyleneimine transfection reagent (Polysciences, catalog number 23966). Five hours after transfection, heparin (Alfa Aesar, catalog number A16198) was added to the culture medium to a final concentration of 0.5 mg/ml. The cells were then cultured for 72-96 hours and the cell culture supernatant was then harvested by centrifugation at 4° C. and sterile-filtered using a 0.22 µm filter (Thermo, catalog number 567-0010). The filtered cell culture supernatant was then concentrated to about 100 ml by tangential flow filtration. The concentrated supernatant was diluted to a volume of 1 Liter with TBS-glycerol buffer (50 mM Tris-HCl, 150 mM NaCl, and 15% glycerol, pH 7.4), and the sample was concentrated to about 200 ml by tangential flow filtration. Anti-Flag M2 agarose resin (Sigma, catalog number 220102-177) pre-equilibrated with TBS-glycerol buffer was then added to the sample, and the resulting solution was gently mixed for 1 hr at 4° C. The agarose resin was then washed 5 times with 25 ml TB S-glycerol, and the bound ANGPTL4 protein was eluted with 20 ml TBS-glycerol containing 0.2 mg/ml Flag peptide (Sigma, catalog number 220176-317). Peroxide-free Tween-20 (AppliChem, catalog number A1284,0025 was added to the eluted protein solution to a final concentration of 0.1%, and the resulting solution was loaded onto a 5 ml HiTrap heparin column (GE Lifesciences, catalog number 17-0407-01) that was pre-equilibrated in TBS-glycerol containing 0.1% Tween-20 (Buffer A). The column was washed with 50 ml Buffer A, followed by 50 ml Buffer A containing 300 mM NaCl. ANGPTL4 protein was then eluted with 20 ml Buffer A containing 600 mM NaCl. The eluted protein was concentrated using a centrifugal concentrator with a 30 kDa molecular weight cutoff (Amicon Ultra, catalog number UFC903024). The purity of the purified ANGPTL4 protein as assessed by SDS-PAGE was >90%.

For some applications, ANGPTL4 proteins were site-specifically biotinylated on the C-terminal Avi tag using 10 µg purified biotin-protein ligase (BirA) (Avidity) per mg of ANGPTL4. The buffer was supplemented with final concentrations of 10 mM ATP, 10 mM magnesium acetate, and 0.5 M d-biotin. The reaction mixture was incubated for 2 hr at 30° C. and then overnight at 4° C., then loaded onto a HiLoad Superdex 200 column (26 mm×600 mm) (GE Lifesciences, catalog number 28-9893-36) that was equilibrated in Buffer A. Fractions from the Superdex 200 column were analyzed using SDS-PAGE, and ANGPTL4 containing fractions were pooled and concentrated using a centrifugal concentrator.

For other preparations, the following procedures were used to express, purify, and biotinylate the human ANGPTL4 protein (Method 2). Plasmid pRS-Ikk-hANGPTL4(26-406)C-Flag6HisAvi ('6His' disclosed as SEQ ID NO: 154) was transiently transfected into HEK293T cells using standard polyethylenimine (PEI) transfection methods. Cells were propagated in suspension culture in Freestyle 293 expression media and transfection was carried out at $1\times10^6$ cells/ml final cell concentration in 4 liters media using 1 liter flasks. Five hours after transfection, heparin at a final concentration of 500 µg/ml was added. Cells were grown at 37° C. and 5% $CO_2$ for 72 hr. Cells were then pelleted by centrifugation, and the supernatant passed through a 0.22 µm sterile filter. The clarified supernatant was concentrated and buffer exchanged into Buffer B (50 mM Tris-HCl, 150 mM NaCl, 10% glycerol, 10 mM imidazole, pH 7.4) using tangential flow filtration (TFF). The concentrated sample was then passed over a 5 ml Ni-NTA affinity column equilibrated with Buffer C (50 mM Tris.HCl, 150 mM NaCl, 10% glycerol, 10 mM imidazole, 0.1% n-octyl-β-maltoside, pH 7.4). After loading the sample, the column was washed with the same buffer until baseline absorbance at 280 nm was reached. The bound ANGPTL4 protein was then eluted by using a gradient of imidazole (10 mM to 500 mM). Elution fractions that contained human ANGPTL4 were pooled, concentrated using an Amicon concentrator (molecular weight cut-off 10 kD), buffered-exchanged using PD-10 columns into storage buffer (50 mM Tris-HCl, 150 mM NaCl, 15% Glycerol, pH 7.4), aliquoted, flash frozen in liquid nitrogen, and stored at −80° C. The purity of the purified human ANGPTL4 protein as assessed by SDS-PAGE was >90%.

For some applications, purified ANGPTL4 protein prepared as described above was site-specifically biotinylated as follows: purified protein in 50 mM Bicine, pH 8.3 buffer at a final concentration of approximately 1 mg/mL was incubated in the presence of 10 mM ATP, 10 mM magnesium acetate, 0.1 mM biotin, and BirA biotin ligase (Avidity) at 30° C. for 1 hr and then at 4° C. overnight. The protein was then concentrated using an Amicon concentrator (molecular weight cut-off 10 kD), buffer-exchanged using PD-10 columns into storage buffer (50 mM Tris-HCl, 150 mM NaCl, 15% glycerol, pH 7.4), aliquoted, flash frozen in liquid nitrogen, and stored at −80° C.

Example 2: Preparation of Purified Recombinant Human ANGPTL4 N-terminal Coiled-coil Domain Protein for use in Antibody Characterization Experiments Expression, purification, and biotinylation of the N-terminal coiled coil domain of human ANGPTL4 (amino acids 26-161) was carried out using essentially the same methods described for human full-length human ANGPTL4 in Example 1, Method 2. The sequence of the purified human ANGPTL4 N-terminal domain protein is shown in Table 2 (SEQ ID NO: 157).

TABLE 2

Amino acid sequences of human ANGPTL4(26-406)-FLAG-His6-Avi ('His6' disclosed as SEQ ID NO: 154) (the signal peptide is highlighted by underlining, and the N-terminal QP sequence after the signal peptide and the C-terminal FLAG-His6-Avi ('His6' disclosed as SEQ ID NO: 154) sequences are highlighted with italics)

| Construct | SEQ ID NO. | Amino Acid Sequence |
|---|---|---|
| Human ANGPTL4(26-406)-FLAG-His6-Avi ('His6' disclosed as SEQ ID NO: 154) | 156 | MKTFILLLWVLLLWVIFLLPGATA*QP*GPVQSK SPRFASWDEMNVLAHGLLQLGQGLREHAERTR SQLSALERRLSACGSACQGTEGSTDLPLAPES RVDPEVLHSLQTQLKAQNSRIQQLFHKVAQQQ RHLEKQHLRIQHLQSQFGLLDHKHLDHEVAKP ARRKRLPEMAQPVDPAHNVSRLHRLPRDCQEL FQVGERQSGLFEIQPQGSPPFLVNCKMTSDGG WTVIQRRHDGSVDFNRPWEAYKAGFGDPHGEF WLGLEKVHSITGDRNSRLAVQLRDWDGNAELL QFSVHLGGEDTAYSLQLTAPVAGQLGATTVPP SGLSVPFSTWDQDHDLRRDKNCAKSLSGGWWF GTCSHSNLNGQYFRSIPQQRQKLKKGIFWKTW RGRYYPLQATTMLIQPMAAEEAAS*DYKDDDDKH HHHHHGGGLNDIFEAQKIEWHE* |
| Human ANGPTL4(26-161)-FLAG-His6-Avi ('His6' disclosed as SEQ ID NO: 154) | 157 | MKTFILLLWVLLLWVIFLLPGATA*QP*GPVQSK SPRFASWDEMNVLAHGLLQLGQGLREHAERTR SQLSALERRLSACGSACQGTEGSTDLPLAPES RVDPEVLHSLQTQLKAQNSRIQQLFHKVAQQQ RHLEKQHLRIQHLQSQFGLLDHKHLDHEVAKP ARRKRLPEMAQPVDPAHNVSRLHRLPR*DYKDD DDKHHHHHHDYKDDDDKHHHHHHGGGLNDIFE AQKIEWHE* |

Example 3: Preparation and Screening of Monoclonal Antibodies

Recombinant human ANGPTL4 protein was prepared in-house as described in Example 1, and was used as immunogen for the generation of anti-ANGPTL4 hybridoma clones. Bcl-2 transgenic mice were immunized with recombinant human ANGPTL4 according to a standard rapid immunization protocol. Hybridomas were generated by using a standard electrofusion-based method.

CHO-K1PD cells stably expressing human ANGPTL4 fused to a transmembrane domain were generated using standard methods. Due to the presence of the transmembrane domain, these cells display ANGPTL4 on the cell surface. Therefore, binding of antibodies to ANGPTL4 on the surface of these cells can be detected using flow cytometry.

Hybridoma supernatants were screened by detecting binding of antibodies present in the supernatant to human ANGPTL4 expressed on the surface of CHO-K1PD cells. Binding of antibodies to the cells was detected using a fluorescently labeled anti-mouse secondary antibody and flow cytometry. Parental CHO-K1PD cells that do not express ANGPTL4 were used as a negative control. For hybridomas that bound to ANGPTL4, antibodies were purified from cell supernatants using standard methods, and the resulting enriched supernatant was tested in the flow cytometry assay with CHO-K1PD/ANGPTL4 and CHO-K1PD-Parental cells.

ANGPTL4 antibody titers in hybridoma supernatants were determined by using a standard direct ELISA assay, in which recombinant human ANGPTL4 protein was immobilized on the surface of the ELISA plate. Confirmed positive hybridomas were subcloned, and the sequences of the monoclonal antibodies produced by these hybridomas was determined using standard methods.

The monoclonal antibodies 14P18, 1761, 19C16 and 37P1 were subsequently shown to inhibit human ANGPTL4 mediated inhibition of human lipoprotein lipase using methods described in Example 7 below. The nucleotide and amino acid sequences of the heavy and light chain variable regions of 14P18, 1761, 19C16 and 37P1 were determined using standard methods.

Example 4: Humanization of Monoclonal Antibodies

The process of humanization is well described in the art (Jones, et al 1986, Queen, et al 1989, Riechmann, et al 1988, Verhoeyen, Milstein and Winter 1988). The term humanization is described as the transfer of the antigen-binding site of a non-human antibody, e.g., a murine derived antibody, to a human acceptor framework, e.g., a human germline sequence (Retter, et al 2005). The main rationale for humanizing an antibody is to minimize the risk of developing an immunogenic response towards the antibody when the antibody is administered as a therapeutic in humans (Rebello, et al 1999).

The antigen-binding site comprises the complementary determining regions (CDRs) (Chothia and Lesk 1987, Kabat, et al 1991) and positions in the framework region of the variable domains (VL and VH) that directly or indirectly affect binding. Framework residues that may directly affect binding can, for example, be found in the so called "outer" loop region located between CDR2 and CDR3. Residues that indirectly affect binding are for example found at so called Vernier Zones (Foote and Winter 1992). They are thought to support CDR conformation. Those positions outside the CDRs are taken into account when choosing a suitable acceptor framework to minimize the number of deviations of the final humanized antibody to the human germline acceptor sequence in the framework regions.

Example 5: Antibody Sequence Optimization and Affinity Maturation

Certain amino acid sequence motifs are known to undergo post-translational modification (PTM) such as glycosylation (e.g., NxS/T, where x is any amino acid except P), oxidation of free cysteines, deamidation (e.g., deamidation of N in NG sequences) or isomerization (e.g., at DG sequences). If present in the CDR regions, those motifs are ideally removed by site-directed mutagenesis in order to increase product homogeneity.

The process of affinity maturation is well described in the art. Among many display systems, phage display (Smith 1985) and display on eukaryotic cells such as yeast (Boder and Wittrup 1997) are the most commonly applied systems to select for antibody-antigen interaction. Advantages of these display systems are that they are suitable for a wide range of antigens and that the selection stringency can be easily adjusted. In phage display, scFv or Fab fragments can be displayed and in yeast display scFv, Fab or full-length IgG can be displayed. These commonly applied methods allow selection of desired antibody variants from larger libraries with diversities of more than $1 \times 10^7$. Libraries with smaller diversity (e.g. 1,000) may be screen by microexpression and ELISA.

Non-targeted or random antibody variant libraries can be generated for example by error-prone PCR (Cadwell and Joyce 1994) and provide a very simple, but sometimes limited approach. Another strategy is the CDR directed diversification of an antibody candidate. One or more positions in one or more CDRs can be targeted specifically using for example degenerate oligonucleotides (Thompson, et al 1996), trinucleotide mutagenesis (TRIM) (Kayushin, et al 1996), or any other approach known to the art.

Example 6: Expression and Purification of Humanized Antibodies

DNA sequences coding for humanized VL and VH domains were ordered at GeneArt (Life Technologies, Inc., Regensburg, Germany) including codon optimization for *Homo Sapiens*. Sequences coding for VL and VH domains were subcloned by cutting and pasting from the GeneArt derived vectors into expression vectors suitable for expression and secretion by mammalian cells. The heavy and light chains were cloned into individual expression vectors to allow co-transfection. Elements of the expression vector include a promoter (Cytomegalovirus (CMV) enhancer-promoter), a signal sequence to facilitate secretion, a polyadenylation signal and transcription terminator (from the Bovine Growth Hormone (BGH) gene), an element allowing episomal replication and replication in prokaryotes (e.g., SV40 origin and ColE1 or others known in the art) and elements to allow selection (ampicillin resistance gene and zeocin marker).

Human Embryonic Kidney cells constitutively expressing the SV40 large T antigen (HEK293-T ATCC11268) are one of the preferred host cell lines for transient expression of humanized and/or optimized IgG proteins. Transfection is performed using PEI (Polyethylenimine, MW 25,000 linear, Polysciences, USA, catalog number 23966) as transfection reagent. The PEI stock solution is prepared by carefully dissolving 1 g of PEI in 900 ml cell culture grade water at room temperature (RT). To facilitate dissolution of PEI, the solution is acidified by addition of HCl to pH 3-5, followed by neutralization with NaOH to a final pH of 7.05. Finally, the volume is adjusted to 1 L and the solution is filtered through a 0.22 µm filter, aliquotted and frozen at −80° C. until further use. HEK 293T cells are cultivated using a Novartis proprietary serum-free culture medium for transfection and propagation of the cells, and ExCell VPRO serum-free culture medium (SAFC Biosciences, USA, Cat. No. 24561C) as production/feed medium. Cells prepared for transient transfections are cultivated in suspension culture.

For small scale (<5 L) transfections, cells are grown in Corning shake flasks (Corning, Tewksbury, Mass.) on an orbital shaker (100-120 rpm) in a humidified incubator at 5% $CO_2$ (seed flasks). Cells in the seed cultures should be maintained in the exponential growth phase (cell densities between $5 \times 10^5$/ml and $3 \times 10^6$/ml) and display a viability of >90% for transfection. For small scale (<5 L) transfection an aliquot of cells is taken out of the seed cultures and adjusted to $1.4 \times 10^6$ cells/ml in 36% of the final volume with Novartis serum-free culture medium. The DNA solution (Solution 1:0.5 mg of heavy chain and 0.5 mg of light chain expression plasmid for a 1 L transfection) is prepared by diluting the DNA to 1 mg/l (final volume) in 7% of the final culture volume followed by gentle mixing. To prevent bacterial contamination, this solution is filtered using a 0.22 µm filter (e.g., Millipore Stericup). Then 3 mg/L (final volume) of PEI solution is also diluted in 7% of final culture volume and mixed gently (Solution 2). Both solutions are incubated for 5-10 min at room temperature (RT). Thereafter solution 2 is added to solution 1 with gentle mixing and incubated for another 5-15 minutes at room temperature. The transfection mix is then added to the cells and the cultivation of cells is continued for 4 to 6 hours. Finally, the remaining 50% of total production volume is achieved by addition of ExCell® VPRO serum-free culture medium. The cell cultivation is continued for eleven days post-transfection.

The culture is harvested by centrifugation at 4500 rpm for 20 minutes at 4° C. (Heraeus®, Multifuge 3 S-R, Thermo Scientific, Rockford, Ill.). The cell supernatant recovered is sterile-filtered through a stericup filter (0.22 µm) and stored at 4° C. until further processing. Purification was performed on an "ÄKTA 100 Explorer Air" chromatography system at 4° C. in a cooling cabinet, using a freshly sanitized (0.25 M NaOH) HiTrap 5 ml Protein A MabSelect®SuRe column. The column was equilibrated with 5 column volumes of phosphate buffered saline (PBS, Gibco, Life Technologies, Carlsbad, Calif.), and then the sterile-filtered supernatant was loaded at 4.0 ml/min. The column was washed with 13 column volumes of PBS. Antibody was then eluted with 5 column volumes of 50 mM citrate, 70 mM NaCl, pH 3.2. The eluate was collected in 3 ml fractions and adjusted to pH 7 with 1 M Tris-HCl, pH 10. The antibody containing fractions were pooled and sterile-filtered (Millipore Steriflip, 0.22 µm), the OD 280 nm was measured using a spectrophotometer (NanoDrop ND-1000), and the protein concentration was calculated based on the OD 280 and the molar extinction coefficient which was calculated based on the protein sequence. The eluate was tested for aggregation by size exclusion chromatography with multi-angle light scattering detector (SEC-MALS) and purity was assessed by gel electrophoresis (SDS-PAGE), endotoxin assay (LAL) and mass spectrometry (MS). For the second purification step, if needed, antibody from the first purification was loaded onto a freshly sanitized (0.5 M NaOH) gel viltration column (Hi Load 16/60 Superdex 200, 120 mL, GE-Helthcare). The column was equilibrated with PBS and the run was done with PBS buffer at a flow rate of 1 ml/min. The eluate was collected in 1.2 ml fractions. Antibody containing proteins were pooled, and the resulting purified antibody analyzed as described for the first purification step.

Using the methods described above, the following humanized antibodies were prepared, expressed and purified: NEG276, NEG276-LALA, NEG278, NEG310, NEG318, NEG318-LALA, NEG319, NEG313, and NEG315. The framework and parental antibodies for these humanized antibodies is shown in Table 3, and the nucleotide and amino acid sequences are shown in Table 1. All humanized antibodies were prepared as human IgG1 antibodies, except for NEG276-LALA and NEG318-LALA, which were prepared using a modified Fc region (human IgG1-LALA) in which the Leu234-Leu235 sequence in the heavy chain is replaced by Ala234-Ala235. Human IgG1-LALA antibodies are known to have reduced antibody effector function compared to wild-type human IgG1 antibodies.

TABLE 3

Humanized ANGPTL4 antibodies of the invention.

| Antibody | VH SEQ ID NO. | VL SEQ ID NO. | Framework | Parental Antibody |
|---|---|---|---|---|
| NEG276 | 13 | 23 | hIgG1/kappa | 19C16 |
| NEG276-LALA | 13 | 23 | hIgG1-LALA/kappa | 19C16 |
| NEG278 | 38 | 48 | hIgG1/kappa | 19C16 |
| NEG310 | 58 | 68 | hIgG1/kappa | 17B1 |
| NEG313 | 78 | 88 | hIgG1/kappa | 37P1 |
| NEG315 | 98 | 108 | hIgG1/kappa | 37P1 |
| NEG318 | 118 | 128 | hIgG1/kappa | 14P18 |
| NEG319 | 138 | 148 | hIgG1/kappa | 14P18 |

Example 7: Human Lipoprotein Lipase Assay

HEK 293T cells cultured in FreeStyle expression medium (Invitrogen) were transfected with a mammalian expression plasmid encoding full-length human lipoprotein lipase (LPL) polypeptide (matching NCBI sequence NM_000237.2) using a standard polyethyleneimine (PEI) transfection method. At 24 hours after transfection, heparin was added to the culture medium to a final concentration of 3 U/ml, to enhance release of secreted hLPL from the cell surface. At 60 hours post-transfection, the culture medium was collected, filtered using a 0.2 µm filter, and glycerol was added to a final concentration of 10% v/v. The resulting solution was loaded onto a 5 ml Heparin Sepharose HiTrap column (GE) which had been pre-equilibrated with Buffer A (50 mM Tris-HCl, 200 mM NaCl, 10% v/v glycerol, pH7.2). The column was washed with Buffer A, and human LPL protein was then eluted with step gradients of 500 mM NaCl, 1M NaCl, and 2M NaCl in Buffer A. The purest and most catalytically active human LPL eluted at 2M NaCl. Aliquots of purified human LPL were flash-frozen and stored at −80° C. until use.

The following protocol was used to assess the ability of antibodies of the invention to block ANGPTL4 inhibition of human lipoprotein lipase. The 384-well assay plate (Corning, catalog number 3573) and sample plate (Greiner Bio-one, catalog number 781201) were washed with 1% bovine serum albumin (BSA) (0.1 ml per well) for 30 min at room temperature. The plates were then washed twice with 0.05% Tween-20 solution.

ANGPTL4 antibody in 100 mM HEPES, pH 7.0 (20 µl per well, serial dilution with final assay concentrations ranging from 0.02 to 500 nM) was added to the sample plate, followed by 20 µl human ANGPTL4 protein (10 nM final assay concentration) in Assay Buffer (100 mM HEPES, 2 mM $MgCl_2$, pH 7.0), and the plate was incubated for 20 min at room temperature with gentle shaking. Lipoprotein lipase diluted in Assay Buffer (20 µl) was then added and the plate was incubated for 10 min at room temperature with gentle shaking.

A Coupling Enzyme Mix containing acyl-coenzyme A oxidase (Sekisui Diagnostics, catalog number T-17), acyl-Coenzyme A synthetase (Sekisui Diagnostics, catalog number T-16), and horseradish peroxidase (Sekisui Diagnostics), ATP (Sigma, catalog number A7699) and coenzyme A (MP Biomedicals, catalog number 100493) in Assay Buffer was prepared. Catalase agarose beads (Sigma, catalog number C9284) were added to the Coupling Enzyme Mix, and the mixture was incubated at 4° C. for 30 min with shaking, and the catalase agarose beads were then removed by centrifugation.

Human VLDL (Millipore, catalog number LP1) was diluted in Assay Buffer, treated with catalase agarose beads for 30 min, and the beads were removed from the solution by centrifugation. Amplex Red (Invitrogen, catalog number A12222) in Assay Buffer was added to a concentration of 33 µM.

To the solution in the sample plate containing LPL, ANGPTL4 and ANGPTL4 antibody, Coupling Enzyme Mix (20 µl) was added, and 54 µl of the resulting solution was transferred to the assay plate. To initiate the lipoprotein lipase reaction, VLDL/Amplex Red solution (18 µl) was added, and resorufin fluorescence was monitored continuously for 30 minutes using an EnVision multiwell plate reader (Perkin Elmer). Final assay concentrations were: 9.4 nM ANGPTL4, ~4 nM human lipoprotein lipase, 2.3 µg/ml human VLDL, 0.75 mM ATP, 90 µM coenzyme A, 0.5 U/ml ACO, 1.25 U/ml ACS, 1.2 U/ml HRP, and 10 µM Amplex Red.

The resulting resorufin fluorescence vs. time data was used to determine lipoprotein lipase enzyme activity (initial rate) for each sample. Control samples without LPL (background control) or without ANGPTL4 or ANGPTL4 antibodies (LPL activity control) were used to normalize the enzyme activity, which was expressed as a percentage of the LPL control activity. Enzyme activity data for different ANGPTL4 antibody concentrations was plotted using GraphPad Prism software, and the data was fitted to generate an $EC_{50}$ value for the ANGPTL4 antibody-mediated increase in lipoprotein lipase enzyme activity. In this assay, human ANGPTL4 at 10 nM concentration typically inhibited LPL activity by 70-95%. ANGPTL4 antibodies of the invention dose-dependently reversed LPL inhibition by ANGPTL4. EC50 results from this assay are shown in Table 4. Representative data for selected antibodies of the invention is shown in FIG. 1.

TABLE 4

ANGPTL4 antibodies of the invention block human ANGPTL4 inhibition of lipoprotein lipase (LPL).

| Antibody | Human ANGPTL4 $EC_{50}$ (nM) |
|---|---|
| NEG276 | 0.6 |
| NEG276-LALA | 0.7 |
| NEG278 | 0.7 |
| NEG310 | 1.6 |
| NEG313 | 3 |
| NEG315 | 3 |
| NEG318 | 1.4 |
| NEG319 | 0.5 |

Example 8: Preparation of Cynomolgus Monkey, Mouse and Rat ANGPTL4 and Human ANGPTL3 Proteins for use in Antibody Characterization The sequence of cynomolgus monkey ANGPTL4 was determined by amplifying the gene sequence from a cynomolgus monkey liver cDNA library (Biochain, catalog number C1534149-Cy, lot no B409051). The primers 5-UT-Cyno 5'-ATCCCCGCTCCCAGGCTAC-3' (SEQ ID NO: 158) and 3-UT-cyno 5'-CAGCAAGGAGTGAAG-CTCCATGCC-3' (SEQ ID NO: 159) were designed based on the 5' and 3' untranslated regions of human ANGPTL4 cDNA (NCBI sequence NM_139314.2). The gel purified PCR product was ligated into pCR4-Blunt-TOPO (Life Technologies, catalog number K2875-40) and sequenced. The cloned cynomolgus monkey ANGPTL4 cDNA encoded a 406 amino acid protein with 95% homology to human ANGPTL4. The nucleic acid sequence encoding amino acids 26-406 of cynomolgus monkey ANGPTL4 was subcloned into the mammalian expression vector pRS5, to produce the plasmid pRS-Ikk-cynoANGPTL4(26-406)-FLAG-6HIS-Avi ('6HIS' disclosed as SEQ ID NO: 154), which has a 20 amino acid Ikk signal sequence, amino acids 26-406 of cyno ANGPTL4, and carboxyl-terminal FLAG, 6HIS (SEQ ID NO: 154), and Avi tags (SEQ ID NO: 160 in Table 5).

The cynomolgus monkey ANGPTL4(26-406)-FLAG-6HIS-Avi protein ('6HIS' disclosed as SEQ ID NO: 154) was expressed and purified using similar methods as described for human ANGPTL4(26-406)-FLAG-6HIS-Avi protein ('6HIS' disclosed as SEQ ID NO: 154) in Example 1. For some applications, the purified cynomolgus monkey ANGPTL4 protein was site-specifically biotinylated using a similar as described for human ANGPTL4 protein in Example 1. The purity of the purified cynomolgus monkey ANGPTL4 protein as assessed by SDS-PAGE was >90%.

Cynomolgus monkey ANGPTL4(26-161)-FLAG-6HIS-Avi protein ('6HIS' disclosed as SEQ ID NO: 154) was prepared using similar methods. The sequence of the cyno ANGPTL4(26-161) protein encoded by its corresponding expression construct is shown in Table 5 (SEQ ID NO: 161).

Expression, purification, and biotinylation of mouse ANGPTL4 (amino acids 26-410) and rat ANGPTL4 (amino acids 24-405) was carried out using essentially the same methods as described for human ANGPTL4 in Example 1, Method 2. The sequences of the mouse and rat ANGPTL4 proteins encoded by the corresponding expression constructs is shown in Table 5 (SEQ ID NO: 162 and 163, respectively). The purity of the purified mouse ANGPTL4 and rat ANGPTL4 proteins as assessed by SDS-PAGE was >90%.

ANGPTL3 (SEQ ID NO: 5, Table 1) is a human protein that is closely related to ANGPTL4. To enable evaluation of possible binding of antibodies of the invention to ANGPTL3, a human ANGPTL3(14-460)-FLAG-His-Avi protein (SEQ ID NO: 164, Table 5) was expressed, purified and biotinylated using similar methods as described for human ANGPTL4 in Example 1, Method 2.

TABLE 5

Amino acid sequences of cynomolgus monkey ANGPTL4(26-406)-FLAG-His6-Avi ('His6' disclosed as SEQ ID NO: 154), mouse ANGPTL4(26-410)-FLAG-His6-Avi ('His6' disclosed as SEQ ID NO: 154), rat ANGPTL4(24-405)-FLAG-His6-Avi ('His6' disclosed as SEQ ID NO: 154), and human ANGPTL3(17-460)-FLAG-His-Avi (signal peptides are highlighted by underlining, and the N-terminal QP sequence after the signal peptide and the C-terminal FLAG-His6-Avi sequences ('His6' disclosed as SEQ ID NO: 154) are highlighted with italics)

| Construct | SEQ ID NO. | Amino Acid Sequence |
|---|---|---|
| Cynomolgus monkey ANGPTL4(26-406)-FLAG-His6-Avi ('His6' disclosed as SEQ ID NO: 154) | 160 | MKTFILLLWVLLLWVIFLLPGATA*QP*GPVQSKSPRFASWDEMNVLAH GLLQLGQGLREHAERTRSQLNALERRLSACGSACQGTEGSTALPLAP ESRVDPEVLHSLQTQLKAQNSRIQQLFHKVAQQQRHLEKQHLRIQRL QSQVGLLDPKHLDHEVAKPARRKRRPEMAQPVDSAHNASRLHRLPRD CQELFEDGERQSGLFEIQPQGSPPFLVNCKMTSDGGWTVIQRRHDGS VDFNRPWEAYKAGFGDPQGEFWLGLEKVHSITGDRNSRLAVQLQDWD GNAESLQFSVHLGGEDTAYSLQLTEPVASQLGATTVPPSGLSVPFST WDQDHDLRRDKNCAKSLSGGWWFGTCSHSNLNGQYFRSIPQQRQELK KGIFWKTWRGRYYPLQATTMLIQPTAAEAAS*DYKDDDDKHHHHHHGG GLNDIFEAQKIEWHE* |
| Cynomolgus monkey ANGPTL4(26-161)-FLAG-His6-Avi ('His6' disclosed as SEQ ID NO: 154) | 161 | MKTFILLLWVLLLWVIFLLPGATA*QP*GPVQSKSPRFASWDEMNVLAH GLLQLGQGLREHAERTRSQLNALERRLSACGSACQGTEGSTALPLAP ESRVDPEVLHSLQTQLKAQNSRIQQLFHKVAQQQRHLEKQHLRIQRL QSQVGLLDPKHLDHEVAKPARRKRRPEMAQPVDSAHNASRLHRLPRD *YKDDDDKHHHHHHGGGLNDIFEAQKIEWHE* |
| Mouse ANGPTL4(26-410)-FLAG-His6-Avi ('His6' disclosed as SEQ ID NO: 154) | 162 | MKTFILLLWVLLLWVIFLLPGATA*QP*RPAQPEPPRFASWDEMNLLAH GLLQLGHGLREHVERTRGQLGALERRMAACGNACQGPKGKDAPFKDS EDRVPEGQTPETLQSLQTQLKAQNSKIQQLFQKVAQQQRYLSKQNLR IQNLQSQIDLLAPTHLDNGVDKTSRGKRLPKMTQLIGLTPNATHLHR PPRDCQELFQEGERHSGLFQIQPLGSPPFLVNCEMTSDGGWTVIQRR LNGSVDFNQSWEAYKDGFGDPQGEFWLGLEKMHSITGNRGSQLAVQL QDWDGNAKLLQFPIHLGGEDTAYSLQLTEPTANELGATNVSPNGLSL PFSTWDQDHDLRGDLNCAKSLSGGWWFGTCSHSNLNGQYFHSIPRQR QERKKGIFWKTWKGRYYPLQATTLLIQPMEATAAS*DYKDDDDKHHHH HHGGGLNDIFEAQKIEWHE* |
| Rat ANGPTL4(24-405)-FLAG-His6-Avi ('His6' disclosed | 163 | MKTFILLLWVLLLWVIFLLPGATA*QP*QGRPAQPEPPRFASWDEMNLL AHGLLQLGHGLREHVERTRGQLGALERRMAACGNACQGPKGTDPKDR VPEGQAPETLQSLQTQLKAQNSKIQQLFQKVAQQQRYLSKQNLRIQN |

TABLE 5-continued

Amino acid sequences of cynomolgus monkey ANGPTL4(26-406)-FLAG-His6-Avi ('His6' disclosed as SEQ ID NO: 154), mouse ANGPTL4(26-410)-FLAG-His6-Avi ('His6' disclosed as SEQ ID NO: 154), rat ANGPTL4(24-405)-FLAG-His6-Avi ('His6' disclosed as SEQ ID NO: 154), and human ANGPTL3(17-460)-FLAG-His6-Avi (signal peptides are highlighted by underlining, and the N-terminal QP sequence after the signal peptide and the C-terminal FLAG-His6-Avi sequences ('His6' disclosed as SEQ ID NO: 154) are highlighted with italics)

| Construct | SEQ ID NO. | Amino Acid Sequence |
|---|---|---|
| as SEQ ID NO: 154) | | LQSQIDLLTPTHLDNGVDKTSRGKRLPKMAQLIGLTPNATRLHRPPR DCQELFQEGERHSGLFQIQPLGSPPFLVNCEMTSDGGWTVIQRRLNG SVDFNQSWEAYKDGFGDPQGEFWLGLEKMHSITGDRGSQLAVQLQDW DGNAKLLQFPIHLGGEDTAYSLQLTEPTANELGATNVSPNGLSLPFS TWDQDHDLRGDLNCAKSLSGGWWFGTCSHSNLNGQYFHSIPRQRQQR KKGIFWKTWKGRYYPLQATTLLIQPMEATAA*SDYKDDDDKHHHHHHG GGLNDIFEAQKIEWHET* |
| Human ANGPTL3(17-460) | 164 | <u>MKTFILLLWVLLLWVIFLLPGATA</u>*QP*SRIDQDNSSFDSLSPEPKSRF AMLDDVKILANGLLQLGHGLKDFVHKTKGQINDIFQKLNIFDQSFYD LSLQTSEIKEEEKELRRTTYKLQVKNEEVKNMSLELNSKLESLLEEK ILLQQKVKYLEEQLTNLIQNQPETPEHPEVTSLKTFVEKQDNSIKDL LQTVEDQYKQLNQQHSQIKEIENQLRRTSIQEPTEISLSSKPRAPRT TPFLQLNEIRNVKHDGIPAECTTIYNRGEHTSGMYAIRPSNSQVFHV YCDVISGSPWTLIQHRIDGSQNFNETWENYKYGFGRLDGEFWLGLEK IYSIVKQSNYVLRIELEDWKDNKHYIEYSFYLGNHETNYTLHLVAIT GNVPNAIPENKDLVFSTWDHKAKGHFNCPEGYSGGWWWHDECGENNL NGKYNKPRAKSKPERRRGLSWKSQNGRLYSIKSTKMLIHPTDSESFE *DYKDDDDKHHHHHHGGGLNDIFEAQKIEWHE* |

Figure 2:
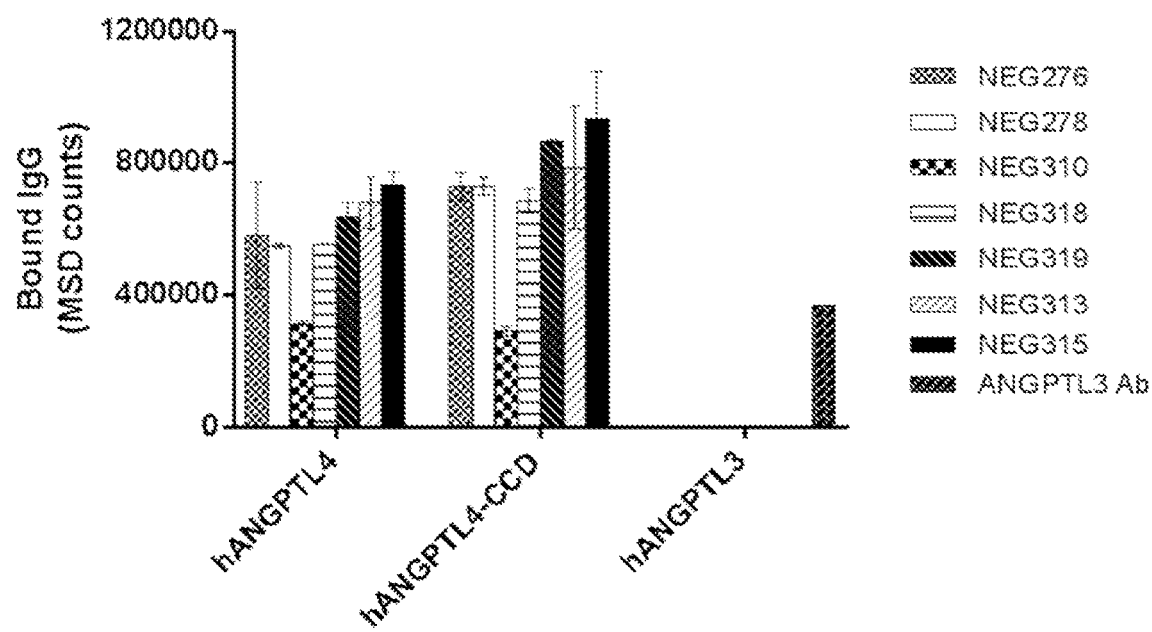
FIG. 2 depicts binding of selected antibodies of the invention to full-length human ANGPTL4 and human ANGPTL4 N-terminal coiled coil domain, and absence of binding to human full-length ANGPTL3. ANGPTL3 Ab=ANGPTL3-specific reference antibody.

Example 9: Characterization of Antibody Binding Specificity by Direct ELISA Assays Direct ELISA assays were conducted to characterize antibody binding specificity of selected antibodies of the invention. The assay was performed as follows. A 384-well streptavidin-coated Meso Scale Discovery (MSD) plate was blocked by incubating the plate with 50 μL Blocking Buffer (PBS, pH 7.4, 5% w/v bovine serum albumin) per well at 22° C. for 1 hour with constant shaking (600 rpm). The blocked MSD plate was then washed 3 times with Wash Buffer (PBS, pH 7.4 and 0.05% v/v Tween-20) using a plate washer (BioTek). Following washing, biotinylated human ANGPTL4 proteins diluted in Assay Buffer (PBS, pH 7.4 without $CaCl_2$ or $MgCl_2$, 0.5% w/v fatty acid-free bovine serum albumin and 0.02% v/v Tween-20) were immobilized on the surface by incubation at 1 nM concentration (15 μL per well) at 22° C. for one hour: full length human ANGPTL4 (hANGPTL4), human ANGPTL4 coiled-coil domain (hANGPTL4-CCD) and full length human ANGPTL3 (hANGPTL3). The plate was then washed 3 times as described earlier. Antibody diluted to 1 nM concentration in Assay Buffer was then applied to the MSD plate (15 μL per well), and the plate was incubated for 1 hour at 22° C. with constant shaking (600 rpm). Bound antibodies were detected by adding 15 μL per well of a 1:500 dilution of Sulfo-tagged goat anti-human IgG. The plate was then incubated for one hour with constant shaking (600 rpm). The plate was washed 3 times, and then 15 μL/well of 1×MSD read buffer T was added and the plate was developed using a Sector Imager 6000 (Meso Scale Discovery). The data were transferred to Microsoft Excel for analysis and plotted using GraphPad Prism v6. These experiments showed that all of the antibodies of the invention tested in this assay bind to full-length human ANGPTL4 and to the N-terminal domain of human ANGPTL4, and do not bind to full-length human ANGPTL3. An ANGPTL3-specific reference antibody was used as a positive control for the ANGPTL3 binding assay (FIG. 2).

Example 10: Antibody Dissociation Constants Determination by Solution Equilibrium Titration (SET) Assay SET assays were performed as follows. In a 96-well polypropylene plate, a constant concentration of ANGPTL4 antibody (10 pM) was mixed with different concentrations of non-biotinylated human, cyno, mouse, or rat full-length ANPGLT4 protein, or human ANGPTL4 N-terminal domain protein (5-fold serial dilution ranging from 0.01 pM to 100 nM) in SET buffer (PBS, pH 7.4 without $CaCl_2$ or $MgCl_2$, 0.5% w/v bovine serum albumin (fatty acid free) and 0.02% v/v Tween-20). The final reaction volume was 80 μL. The plate was sealed using an adhesive film and incubated at 22° C. for 14 hours with constant shaking (300 rpm). During the same period of time, a 384-well streptavidin-coated Meso Scale Discovery (MSD) plate was blocked by incubating the plate with 50 μL blocking buffer (PBS, pH 7.4, 5% w/v bovine serum albumin) per well at 4° C. The blocked MSD plate was washed 3 times with wash buffer (PBS, pH 7.4 and 0.05% v/v Tween-20) using a plate washer (BioTek). Biotinylated ANGPTL4 (full-length human, cyno, mouse, or rat ANGPTL4, or human ANGPTL4 N-terminal domain) protein (1 nM, 15 μL per well) was immobilized on the surface of the streptavidin-coated MSD plate by incubation at 22° C. for one hour with constant shaking (600 rpm). The plate was then washed 3 times as described earlier.

The equilibrium binding reactions (15 μL per well) were applied to the MSD plate with immobilized ANGPTL4 and incubated for 20 min at 22° C. The unbound material was removed by washing the plate 3 times with wash buffer, and the captured antibody was detected by adding 15 μL per well of a 1:500 dilution of Sulfo-tagged goat anti-human IgG (Meso Scale Discovery). The plate was then incubated for one hour with constant shaking (600 rpm). The plate was washed 3 times, and then 15 μL/well of 1×MSD read buffer T was added and the plate was developed using a Sector Imager 6000 (Meso Scale Discovery). The data were transferred to Microsoft Excel for analysis and plotted using GraphPad Prism v6. The $K_D$ values were determined by fitting the data to the following equation:

$$y=(B_{max}/(C_{Ab}/2))*((C_{Ab}/2)-(((((C_{Ag}+C_{Ab})+K_D)/2)-((((((C_{Ag}+C_{Ab})+K_D)^2)/4)-(C_{Ag}*C_{Ab}))^0.5))^2)/(2*C_{Ab}))),$$

where $B_{max}$ is the signal when no ANGPTL4 protein is present in solution, $C_{Ab}$ is the constant concentration of ANGPTL4 antibody in solution, $C_{Ag}$ is the concentration of ANGPTL4 in solution, and $K_D$ is the equilibrium dissociation constant. Equilibrium dissociation constants determined using this method are shown in Table 6.

TABLE 6

Dissociation constants ($K_D$) for antibodies of the invention binding to ANGPTL4 proteins determined by Solution Equilibrium Titration (SET) assays

| Antibody (IgG) | Human ANGPTL4 (26-406) $K_D$ (pM) | Cyno ANGPTL4 (26-406) $K_D$ (pM) | Rat ANGPTL4 (24-405) $K_D$ (pM) | Mouse ANGPTL4 (26-410) $K_D$ (pM) |
|---|---|---|---|---|
| NEG276 | 24 | 14 | >500* | >500* |
| NEG276-LALA | 8 | 7 | >500* | >500* |
| NEG278 | 15 | 20 | >500* | >500* |
| NEG310 | 21 | 22 | >500* | >500* |
| NEG313 | 9 | 15 | >500* | >500* |
| NEG315 | 12 | 21 | >500* | >500* |
| NEG318 | 9 | 17 | >500* | >500* |
| NEG319 | 16 | 8 | >500* | >500* |
| Ref Ab* | 17 | 4 | 517 | 194 |

*No binding signal was detected with the experimental conditions used, indicating a $K_D$ value >500 pM. A $K_D$ value of 517 pM was determined for binding of an ANGPTL4 reference antibody to rat ANGPTL4.

Example 11: Antibody Binding Kinetics and Dissociation Constants Determined by Octet Kinetic Binding Assay Dissociation constants ($K_D$) were determined for selected antibodies of the invention by using an Octet (ForteBio) kinetic binding assay. ForteBio 10× Kinetics Buffer (ForteBio, catalog number 18-5032) was diluted 10-fold with DPBS (Life Technologies, catalog number 14190-136), and the resulting solution was added (0.2 ml per well) to a 96-well plate (Greiner, catalog number 65520). Streptavidin sensors (ForteBio, catalog number 18-5020) were immersed in the solution and equilibrated for at least 10 min at room temperature. In a second 96-well plate (Greiner, catalog number 65520), sensors were washed in 1× Kinetics buffer, and then immersed in 200 ul of 25 nM biotinylated human ANGPTL4 or a biotinylated reference protein (for background substraction) for 1000 sec at seconds at room temperature. The sensors were then washed in 1× Kinetics buffer for 120 sec, and immersed in 200 μl of ANGPTL4 antibody diluted in 1× Kinetics buffer at various concentrations (serial 2-fold dilutions; the highest concentrations were 12.5 nM or 25 nM; the lowest concentrations ranged from 0.8 to 3.1 nM; 4-6 different antibody concentrations were used for each $K_D$ determination), and antibody association was monitored for 480 seconds. The sensors were then transferred to a well containing 200 μl 1× Kinetics buffer, and antibody dissociation was monitored for 1200 seconds. Background-corrected association and dissociation curves were globally fitted by Octet Software (ForteBio) to generate association ($k_a$) and dissociation ($k_d$) rate constants, which in turn were used to calculate equilibrium dissociation constants ($K_D$). The resulting data for selected antibodies of the invention is shown in Table 7 and Table 8.

TABLE 7

Human ANGPTL4(26-406) antibody dissociation constants ($K_D$) determined by ForteBio kinetic binding assay

| | Human ANGPTL4(26-406) | | |
|---|---|---|---|
| Antibody | $k_a$ (M$^{-1}$s$^{-1}$) | $k_d$ (s$^{-1}$) | $K_D$ (pM) |
| NEG276 | 3.4 × 10$^5$ | 8.0 × 10$^{-6}$ | 23 |
| NEG278 | 3.0 × 10$^5$ | 6.7 × 10$^{-7}$ | ≤17* |
| NEG310 | 2.2 × 10$^5$ | 1.1 × 10$^{-5}$ | 25 |
| NEG313 | 2.8 × 10$^5$ | 1.1 × 10$^{-5}$ | 40 |
| NEG315 | 2.8 × 10$^5$ | 7.9 × 10$^{-6}$ | 29 |
| NEG318 | 2.7 × 10$^5$ | 1.2 × 10$^{-5}$ | 45 |
| NEG319 | 2.8 × 10$^5$ | 1.0 × 10$^{-5}$ | 36 |

*Upper limit reported because off-rate is slower than the limit of detection, which is approximately 5 × 10$^{-6}$ s$^{-1}$.

TABLE 8

NEG276-LALA dissociation constants ($K_D$) determined by ForteBio kinetic binding assays

| Antibody | ANGPTL4 Protein | $k_a$ (M$^{-1}$s$^{-1}$) | $k_d$ (s$^{-1}$) | $K_D$ (pM) | Average $K_D$ (pM) |
|---|---|---|---|---|---|
| NEG276-LALA | Human ANGPTL4(26-406) | 4.1 × 10$^5$ | 5.9 × 10$^{-6}$ | 14 | 13 |
| | | 3.6 × 10$^5$ | 6.0 × 10$^{-6}$ | 17 | |
| | | 4.3 × 10$^5$ | 4.9 × 10$^{-7}$ | ≤12* | |
| | | 6.8 × 10$^5$ | 7.0 × 10$^{-6}$ | 10 | |
| | Cyno ANGPTL4(26-406) | 3.6 × 10$^5$ | 5.4 × 10$^{-6}$ | 15 | 15 |
| | | 3.7 × 10$^5$ | 4.1 × 10$^{-6}$ | ≤14* | |
| | Rat ANGPTL4(24-405) | 1.6 × 10$^5$ | 1.2 × 10$^{-3}$ | 7470 | 6343 |
| | | 1.7 × 10$^5$ | 1.1 × 10$^{-3}$ | 6030 | |
| | | 5.2 × 10$^4$ | 2.8 × 10$^{-5}$ | 5530 | |
| | Mouse ANGPTL4(26-410) | 3.6 × 10$^5$ | 2.9 × 10$^{-3}$ | 8250 | 6200 |
| | | 4.3 × 10$^5$ | 1.8 × 10$^{-3}$ | 4150 | |

TABLE 8-continued

NEG276-LALA dissociation constants ($K_D$) determined by ForteBio kinetic binding assays

| Antibody | ANGPTL4 Protein | $k_a$ (M$^{-1}$s$^{-1}$) | $k_d$ (s$^{-1}$) | $K_D$ (pM) | Average $K_D$ (pM) |
|---|---|---|---|---|---|
| | Human ANGPTL4(26-161) | 2.2 × 10$^5$ | 3.1 × 10$^{-6}$ | ≤23* | 38 |
| | | 1.8 × 10$^5$ | 9.2 × 10$^{-6}$ | 52 | |
| | Cyno ANGPTL4(26-161) | 2.7 × 10$^5$ | 6.4 × 10$^{-6}$ | 24 | 56 |
| | | 1.9 × 10$^5$ | 1.7 × 10$^{-5}$ | 87 | |
| | Human ANGPTL3(17-460) | —* | —* | >6000** | >6000** |
| | | —* | —* | >6000** | |

*Upper limit reported because the dissociation rate is slower that the limit of detection, which is approximately 5 × 10$^{-6}$ s$^{-1}$.
**No binding was detected at the highest concentration of antibody tested, 25 nM.

Example 12: Epitope Mapping by Hydrogen-deuterium Exchange/Mass Spectrometry

Hydrogen-deuterium exchange (HDx) in combination with mass spectrometry (MS) (Woods, 2001) was used to map the binding site of antibodies NEG276 and NEG318 on the ANGPTL4 N-terminal domain. In HDx, exchangeable amide hydrogens of proteins are replaced by deuterium. This process is sensitive to protein structure/dynamics and solvent accessibility and, therefore, able to report on ligand binding. The goal of these experiments was the identification of the epitopes of NEG276 and NEG318 on ANGPTL4.

Automated HDx/MS experiments were performed using methods similar to those described in the literature (Chalmers, 2006). The experiments were performed on a Waters HDx-MS platform, which includes a LEAP autosampler, nanoACQUITY UPLC System, and Synapt G2 mass spectrometer. The deuterium buffer used to label the protein backbone with deuterium was 50 mM D-Tris-HCl (pH 7.4), 500 mM NaCl, 15% glycerol, and 0.1% n-octyl β-D-maltoside; the overall percentage of deuterium in the solution was 82.5%. For human ANGPTL4(26-161) deuterium labeling experiments in the absence of ANGPTL4 antibody, 300 pmol of human ANGPLT4(26-161) (1.3 µl) was diluted using 100 µl of the deuterium buffer in a chilled tube and incubated for 25 minutes on a rotator at 4° C. The labeling reaction was then quenched with 100 µl of chilled quench buffer on ice for three minutes. After three minutes, the quenched solution was injected onto the LC-MS system for automated pepsin digestion and peptide analysis. For human ANGPTL4(26-161) deuterium labeling experiments in the presence of bound ANGPTL4 antibody, 300 pmol of the ANGPTL4 antibody was first immobilized on Thermo Protein G Plus beads and cross-linked using disuccinimidyl suberate (DSS). To perform the labeling experiments, the antibody beads (containing 300 pmol antibody) were incubated with 300 pmol human ANGPTL4(26-161) for 30 minutes at 4° C. After 30 minutes the beads were washed with 200 µl of Tris buffer. Then 200 µl of chilled deuterium buffer was added and the complex was incubated for 25 minutes at 4° C. After 25 minutes, the labeling reaction was quenched with 125 µl of chilled quench buffer on ice for 2.5 minutes. After spinning the sample for 30 seconds in a centrifuge, the quenched solution was injected onto the LC-MS system for automated pepsin digestion and peptide analysis.

All measurements were carried out using a minimum of three analytical triplicates. All deuterium exchange experiments were quenched using 0.5 M TCEP and 3 M urea (pH 2.5). After quenching, the exchanged antigen was subjected to on-line pepsin digestion using a Poroszyme Immobilized Pepsin column (2.1×30 mm) at 12° C. followed by trapping on a Waters Vanguard HSS T3 trapping column. Peptides were eluted from the trapping column and separated on a Waters CSH C18 1×100 mm column (maintained at 1° C.) at a flow rate of 40 µl/min using a binary eight minute gradient of 2 to 35% B (mobile phase A was 99.9% water and 0.1% formic acid; mobile phase B was 99.9% acetonitrile and 0.1% formic acid).

In these deuterium exchange experiments, peptides covering 87% of the ANGPTL4 N-terminal domain sequence were detected. The detected peptides, and the reduction in deuterium incorporation for each peptide, are indicated in Table 9. The HDxMS mapping experiment identified three regions of the ANGPTL4 N-terminal domain that were significantly protected by both NEG276 and NEG318: amino acids 26-35 ($G_{26}$PVQSKSPRF$_{35}$) (SEQ ID NO: 165), amino acids 42-68 ($N_{42}$VLAHGLLQLGQGLREHAERTRSQLSA$_{68}$) (SEQ ID NO: 174) and amino acids 69-95 ($L_{69}$ERRLSACGSACQTEGSTDLPLAPES$_{95}$) (SEQ ID NO: 190). The observation that NEG276 and NEG318 protect multiple regions of the ANGPTL4 N-terminal domain from deuterium incorporation is consistent with results from linear peptide epitope mapping which suggest that NEG276 and NEG318 have conformational rather than linear epitopes (see Example 13).

TABLE 9

Effect of NEG276 and NEG318 binding on deuterium incorporation into human ANGPLT4(26-161). For each peptide detected by mass spectrometry, the reduction in deuterium incorporation (in Daltons) for the antibody/ANGPTL4 complex relative to ANGPTL4 alone is shown.

| Peptide Name | Sequence | SEQ ID NO | Reduction in deuterium incorporation (Daltons) NEG276 | NEG318 |
|---|---|---|---|---|
| 26-35 | GPVQSKSPRF | 165 | 1.1 | 1.2 |
| 28-38 | VQSKSPRFASW | 166 | 1.0 | 0.9 |
| 42-49 | NVLAHGLL | 167 | <0.5 | <0.5 |
| 42-51 | NVLAHGLLQL | 168 | <0.5 | <0.5 |
| 44-51 | LAHGLLQL | 169 | <0.5 | <0.5 |

TABLE 9-continued

Effect of NEG276 and NEG318 binding on deuterium incorporation into human ANGPLT4(26-161). For each peptide detected by mass spectrometry, the reduction in deuterium incorporation (in Daltons) for the antibody/ANGPTL4 complex relative to ANGPTL4 alone is shown.

| Peptide Name | Sequence | SEQ ID NO | Reduction in deuterium incorporation (Daltons) NEG276 | NEG318 |
|---|---|---|---|---|
| 42-54 | NVLAHGLLQLGQG | 170 | 0.8 | 0.8 |
| 42-55 | NVLAHGLLQLGQGL | 171 | 0.9 | 0.8 |
| 42-57 | NVLAHGLLQLGQGLRE | 172 | 0.9 | 0.9 |
| 42-66 | NVLAHGLLQLGQGLREHAERTRSQL | 173 | 1.2 | 1.6 |
| 42-68 | NVLAHGLLQLGQGLREHAERTRSQLSA | 174 | 1.3 | 1.8 |
| 44-66 | LAHGLLQLGQGLREHAERTRSQL | 175 | 1.1 | 1.6 |
| 45-57 | AHGLLQLGQGLRE | 176 | 0.7 | 0.9 |
| 45-66 | AHGLLQLGQGLREHAERTRSQL | 177 | 1.0 | 1.5 |
| 49-66 | LQLGQGLREHAERTRSQL | 178 | 0.5 | 1.0 |
| 52-66 | GQGLREHAERTRSQL | 179 | <0.5 | 0.9 |
| 69-102 | LERRLSACGSACQTEGSTDLPAPESRVDPEVL | 180 | 1.4 | 1.9 |
| 76-102 | CGSACQTEGSTDLPAPESRVDPEVL | 181 | 1.0 | 1.2 |
| 86-102 | STDLPAPESRVDPEVL | 182 | 1.1 | 1.1 |
| 96-102 | RVDPEVL | 183 | <0.5 | <0.5 |
| 103-109 | HSLQTQL | 184 | 0.5 | 0.5 |
| 110-119 | KAQNSRIQQL | 185 | <0.5 | <0.5 |
| 110-135 | KAQNSRIQQLFHKVAQQQRHLEKQHL | 186 | <0.5 | <0.5 |
| 120-135 | FHKVAQQQRHLEKQHL | 187 | <0.5 | <0.5 |
| 141-147 | QSQFGLL | 188 | 0.6 | 0.6 |
| 144-155 | FGLLDHKHLDHE | 189 | <0.5 | <0.5 |

Example 13: Epitope Mapping by Linear Peptide Binding

The ability of selected antibodies of invention, namely NEG276 and NEG318, to bind to linear 15-amino-acid peptides derived from the N-terminal coiled coil domain of human ANGPTL4 was tested. A total of 43 peptides were synthesized and purified using standard methods; the sequence of the peptides are shown in Table 10. The peptides were immobilized on a glass surface, and the ability of NEG276 and NEG318 to bind to the immobilized peptides was evaluated using experimental methods optimized for linear peptide epitope mapping at JPT Peptide Technologies (Berlin, Germany). An antibody that does not bind to ANGPTL4 was used as a control for non-specific binding. No specific binding of NEG276 or NEG318 to any of the 43 15-mer peptides was observed in these experiments. These results strongly suggest that the epitopes of NEG276 and NEG318 are not linear ANGPTL4 peptides, but instead are conformational epitopes.

TABLE 10

Sequences of linear ANGPTL4-derived peptides used for peptide binding experiments.

| Peptide | Name (SEQ ID NO.) |
|---|---|
| GPVQSKSPRFASWDE | P1 (191) |
| QSKSPRFASWDEMNV | P2 (192) |
| SPRFASWDEMNVLAH | P3 (193) |
| FASWDEMNVLAHGLL | P4 (194) |
| WDEMNVLAHGLLQLG | P5 (195) |
| MNVLAHGLLQLGQGL | P6 (196) |
| LAHGLLQLGQGLREH | P7 (197) |
| GLLQLGQGLREHAER | P8 (198) |
| QLGQGLREHAERTRS | P9 (199) |
| QGLREHAERTRSQLS | P10 (200) |
| REHAERTRSQLSALE | P11 (201) |
| AERTRSQLSALERRL | P12 (202) |
| TRSQLSALERRLSAS | P13 (203) |
| QLSALERRLSASGSA | P14 (204) |
| ALERRLSASGSASQG | P15 (205) |
| RRLSASGSASQGTEG | P16 (206) |
| SASGSASQGTEGSTD | P17 (207) |
| GSASQGTEGSTDLPL | P18 (208) |
| SQGTEGSTDLPLAPE | P19 (209) |
| TEGSTDLPLAPESRV | P20 (210) |
| STDLPLAPESRVDPE | P21 (211) |
| LPLAPESRVDPEVLH | P22 (212) |
| APESRVDPEVLHSLQ | P23 (213) |
| SRVDPEVLHSLQTQL | P24 (214) |
| DPEVLHSLQTQLKAQ | P25 (215) |
| VLHSLQTQLKAQNSR | P26 (216) |
| SLQTQLKAQNSRIQQ | P27 (217) |
| TQLKAQNSRIQQLFH | P28 (218) |
| KAQNSRIQQLFHKVA | P29 (219) |
| NSRIQQLFHKVAQQQ | P30 (220) |
| IQQLFHKVAQQQRHL | P31 (221) |
| LFHKVAQQQRHLEKQ | P32 (222) |
| KVAQQQRHLEKQHLR | P33 (223) |
| QQQRHLEKQHLRIQH | P34 (224) |

TABLE 10-continued

Sequences of linear ANGPTL4-derived peptides used for peptide binding experiments.

| Peptide | Name (SEQ ID NO.) |
| --- | --- |
| RHLEKQHLRIQHLQS | P35 (225) |
| EKQHLRIQHLQSQFG | P36 (226) |
| HLRIQHLQSQFGLLD | P37 (227) |
| IQHLQSQFGLLDHKH | P38 (228) |
| LQSQFGLLDHKHLDH | P39 (229) |
| QFGLLDHKHLDHEVA | P40 (230) |
| LLDHKHLDHEVAKPA | P41 (231) |
| HKHLDHEVAKPARRK | P42 (232) |
| KHLDHEVAKPARRKR | P43 (233) |

Example 14: Effect of ANGPTL4 Antibodies of the Invention on Plasma Triglyceride Concentrations in Human ANGPTL4 Transgenic Mice A construct to express transgenic human ANGPTL4 in mice was made by inserting the full-length human ANGPTL4 cDNA sequence into the polylinker region of the pLIVLE6 vector, which contains the human apolipoprotein E gene promoter and its hepatic control region. ANGPTL4 transgenic mice were generated on a C57BL/6J background and bred at Novartis (East Hanover, N.J.). Transgenic mice were tail-clipped at 7 days of age and DNA was extracted from the tails using a REDExtract-N-Amp Tissue PCR Kit (Sigma-Aldrich; St. Louis, Mo.; cat #XNATR). The human ANGPTL4 transgene was detected by using primer pairs targeting the pLIVLE6 vector and targeting ANGPTL4 cDNA. Mice were housed in solid-bottom cages on a rack equipped to automatically provide water ad libitum, maintained on a 12 hr light/dark cycle (6 am to 6 pm), and given standard rodent chow (Harlan-Teklad; Frederick, Md.; cat #8604). The vivarium was maintained between 68-76° F. with 30-70% humidity. Mice were housed with littermates and received food and water ad libitum during the study, except for 4 hr fasts prior to sample collection.

Animals were fasted for 4 hr and briefly anesthetized for submandibular blood collection to measure baseline plasma triglyceride concentrations. Mice were then injected intraperitoneally (i.p.) with 30 mg/kg antibody diluted in PBS (10 mL/kg injection volume). Blood was collected after 4 hr fasts on days 1, 2, and 5 post-dose to measure plasma triglyceride and total human IgG concentrations. Blood was collected into BD Microtainer collection/separator tubes with EDTA (Becton, Dickinson, and Company; Franklin Lakes, N.J., catalog number 365973). Samples were centrifuged for 10 min at 20,817×g, and plasma was transferred to a 0.2 mL Thermo-strip tube (Thermo-Scientific; Pittsburgh, Pa.; cat #AB 0451) and frozen and stored at −80° C.

Plasma triglyceride concentrations were measured using the Triglyceride (GPO) Liquid Reagent set (Pointe Scientific, Canton, Mich., catalog number T7532-500). Briefly, 300 µL of assay reagent, pre-warmed to 37° C., was added to 5 µL of plasma in a clear, flat-bottom 96-well plate (Thermo Scientific, catalog number 269620). The plate was mixed on a plate shaker for 30 sec and then placed in a 37° C. incubator for 5 min. Following a 20 sec mix, absorbance at 500 nm was measured using a Molecular Devices SPECTRAmax PLUS plate reader. Triglyceride concentrations were calculated by using a calibration curve generated using known quantities of a triglyceride standard (Pointe Scientific, catalog number T7531-STD).

Figure 3A:
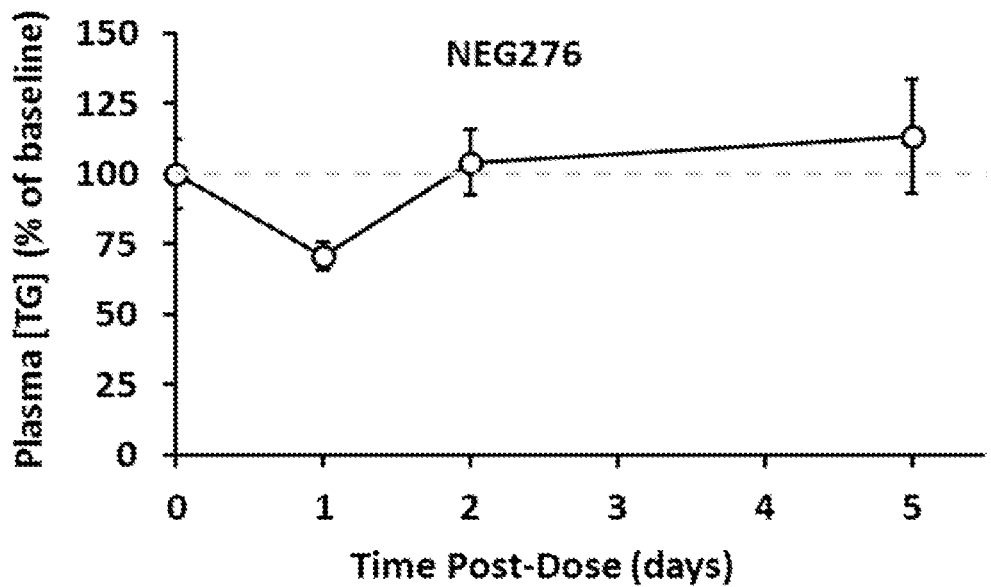
FIG. 3A-3B depicts changes in plasma triglyceride levels in human ANGPTL4 transgenic mice following administration of selected ANGPTL4 antibodies of the invention.
Figure 3B:
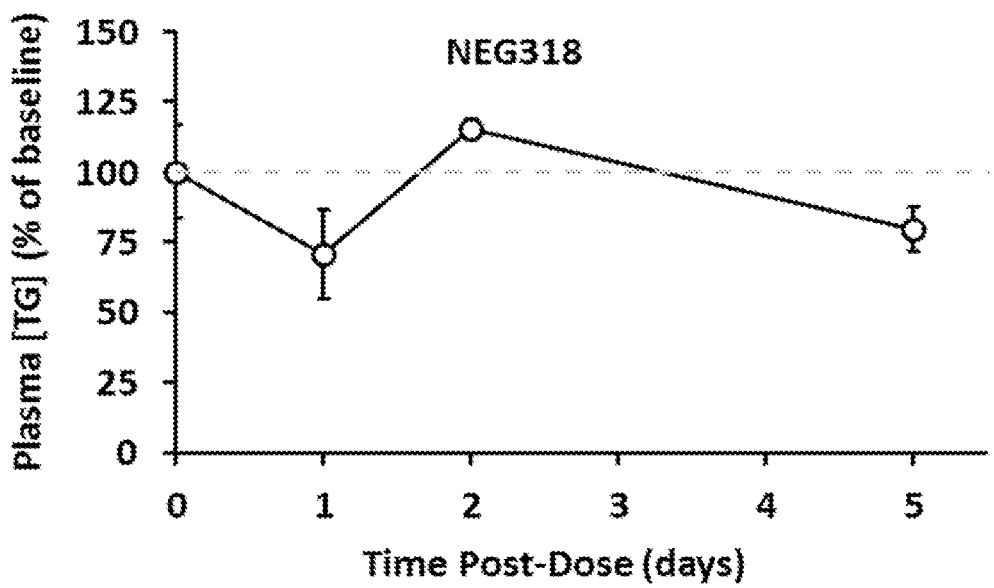

The antibodies NEG276 and NEG318 both reduced plasma triglyceride levels when administered to the human ANGPTL4 transgenic mice (FIG. 3).

Example 15: Effects of Administering One of the ANGPTL4 Antibodies of the Invention to Obese, Diabetic, Hypertriglyceridemic Cynomolgus Monkeys To evaluate the pharmacokinetic profile and pharmacological effects of NEG276-LALA, we administered a single, subcutaneous, 3 mg/kg dose to four hypertriglyceridemic cynomolgus monkeys. The monkeys used in this study had baseline plasma triglyceride levels ranging from 207 mg/dL to 2438 mg/dL. At various timepoints over 5 weeks after NEG276-LALA dosing, plasma samples were collected (blood samples were drawn from animals prior to morning feeding, but the animals were not fasted overnight).

Figure 4:
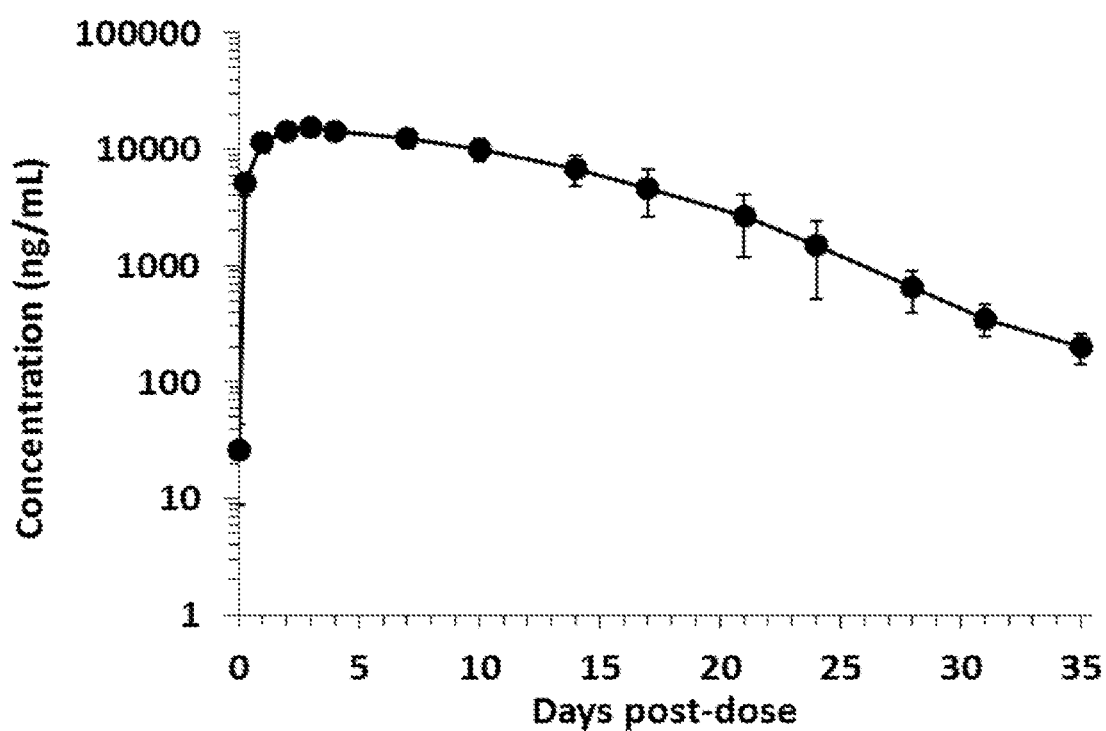
FIG. 4 depicts plasma total human antibody concentrations in obese, diabetic cynomolgus monkeys following administration of one ANGPTL4 antibody of the invention (NEG276-LALA).

Total NEG276-LALA plasma concentrations were determined by standard methods. NEG276-LALA reached an average maximum plasma concentration ($C_{max}$) of 15,536±2281 ng/mL at 3 days post-dose. At day 21 post-dose, the average NEG276-LALA plasma concentration was 2663 ng/mL (FIG. 4).

Plasma TG, total cholesterol, high-density lipoprotein (HDL) cholesterol, total apolipoprotein B (apoB), and apolipoprotein CIII (apoCIII) concentrations were determined using commercially available assay kits (TG: Triglyceride (GPO) Liquid Reagent set, Pointe Scientific, catalog number T7532-500; total cholesterol: Cholesterol Reagent Set, Pointe Scientific, catalog number C7510-500; HDL: Cholesterol Precipitating Reagent from manual HDL reagent kit, Wako, catalog number 431-52501; total ApoB: K-Assay Apo B, Kamiya Biomedical Company, catalog number KAI-004; ApoC-III: ApoC-III Assay Reagent, Randox, catalog number LP-3865).

Figure 5:
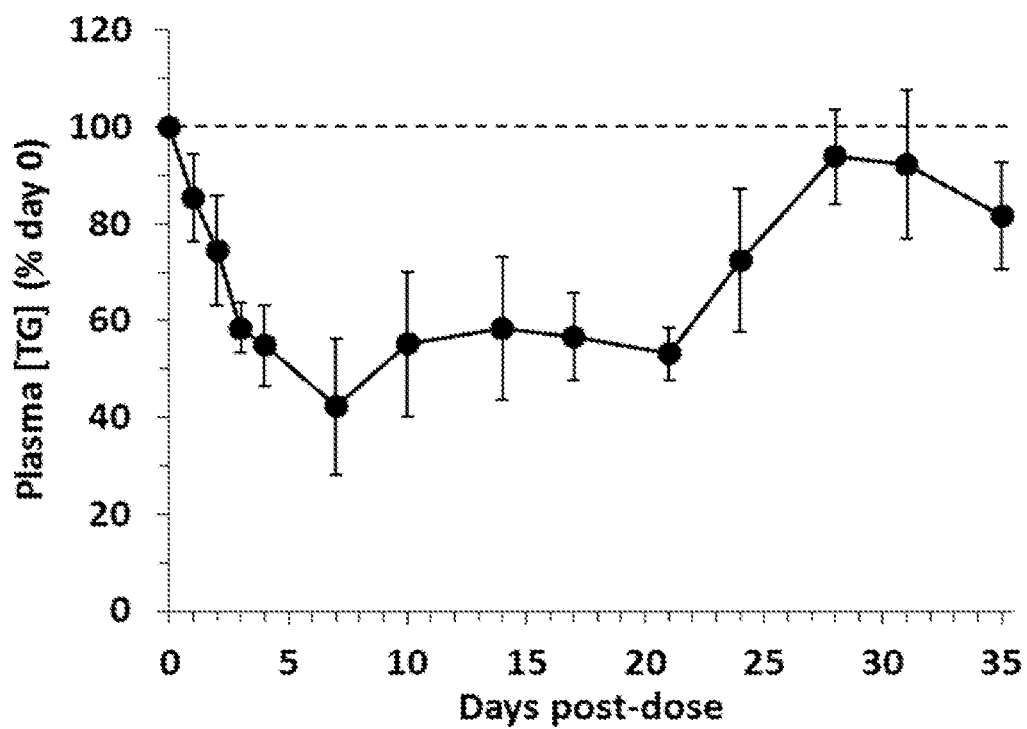
FIG. 5 depicts changes in plasma triglyceride (TG) concentrations in obese, diabetic cynomolgus monkeys following administration of one ANGPTL4 antibody of the invention (NEG276-LALA).
Figure 6:
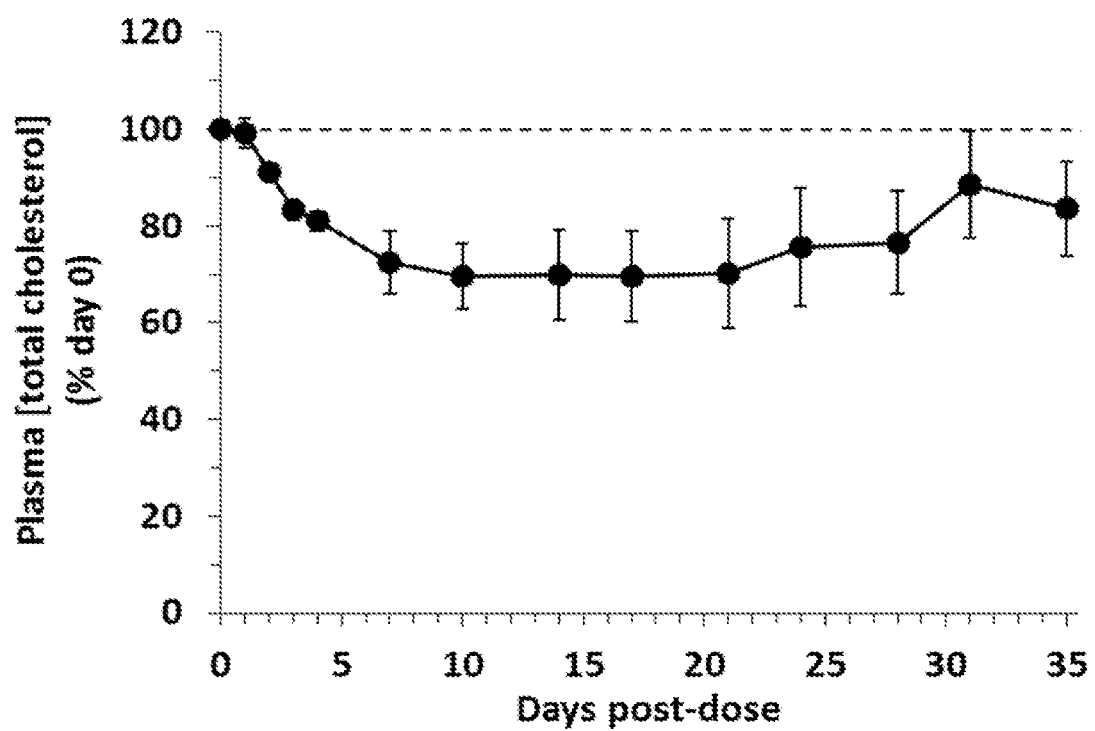
FIG. 6 depicts changes in plasma total cholesterol concentration in obese, diabetic cynomolgus monkeys following administration of one ANGPTL4 antibody of the invention (NEG276-LALA).
Figure 7:
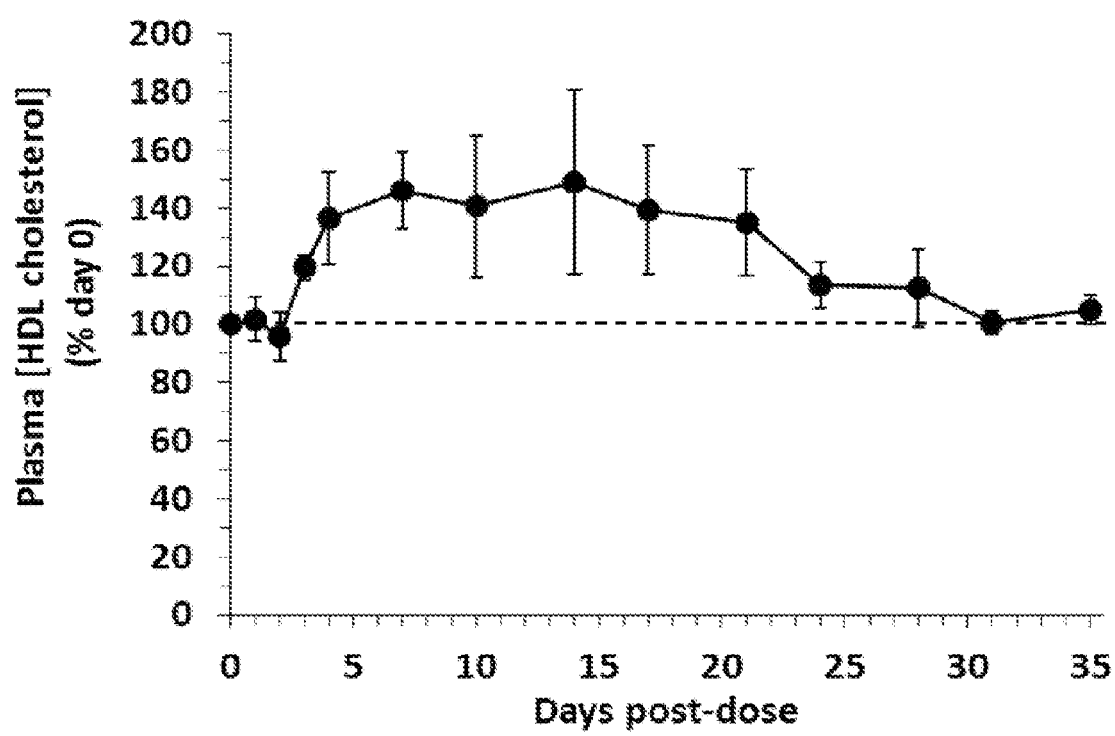
FIG. 7 depicts changes in plasma high-density lipoprotein (HDL) concentrations in obese, diabetic cynomolgus monkeys following administration of one ANGPTL4 antibody of the invention (NEG276-LALA).
Figure 8:
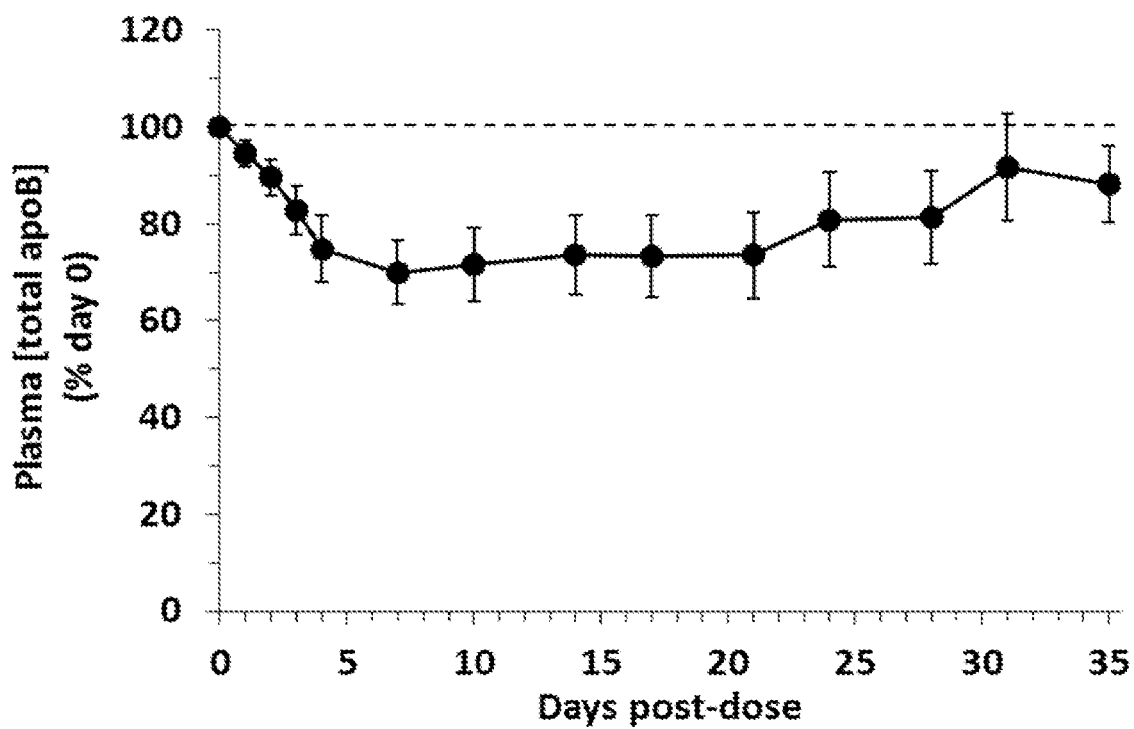
FIG. 8 depicts changes in plasma total apolipoprotein B (ApoB) concentrations in obese, diabetic cynomolgus monkeys following administration of one ANGPTL4 antibody of the invention (NEG276-LALA).
Figure 9:
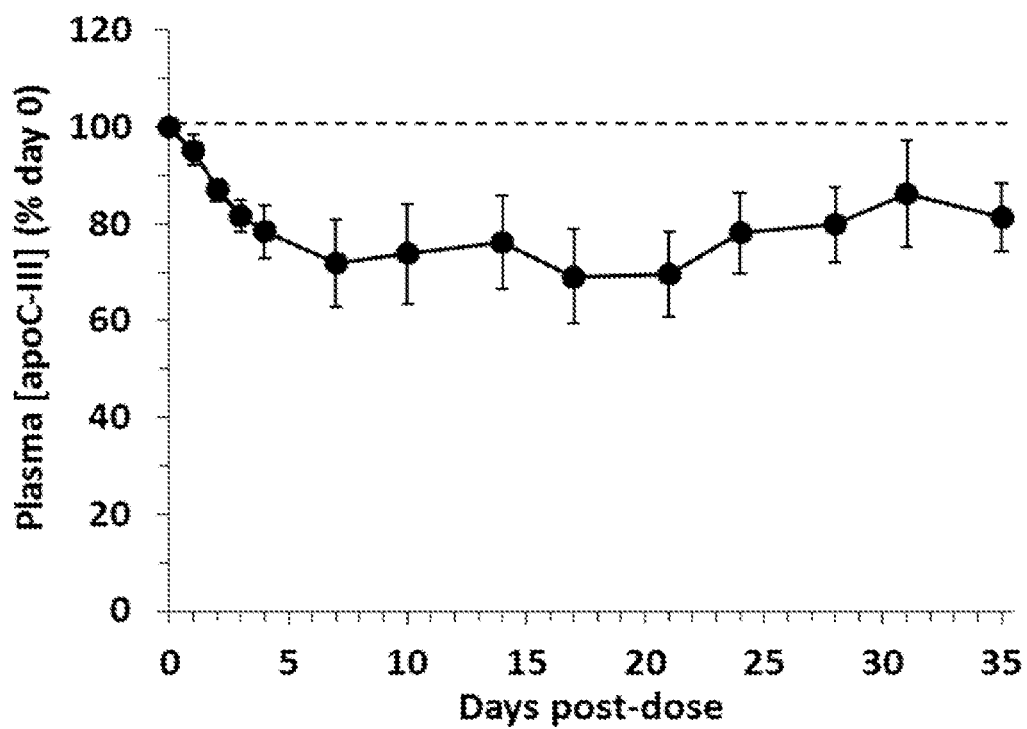
FIG. 9 depicts changes in plasma apolipoprotein C-III (ApoC-III) concentrations in obese, diabetic cynomolgus monkeys following administration of one ANGPTL4 antibody of the invention (NEG276-LALA).
Figure 10:
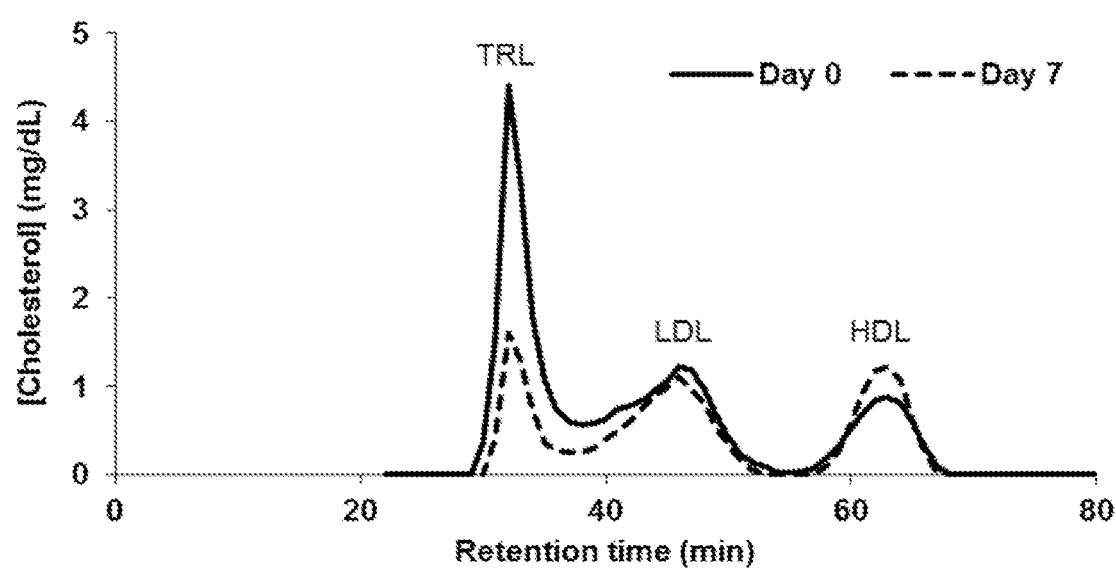
FIG. 10 depicts changes in plasma lipoprotein-associated cholesterol levels as assessed by fast-protein liquid chromatography (FPLC) separation of plasma lipoprotein following administration of one ANGPTL4 antibody of the invention. Data from one monkey is shown (NEG276-LALA, monkey #6296). Abbreviations: TRL, triglyceride-rich lipoproteins; LDL, low-density lipoprotein; HDL, high-density lipoprotein.
Figure 11:
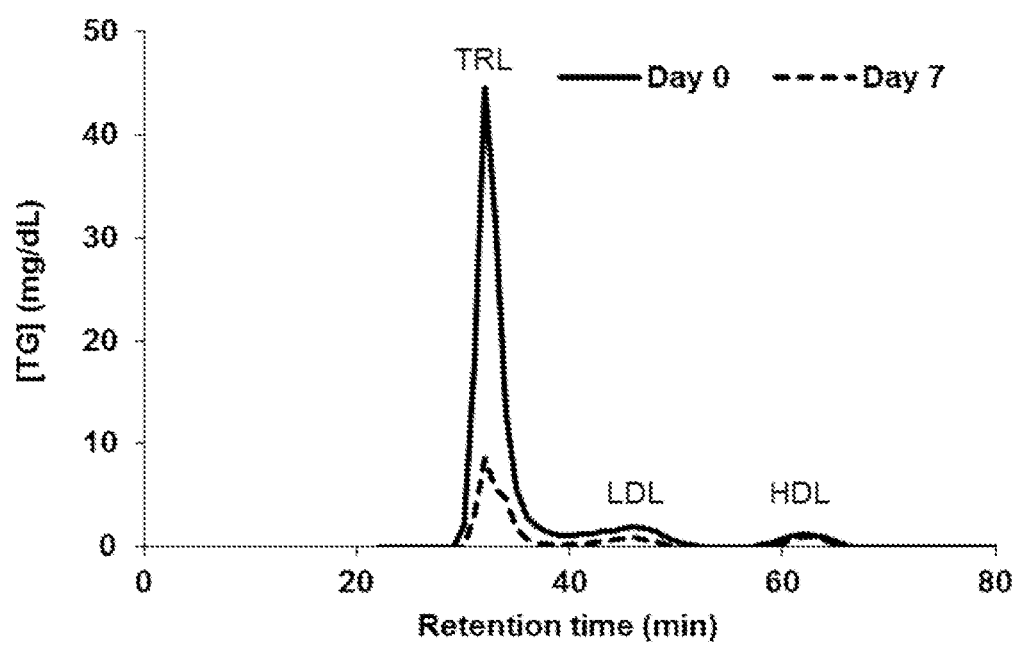
FIG. 11 depicts changes in plasma lipoprotein-associated triglyceride (TG) levels as assessed by fast-protein liquid chromatography (FPLC) separation of plasma lipoprotein following administration of one ANGPTL4 antibody of the invention. Data from one monkey is shown (NEG276-LALA, monkey #6296). Abbreviations: TRL, triglyceride-rich lipoproteins; LDL, low-density lipoprotein; HDL, high-density lipoprotein.

NEG276-LALA administration resulted in a marked decrease in plasma triglyceride (TG) levels. Peak plasma TG lowering was observed on day 7 post-dosing; at this time point plasma TG concentrations were 58% lower than baseline plasma TG levels. After peak TG lowering occurred on day 7 post-dose, plasma TG concentrations remained suppressed by greater than 40% relative to baseline concentrations through day 21 post-dose, then returned to baseline (FIG. 5). In addition to its effect on plasma TG, NEG276-LALA administration reduced plasma total cholesterol concentrations by approximately 30% relative to baseline (FIG. 6) and increased HDL cholesterol concentrations by more than 20% from baseline on days 7 through 21 post-dosing (FIG. 7). In addition, an approximately 30% decrease in plasma total apoB concentrations was observed on days 7 through 21 post-dose (FIG. 8), and an approximately 25% decrease in plasma apoC-III concentrations relative to baseline was observed on days 7 through 21 (FIG. 9). We also evaluated the effect of NEG276-LALA administration on lipoprotein-associated triglyceride and cholesterol levels by separating lipoprotein components using standard size-exclusion chromatography methods. Comparison of lipoprotein profiling data for pre-dose (day 0) and day 7 post-dose samples showed that NEG276-LALA administration resulted in marked decreases in triglyceride-rich lipoprotein (TRL) associated cholesterol and triglyceride concentrations (results from one monkey are shown in FIG. 10 and FIG. 11).

INCORPORATION BY REFERENCE

All references cited herein, including patents, patent applications, papers, text books, and the like, and the references cited therein, to the extent that they are not already, are hereby incorporated herein by reference in their entirety.

EQUIVALENTS

The foregoing written specification is considered to be sufficient to enable one skilled in the art to practice the invention. The foregoing description and examples detail certain preferred embodiments of the invention and describe the best mode contemplated by the inventors. It will be appreciated, however, that no matter how detailed the foregoing may appear in text, the invention may be practiced in many ways and the invention should be construed in accordance with the appended claims and any equivalents thereof.

The invention claimed is:

1. A method for achieving one or more biological activities selected from the group consisting of: decreasing plasma triglyceride levels, decreasing plasma lipoprotein-associated triglyceride levels, decreasing plasma total cholesterol levels, decreasing plasma lipoprotein-associated cholesterol levels, decreasing plasma apolipoprotein B (ApoB) levels, decreasing plasma apolipoprotein C-III (ApoC-III) levels, decreasing triglyceride-rich lipoprotein (TRL) associated cholesterol levels, and increasing plasma high-density lipoprotein (HDL) in a subject, the method comprising administering to the subject a therapeutically-effective amount of a pharmaceutical composition comprising an antibody or fragment thereof that binds specifically to human ANGPTL4, wherein the antibody or fragment thereof comprises:

(I)
a heavy chain variable region comprising a HCDR1 comprising the amino acid sequence of SEQ ID NO:7, a HCDR2 comprising the amino acid sequence of SEQ ID NO:8, and a HCDR3 comprising the amino acid sequence of SEQ ID NO:9; and
a light chain variable region comprising a LCDR1 comprising the amino acid sequence of SEQ ID NO:17, a LCDR2 comprising the amino acid sequence of SEQ ID NO:18, and a LCDR3 comprising the amino acid sequence of SEQ ID NO:19; or (II)
a heavy chain variable region comprising a HCDR1 comprising the amino acid sequence of SEQ ID NO:10, a HCDR2 comprising the amino acid sequence of SEQ ID NO:11, and a HCDR3 comprising the amino acid sequence of SEQ ID NO:12; and
a light chain variable region comprising a LCDR1 comprising the amino acid sequence of SEQ ID NO:20, a LCDR2 comprising the amino acid sequence of SEQ ID NO:21, and a LCDR3 comprising the amino acid sequence of SEQ ID NO:22.

2. The method of claim 1, wherein the subject has an ANGPTL4-associated disorder.

3. The method of claim 2, wherein the ANGPTL4-associated disorder is selected from the group consisting of severe hypertriglyceridemia, hypertriglyceridemia associated with obesity, type V hypertriglyceridemia, chylomicronemia, primary dyslipidemia, metabolic syndrome, and type 2 diabetes.

4. The method of claim 3, wherein the severe hypertriglyceridemia is associated with plasma triglyceride concentration of >500 mg/dL.

5. The method of claim 1, wherein the antibody or fragment thereof is a monoclonal antibody, humanized antibody, single chain antibody, Fab fragment, Fv fragment, $F(ab')_2$ fragment, or scFv fragment.

6. The method of claim 1, wherein the antibody or fragment thereof is an IgG1 or IgG4 isotype antibody or fragment thereof.

7. The method of claim 1, wherein the antibody or fragment thereof comprises a heavy chain variable region comprising an amino acid sequence that is at least 90% identical to SEQ ID NO:13, and a light chain variable region comprising an amino acid sequence that is at least 90% identical to SEQ ID NO:23.

8. The method of claim 1, wherein the antibody or fragment thereof comprises a heavy chain variable region comprising the amino acid sequence of SEQ ID NO:13, and a light chain variable region comprising the amino acid sequence of SEQ ID NO:23.

9. The method of claim 1, wherein the antibody or fragment thereof comprises a heavy chain comprising an amino acid sequence that is at least 90% identical to SEQ ID NO:15, and a light chain comprising an amino acid sequence that is at least 90% identical to SEQ ID NO:25.

10. The method of claim 1, wherein the antibody or fragment thereof comprises a heavy chain comprising the amino acid sequence of SEQ ID NO:15, and a light chain comprising the amino acid sequence of SEQ ID NO:25.

11. The method of claim 1, wherein the antibody or fragment thereof comprises a heavy chain comprising an amino acid sequence that is at least 90% identical to SEQ ID NO:28, and a light chain comprising an amino acid sequence that is at least 90% identical to SEQ ID NO:25.

12. The method of claim 1, wherein the antibody or fragment thereof comprises a heavy chain comprising the amino acid sequence of SEQ ID NO:28, and a light chain comprising the amino acid sequence of SEQ ID NO:25.

13. The method of claim 1, wherein the antibody or fragment thereof is a bispecific antibody or fragment thereof.

* * * * *